United States Patent
Oslob et al.

(10) Patent No.: US 11,123,337 B2
(45) Date of Patent: *Sep. 21, 2021

(54) 4-METHYLSULFONYL-SUBSTITUTED PIPERIDINE UREA COMPOUNDS

(71) Applicant: MYOKARDIA, INC., Brisbane, CA (US)

(72) Inventors: Johan Oslob, Sunnyvale, CA (US); Danielle Aubele, San Mateo, CA (US); Jae Kim, Thousand Oaks, CA (US); Robert McDowell, San Francisco, CA (US); Yonghong Song, Foster City, CA (US); Arvinder Sran, Fremont, CA (US); Min Zhong, Palo Alto, CA (US)

(73) Assignee: MyoKardia, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/934,463

(22) Filed: Jul. 21, 2020

(65) Prior Publication Data

US 2020/0345716 A1   Nov. 5, 2020

Related U.S. Application Data

(63) Continuation of application No. 16/149,912, filed on Oct. 2, 2018, now Pat. No. 10,758,525, which is a continuation of application No. 15/888,775, filed on Feb. 5, 2018, now abandoned, which is a continuation of application No. 15/003,662, filed on Jan. 21, 2016, now Pat. No. 9,925,177.

(60) Provisional application No. 62/106,571, filed on Jan. 22, 2015.

(51) Int. Cl.
| | |
|---|---|
| *C07D 401/14* | (2006.01) |
| *C07D 413/14* | (2006.01) |
| *C07D 417/12* | (2006.01) |
| *C07D 401/12* | (2006.01) |
| *C07D 413/12* | (2006.01) |
| *C07D 471/04* | (2006.01) |
| *C07D 417/14* | (2006.01) |
| *A61K 31/4545* | (2006.01) |
| *A61K 31/454* | (2006.01) |
| *A61K 31/496* | (2006.01) |
| *A61K 31/506* | (2006.01) |
| *A61K 45/06* | (2006.01) |
| *C07D 405/14* | (2006.01) |
| *C07D 411/14* | (2006.01) |
| *C07D 409/02* | (2006.01) |
| *C07D 407/14* | (2006.01) |
| *C07D 407/02* | (2006.01) |
| *C07D 401/02* | (2006.01) |
| *A61K 31/501* | (2006.01) |

(52) U.S. Cl.
CPC ........ *A61K 31/4545* (2013.01); *A61K 31/454* (2013.01); *A61K 31/496* (2013.01); *A61K 31/501* (2013.01); *A61K 31/506* (2013.01); *A61K 45/06* (2013.01); *C07D 401/02* (2013.01); *C07D 401/12* (2013.01); *C07D 401/14* (2013.01); *C07D 405/14* (2013.01); *C07D 407/02* (2013.01); *C07D 407/14* (2013.01); *C07D 409/02* (2013.01); *C07D 411/14* (2013.01); *C07D 413/12* (2013.01); *C07D 413/14* (2013.01); *C07D 417/12* (2013.01); *C07D 471/04* (2013.01)

(58) Field of Classification Search
CPC .. C07D 401/12; C07D 413/12; C07D 413/14; C07D 417/12; C07D 417/14; C07D 401/14; C07D 471/04
See application file for complete search history.

(56) References Cited

U.S. PATENT DOCUMENTS

| | | |
|---|---|---|
| 9,925,177 B2 | 3/2018 | Oslob et al. |
| 2005/0250789 A1 | 11/2005 | Burns et al. |
| 2010/0113377 A1 | 5/2010 | Simpson |
| 2010/0228026 A1 | 9/2010 | Yoshida et al. |
| 2016/0145249 A1 | 5/2016 | Terakado et al. |

FOREIGN PATENT DOCUMENTS

| | | |
|---|---|---|
| CA | 2598610 A1 | 9/2006 |
| CN | 102596949 A | 7/2012 |
| EP | 2500345 A1 | 9/2012 |
| EP | 2203437 B1 | 11/2012 |
| WO | 2000/044723 A1 | 8/2000 |
| WO | 2006/009726 A2 | 1/2006 |
| WO | 2006/074025 A1 | 7/2006 |
| WO | 2008/120759 A1 | 10/2008 |
| WO | 2009/011850 A2 | 1/2009 |
| WO | 2009/038974 A1 | 3/2009 |
| WO | 2009/043747 A2 | 4/2009 |
| WO | 2009/154300 A2 | 12/2009 |

(Continued)

OTHER PUBLICATIONS

International Search Report and Written Opinion dated Apr. 29, 2016 in connection with PCT/US2016/014365.

(Continued)

*Primary Examiner* — Emily A Bernhardt
(74) *Attorney, Agent, or Firm* — Honigman LLP; Andrew S. Chipouras; Jonathan P. O'Brien

(57) ABSTRACT

The present invention provides novel 4-methylsulphone-substituted piperidine urea compounds that are useful for the treatment of dilated cardiomyopathy (DCM) and conditions associated with left and/or right ventricular systolic dysfunction or systolic reserve. The synthesis and characterization of the compounds is described, as well as methods for treating DCM and other forms of heart disease.

14 Claims, 3 Drawing Sheets

(56) References Cited

FOREIGN PATENT DOCUMENTS

| WO | 2010/113377 A1 | 10/2010 |
| WO | 2011/059021 A1 | 5/2011 |
| WO | 2015/005305 A1 | 1/2015 |
| WO | 2015/018475 A1 | 2/2015 |
| WO | 2015/112806 A2 | 7/2015 |
| WO | 2016/118774 A1 | 7/2016 |

OTHER PUBLICATIONS

Written Opinion for Singapore Patent Application No. 11201705928 dated Apr. 20, 2018, 6 pages.

Andrei, et al., New Perspective in Heart Failure Management: Could Myosin Activators be the Answer? Discoveries Journals. Oct. 2014;2(4):e33, 8 pages. Doi:10.15190/d.2014.25.

Malik, et al., Cardiac myosin activation: a potential therapeutic approach for systolic heart failure. Science. Mar. 18, 2011;331(6023):1439-43. doi:10.1126/science.1200113.

Shen et al. Discovery of a highly potent, selective, and bioavailable soluble epoxide hydrolase inhibitor with excellent ex vivo target engagement. J Med Chem. Aug. 27, 2009;52(16):5009-12. doi: 10.1021/jm900725r. PubMed PMID: 19645482.

Teerlink, J.R., "A novel approach to improve cardiac performance: cardiac myosin activators", Heart Fail Rev. Dec. 2009;14(4), pp. 289-298.

4-METHYLSULFONYL-SUBSTITUTED PIPERIDINE UREA COMPOUNDS

CROSS-REFERENCES TO RELATED APPLICATIONS

This application is a continuation of U.S. patent application Ser. No. 16/149,912, filed Oct. 2, 2018, which is a continuation application of U.S. patent application Ser. No. 15/888,775, filed Feb. 5, 2018, which is a continuation application of U.S. patent application Ser. No. 15/003,662, filed Jan. 21, 2016, which claims the benefit of priority to U.S. Provisional Application Ser. No. 62/106,571, filed Jan. 22, 2015, the entire contents of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Dilated cardiomyopathy (DCM) comprises a group of myocardial disorders that lead to left ventricular dilatation and systolic dysfunction (abnormality of contraction). DCM can be subdivided into ischemic (attributed due to coronary artery disease) or non-ischemic (primary diseases of the myocardium). Hereafter, DCM refers to non-ischemic primary diseases of the myocardium. DCM can be assigned a clinical diagnosis of "idiopathic" DCM if no identifiable cause (except genetic) can be found. Idiopathic DCM can be further subcategorized based upon whether a genetic cause can be identified. Mutations in over 30 genes, including sarcomere genes, perturb a diverse set of myocardial proteins to cause a DCM phenotype. Epidemiologic data indicate that approximately 1 in 2,500 individuals in the general population have idiopathic DCM.

Sarcomere gene mutations that cause DCM are highly penetrant, but there is wide variability in clinical severity and clinical course. Some genotypes are associated with a more malignant course, but there is considerable variability between and even within families carrying the same mutation. While many patients with DCM report minimal or no symptoms for extended periods of time, DCM is a progressive disease with a significant cumulative burden of morbidity and mortality. The hallmark of DCM is a dilated left ventricle, more spherical in shape than usual, and with decreased systolic function. Patients usually present with symptoms of heart failure: dyspnea, orthopnea, exercise intolerance, fatigue, abdominal discomfort and poor appetite. Signs include sinus tachycardia, a gallop rhythm, murmur of mitral regurgitation, rales, jugular venous distension, hepatomegaly, peripheral edema and cool extremities can be found. As with many other disorders, symptoms tend to worsen with age. The patient journey is punctuated by hospitalizations for decompensated heart failure and an increased risk for sudden arrhythmic death and death from pump failure.

Diagnosis is dependent upon patient history and physical examination. Plasma biomarkers such as B-type natriuretic peptide (BNP) or its N-terminal pro-protein (NT-proBNP) can help with diagnosis and management of DCM, especially to distinguish heart failure from comorbid pulmonary disease. Coronary angiography can identify if heart failure is due to ischemic etiology. Endomyocardial biopsy can distinguish DCM from disease processes that might require alternative management strategy, such as myocarditis, storage disease, sarcoidosis or hemochromatosis.

Medical therapy remains the mainstay in patients with DCM and heart failure. Beta-blocker, ACE inhibitor or ARB, mineral corticoid receptor blocker, and loop diuretics continue to be standard treatment options for the treatment of heart failure symptoms and reduction of risk for cardiovascular death and heart failure hospitalization. Implantable cardioverter defibrillators (ICD) for patients with left ventricular ejection fraction of less than 30% can reduce sudden arrhythmic death. Additionally, cardiac resynchronization therapy (CRT) has been shown to improve heart failure-free survival in select patients. Despite these interventions, morbidity and mortality for heart failure remain high, and hospitalization for heart failure remains the most common reason for hospitalization in the elderly. The present invention provides new therapeutic agents and methods that remedy the unmet need for improved treatment of DCM and related cardiac disorders.

BRIEF SUMMARY OF THE INVENTION

In one aspect, provided is a compound having formula (I):

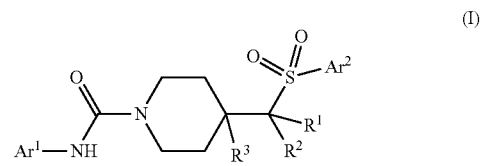

or a pharmaceutically acceptable salt thereof.

In formula (I), $Ar^1$ is a 5- to 6-membered heteroaryl having at least one nitrogen atom ring member; and is optionally substituted with from 1-3$R^a$. $Ar^2$ is a 5- to 10-membered aryl or heteroaryl which is optionally substituted with from 1-5$R^b$. The symbols $R^1$ and $R^2$ are each independently a member selected from H, F, $C_1$-$C_4$ alkyl, $C_1$-$C_4$ deuteroalkyl, and $C_1$-$C_4$ haloalkyl; or optionally $R^1$ and $R^2$ can be combined to form a $C_3$- to $C_5$ carbocyclic ring which is optionally substituted with one or two F. The symbol $R^3$ represents a member selected from H, F, OH and $C_1$-$C_4$ alkyl.

The substituents for each of $Ar^1$ and $Ar^2$ are as follows: each $R^a$ is independently selected from the group consisting of halo, CN, hydroxyl, $C_1$-$C_4$ alkyl, $C_1$-$C_4$ haloalkyl, $C_1$-$C_4$ hydroxyalkyl, $C_1$-$C_4$ alkoxy, $C_1$-$C_4$ haloalkoxy, —$COR^{a1}$, —$CO_2R^{a1}$, —$SO_2R^{a1}$, —$SO_2NR^{a1}$, and —$CONR^{a1}R^{a2}$, wherein each $R^{a1}$ and $R^{a2}$ is independently selected from the group consisting of H and $C_1$-$C_4$ alkyl or optionally $R^{a1}$ and $R^{a2}$ when attached to a nitrogen atom are combined to form a 4- to 6-membered ring; or optionally, two $R^a$ substituents on adjacent ring members are combined to form a 5- or 6-membered ring having 0, 1 or 2 ring members selected from O, N and S; and each $R^b$ is independently selected from the group consisting of halo, CN, hydroxyl, $C_1$-$C_4$ alkyl, $C_1$-$C_4$ deuteroalkyl, $C_1$-$C_4$ haloalkyl, $C_1$-$C_4$ alkoxy, $C_1$-$C_4$ haloalkoxy, $C_3$-$C_6$ cycloalkyl, —$NR^{b1}R^{b2}$, —$COR^{b1}$, —$CO_2R^{b1}$, —$SO_2R^{b1}$, —$SO_2NR^{b1}R^{b2}$, —$CONR^{b1}R^{b2}$, and a 5- or 6-membered heteroaryl which is optionally substituted with $C_1$-$C_4$ alkyl, and wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4- to 6-membered ring; or optionally, two $R^b$ substituents on adjacent ring members are combined to form a 5- or 6-membered ring having 0, 1 or 2 ring members selected from O, N and S.

In another aspect, the invention provides a pharmaceutical composition containing a compound or a pharmaceutically acceptable salt thereof as described herein and a pharmaceutically acceptable excipient.

In another aspect, the invention provides a method of treating dilated cardiomyopathy. The method includes administering to a subject in need thereof an effective amount of a compound or pharmaceutically acceptable salt thereof as described herein.

DETAILED DESCRIPTION OF THE INVENTION

I. General

Figure 1A:
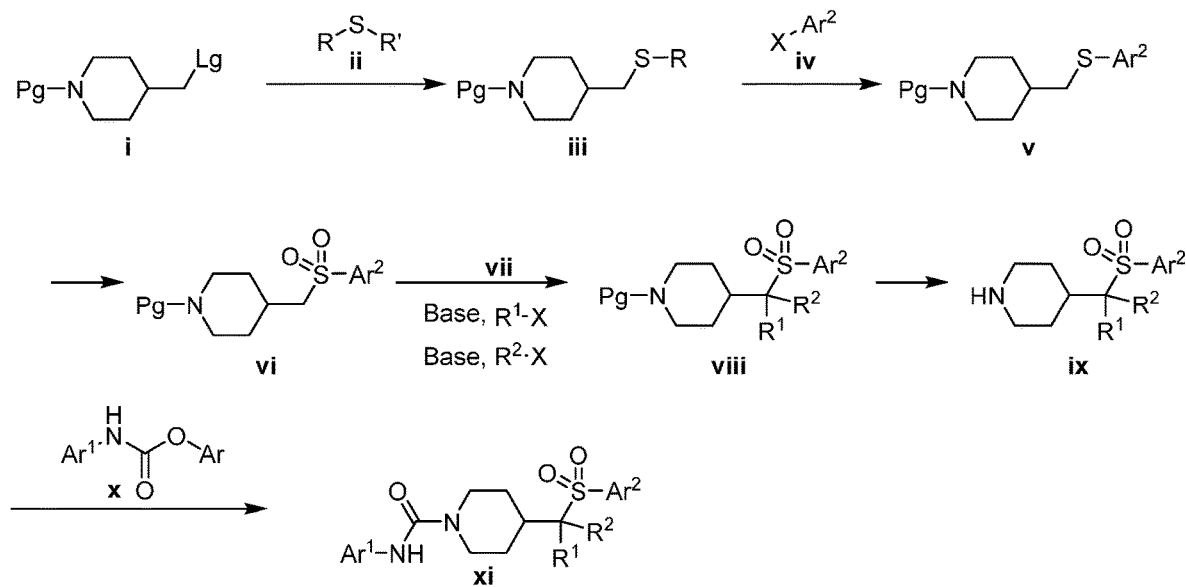
FIGS. 1A, 1B, 1C, 1D and 1E shows schematic routes for the synthesis of the compounds or pharmaceutically acceptable salts described herein.

A series of 4-methylsulfonyl-substituted piperidine ureas and pharmaceutically acceptable salts thereof has been found to increase contractility by enhancing phosphate release from myosin without prolonging systole or shortening diastole. As such, the compounds can improve systolic function in patients with DCM, helping them to overcome the debilitating exertional dyspnea and fatigue that often accompanies the disease. The compounds can also be used to treat other cardiac disorders characterized by diminished cardiac output.

II. Definitions

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Unless stated otherwise, alkyl groups are unsubstituted. A "substituted alkyl" group can be substituted with one or more moieties selected from halo, hydroxy, amino, alkylamino, nitro, cyano, and alkoxy.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

Unless otherwise stated, cycloalkyl groups are unsubstituted. A "substituted cycloalkyl" group can be substituted with one or more moieties selected from halo, hydroxy, amino, alkylamino, nitro, cyano, and alkoxy.

As used herein, the term "heterocycloalkyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocycloalkyl groups can include any number of ring atoms, such as, 3 to 6, 4 to 6, 5 to 6, or 4 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Examples of heterocycloalkyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocycloalkyl groups are unsubstituted, but can be described, in some embodiments as substituted. "Substituted heterocycloalkyl" groups can be substituted with one or more moieties selected from halo, hydroxy, amino, alkylamino, nitro, cyano, and alkoxy.

The term "aryl" or "aromatic ring" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms including, but not limited to, B, Al, Si and P can also be present in a heteroaryl group. The heteroatoms can be oxidized to form moieties such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. Examples of heteroaryl groups include, but are not limited to, pyrrole, pyridine, imidazole, pyrazole, triazole, tetrazole, pyrazine, pyrimidine, pyridazine, triazine (1,2, 3-, 1,2,4- and 1,3,5-isomers), thiophene, furan, thiazole, isothiazole, oxazole, and isoxazole. Heteroaryl groups are unsubstituted, but can be described, in some embodiments as substituted. "Substituted heteroaryl" groups can be substituted with one or more moieties selected from halo, hydroxy, amino, alkylamino, nitro, cyano, and alkoxy.

As used herein, the term "alkoxy" refers to an alkyl group having an oxygen atom that connects the alkyl group to the point of attachment: i.e., alkyl-O—. As for the alkyl portions, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups are unsubstituted, but can be described, in some embodiments as substituted. "Substituted alkoxy" groups can be substituted with one or more moieties selected from halo, hydroxy, amino, alkylamino, nitro, cyano, and alkoxy.

As used herein, the terms "halo" and "halogen" refer to fluorine, chlorine, bromine and iodine.

As used herein, the term "pharmaceutically acceptable" refers to a substance that is compatible with a compound of the invention, as well as with any other ingredients with which the compound is formulated. Furthermore, a pharmaceutically acceptable substance is not deleterious to the recipient of the substance.

As used herein, the term "salt" refers to an acid or base salt of a compound of the invention. Pharmaceutically acceptable salts can be derived, for example, from mineral acids (hydrochloric acid, hydrobromic acid, phosphoric acid, and the like), organic acids (acetic acid, propionic acid, glutamic acid, citric acid and the like), and quaternary ammonium ions. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The neutral form of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. "Substantially free of" another isomer indicates at least a 70/30 ratio of the two isomers at the stereochemical center shown, more preferably 80/20, 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics, which can contribute to enhanced safety, tolerability or efficacy during treatment. All isotopic variations of the compounds of the present invention, whether radioactive or not, are intended to be encompassed within the scope of the present invention.

When specifically referred to, such as, $C_1$-$C_4$ deuteroalkyl—the term refers to an alkyl group with the indicated number of carbon atoms and having hydrogen atoms replaced by deuterium in a number of from one to a per-deutero form, wherein the deuterium replacement is greater than the natural abundance of deuterium—typically 50%, 60%, 70%, 80%, 90%, 95% or more deuterium replacement. Examples of $C_1$-$C_4$ deuteroalkyl are —$CD_3$, —$CH_2CD_3$, —$CD_2CD_3$, —$CH_2CH_2CH_2D$, and the like.

As used herein, the term "pharmaceutical composition" refers to a product comprising a compound of the invention, an excipient as defined herein, and other optional ingredients in specified amounts, as well as any product which results directly or indirectly from combination of the specified ingredients in the specified amounts.

As used herein, the term "excipient" refers to a substance that aids the administration of an active agent to a subject. Pharmaceutical excipients useful in the present invention include, but are not limited to, binders, fillers, disintegrants, lubricants, coatings, sweeteners, flavors and colors. One of skill in the art will recognize that other excipients can be useful in the present invention.

As used herein, the terms "treat," "treating" and "treatment" refer to any indicia of success in the treatment or amelioration of a pathology, injury, condition, or symptom related to dilated cardiomyopathy, including any objective or subjective parameter such as abatement; remission; diminishing of symptoms; making the pathology, injury, condition, or symptom more tolerable to the patient; decreasing the frequency or duration of the pathology, injury, condition, or symptom; or, in some situations, preventing the onset of the pathology, injury, condition, or symptom. Treatment or amelioration can be based on any objective or subjective parameter; including, e.g., the result of a physical examination.

III. Compounds

In one aspect, provided herein are compounds having the formula:

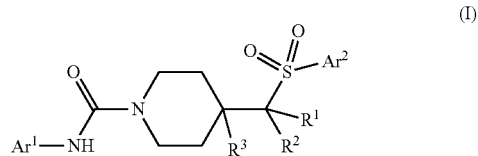

(I)

or a pharmaceutically acceptable salt thereof, wherein
$Ar^1$ is a 5- to 6-membered heteroaryl having at least one nitrogen atom ring member; and which is optionally substituted with from 1-3$R^a$;
$Ar^2$ is a 5- to 10-membered aryl or heteroaryl which is optionally substituted with from 1-5$R^b$;
$R^1$ and $R^2$ are each independently a member selected from the group consisting of H, F, $C_1$-$C_4$ alkyl, $C_1$-$C_4$ deuteroalkyl, and $C_1$-$C_4$ haloalkyl; or optionally $R^1$ and $R^2$ can be combined to form a $C_3$- to $C_5$ carbocyclic ring which is optionally substituted with one or two F;
$R^3$ is a member selected from the group consisting of H, F, OH and $C_1$-$C_4$ alkyl;
each $R^a$ is independently selected from the group consisting of halo, CN, hydroxyl, $C_1$-$C_4$ alkyl, haloalkyl, hydroxyalkyl, alkoxy, haloalkoxy, —$COR^{a1}$, —$CO_2R^{a1}$, —$SO_2R^{a1}$, —$SO_2NR^{a1}R^{a2}$, and —$CONR^{a1}R^{a2}$, wherein each $R^{a1}$ and $R^{a2}$ is independently selected from the group consisting of H and $C_1$-$C_4$ alkyl or optionally $R^{a1}$ and $R^{a2}$ when attached to a nitrogen atom are combined to form a 4- to 6-membered ring; or optionally, two $R^b$ substituents on adjacent ring members are combined to form a 5- or 6-membered ring having 0, 1 or 2 ring members selected from O, N and S; and each $R^b$ is independently selected from the group consisting of halo, CN, hydroxyl, $C_1$-$C_4$ alkyl, deuteroalkyl, haloalkyl, alkoxy, haloalkoxy, $C_3$-$C_6$ cycloalkyl, —$NR^{b1}R^{b2}$, —$COR^{b1}$, —$CO_2R^{b1}$, —$SO_2R^{b1}$—$SO_2NR^{b1}R^{b2}$, —$CONR^{b1}R^{b2}$, and a 5- or 6-membered heteroaryl which is optionally substituted with $C_1$-$C_4$ alkyl, and wherein each $R^{b1}$ and $R^{b2}$ is independently selected from the group consisting of H and $C_1$-$C_4$ alkyl or optionally $R^{b1}$ and $R^{b2}$ when attached to a nitrogen atom are combined to form a 4- to 6-membered ring; or optionally, two $R^b$ substituents on adjacent ring members are combined to form a 5- or 6-membered ring having 0, 1 or 2 ring members selected from O, N and S.

In some embodiments, compounds are provided of Formula I, or a pharmaceutically acceptable salt thereof, wherein $Ar^1$ is selected from the group consisting of pyridyl, pyridazinyl, oxazolyl, isoxazolyl, pyrazolyl, 1,2,3-thiadiazolyl, isothiazolyl, and thiazolyl, each of which is optionally substituted with from 1 or 2 $R^a$.

In other embodiments, compounds are provided of Formula I, or a pharmaceutically acceptable salt thereof, wherein AP is selected from the group consisting of phenyl, pyridyl and pyrazolyl, each of which is optionally substituted with from 1 to 3 $R^b$. In some of these embodiments, $R^b$ is selected from the group consisting of halo, CN, $C_1$-$C_4$ alkyl, $C_1$-$C_4$ haloalkyl, $C_1$-$C_4$ alkoxy and $C_1$-$C_4$ haloalkoxy.

In yet other embodiments, compounds are provided of Formula I, or a pharmaceutically acceptable salt thereof, wherein $R^1$ is selected from the group consisting of H, F and $CH_3$.

In still other embodiments, compounds are provided of Formula I, or a pharmaceutically acceptable salt thereof, wherein $R^2$ is selected from the group consisting of H, F and $CH_3$.

In some embodiments, compounds are provided of Formula I, or a pharmaceutically acceptable salt thereof, $R^1$ and $R^2$ taken together with the carbon atom to which each is attached to form a cyclopropane or cyclobutane ring.

In other embodiments, compounds are provided of Formula I, or a pharmaceutically acceptable salt thereof, wherein $R^1$ and $R^2$ are each F.

In other embodiments, compounds are provided of Formula I, or a pharmaceutically acceptable salt thereof, wherein $R^1 \neq R^2$, and one of $R^1$ or $R^2$ is selected from F and $CH_3$ to form a quaternary chiral center.

In other embodiments, compounds are provided of Formula I, or a pharmaceutically acceptable salt thereof, wherein $R^1 \neq R^2$, and one of $R^1$ or $R^2$ is selected from F and $CH_3$ to form a quaternary chiral center having a R configuration.

In yet other embodiments, compounds are provided of Formula I, or a pharmaceutically acceptable salt thereof, wherein $R^3$ is H or F.

In some particular embodiments, compounds are provided of Formula I, or a pharmaceutically acceptable salt thereof, wherein $Ar^1$ is 4-pyridinyl and $Ar^2$ is phenyl, optionally substituted with from 1 to 3 $R^b$. In still other embodiments, $R^3$ is H, and each of $R^1$ and $R^2$ is F. In yet other embodiments, $R^3$ is H, and each of $R^1$ and $R^2$ is $CH_3$. In other embodiments, $R^3$ is H, $R^1$ is $CH_3$, and $R^2$ is F.

In other particular embodiments, compounds are provided of Formula I, or a pharmaceutically acceptable salt thereof, wherein $Ar^1$ is 4-pyridazinyl and $Ar^2$ is phenyl, optionally substituted with from 1 to 3 $R^b$. In still other embodiments, $R^3$ is H, and each of $R^1$ and $R^2$ are F. In yet other embodiments, $R^3$ is H, and each of $R^1$ and $R^2$ are $CH_3$. In other embodiments, $R^3$ is H, $R^1$ is $CH_3$, and $R^2$ is F.

In still other particular embodiments, compounds are provided of Formula I, or a pharmaceutically acceptable salt thereof, wherein $Ar^1$ is selected from the group consisting of oxazol-5-yl, isoxazol-3-yl, isoxazol-4-yl, pyrazol-3-yl, pyrazol-4-yl, 1,2,3-thiadiazol-5-yl, isothiazol-5-yl, and thiazol-5-yl, each of which is optionally substituted with one $R^a$. In still other embodiments, $R^3$ is H, and each of $R^1$ and $R^2$ are F. In yet other embodiments, $R^3$ is H, and each of $R^1$ and $R^2$ are $CH_3$. In other embodiments, $R^3$ is H, $R^1$ is $CH_3$, and $R^2$ is F.

In other selected embodiments, compounds are provided of Formula I, or a pharmaceutically acceptable salt thereof, wherein $R^1$ and $R^2$ are not the same, and at least one of $R^1$ and $R^2$ is F or $CH_3$ to form a chiral center at the carbon atom bearing $R^1$ and $R^2$ that has a R-configuration.

In some selected embodiments, compounds are provided of Formula I, or a pharmaceutically acceptable salt thereof, selected from Table 2 and having an activity level of ++ or +++.

In some embodiments, compounds are provided of Formula I, or a pharmaceutically acceptable salt thereof, selected from:

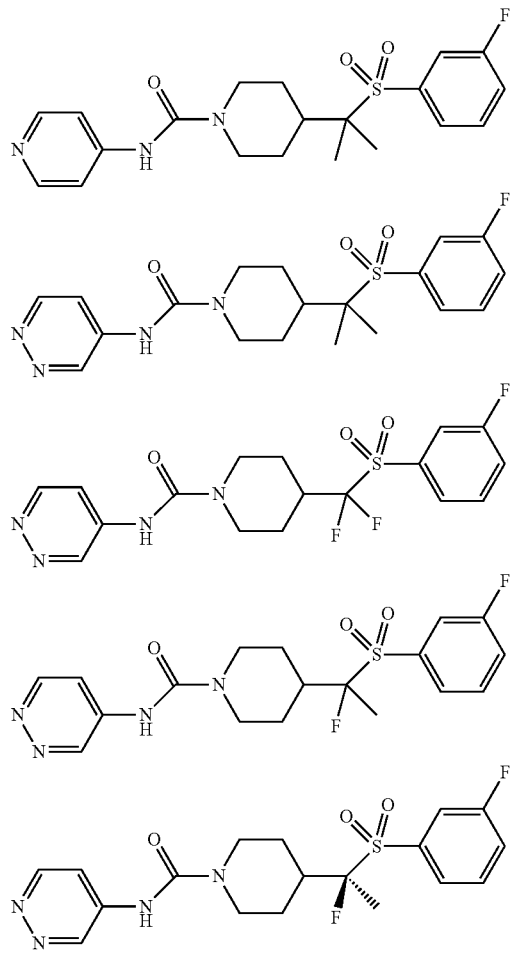

-continued

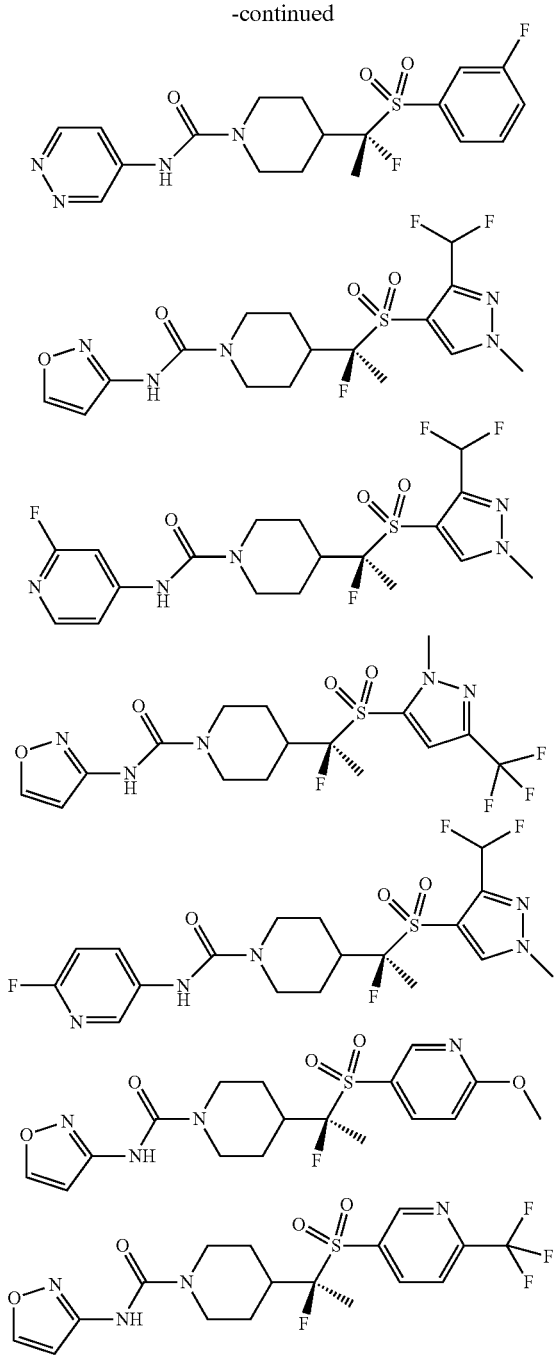

The compounds or their pharmaceutically acceptable salts provided herein can have any combination of the $Ar^1$, $Ar^2$, $R^1$, $R^2$, $R^3$, $R^a$, $R^{a1}$, $R^{a2}$, $R^b$, $R^{b1}$ and $R^{b2}$ groups recited above. Selected embodiments recited for $R^2$, for example, can be combined with any of the selected embodiments recited for $R^1$ which, in turn, can be combined with any of the selected embodiments recited for $R^3$ or $Ar^1$ or $Ar^2$.

Figure 1B:
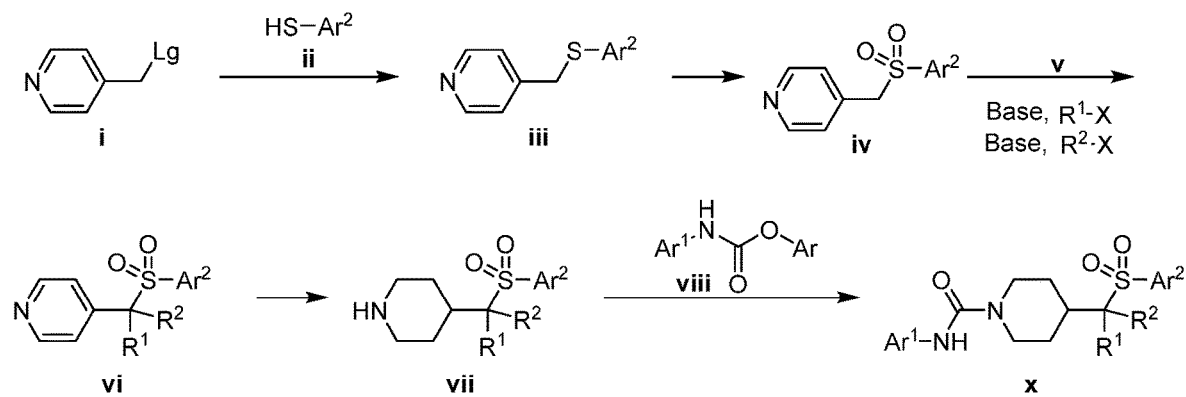
Figure 1C:
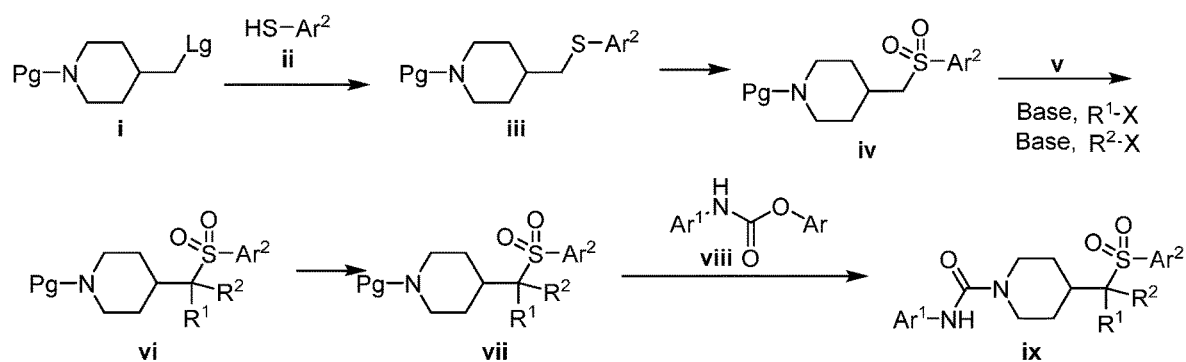
Figure 1D:
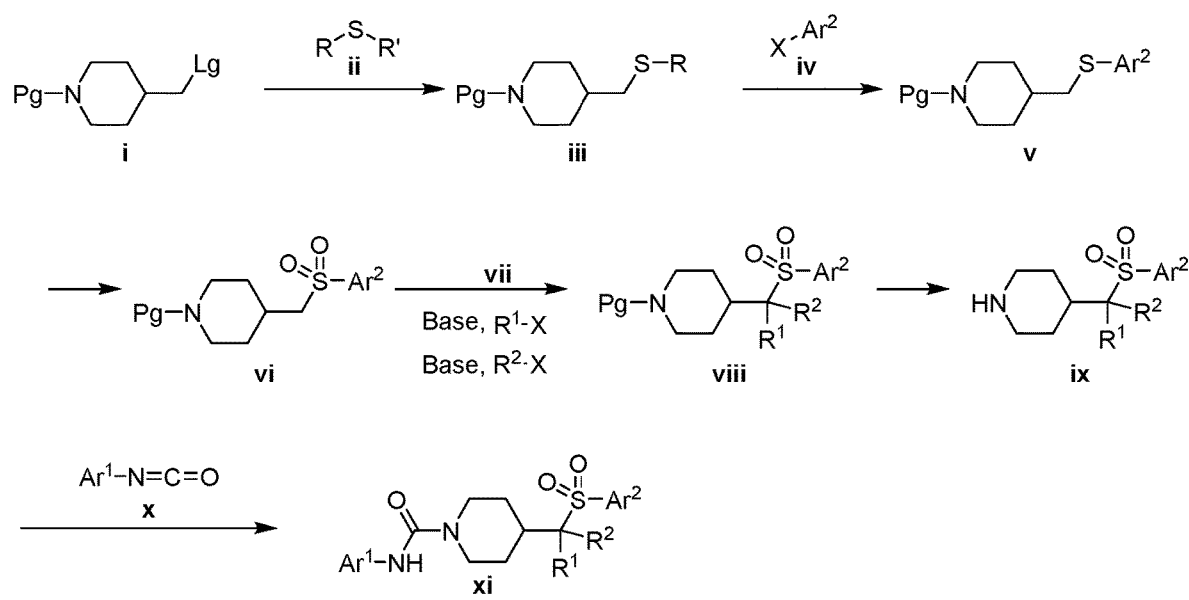
Figure 1E:
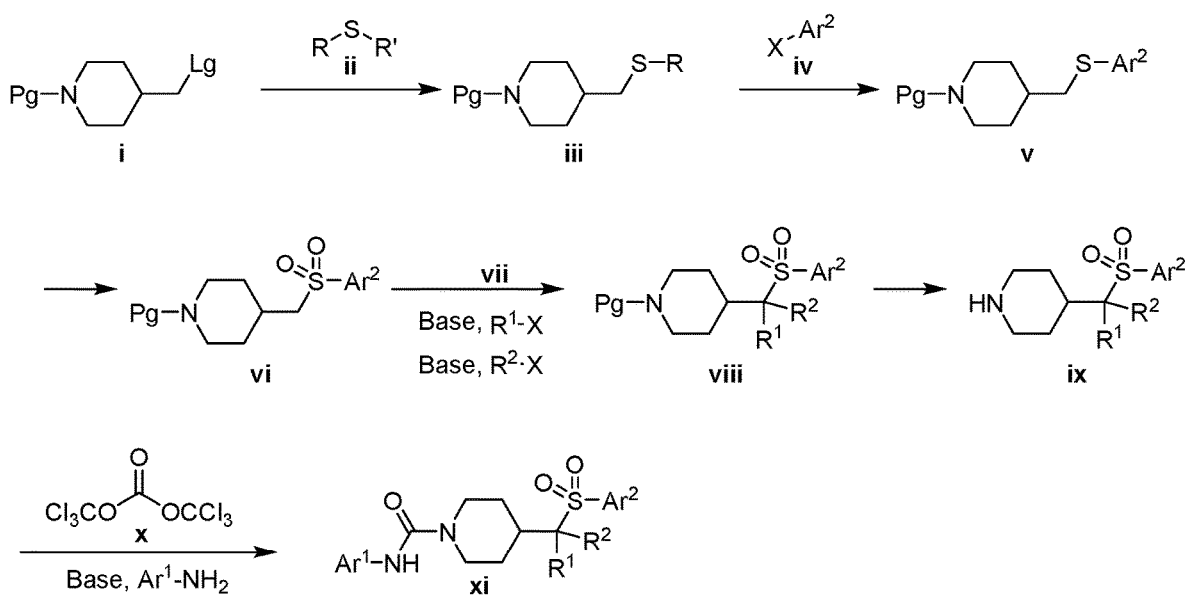

The compounds of formula (I) can be prepared by methods as generally outlined in FIGS. 1A, 1B and 1C, or as provided in the Examples and outlined in Table 1. One skilled in the art will appreciate that the compounds of invention can be prepared using other synthetic methods, including transformations as described in, for example, LaRock (*Comprehensive Organic Transformations: A Guide to Functional Group Preparations*, Wiley, 1999), as substitutes for transformations provided in the Examples.

IV. Compositions

In another aspect, provided herein is a pharmaceutical composition containing a compound of formula I or a pharmaceutically acceptable salt thereof and a pharmaceutically acceptable excipient. The compositions are useful for treating dilated cardiomyopathy in humans and other subjects.

The pharmaceutical compositions for the administration of the compounds or their pharmaceutically acceptable salts provided herein may conveniently be presented in unit dosage form and may be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active agent is generally included in an amount sufficient to increase myocardial contractility (i.e. to improve the systolic dysfunction in DCM) and to improve or not worsen left ventricular relaxation in diastole. Such improved relaxation can alleviate symptoms in dilated cardiomyopathy and other etiologies of diastolic dysfunction, such as heart failure with preserved ejection fraction (HFpEF). It can also ameliorate the effects of diastolic dysfunction causing impairment of coronary blood flow, improving the latter as an adjunctive agent in angina pectoris and ischemic heart disease. It can also confer benefits on salutary left ventricular remodeling in DCM and other causes of left ventricular dysfunction due to ischemic heart disease or chronic volume or pressure overload from, e.g., myocardial infarction, valvular heart disease or systemic hypertension The pharmaceutical compositions containing the active ingredient may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions provided herein may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds or their pharmaceutically acceptable salts provided herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds or their pharmaceutically acceptable salts provided herein are employed. As used herein, topical application is also meant to include the use of mouth washes and gargles.

The compounds of this invention may also be coupled to a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds or their pharmaceutically acceptable salts provided herein may be coupled to a carrier that is a biodegradable polymer useful in achieving controlled release of a drug, such as polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

V. Methods of Treating Cardiac Disorders

The mutations that lead to DCM cause significant perturbations in myosin mechanics. These mutations exert their effects via distinct mechanisms depending on their locations in the myosin gene. Without wishing to be bound by any particular theory, it is believed that the compounds or their pharmaceutically acceptable salts provided herein can bind directly to the mutant sarcomeric proteins and correct for their aberrant function, either in cis (by affecting the same specific function) or in trans (by altering a complementary function). As such, they can provide therapeutic benefit for DCM patients by counteracting the hypocontractile and/or impaired relaxation associated with this disease. Additionally, these compounds that increase systolic function hold promise of treating a wide spectrum of disorders in which symptoms and/or clinical outcomes are attributable to systolic dysfunction (left or right sided heart failure) or a reduction in systolic reserve (eg. HFpEF).

Accordingly, the invention provides a method of treating dilated cardiomyopathy (DCM) or a cardiac disorder having one or more pathophysiological features associated with DCM, such as disorders with systolic dysfunction or a reduction in systolic reserve. The method includes administering to a subject in need thereof an effective amount of a compound provided herein.

The compounds of the invention or their pharmaceutically acceptable salts can alter the natural history of DCM and other diseases rather than merely palliating symptoms. The mechanisms conferring clinical benefit to DCM patients can extend to patients with other forms of heart disease sharing similar pathophysiology, with or without demonstrable genetic influence. For example, an effective treatment for DCM, by improving ventricular contraction, can also be effective in a broader population characterized by systolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from heart failure with reduced ejection fraction (HFrEF), HFpEF, chronic congestive heart failure, acute heart failure, right-sided (or right ventricular) heart failure, cardiogenic shock and inotropic support after cardiac surgery. Compounds of the invention or their pharmaceutically acceptable salts can potentially improve cardiac function in the following patient segments: idiopathic dilated cardiomyopathy, genetically defined or familial dilated cardiomyopathy, ischemic or post-infarction mardiomyopathy, viral cardiomyopathy or myocarditis, toxic cardiomyopathies (eg. post-anthracycline anticancer therapy), metabolic cardiomyopathies (in conjunction with enzyme replacement therapy), diastolic heart failure (with diminished systolic reserve), right heart failure due to pulmonary hypertension, and ventricular dysfunction due to on-bypass cardiovascular surgery. Compounds of the invention or their pharmaceutically acceptable salts can also promote salutary ventricular reverse remodeling of left ventricular dysfunction due to ischemia or volume or pressure overload; e.g., myocardial infarctions, chronic mitral regurgitation, chronic aortic stenosis, or chronic systemic hypertension. By reducing left ventricular filling pressures the compounds could improve the symptom of dyspnea and reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. The compounds or their pharmaceutically acceptable salts may reduce the severity of the chronic ischemic state associated with DCM and thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug-drug interactions, and/or side effects. The compounds or their pharmaceutically acceptable salts may reduce interstitial myocardial fibrosis and/or slow the progression, arrest, or reverse left ventricular stiffness and diastolic dysfunction.

Depending on the disease to be treated and the subject's condition, the compounds or their pharmaceutically acceptable salts provided herein may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require improved ventricular contraction without impairment of diastolic relaxation, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Compounds and compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Suitable additional active agents include, for example: therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The compounds or their pharmaceutically acceptable salts may be used in combination with a beta-blocker (a drug class with known side-effects due to negative inotropic effect) to confer unique tolerability of beta-blocker titration to target doses. The compounds or their pharmaceutically acceptable salts may be used in combination with a lusitropic agent for the treatment of diastolic heart failure (or HFpEF, a disorder with diastolic dysfunction and reduced systolic reserve). The weight ratio of the compound provided herein to the second active ingredient may be varied and will depend upon the effective dose of each ingredient. Generally, an effective dose of each will be used.

VI. Examples aq: aqueous; BBr$_3$: boron tribromide; BTC: Bis(trichloromethyl) carbonate; CH$_2$Cl$_2$: dichloromethane; CH$_3$CN: acetonitrile; CH$_3$OH: methanol; DAST: Diethylaminosulfur trifluoride; DIAD: diisopropyl azodicarboxylate; DIEA: diisopropyl ethylamine; DMF: dimethyl formamide; DMSO: dimethyl sulfoxide; dppf: [1,1'-Bis(diphenylphosphino)ferrocene]dichloropalladium(II), complex with dichloromethane; DPPA: Diphenylphosphoryl azide; equiv.: equivalent(s); Et$_3$N: trimethylamine; Et$_2$O: diethyl ether; EtOH: ethanol; h, hr: hour(s); HATU: (1-[Bis(dimethylamino)methylene]-1H-1,2,3-triazolo[4,5-b]pyridinium 3-oxid hexafluorophosphate); HCl: hydrogen chloride; H$_2$O: water; K$_2$CO$_3$: potassium carbonate; KHSO$_4$: potassium bisulfate; KNCO: potassium isocyanate; LDA: lithium diisopropylamide; mCPBA: meta-chloroperbenzoic acid; MgSO$_4$: magnesium sulfate; mL: milliliter(s); MW: microwave (reaction done in a microwave reactor); NaCl: sodium chloride; NaH: sodium hydride; NaHCO$_3$: sodium bicarbonate; NaOEt: sodium ethoxide; NaOH: sodium hydroxide; NaOMe: sodium methoxide; Na$_2$SO$_4$: sodium sulfate; Na$_2$SO$_3$: sodium sulfite; NBS: N-Bromosuccinimide; NFSI: N-Fluorobenzenesulfonimide; NH$_4$Cl: ammonium chloride; NMP: n-methyl pyrrolidinone; pH: −log [H$^+$]; POCl$_3$: phosphoryl trichloride; PPTS: pyridinium p-toluenesulfonate; RP-HPLC: reversed phase high pressure liquid chromatography; RT: room temperature; RT$_x$: retention time; SFC: Supercritical fluid chromatography; TEBAC: triethylbenzylammonium chloride; TFA: trifluoroacetic acid; and THF: tetrahydrofuran.

Example 1. Preparation of 4-(((1-isopropyl-1H-pyrazol-4-yl)sulfonyl)methyl)-N-(pyridin-4-yl)piperidine-1-carboxamide

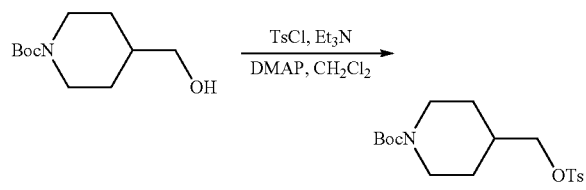

Compound 1.1. tert-Butyl 4-((tosyloxy)methyl)piperidine-1-carboxylate

A solution of tert-butyl 4-(hydroxymethyl)piperidine-1-carboxylate (50 g, 232.25 mmol, 1.00 equiv), triethylamine (35.2 g, 347.86 mmol, 1.50 equiv), 4-dimethylaminopyridine (2.8 g, 22.92 mmol, 0.10 equiv) and 4-methylbenzene-1-sulfonyl chloride (53 g, 278.00 mmol, 1.20 equiv) in CH$_2$Cl$_2$ (500 mL) was stirred under argon overnight at room temperature. The solids were removed by filtration, and the filtrate was concentrated under reduced pressure. The resulting residue was purified by silica gel column (Ethyl Acetate/Petroleum ether=1/3 9 v/v)) to provide 78 g (91%) as a yellow solid. $^1$H-NMR (400 MHz, DMSO-d6): δ 7.78 (d, J=8.4 Hz, 2H), 7.48 (d, J=8.4 Hz, 2H), 3.87 (m, 4H), 2.49 (m, 2H), 2.42 (s, 3H), 1.76 (m, 1H), 1.53 (m, 2H), 1.36 (s, 9H), 0.96 (m, 2H) ppm.

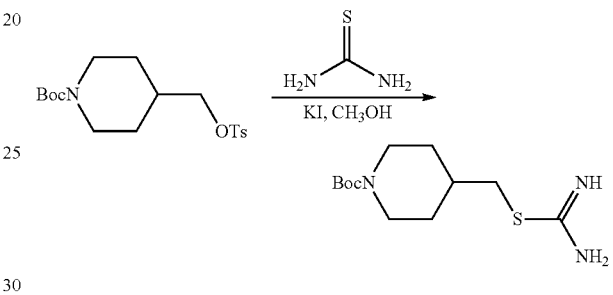

Compound 1.2. tert-Butyl 4-((carbamimidoylthio)methyl)piperidine-1-carboxylate

A solution of tert-butyl 4-((tosyloxy)methyl)piperidine-1-carboxylate (1.1, 11 g, 29.77 mmol, 1.00 equiv), thiourea (4.5 g, 59.13 mmol, 2.00 equiv) and potassium iodide (2.47 g, 14.88 mmol, 0.50 equiv) in CH$_3$OH (110 mL) was stirred overnight at 70° C. under argon. The reaction mixture was cooled to room temperature and concentrated under reduced pressure. The resulting product (15 g, crude) was used as is in the next reaction without further purification.

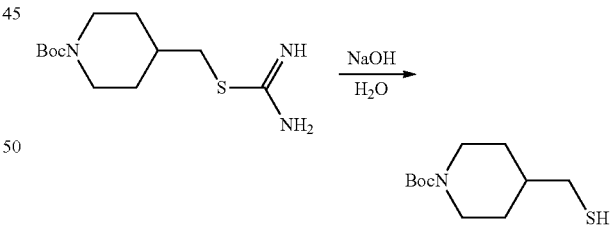

Compound 1.3. tert-Butyl 4-(mercaptomethyl)piperidine-1-carboxylate

A solution of tert-butyl 4-((carbamimidoylthio)methyl)piperidine-1-carboxylate (1.2, 15 g, 1.00 equiv, crude) and sodium hydroxide (2.2 g, 55.00 mmol, 1.00 equiv) in 1:2 (v/v) CH$_3$OH/H$_2$O (150 mL) was stirred for 2 h at 60° C. under argon. Then the reaction mixture was cooled to room temperature. The pH value of the solution was adjusted to 7 with HCl$_{(aq)}$ (35%). The resulting solution was extracted with EtOAc (3×50 mL) and the organic layers were combined. The organic layer was washed with brine (2×50 mL).

The mixture was dried over anhydrous Na₂SO₄, filtered and concentrated under reduced pressure. The resulting residue was purified by silica gel chromatography (EtOAc/petroleum ether=1:8 (v/v)) to provide 5.6 g (44%) as yellow oil. ¹H-NMR (400 MHz, CDCl₃): δ 4.13 (m, 2H), 2.69 (m, 2H), 2.46 (m, 2H), 1.82 (m, 2H), 1.50 (s, 9H), 1.32 (m, 1H), 1.18 (m, 2H) ppm.

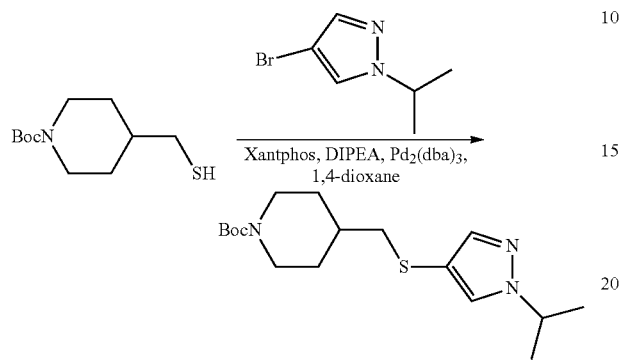

Compound 1.4. tert-Butyl 4-(((1-isopropyl-1H-pyrazol-4-yl)thio)methyl)piperidine-1-carboxylate A solution of tert-butyl 4-(mercaptomethyl)piperidine-1-carboxylate (1.3, 300 mg, 1.30 mmol, 1.00 equiv), Xantphos (123 mg, 0.21 mmol, 0.20 equiv), Pd₂(dba)₃·CHCl₃ (144 mg, 0.10 equiv), 4-bromo-1(propan-2-yl)-1H-pyrazole (246 mg, 1.30 mmol, 1.00 equiv) and N,N-diisopropylethylamine (195 mg, 1.51 mmol, 1.50 equiv) in 1,4-dioxane (5 mL) was stirred overnight at 90° C. under argon. The reaction mixture was cooled to room temperature and concentrated under reduced pressure. The resulting residue was purified by silica gel chromatography (EtOAc/petroleum ether=7:3 (v/v)) to provide 400 mg (crude) of a yellow oil. The product was used directly in the next step without further purification.

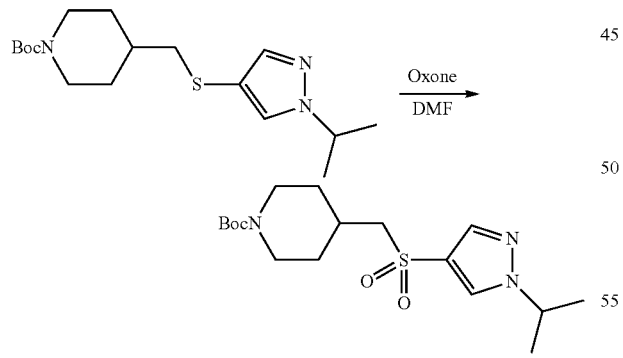

Compound 1.5. tert-Butyl 4-(((1-isopropyl-1H-pyrazol-4-yl)sulfonyl)methyl)piperidine-1-carboxylate A solution of tert-butyl 4-(((isopropyl-1H-pyrazol-4-yl)thio)methyl)piperidine-1-carboxylate (1.4, 400 mg, 1.18 mmol, 1.00 equiv) and Oxone (2.17 g, 3.00 equiv) in DMF (10 mL) was stirred overnight at room temperature under argon. The solids were removed by filtration, and the filtrate was diluted with EtOAc (25 mL). The filtrate was washed with H₂O (3×15 mL), dried over anhydrous Na₂SO₄, filtered, and concentrated under reduced pressure to provide 200 mg (crude) of a yellow oil. The product was used directly in the next step without further purification.

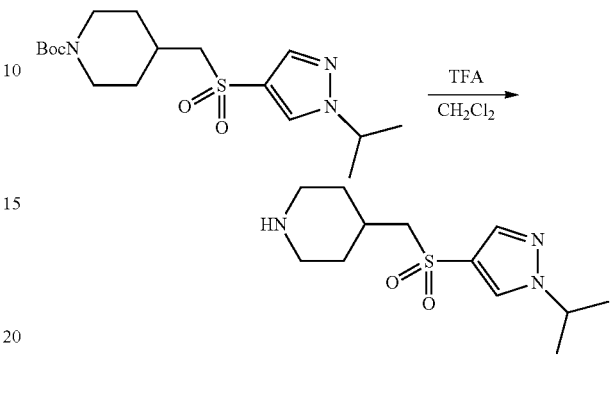

Compound 1.6. 4-(((1-Isopropyl-1H-pyrazol-4-yl)sulfonyl)methyl)piperidine

A solution of tert-butyl 4-(((1-isopropyl-1H-pyrazol-4-yl)sulfonyl)methyl)piperidine-1-carboxylate (1.5, 200 mg, 0.54 mmol, 1.00 equiv) in trifluoroacetic acid/CH₂Cl₂ (1:1 (v/v), 10 mL) was stirred for 2 h at room temperature under argon, and then was concentrated under reduced pressure to provide 100 mg (crude) of a yellow oil. The product was used directly used in the next step without further purification.

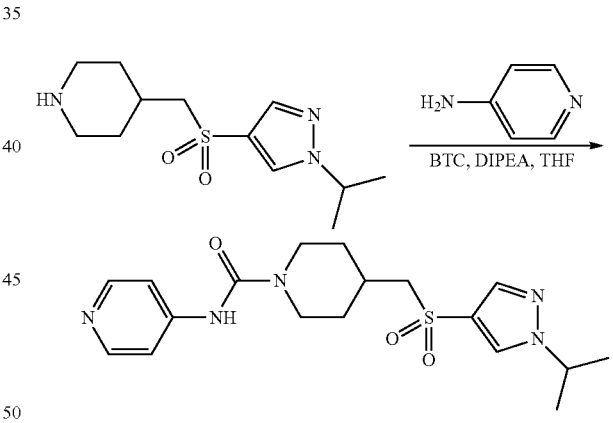

Compound 1. 4-(((1-Isopropyl-1H-pyrazol-4-yl)sulfonyl)methyl)-N-(pyridin-4-yl)piperidine-1-carboxamide To a solution of pyridin-4-amine (34.7 mg, 0.368 mmol, 1.00 equiv.) and BTC (43.7 mg, 0.40 equiv.) in THF (3 mL) under argon was added N,N-diisopropylethylamine (143 mg, 1.11 mmol, 3.00 equiv) dropwise with stirring at 0° C. The resulting solution was stirred for 20 min at 0° C. before a solution of 4-(((1-isopropyl-1H-pyrazol-4-yl)sulfonyl)methyl)piperidine (1.6, 100 mg, 0.37 mmol, 1.00 equiv.) in THF (1 mL) was added dropwise with stirring at 0° C. The resulting solution was stirred for 1 h at 0° C. before being quenched by the addition of saturated Na₂CO₃$_{(aq)}$ (10 mL). The resulting solution was extracted with EtOAc (2×20 mL), and the combined organic layers were concentrated under reduced pressure. The residue was purified by Prep-HPLC [Column: X Bridge C18, 19*150 mm, 5 um; Mobile Phase A: Water/10 mmol/L NH$_4$HCO$_3$, Mobile Phase B: ACN; Flow rate: 30 mL/min; Gradient: 25% B to 65% B in 8 min; Detector UV, 254 nm] to provide 8.7 mg (6%) of a white solid. LC-MS (ES, m/z): 392 [M+H]$^+$; $^1$H-NMR (400 MHz, DMSO-d$_6$): δ 8.89 (s, 1H), 8.48 (s, 1H), 8.29 (d, J=6.4 Hz, 2H), 7.91 (s, 1H), 7.46 (m, 2H), 4.60 (m, 1H), 4.01 (m, 2H), 3.29 (m, 2H), 2.87 (m, 2H), 2.07 (m, 1H), 1.81 (m, 2H), 1.45 (m, 6H), 1.27 (m, 2H) ppm.

Example 2. Preparation of N-(Pyridazin-4-yl)-4-(1-((4-(trifluoromethoxy)phenyl)sulfonyl)cyclopropyl)piperidine-1-carboxamide

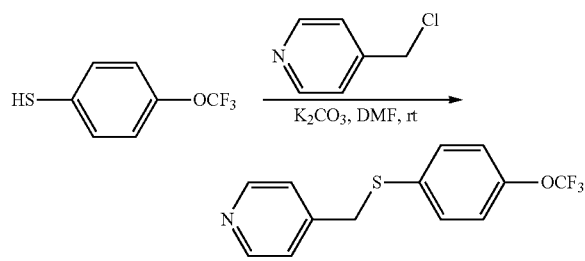

Compound 2.1. 4-(((4-(Trifluoromethoxy)phenyl)thio)methyl)pyridine

A solution of 4-(chloromethyl)pyridine (625 mg, 4.90 mmol, 1.00 equiv), K$_2$CO$_3$ (1.35 g, 9.70 mmol, 2.00 equiv) and 4-(trifluoromethoxy)benzene-1-thiol (950 mg, 4.89 mmol, 1.00 equiv) in DMF (10 mL) was stirred overnight at room temperature under argon, and the solids were removed by filtration. The filtrate was diluted with H$_2$O (30 mL), and the resulting solution was extracted with EtOAc (3×20 mL). The combined organic layers were washed with brine (2×20 mL), dried over anhydrous Na$_2$SO$_4$, filtered and concentrated under reduced pressure. The resulting residue was purified on silica gel (EtOAc/petroleum ether) to provide 1.3 g (93%) of a light yellow oil.

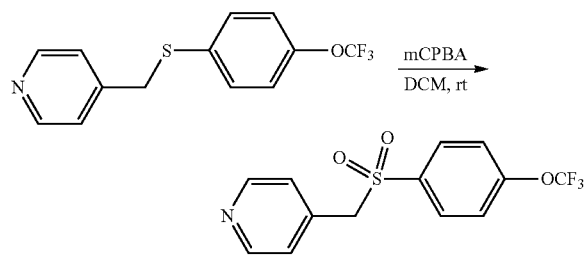

Compound 2.2. 4-(((4-(Trifluoromethoxy)phenyl)sulfonyl)methyl)pyridine

A solution of 4-(((4-(trifluoromethoxy)phenyl)thio)methyl)pyridine (2.1, 800 mg, 2.80 mmol, 1.00 equiv) and mCPBA (1.07 g, 6.17 mmol, 2.20 equiv) in CH$_2$Cl$_2$ (20 mL) was stirred for 2 h at room temperature under argon. The solution was then washed with saturated Na$_2$CO$_{3(aq)}$ (2×20 mL) and brine (20 mL). The organic layer was dried over anhydrous Na$_2$SO$_4$, filtered and concentrated under reduced pressure. The resulting residue was purified on silica gel (EtOAc/petroleum ether=1/1 (v/v)) to provide 900 mg (96%) of a white solid. MS (ES, m/z): 318 [M+H]$^+$.

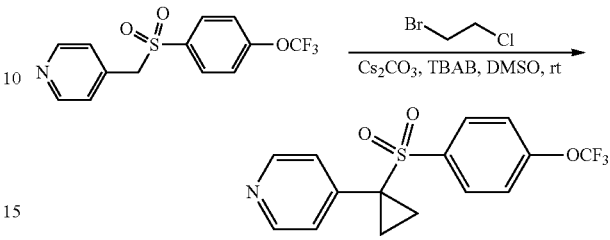

Compound 2.3. 4-(1-((4-(Trifluoromethoxy)phenyl)sulfonyl)cyclopropyl)pyridine

A solution of 4-((4-(trifluoromethoxy)phenylsulfonyl)methyl)pyridine (2.2, 770 mg, 2.43 mmol, 1.00 equiv), 1-bromo-2-chloroethane (1.47 g, 10.25 mmol, 3.00 equiv), Cs$_2$CO$_3$ (2.37 g, 7.27 mmol, 3.00 equiv) and tetrabutylammonium bromide (157 mg, 0.49 mmol, 0.20 equiv) in DMSO (20 mL) was stirred for 2 h at room temperature under argon. The reaction was then quenched by the addition of H$_2$O (30 mL), and was extracted with EtOAc (2×30 mL). The combined organic layers were washed with brine (2×20 mL), dried over anhydrous Na$_2$SO$_4$, filtered, and concentrated under reduced pressure. The resulting residue was purified on silica gel (EtOAc/petroleum ether=2/3 (v/v)) to provide 600 mg (72%) of a light yellow solid. MS (ES, m/z): 344 [M+H]$^+$; $^1$H-NMR (300 MHz, CDCl$_3$): δ 8.51 (d, J=6.0 Hz, 2H), 7.55 (d, J=7.6 Hz. 2H), 7.25 (d, J=7.6 Hz. 2H), 7.13 (d, J=6.0 Hz, 2H), 1.97-2.09 (m, 2H), 1.28-1.34 (m, 2H) ppm.

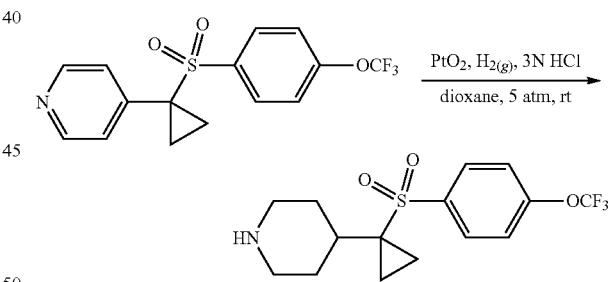

Compound 2.4. 4-(1-((4-(Trifluoromethoxy)phenyl)sulfonyl)cyclopropyl)piperidine

A mixture of 4-(1-((4-(trifluoromethoxy)phenyl)sulfonyl)cyclopropyl)pyridine (2.3, 400 mg, 1.17 mmol, 1.00 equiv) and PtO$_2$ (80 mg) in 3N HCl/dioxane (10 mL) was stirred for 5 h at room temperature in a sealed tube under an atmosphere of H$_{2(g)}$ (5 atm). [Caution: the reaction flask was purged with N$_{2(g)}$ prior to being purged with H$_{2(g)}$.] The solids were removed by filtration. The filtrate was concentrated under reduced pressure to provide 400 mg (98%) of a light yellow solid. $^1$H-NMR (300 MHz, DMSO-d6): δ 8.08 (d, J=8.1 Hz, 2H), 7.65 (d, J=8.1 Hz. 2H), 3.16 (m, 2H), 2.76 (m, 2H), 2.08 (m, 1H), 1.65 (m, 2H), 1.46 (m, 2H), 1.29 (m, 2H), 1.07 (m, 2H) ppm.

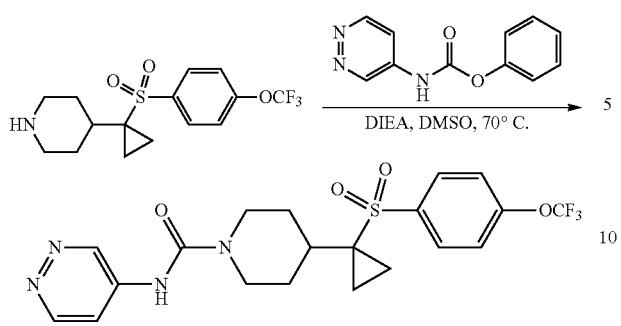

Compound 2. N-(Pyridazin-4-yl)-4-(1-((4-(trifluoromethoxy)phenyl)sulfonyl)cyclopropyl) piperidine-1-carboxamide A solution of 4-(1-((4-(trifluoromethoxy)phenyl)sulfonyl) cyclopropyl)piperidine (2.4, 58 mg, 0.17 mmol, 1.00 equiv), phenyl pyridazin-4-ylcarbamate (5.1, 36 mg, 0.17 mmol, 1.00 equiv) and N-ethyl-N-isopropylpropan-2-amine (65 mg, 0.50 mmol, 3.00 equiv) in DMSO (1 mL) was stirred for 2 h at 70° C. under argon. After cooling to room temperature the reaction was quenched by the addition of H$_2$O (10 mL), and the resulting mixture was extracted with CH$_2$Cl$_2$ (3×20 mL). The combined organic layers were washed with brine (2×10 mL), dried over anhydrous MgSO$_4$, filtered, and concentrated under reduced pressure. The resulting residue was purified by Prep-HPLC [Column: XBridge Prep C18 OBD Column 19*150 mm Sum 13 nm; Mobile Phase A: Water with 10 mmol NH4HCO3, Mobile Phase B: ACN; Gradient: 25% B to 55% B in 10 min; Detector, UV 254 nm] to provide 32.0 mg (41%) of a white solid. MS (ES, m/z): 471 [M+H]$^+$; $^1$H-NMR (300 MHz, DMSO-d6): δ 9.23 (d, J=1.8 Hz, 1H), 9.08 (s, 1H), 8.85 (d, J=6.0 Hz, 1H), 8.08 (d, J=8.7 Hz, 2H), 7.72 (dd, J=1.8 Hz, 6.0 Hz. 1H), 7.67 (d, J=8.7 Hz, 1H), 4.03-4.14 (m, 2H), 2.73-2.86 (m, 2H), 1.97-2.08 (m, 1H), 1.41-1.52 (m, 4H), 0.92-1.13 (m, 4H) ppm.

Example 3. Preparation of 4-(((2-Cyano-4-(trifluoromethyl)phenyl)sulfonyl)-difluoromethyl)-N-(pyridazin-4-yl)piperidine-1-carboxamide

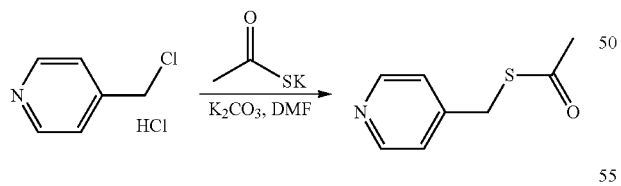

Compound 3.1. S-(Pyridin-4-ylmethyl) ethanethioate

To a mixture of 4-(chloromethyl)pyridine hydrochloride (9 g, 54.87 mmol, 1.00 equiv) and K$_2$CO$_3$ (7.6 g, 54.99 mmol, 1.50 equiv) in DMF (50 mL) under argon was added potassium thioacetate (9.38 g, 82.13 mmol, 1.00 equiv) in several batches at 0° C. The resulting mixture was stirred for 1 h at 50° C. in an oil bath. After cooling to room temperature the reaction was quenched by the addition of ice water (500 mL). The resulting solution was extracted with EtOAc (3×300 mL). The combined organic layers were washed with brine (2×500 mL), dried over anhydrous Na$_2$SO$_4$, filtered, and concentrated under reduced pressure to provide 9 g (98%) of a brown liquid. MS (ES, m/z): 168 [M+H]$^+$.

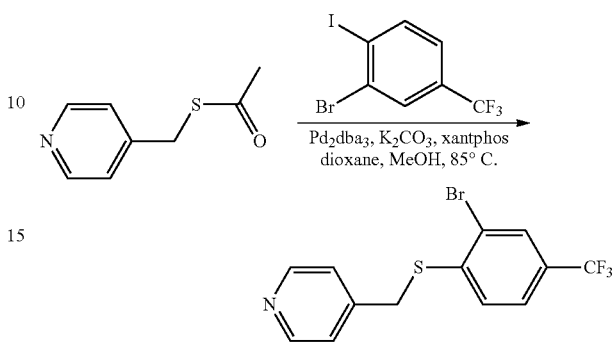

Compound 3.2. 4-(((2-Bromo-4-(trifluoromethyl)phenyl)thio)methyl)pyridine

A mixture of S-(pyridin-4-ylmethyl) ethanethioate (3.1, 4.75 g, 28.40 mmol, 1.20 equiv), Pd$_2$(dba)$_3$-CHCl$_3$ (2.94 g, 2.84 mmonl, 0.10 equiv), potassium carbonate (9.8 g, 70.91 mmol, 2.50 equiv), 2-bromo-1-iodo-4-(trifluoromethyl)benzene (8.3 g, 23.65 mmol, 1.00 equiv) and Xantphos (3.29 g, 5.69 mmol, 0.20 equiv) in 1,4-dioxane (50 mL) was stirred for 10 min at 85° C. in an oil bath in a sealed tube. This was followed by the addition of MeOH (9.1 g, 284.02 mmol, 10.00 equiv) dropwise at 85° C. The resulting mixture was stirred for 2 h at 85° C. in an oil bath. After cooling to room temperature the solids were removed by filtration, and the filtrate was concentrated under reduced pressure. The resulting residue was purified by silica gel chromatography (EtOAc/petroleum ether=1/1 (v/v)) to provide 6 g (73%) of brown oil. MS (ES, m/z): 349 [M+H]$^+$, 388 [M+H+CH$_3$CN]$^+$.

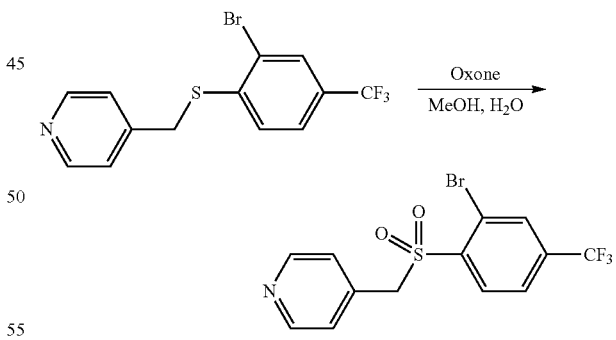

Compound 3.3. 4-(((2-Bromo-4-(trifluoromethyl)phenyl)sulfonyl)methyl)pyridine

A solution of 4-(((2-bromo-4-(trifluoromethyl)phenyl) thio)methyl)pyridine (3.2, 4.6 g, 13.21 mmol, 1.00 equiv) and Oxone (20.35 g, 33.02 mmol, 2.5 equiv) in methanol/water (1:1, 50 mL) was stirred overnight at room temperature. The mixture was dissolved with water (800 mL), and the pH value of the solution was adjusted to 9-10 with K$_2$CO$_{3(aq.)}$ The solids were collected by filtration to provide 5 g (100%) of a yellow solid. ¹H-NMR (400 MHz, DMSO-d6, ppm): δ 8.53 (d, J=6.0 Hz, 2H), 8.40 (m, 1H), 7.97 (m, 2H), 7.24-7.25 (d, J=6.0 Hz, 2H), 5.03 (s, 2H).

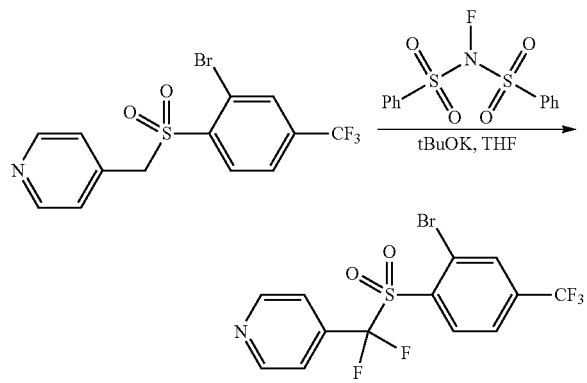

Compound 3.4. 4-(((2-bromo-4-(trifluoromethyl)phenyl)sulfonyl)difluoromethyl)pyridine To a solution of 4-(((2-bromo-4-(trifluoromethyl)phenyl)sulfonyl)methyl)pyridine (3.3, 2.45 g, 6.44 mmol, 1.00 equiv) in THF (40 mL) was added dropwise t-BuOK (1M in THF, 19.4 mL, 19.32 mmol, 3 equiv) at −10° C. under argon. The resulting solution was stirred for 30 min at −10° C. This was followed by the addition of N-Fluorobenzenesulfonimide (5.1 g, 16.17 mmol, 2.50 equiv) in THF (5 mL) dropwise with stirring at −10° C. The resulting solution was stirred for 1 hour at −10° C. The reaction was then quenched by the addition of NH₄Cl$_{(sat.)}$ (50 mL). The resulting mixture was extracted with EtOAc (3×50 mL) and the organic layers were combined. The solution was concentrated under vacuum. The resulting residue was purified by Flash-Prep-HPLC [Column, C18; mobile phase, CH₃CN:H2O=0:100 increasing to CH₃CN:H2O=100:0 within 35 min; Detector, UV 254 nm] to provide 1 g (37%) of as a yellow solid. MS (ES, m/z): [M+H+CH₃CN]+ 458.

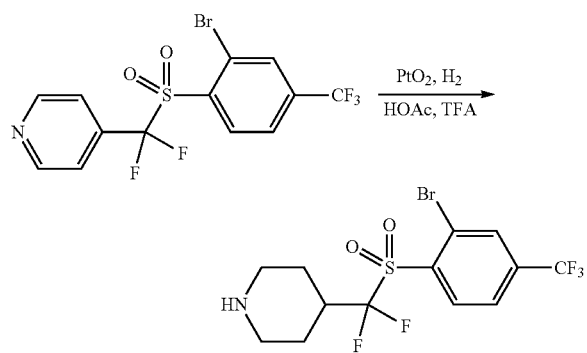

Compound 3.5. 4-(((2-Bromo-4-(trifluoromethyl)phenyl)sulfonyl)difluoromethyl) piperidine To a mixture of 4-(((2-bromo-4-(trifluoromethyl)phenyl)sulfonyl)difluoromethyl)-pyridine (3.4, 500 mg, 1.20 mmol, 1.00 equiv) and PtO₂ (200 mg, 40%) in a pressure tank reactor was added HOAc (6 mL) and trifluoroacetic acid (6 mL). The reaction mixture was purged with H$_{2(g)}$ (20 atm) and the solution was stirred for 2 days at 60° C. in an oil bath. [Caution: the reaction flask was purged with N$_{2(g)}$ prior to being purged with H$_{2(g)}$.] The solids were removed by filtration. A second aliquot of PtO₂ (200 m g, 40%) was added and the resulting solution was stirred for another 2 days at 60° C. in an oil bath. The solids were removed by filtration and the filtrate was concentrated under reduced pressure to provide 500 mg (crude) of a brown solid. The product was used to next step directly without further purification.

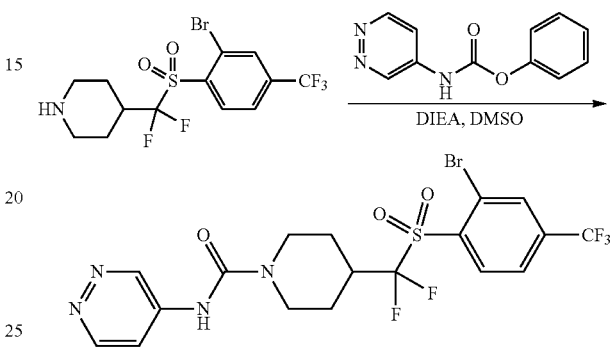

Compound 3.6. 4-(((2-Bromo-4-(trifluoromethyl)phenyl)sulfonyl)difluoromethyl)-N-(pyridazin-4-yl)piperidine-1-carboxamide A solution of 4-(((2-bromo-4-(trifluoromethyl)phenyl)sulfonyl)difluoromethyl)-piperidine (3.5, 0.5 g, 1.15 mmol, 1.00 equiv), DIEA (1.5 g, 5.75 mmol, 5.00 equiv) and phenyl pyridazin-4-ylcarbamate (5.1, 0.5 g, 2.30 mmol, 2.00 equiv) in DMSO (10 mL) was stirred for 3 h at 70° C. in an oil bath under argon. The mixture was purified directly by Flash-Prep-HPLC [Column, C18; mobile phase, CH₃CN:H2O=0:100 increasing to CH₃CN:H2O=100:0 within 35 min; Detector, UV 254 nm] to provide 240 mg (36%) of a brown solid. MS (ES, m/z): [M+H]+ 543, [M+H+CH₃CN]+ 584.

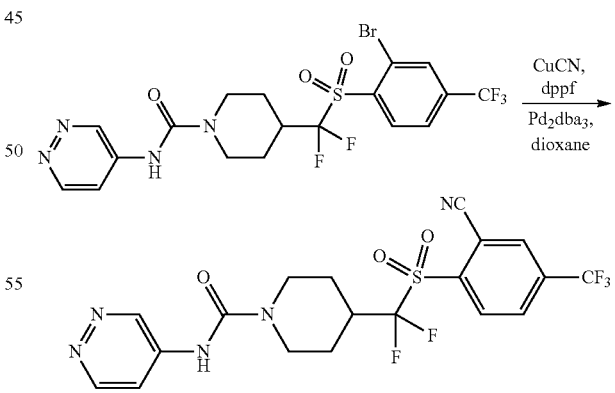

Compound 3. 4-(((2-Cyano-4-(trifluoromethyl)phenyl)sulfonyl)difluoromethyl)-N-(pyridazin-4-yl)piperidine-1-carboxamide A mixture of 4-(((2-bromo-4-(trifluoromethyl)phenyl)sulfonyl)difluoromethyl)-N-(pyridazin-4-yl)piperidine-1- carboxamide (3.6, 190 mg, 0.35 mmol, 1.00 equiv), CuCN (125 mg, 1.4 mmol, 4.00 equiv), dppf (156 mg, 0.28 mmol, 0.80 equiv) and $Pd_2(dba)_3CHCl_3$ (145 mg, 0.14 mmol, 0.40 equiv) in 1,4-dioxane (10 mL) was stirred for 1 hour at 100° C. in an oil bath under argon. After cooling to room temperature, the resulting mixture was diluted with $H_2O$ (40 mL) and was extracted with EtOAc (2×50 mL). The combined organic layers were washed with $FeSO_{4(sat.)}$ (30 mL) and dried over anhydrous magnesium sulfate. The solution was concentrated under vacuum, and the resulting residue was purified by Prep-HPLC [Column, SUNFIRE, 19*150 mm, 5 um; mobile phase, Mobile Phase A: Water/10 mM $NH_4HCO3$, Mobile Phase B: $CH_3CN$; Flow rate: 20 mL/min; Gradient: 25-75% B in 8 min; Detector, 254 nm] to provide 53.1 mg (31%) of a light yellow solid. MS (ES, m/z): [M+H]+ 490, [M+Na]+ 512; $^1$H-NMR (400 MHz, DMSO-d6, ppm): δ 9.28 (m, 2H), 8.88 (m, 2H), 8.45 (m, 2H), 7.75 (d, J=3.2 Hz, 1H), 4.26 (m, 2H), 2.93-3.04 (m, 3H), 2.05 (m, 2H), 1.51-1.60 (m, 2H). $^{19}$F-NMR (400 MHz, DMSO-d6, ppm): 62.107, 104.437.

Example 4. Preparation of 4-(((2-(difluoromethyl) phenyl)sulfonyl)difluoromethyl)-N-(pyridazin-4-yl) piperidine-1-carboxamide

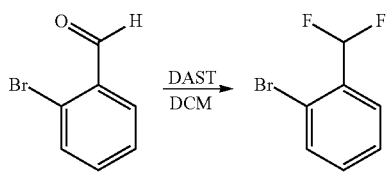

Compound 4.1. 1-bromo-2-(difluoromethyl)benzene

To a solution of 2-bromobenzaldehyde (10.0 g, 54.05 mmol, 1.00 equiv) in $CH_2Cl_2$ (100 mL) under argon was added DAST (17.4 g, 107.95 mmol, 2.00 equiv) dropwise with stirring at 0° C. The resulting solution was stirred for 3 h at room temperature. The reaction was then quenched by the slow and careful addition of $NaHCO_{3(sat.)}$ (200 mL). The resulting mixture was extracted with $CH_2Cl_2$ (3×100 mL) and the combined organic layers were washed with brine (150 mL), dried over anhydrous sodium sulfate, filtered, and concentrated under reduced pressure. The resulting residue was purified by silica gel chromatography (EtOAc/petroleum ether (1:40)) to provide 9.0 g (80%) of a colorless oil. $^1$H-NMR (CDCl3, 400 MHz, ppm): δ 7.68 (m, 1H), 7.61 (m, 1H), 7.42 (m, 1H), 7.33 (m, 1H), 6.79-7.05 (t, J=52 Hz, 1H). $^{19}$F-NMR (CDCl3, 400 MHz, ppm): δ 114.63.

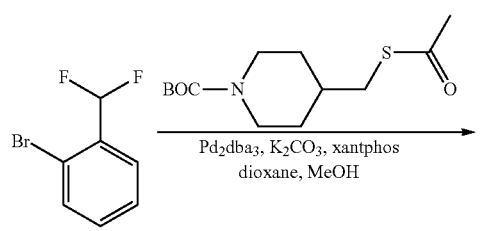

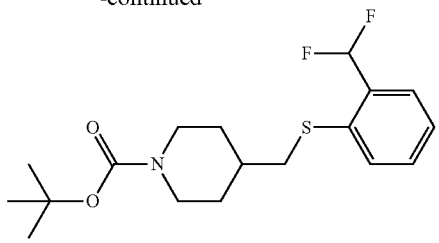

Compound 4.2. tert-Butyl 4-(((2-(difluoromethyl) phenyl)thio)methyl)piperidine-1-carboxylate A mixture of 1-bromo-2-(difluoromethyl)benzene (4.1, 3.0 g, 14.49 mmol, 1.00 equiv), $Pd_2(dba)_3$-$CHCl_3$ (750 mg, 0.82 mmol, 0.05 equiv), potassium carbonate (6.04 g, 43.70 mmol, 3.00 equiv), Xantphos (838 mg, 1.45 mmol, 0.10 equiv) and tert-butyl 4-[(acetylsulfanyl)methyl]piperidine-1-carboxylate (3.96 g, 14.48 mmol, 1.00 equiv) in 1,4-dioxane (80 mL) was stirred for 10 min at 80° C. in an oil bath under argon. This was followed by the addition of methanol (4.6 g, 143.57 mmol, 10.00 equiv) dropwise at 80° C. The resulting solution was stirred for 1 h at 80° C. in an oil bath. The reaction mixture was cooled to room temperature, and then was concentrated under reduced pressure. The resulting residue was purified by silica gel chromatography (EtOAc/petroleum ether (1:10)) to provide 3.0 g (58%) of a colorless oil. $^1$H-NMR (400 MHz, CDCl3, ppm): δ 7.65 (m, 1H), 7.35-7.48 (m, 3H), 6.97-7.24 (t, J=52 Hz, 1H), 4.10 (m, 2H), 2.83 (m, 2H), 2.66 (m, 2H), 1.57 (m, 2H), 1.45 (s, 9H), 1.16-1.27 (m, 3H).

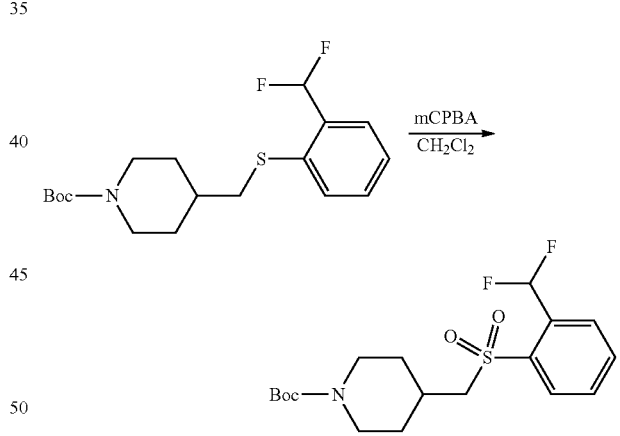

Compound 4.3. tert-Butyl 4-(((2-(difluoromethyl) phenyl)sulfonyl)methyl)piperidine-1-carboxylate To a solution of tert-butyl 4-(((2-(difluoromethyl)phenyl) thio)methyl)piperidine-1-carboxylate (4.2, 2.0 g, 5.60 mmol, 1.00 equiv) in $CH_2Cl_2$ (40 mL) was added mCPBA (4.8 g, 27.82 mmol, 4.00 equiv) in several batches at 0° C. The resulting solution was stirred for 2 h at room temperature. The reaction was then quenched by the addition of $NaHCO_{3(sat.)}$ (150 mL). The resulting solution was extracted with $CH_2Cl_2$ (3×100 mL). The combined organic layers were washed with $H_2O$ (2×100 mL) and brine (150 mL), dried over anhydrous sodium sulfate and concentrated under reduced pressure. The resulting residue was purified by silica gel chromatography (EtOAc/petroleum ether (1:10)) to provide 800 mg (37%) of a colorless oil. ¹H-NMR (400 MHz, CDCl3, ppm): δ 8.09 (m, 1H), 7.92 (m, 1H), 7.79 (m, 1H), 7.71 (m, 1H), 7.49-7.70 (t, J=44 Hz, 1H), 4.07 (m, 2H), 3.10 (m, 2H), 2.74 (m, 2H), 2.23 (m, 1H), 1.87 (m, 2H), 1.47 (s, 9H), 1.26 (m, 2H).

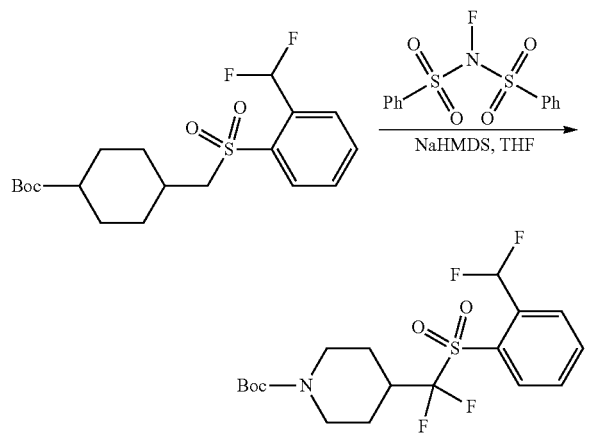 [SMILES: CC(C)(C)OC(=O)C1CCC(CS(=O)(=O)c2ccccc2C(F)F)CC1 ; O=S(=O)(c1ccccc1)N(F)S(=O)(=O)c1ccccc1 ; CC(C)(C)OC(=O)N1CCC(C(F)(F)S(=O)(=O)c2ccccc2C(F)F)CC1]

Compound 4.4. tert-Butyl 4-(((2-(difluoromethyl)phenyl)sulfonyl)difluoromethyl) piperidine-1-carboxylate To a mixture of tert-butyl 4-(((2-(difluoromethyl)phenyl)sulfonyl)methyl)piperidine-1-carboxylate (4.3, 800 mg, 2.05 mmol, 1.00 equiv) and NFSI (3.2 g, 5.00 equiv) in THF (20 mL) under argon was added a solution of NaHMDS (2.0M in THF, 8 mL, 8.00 equiv) dropwise with stirring at −78° C. The resulting solution was stirred for 1 hour at −78° C., and the reaction was then quenched by the addition of NH₄Cl₍sat.₎ (100 mL). The resulting solution was extracted with EtOAc (3×100 mL) and the combined organic layers were washed with H₂O (2×100 mL), brine (150 mL), dried over anhydrous sodium sulfate and concentrated under reduced pressure. The resulting residue was purified by silica gel chromatography (EtOAc/petroleum ether=1/3 (v/v)) to provide 600 mg (69%) of a colorless oil. ¹H-NMR (400 MHz, CDCl₃): δ 8.006 (m, 2H), 7.90 (m, 1H), 7.74 (m, 1H), 7.26-7.48 (t, J=44 Hz, 1H), 4.26 (m, 2H), 2.76 (m, 3H), 2.07 (m, 2H), 1.61 (m, 2H), 1.47 (s, 9H) ppm. ¹⁹F-NMR (376 MHz, CDCl₃): δ −106.80, −109.33 ppm.

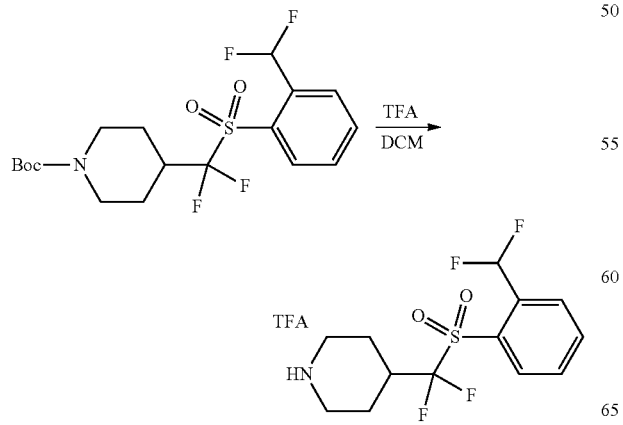

Compound 4.5. 4-(((2-(Difluoromethyl)phenyl)sulfonyl)difluoromethyl)piperidine trifluoroacetic acid salt A solution of tert-butyl 4-((2-(difluoromethyl)phenyl)sulfonyl)difluoromethyl)piperidine-1-carboxylate (4.4, 600 mg, 1.41 mmol, 1.00 equiv) and trifluoroacetic acid (4 mL) in CH₂Cl₂ (4 mL) was stirred for 1 hour at room temperature under argon. The resulting mixture was concentrated under reduced pressure to provide 600 mg of crude of a brown oil. The product was used to next step directly without further purification. MS (ES, m/z): 325 [M+H]⁺, 367 [M+CH₃CN+H]⁺.

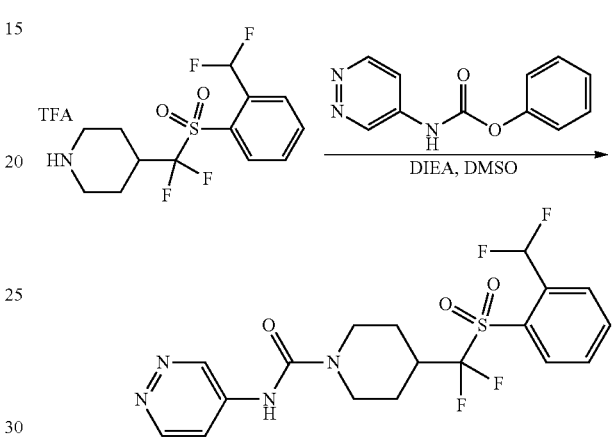

Compound 4. 4-(((2-(Difluoromethyl)phenyl)sulfonyl)difluoromethyl)-N-(pyridazin-4-yl)piperidine-1-carboxamide A mixture of 4-(((2-(difluoromethyl)phenyl)sulfonyl)difluoromethyl)piperidine trifluoroacetic acid salt (4.5, 460 mg, 1.05 mmol, 1.00 equiv), DIEA (731 mg, 5.66 mmol, 4.00 equiv) and phenyl pyridazin-4-ylcarbamate (5.1, 609 mg, 2.83 mmol, 2.00 equiv) in DMSO (5 mL) was stirred for 1 hour at 80° C. in an oil bath under argon. The reaction mixture was cooled to room temperature and was directly purified by Flash-Prep-HPLC [Column, C18; mobile phase, CH₃CN:H2O=0:100 (v/v) increasing to CH₃CN:H2O=100:0 (v/v) within 35 min; Detector, UV 254 nm] to provide 350 mg (75%) of an off-white solid. LC-MS (ES, m/z): 447 [M+H]⁺, 488 [M+CH₃CN+H]⁺; ¹H-NMR (400 MHz, CD₃OD): δ 9.24 (m, 1H), 8.87 (m, 1H), 8.02-8.14 (m, 3H), 7.88 (m, 2H), 7.37-7.64 (t, J=56 Hz, 1H), 4.34 (m, 2H), 2.91-3.13 (m, 3H), 2.18 (m, 2H), 1.74 (m, 2H) ppm.

Example 5. Preparation of 4-(difluoro((3-fluorophenyl)sulfonyl)methyl)-N-(pyridazin-4-yl)piperidine-1-carboxamide

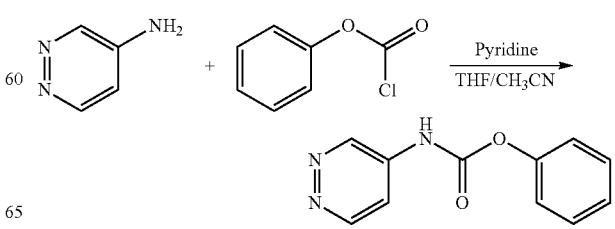

Compound 5.1. Phenyl pyridazin-4-ylcarbamate

To a suspension of 4-aminopyridazine (1.00 g, 10.51 mmol) in a 1:1 mix of THF (10 mL) and acetonitrile (10 mL) at 0° C. was added pyridine (1.03 mL, 12.62 mmol), followed by the dropwise addition of phenyl chloroformate (1.58 mL, 12.62 mmol) over a period of 10 minutes. The reaction mixture was stirred for 2 h while warming to room temperature. The precipitate was isolated by filtration and dried for 1 h under high vacuum to provide the desired product as an off-white powder (0.923 g, 41%). LC-MS (ES, m/z): 216 [M+H]$^+$; $^1$H-NMR (400 MHz, CDCl$_3$): δ 11.00 (br. s., 1H), 9.25 (d, J=1.96 Hz, 1H), 9.03 (d, J=5.87 Hz, 1H), 7.76 (dd, J=5.87, 2.74 Hz, 1H), 7.38-7.51 (m, 2H), 7.19-7.35 (m, 3H) ppm.

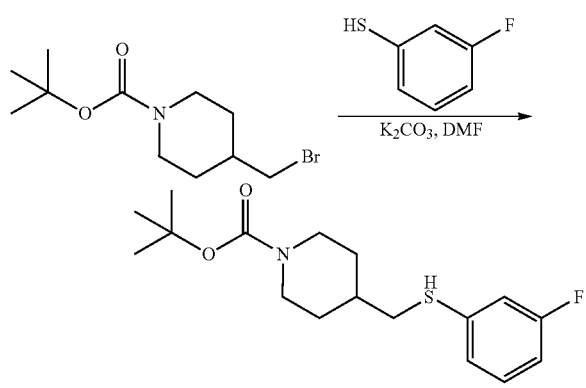

Compound 5.2. tert-Butyl 4-(((3-fluorophenyl)-l3-sulfanyl)methyl)piperidine-1-carboxylate To a solution of tert-butyl 4-(bromomethyl)piperidine-1-carboxylate (10.0 g, 35.94 mmol) in DMF (100 mL) was added potassium carbonate (7.45 g, 53.90 mmol), followed by 3-fluorothiophenol (3.20 mL, 37.87 mmol). The reaction mixture was stirred at room temperature for 24 h. The reaction mixture was diluted with H$_2$O, and extracted with EtOAc. The organic layer was washed with H$_2$O, saturated NaCl, dried over Na$_2$SO$_4$, filtered and concentrated. The desired product was obtained as a clear oil (11.8 g) and was used without purification. LC-MS (ES, m/z): 324 [M−H]$^−$.

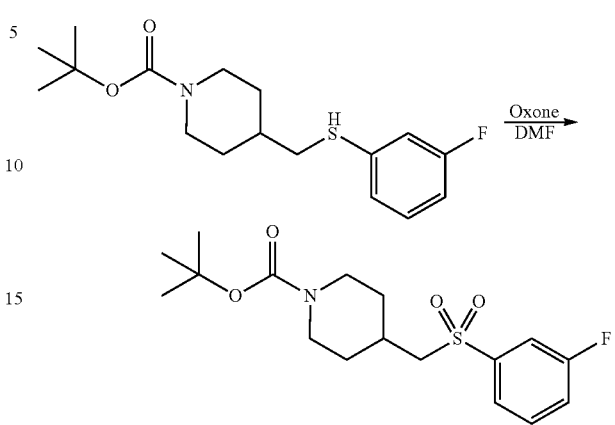

Compound 5.3. tert-Butyl 4-(((3-fluorophenyl)sulfonyl)methyl)piperidine-1-carboxylate To a solution of tert-butyl 4-(((3-fluorophenyl)-l3-sulfanyl)methyl)piperidine-1-carboxylate (5.2, 11.8 g) in DMF (110 mL) was added Oxone (66.4 g, 107.9 mmol). The reaction mixture was stirred at room temperature for 18 h. The reaction mixture was diluted with H$_2$O, and extracted into EtOAc. The organic layer was washed with 0.5 N NaOH, saturated NaCl, dried with Na$_2$SO$_4$, filtered and concentrated. The resulting residue was purified by flash chromatography (20%-40% EtOAc in hexanes) to provide the desired product as a white solid (7.48 g, 56% over two steps). LC-MS (ES, m/z): 302 [M-56+H]$^+$; $^1$H-NMR (400 MHz, CDCl$_3$): δ 7.72 (d, J=7.83 Hz, 1H), 7.54-7.65 (m, 2H), 7.37 (td, J=8.22, 2.74 Hz, 1H), 3.97-4.20 (m, 2H), 3.02 (d, J=6.26 Hz, 2H), 2.74 (m, 2H), 2.13-2.26 (m, 1H), 1.89-1.86 (m, 2H), 1.44 (s, 9H), 1.19-1.33 (m, 2H) ppm.

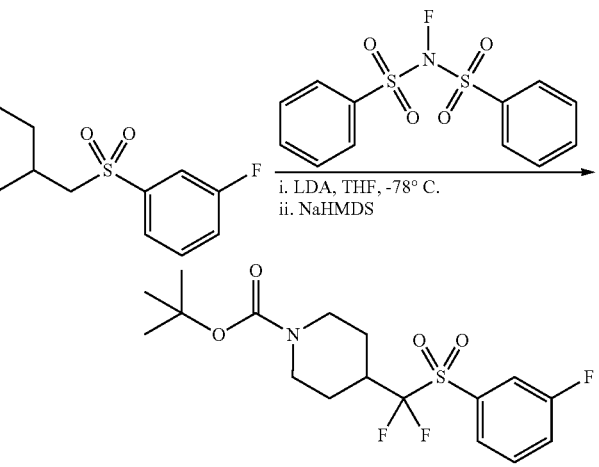

Compound 5.4. tert-Butyl 4-(difluoro((3-fluorophenyl)sulfonyl)methyl)piperidine-1-carboxylate To a solution of tert-butyl 4-(((3-fluorophenyl)sulfonyl)methyl)piperidine-1-carboxylate (5.3, 1.00 g, 2.80 mmol) and N-fluorobenzene sulfinimde (3.50 g, 11.1 mmol) in dry THF (50 mL) at −78° C. under nitrogen was added LDA (2.0M in THF, 3.5 mL, 3.50 mmol)) dropwise. The reaction mixture was stirred for 25 minutes at −78° C. A second aliquot of LDA (2.0M in THF, 2.0 mL, 2.00 mmol) was added dropwise, and the reaction mixture was stirred at −78° C. for 40 minutes. The NaHMDS (1.0M in THF, 7.0 mL, 7.00 mmol) was added slowly and the reaction mixture was stirred at −78° C. for 1.5 h. Hexanes (150 mL) was added to the reaction mixture, and the precipitate was removed by filtration. The filtrate was washed with saturated NaHCO$_3$, saturated NaCl, dried with Na$_2$SO$_4$, filtered and concentrated. The resulting residue was purified by flash chromatography (0-20% EtOAc in hexanes) to provide the desired product as a white solid (0.6 g, 54%). LC-MS (ES, m/z): 338 [M-56+H]$^+$; $^1$H-NMR (400 MHz, CDCl$_3$): δ 7.77 (d, J=7.83 Hz, 1H), 7.65-7.70 (m, 1H), 7.62 (m, 1H), 7.46 (m, 1H), 4.25 (br. s., 2H), 2.60-2.87 (m, 3H), 2.07 (d, J=13.30 Hz, 2H), 1.55-1.67 (m, 2H), 1.46 (s, 9H) ppm.

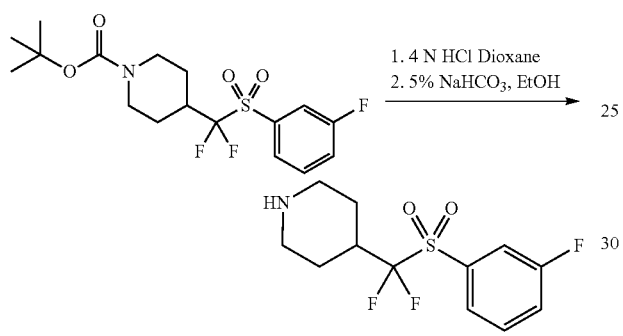

Compound 5.5. 4-(Difluoro((3-fluorophenyl)sulfonyl)methyl)piperidine

To a solution of tert-butyl 4-(difluoro((3-fluorophenyl)sulfonyl)methyl)piperidine-1-carboxylate (5.4, 8.0 g, 20.35 mmol) in dioxane (30 mL) was added 4N HCl/dioxane (30 mL). The reaction mixture was stirred at room temperature for 1 h, and then was concentrated. The resulting residue was dissolved in EtOH (30 mL) and 150 mL 5% NaHCO$_3$ in water was added. The crashed solid was stirred at room temperature for 30 minutes. The solid was filtered, washed with water and dried to provide the desired product as a white solid which was used without further purification (4.68 g). LC-MS (ES, m/z): 294 [M+H]$^+$.

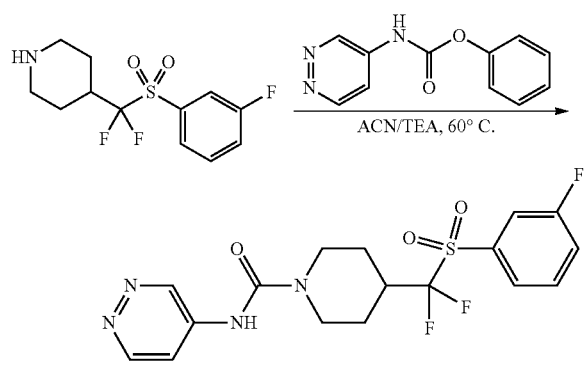

Compound 5. 4-(Difluoro((3-fluorophenyl)sulfonyl)methyl)-N-(pyridazin-4-yl)piperidine-1-carboxamide To a solution of 4-(difluoro((3-fluorophenyl)sulfonyl)methyl)piperidine (5.5, 4.68 g, 15.95 mmol) and 1-phenyl-3-(pyridazine-4-yl)urea (3.50 g, 16.27 mmol) in acetonitrile (50 mL) was added triethylamine (31.9 mmol, 3.22 g) in sealed tube. The reaction mixture was heated at 60° C. for 2 h behind a blast shield. The resulting residue was purified by flash chromatography (0-7% (v/v) MeOH/DCM) to provide the desired product as white solid (6.2 g). LC-MS (ES, m/z): 415 [M+H]$^+$; $^1$H NMR (400 MHz, CD$_3$OD): δ 9.23 (dd, J=2.7, 0.8 Hz, 1H), 8.80-8.94 (m, 1H), 7.82-7.96 (m, 2H), 7.70-7.80 (m, 2H), 7.58-7.68 (m, 1H), 4.32 (d, J=14.1 Hz, 2H), 3.03 (t, J=12.3 Hz, 2H), 2.83-2.97 (m, 1H), 2.16 (d, J=12.9 Hz, 2H), 1.63-1.78 (m, 2H) ppm.

Example 6. Preparation of 4-(1-fluoro-1-((3-fluorophenyl)sulfonyl)ethyl)-N-(pyridazin-4-yl)piperidine-1-carboxamide

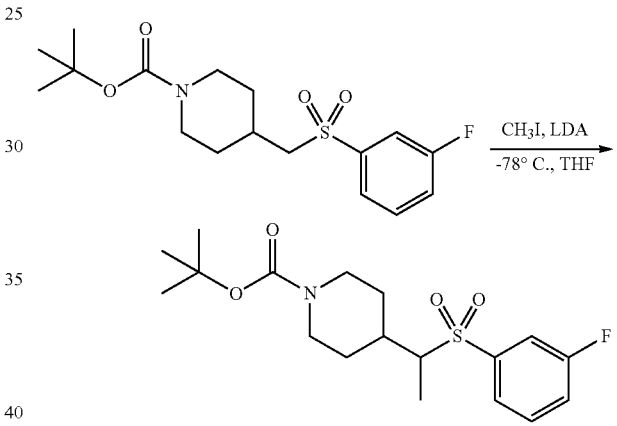

Compound 6.1. tert-Butyl 4-(1-((3-fluorophenyl)sulfonyl)ethyl)piperidine-1-carboxylate To a solution of tert-butyl 4-(((3-fluorophenyl)sulfonyl)methyl)piperidine-1-carboxylate (5.3, 0.10 g, 0.279 mmol) in dry THF (1 mL) at −78° C. was added LDA (2.0M in THF, 0.168 mL, 0.336 mmol). The reaction mixture was stirred at −78° C. under nitrogen for 15 minutes before methyl iodide (0.017 mL, 0.279 mmol) was added. The reaction mixture was allowed to stir for 18 h while warming to room temperature. The reaction mixture was diluted with H$_2$O and extracted into EtOAc. The organic layer was dried with Na$_2$SO$_4$, filtered and concentrated. The resulting residue was purified by flash chromatography (20% EtOAc in hexanes) to provide the desired product as a colorless oil (0.103 g, 98%). LC-MS (ES, m/z): 316 [M-56+H]$^+$; $^1$H-NMR (400 MHz, CDCl$_3$): δ 7.66-7.71 (m, 1H), 7.53-7.62 (m, 2H), 7.33-7.40 (m, 2H), 3.98-4.33 (m, 2H), 3.00-2.94 (m, 1H), 2.63-2.80 (m, 2H), 2.44-2.37 (m, 1H), 1.96-1.92 (m, 1H), 1.45 (s, 9H), 1.23-1.42 (m, 2H), 1.20 (d, J=7.04 Hz, 3H) ppm.

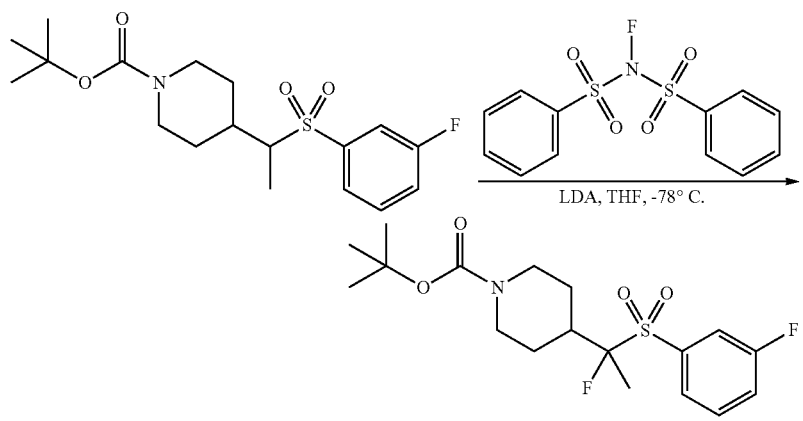

Compound 6.2. tert-Butyl 4-(1-fluoro-1-((3-fluorophenyl)sulfonyl)ethyl)piperidine-1-carboxylate To a solution of tert-butyl 4-(1-((3-fluorophenyl)sulfonyl)ethyl)piperidine-1-carboxylate (6.1, 0.103 g, 0.277 mmol) in dry THF (1 mL) at −78° C. was added LDA (2.0M in THF, 0.173 mL, 0.346 mmol). The reaction mixture was stirred at −78° C. for 15 minutes before N-fluorobenzene sulfinimde (0.087 g, 0.277 mmol) was added. The reaction mixture was stirred for 2 h at −78° C. A second aliquot of both LDA (2.0M in THF, 0.173 mL, 0.346 mmol) and N-fluorobenzene sulfinimde (0.087 g, 0.277 mmol) were added, and the reaction mixture was stirred for an additional 30 minutes at −78° C. The reaction mixture was diluted with $H_2O$, warmed to room temperature and extracted into EtOAc. The organic layer was dried with $Na_2SO_4$, filtered and concentrated. The resulting residue was purified by flash chromatography (20% EtOAc in hexanes to provide the desired product as a colorless oil (0.028 g, 26%). LC-MS (ES, m/z): 334 [M-56+H]$^+$; $^1$H-NMR (400 MHz, CDCl3): δ 7.74-7.72 (m, 1H), 7.54-7.67 (m, 2H), 7.42 (ddt, J=8.27, 6.99, 1.37, 1.37 Hz, 1H), 4.30-4.15 (m, 2H), 2.77-2.64 (m, 3H), 2.40-2.53 (m, 1H), 2.21-2.17 (m, 1H), 1.81-1.78 (m, 2H), 1.48-1.58 (m, 3H), 1.46 (s, 9H) ppm.

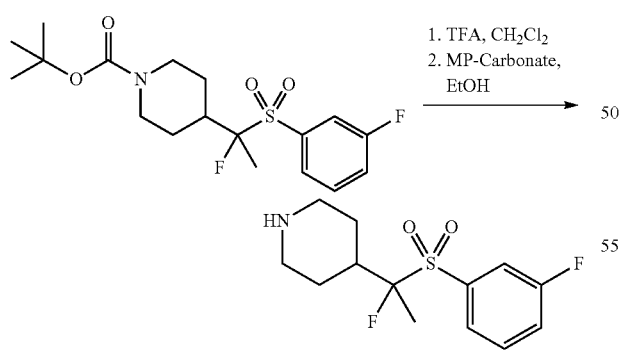

Compound 6.3. 4-(1-Fluoro-1-((3-fluorophenyl)sulfonyl)ethyl)piperidine

To a solution of tert-butyl 4-(1-fluoro-1-((3-fluorophenyl)sulfonyl)ethyl)piperidine-1-carboxylate (6.2, 0.046 g, 0.119 mmol) in $CH_2Cl_2$ (1 mL) was added TFA (0.20 mL). The reaction mixture was stirred at room temperature for 18 h, and then was concentrated. The resulting residue was dissolved in EtOH (1 mL) and MP-carbonate (0.376 g, 1.19 mmol) was added. The reaction mixture was stirred for 30 minutes at room temperature. The solid was removed by filtration and the filtrate was concentrated to provide the desired product as a colorless oil which was used without further purification (0.026 g, 75%). LC-MS (ES, m/z): 290 [M+H]$^+$.

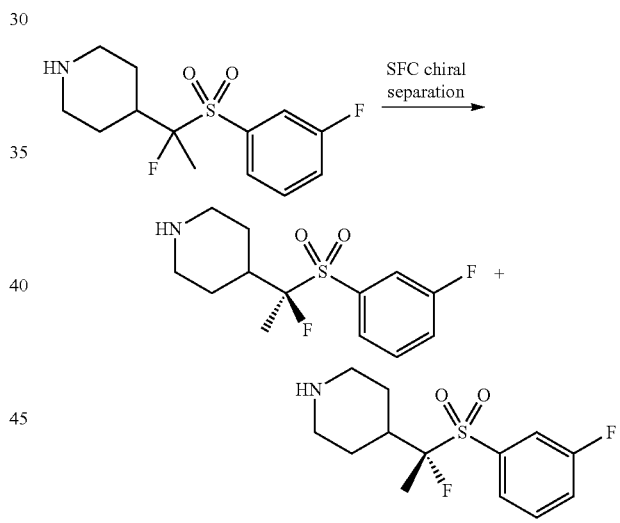

Compound 6.3a. (R)-4-(1-fluoro-1-((3-fluorophenyl) sulfonyl)ethyl)piperidine and

Compound 6.3b. (S)-4-(1-fluoro-1-((3-fluorophenyl) sulfonyl)ethyl)piperidine

The enantiomers of 4-(1-fluoro-1-((3-fluorophenyl)sulfonyl)ethyl)piperidine (6.3, 1.89 g) were separated using by Prep-SFC (Column: Phenomenex Lux® 3u Celloluse-2, 4.6*100 mm, 3 um; Mobile Phase A: $CO_2$, Mobile Phase B: EtOH (0.1% DEA) gradient 10% to 50% in 4.0 min, hold 2.0 min at 50%; Flow rate: 150 mL/min; 220 nm) to provide RT$_1$=2.16 min (6.3a, 0.938 g, 98%) as a white solid and RT$_2$=2.75 min (6.3b, 0.948 g, 98%) as a white solid.

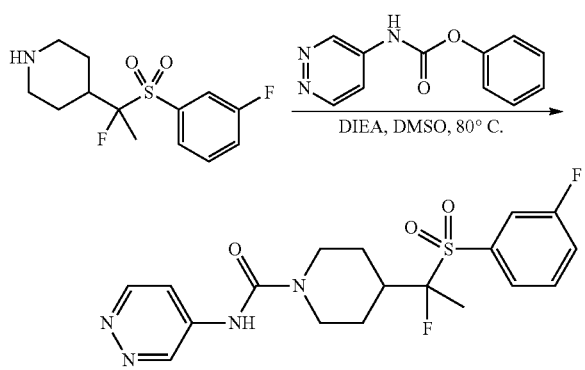

Compound 6. 4-(1-Fluoro-1-((3-fluorophenyl)sulfonyl)ethyl)-N-(pyridazin-4-yl)piperidine-1-carboxamide trifluoroacetic acid salt To a solution of 4-(1-fluoro-1-((3-fluorophenyl)sulfonyl)ethyl)piperidine (6.3, 0.026 g, 0.089 mmol) in in DMSO (1 mL) was added phenyl pyridazin-4-ylcarbamate (5.1, 0.028 g, 0.132 mmol), followed by DIEA (0.055 mL, 0.309 mmol). The reaction mixture was plunged into a preheated 80° C. oil bath and was stirred for 2 h. The reaction mixture was cooled to room temperature and diluted with EtOAc and H$_2$O. The two layers were separated. The organic layer was dried with Na$_2$SO$_4$, filtered and concentrated. The resulting residue was purified using reverse phase high pressure liquid chromatography (0-90% (v/v) CH$_3$CN in H$_2$O (both containing 0.1% TFA)) to provide the desired product as a white solid (0.015 g, 42%). LC-MS– (ES, m/z): 411 [M+H]$^+$; $^1$H-NMR (400 MHz, CDCl$_3$): δ 10.55 (s, 1H), 9.60 (d, J=1.96 Hz, 1H), 8.77 (d, J=7.04 Hz, 1H), 8.67 (dd, J=6.85, 2.15 Hz, 1H), 7.74 (d, J=7.43 Hz, 1H), 7.56-7.67 (m, 2H), 7.43 (td, J=8.12, 2.15 Hz, 1H), 4.49 (t, J=12.91 Hz, 2H), 2.96 (br. s., 2H), 2.55-2.68 (m, 1H), 2.33 (d, J=12.91 Hz, 1H), 1.96 (d, J=13.30 Hz, 1H), 1.42-1.59 (m, 5H) ppm.

Example 7. Preparation of 4-(2-((3-Fluorophenyl)sulfonyl)propan-2-yl)-N-(pyridazin-4-yl)piperidine-1-carboxamide

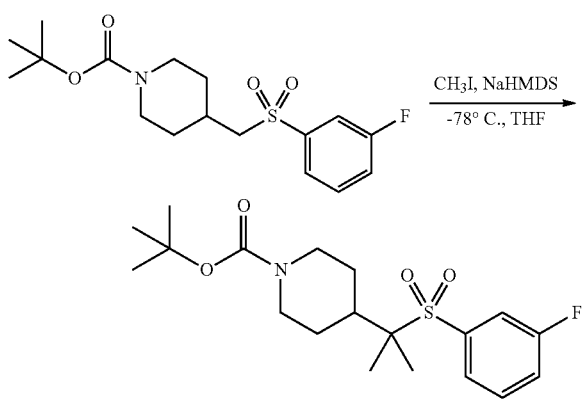

Compound 7.1. tert-butyl 4-(2-((3-fluorophenyl)sulfonyl)propan-2-yl)piperidine-1-carboxylate Compound 7.1 was prepared in a similar manner as compound 6.1 with the exception of the substitution of sodium bis(trimethylsilyl)amide for LDA and the use of 3.5 equivalents of methyl iodide to provide the desired product as a white solid (1.8 g, 83%) which was used without purification in the next reaction.

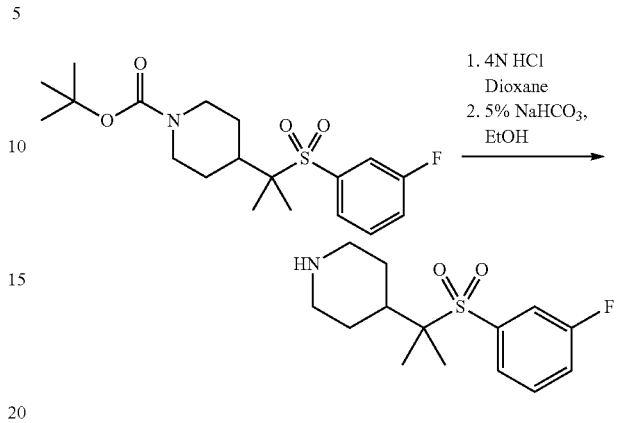

Compound 7.2. 4-(2-((3-Fluorophenyl)sulfonyl)propan-2-yl)piperidine

Compound 7.2 was prepared in a similar manner as compound 5.5 to provide the desired product which was used without purification in the next reaction.

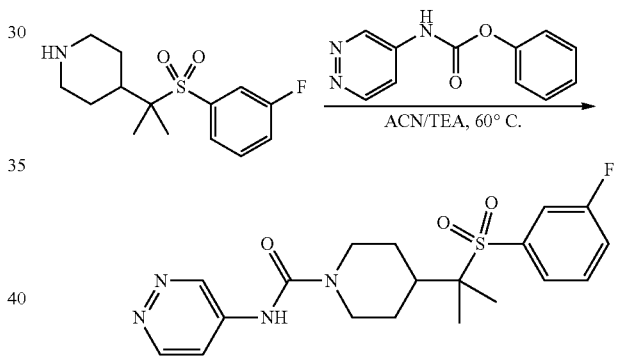

Compound 7. 4-(2-((3-fluorophenyl)sulfonyl)propan-2-yl)-N-(pyridazin-4-yl)piperidine-1-carboxamide Compound 7 was prepared in a similar manner as compound 5 to provide the desired product as a white solid (0.56 g, 72%). LC-MS (ES, m/z): 407 [M+H]$^+$; $^1$H-NMR (400 MHz, DMSO-d6, ppm): δ 9.28 (s, 1H), 9.17 (s, 1H), 8.88 (d, J=6.0 Hz, 1H), 7.78-7.66 (m, 5H), 4.23-4.20 (m, 2H), 2.83-2.77 (m, 2H), 2.08-1.94 (m, 3H), 1.40-1.37 (m, 2H), 1.19 (s, 6H) ppm.

Example 8. Preparation of 4-(1-fluoro-1-((4-(trifluoromethyl)phenyl)sulfonyl)ethyl)-N-(isoxazol-3-yl)piperidine-1-carboxamide

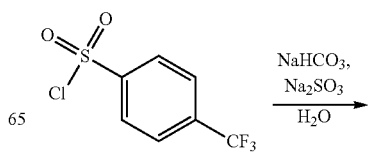

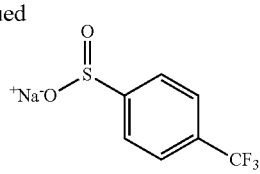

Compound 8.1. Sodium 4-(trifluoromethyl)benzenesulfinate

To a solution of 4-(trifluoromethyl)benzenesulfonyl chloride (0.424 g, 1.73 mmol) in H$_2$O (2.5 mL) was added NaHCO$_3$ (0.291 g, 3.46 mmol) and Na$_2$SO$_3$ (0.437 g, 3.46 mmol). The reaction mixture was plunged into a preheated 80° C. oil bath and was stirred for 3 h. The reaction mixture was cooled to room temperature and was concentrated under reduced pressure. The resulting residue was suspended in EtOH (5 mL) and the solids were removed by filtration. The filtrate was concentrated under reduced pressure to provide the desired product as a white solid which was used without further purification (0.40 g, 99%). LC-MS (ES, m/z): 232 [M+H]$^+$.

Compound 8.2. tert-Butyl 4-(((4-(trifluoromethyl)phenyl)sulfonyl)methyl)piperidine-1-carboxylate To a solution of tert-butyl 4-(((4-(trifluoromethyl)phenyl)sulfonyl)methyl)piperidine-1-carboxylate (8.1, 0.40 g, 1.79 mmol) in DMF (10 mL) was added K$_2$CO$_3$ (0.495 g, 3.58 mmol) and tert-butyl 4-(bromomethyl)piperidine-1-carboxylate (0.499 g, 1.79 mmol). The reaction mixture was plunged into a preheated 80° C. oil bath and was stirred for 3 h. The reaction mixture was then stirred overnight while cooling to room temperature. The solids were removed by filtration. The filtrate was diluted with EtOAc (15 mL) and H$_2$O (10 mL) and the two layers were separated. The organic layer was dried with Na$_2$SO$_4$, filtered and concentrated. The resulting residue was purified by flash chromatography (20% EtOAc in hexanes to provide the desired product as a colorless oil (0.21 g, 73%). LC-MS (ES, m/z): 222 [M-56+H]$^+$; 1H-NMR (400 MHz, CDCl$_3$): δ 8.09 (d, J=8.07 Hz, 2H), 7.88 (d, J=8.19 Hz, 2H), 4.10 (d, J=13.69 Hz, 2H), 3.05 (d, J=6.36 Hz, 2H), 2.77 (t, J=12.72 Hz, 2H), 2.24 (br. s., 1H), 1.92 (d, J=12.23 Hz, 2H), 1.47 (s, 9H), 1.22-1.38 (m, 2H) ppm.

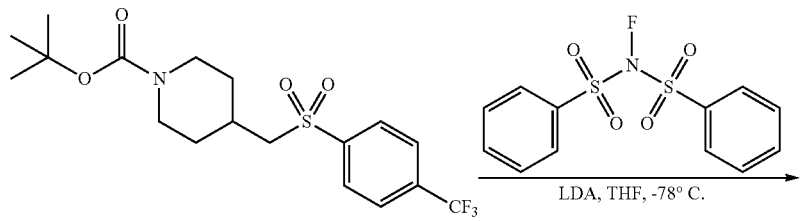

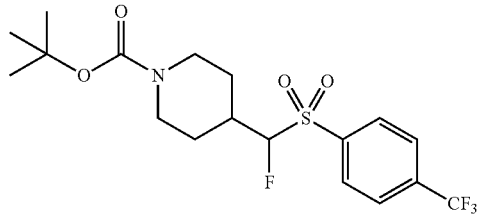

Compound 8.3. tert-Butyl 4-(fluoro((4-(trifluoromethyl)phenyl)sulfonyl)methyl)piperidine-1-carboxylate To a solution of tert-butyl 4-(((4-(trifluoromethyl)phenyl)sulfonyl)methyl)piperidine-1-carboxylate (8.2, 0.207 g, 0.508 mmol) in THF (3 mL) at −78° C. was added LDA (2.0 M in THF, 0.279 mL, 0.559 mmol). The reaction mixture was stirred for 25 minutes before NFSI (0.241 g, 0.762 mmol) was added. The reaction mixture was stirred for 4 h at −78° C., then was diluted with EtOAc (5 mL) and was warmed to room temperature. The reaction mixture was diluted with H$_2$O (5 mL) and the two layers were separated. The organic layer was dried with Na$_2$SO$_4$, filtered and then concentrated. The resulting residue was purified by flash chromatography (20% EtOAc in hexanes to provide the desired product as a colorless oil (0.16 g, 21%) which was used as is in the next reaction. LC-MS (ES, m/z): 370 [M-56+H]$^+$.

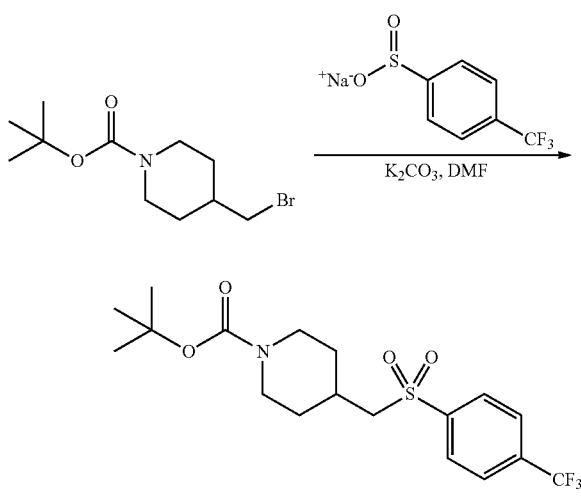

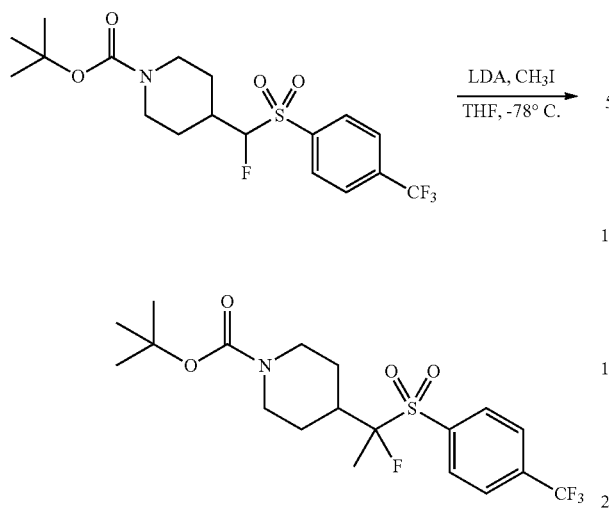

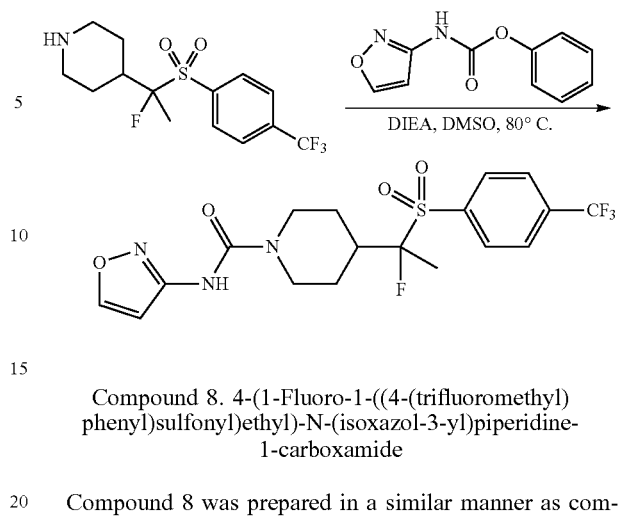

Compound 8. 4-(1-Fluoro-1-((4-(trifluoromethyl)phenyl)sulfonyl)ethyl)-N-(isoxazol-3-yl)piperidine-1-carboxamide Compound 8 was prepared in a similar manner as compound 6 to provide the desired product as a white solid (0.010 g, 33%). LC-MS (ES, m/z): 450.1 [M+H]+; 1H NMR (400 MHz, CDCl3): δ 8.41 (s, 1H), 8.16 (s, 1H), 8.00 (d, J=7.95 Hz, 2H), 7.80 (d, J=8.19 Hz, 2H), 6.92 (s, 1H), 4.16-4.30 (m, 2H), 2.83-2.95 (m, 2H), 2.51-2.61 (m, 1H), 2.25 (d, J=13.00 Hz, 1H), 1.86 (d, J=12.96 Hz, 1H), 1.35-1.54 (m, 5H) ppm.

Compound 8.4. tert-Butyl 4-(1-fluoro-1-((4-(trifluoromethyl)phenyl)sulfonyl)ethyl)piperidine-1-carboxylate To a solution of tert-butyl 4-(((4-(trifluoromethyl)phenyl)sulfonyl)methyl)piperidine-1-carboxylate (8.3, 0.160 g, 0.377 mmol) in THF (3 mL) at −78° C. was added LDA (2.0 M in THF, 0.235 mL, 0.471 mmol). The reaction mixture was stirred for 20 minutes before the iodomethane (0.094 g, 0.659 mmol) was added. The reaction mixture was diluted with EtOAc (6 mL) and H2O (2 mL) and was warmed to room temperature. The two layers were separated and the organic layer was dried with Na2SO4, filtered and then concentrated. The resulting residue was purified by flash chromatography (20% (v/v) EtOAc in hexanes to provide the desired product as a colorless oil (0.09 g, 55%), which was used as is in the next reaction. LC-MS (ES, m/z): 384 [M-56+H]+.

Example 9. Preparation of 4-(1-fluoro-1-((6-methoxypyridin-3-yl)sulfonyl)ethyl)-N-(pyridazin-4-yl)piperidine-1-carboxamide

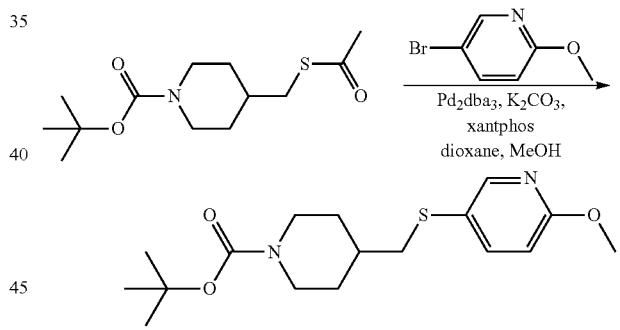

Compound 9.1. tert-Butyl 4-(((6-methoxypyridin-3-yl)thio)methyl)piperidine-1-carboxylate Compound 9.1 was prepared in a similar manner to compound 4.2 to provide the desired product as a yellow solid (1.78 g, 48%). 1H NMR (400 MHz, CDCl3) δ 8.17-8.23 (dd, J=2.4, 0.7 Hz, 1H), 7.59-7.67 (dd, J=8.6, 2.5 Hz, 1H), 6.68-6.75 (dd, J=8.6, 0.7 Hz, 1H), 4.05-4.15 (m, 2H), 3.94 (s, 3H), 2.59-2.75 (m, 4H), 1.76-1.87 (m, 2H), 1.50-1.64 (m, 1H), 1.42-1.48 (s, 9H), 1.06-1.21 (m, 2H) ppm.

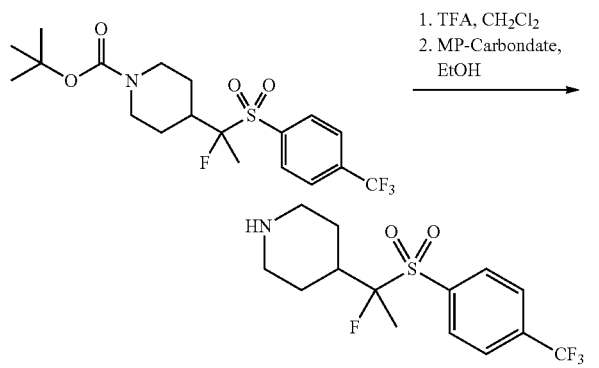

Compound 8.5. 4-(1-Fluoro-1-((4-(trifluoromethyl)phenyl)sulfonyl)ethyl)piperidine Compound 8.5 was prepared in a similar manner as compound 6.3 to provide the desired product which was used without purification in the next reaction.

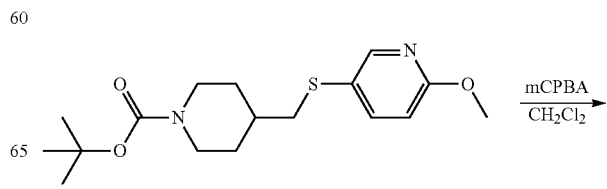

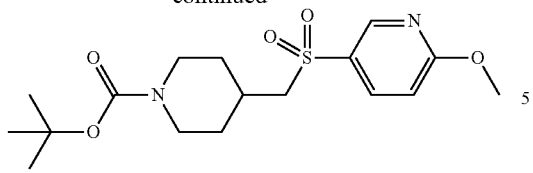

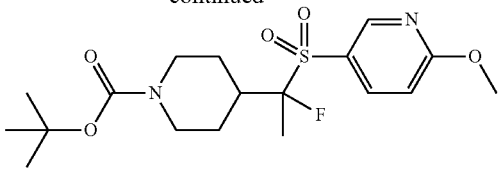

Compound 9.2. tert-Butyl 4-(((6-methoxypyridin-3-yl)sulfonyl)methyl)piperidine-1-carboxylate Compound 9.2 was prepared in a similar manner to compound 4.3 to provide the desired product as a white solid (0.20 g, 81%). $^1$H NMR (400 MHz, CDCl$_3$) δ ppm 8.63-8.70 (d, J=2.5 Hz, 1H), 7.91-8.04 (dd, J=8.8, 2.6 Hz, 1H), 6.79-6.89 (d, J=8.8 Hz, 1H), 3.97-4.11 (m, 5H), 2.94-3.02 (d, J=6.3 Hz, 2H), 2.63-2.79 (m, 2H), 2.08-2.22 (m, 1H), 1.72-1.91 (m, 2H), 1.41 (s, 9H), 1.15-1.34 (m, 2H) ppm.

Compound 9.4. tert-Butyl 4-(1-fluoro-1-((6-methoxypyridin-3-yl)sulfonyl)ethyl)piperidine-1-carboxylate To a solution of tert-butyl 4-[fluoro(6-methoxypyridine-3-sulfonyl)methyl]piperidine-1-carboxylate (9.3, 0.700 g, 1.80 mmol) in THF (15 mL) at −78° C. was added NaHMDS (2.0 M in THF, 1 mL, 2.00 mmol) followed by the dropwise addition of iodomethane (0.282 g, 1.98 mmol). The resulting solution was stirred for 2 h while warming to room tem-

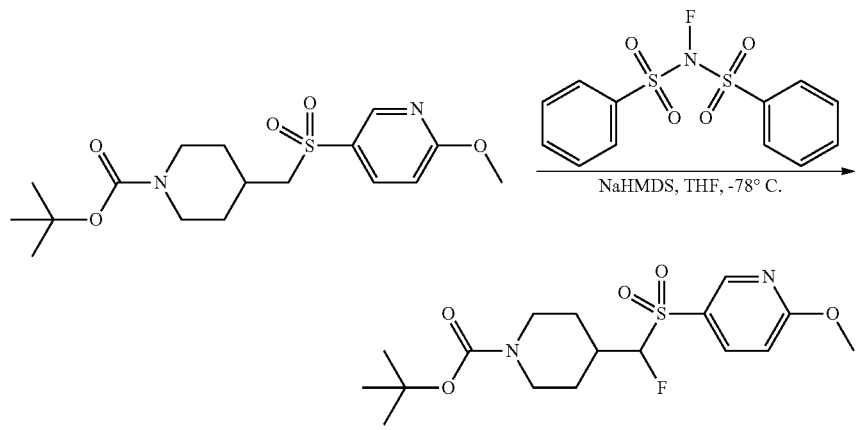

Compound 9.3. tert-Butyl 4-(fluoro((6-methoxy-pyridin-3-yl)sulfonyl)methyl)piperidine-1-carboxylate To a solution of tert-butyl 4-[(6-methoxypyridine-3-sulfonyl)methyl]piperidine-1-carboxylate (9.2, 1.00 g, 2.70 mmol) in THF (10 mL) at −78° C. was added dropwise NaHMDS (2.0 M in THF, 1.4 mL, 0.700 mmol) followed by the dropwise addition of a solution of NFSI (840 mg, 2.66 mmol) in THF (5 mL). The resulting solution was stirred for 2 h while warming to room temperature. The resulting solution was diluted with hexanes (100 mL), and the solids were removed by filtration. The filtrate was washed with saturated NaCl (50 mL), dried over anhydrous Na$_2$SO$_4$, and was concentrated. The resulting residue was purified by silica gel chromatography (EtOAc/petroleum ether (1:10-1:5 (v/v))) to provide the desired product as an off-white solid (0.75 g, 72%). LC-MS (ES, m/z): 288.9 [M-56+H]$^+$.

perature. The reaction was then quenched by the addition of saturated NH$_4$Cl$_{(aq)}$ (40 mL). The resulting solution was extracted with EtOAc (3×10 mL) and the combined organic layers were washed with saturated NaCl (50 mL), dried over Na$_2$SO$_4$, filtered and concentrated. The resulting residue was purified by silica gel column with (EtOAc/petroleum ether (1:10-1:5 (v/v))) to provide the desired product as a yellow oil (0.600 g, 83%). $^1$H NMR (300 MHz, DMSO-d6) δ 8.64 (d, J=2.7 Hz, 1H), 8.10 (dd, J=8.7, 1.5 Hz, 1H), 7.10 (d, J=8.7 Hz, 1H), 4.03 (m, 2H), 3.99 (s, 3H), 2.71 (s, 1H), 2.32 (m, 1H), 2.02 (m, 1H), 1.62 (m, 1H), 1.52 (d, J=22.8 Hz, 1H), 1.40 (s, 9H), 1.24-1.39 (m, 5H) ppm.

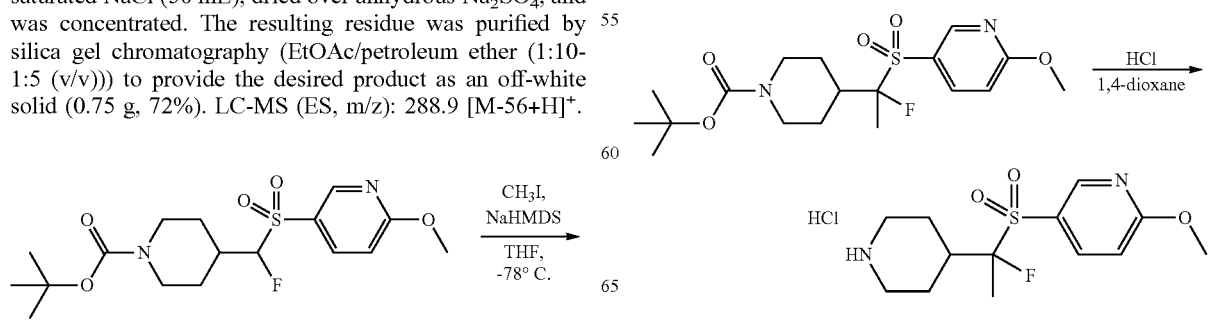

Compound 9.5. 5-(1-Fluoro-1-(piperidin-4-yl)ethyl-sulfonyl)-2-methoxypyridine hydrochloride To a solution of tert-butyl 4-[1-fluoro-1-(6-methoxypyridine-3-sulfonyl)ethyl]piperidine-1-carboxylate (9.4, 0.600 g, 1.49 mmol) in 1,4-dioxane (5 mL) was added 4N HCl in 1,4-dioxane (5 mL) dropwise. The resulting solution was stirred for 1 h at room temperature and then was concentrated. The resulting residue (0.500 g, crude) was used as is in the next reaction without purification. LC-MS (ES, m/z): 302.7 [M+H]$^+$.

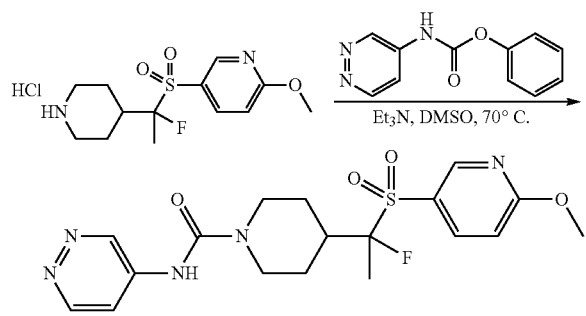

Compound 9. 4-(1-Fluoro-1-((6-methoxypyridin-3-yl)sulfonyl)ethyl)-N-(pyridazin-4-yl)piperidine-1-carboxamide To a solution of 5-(1-fluoro-1-(piperidin-4-yl)ethylsulfonyl)-2-methoxypyridine hydrochloride (9.5, 0.300 g, crude) in DMSO (7 mL) was added triethylamine (0.400 g, 3.95 mmol) and phenyl N-(pyridazin-4-yl)carbamate (0.312 mg, 1.45 mmol). The reaction mixture was stirred for 1 h at 70° C. The reaction mixture was cooled to room temperature and was then quenched by the addition of H$_2$O (20 mL). The resulting solution was extracted with EtOAc (3×10 mL) and the combined organic layers were washed with saturated NaCl (50 mL), dried over Na$_2$SO$_4$, filtered and concentrated. The resulting residue was purified by Prep-HPLC (Column: X Bridge RP, 19*150 mm, 5 μm; Mobile Phase A: H$_2$O/10 mM NH$_4$HCO$_3$, Mobile Phase B: ACN; Flow rate: 20 mL/min; Gradient: 24% B to 33% B in 10 min; 254 nm) to provide the desired product as a white solid (0.216 g, 39%). LC-MS (ES, m/z): 424.1 [M+H]$^+$; $^1$H-NMR (300 MHz, CD$_3$OD): δ 9.24 (d, J=2.7 Hz, 1H), 8.86 (d, J=6.0 Hz, 1H), 8.65 (d, J=2.4 Hz, 1H), 8.09 (d, J=8.7 Hz, 1H), 7.86 (dd, J=2.7, 6.0 Hz, 1H), 7.02 (d, J=9.0 Hz, 1H), 4.40-4.25 (m, 2H), 4.05 (s, 3H), 2.96 (t, J=13.2 Hz, 2H), 2.68-2.48 (m, 1H), 2.27 (d, J=12.9 Hz, 1H), 1.89 (d, J=12.9 Hz, 1H), 1.65-1.45 (m, 2H), 1.58 (d, J=22.5 Hz, 3H) ppm.

Example 10. Preparation of 1-(4-(1-fluoro-1-((3-fluorophenyl)sulfonyl)ethyl)piperidin-1-yl)-2-(pyridazin-4-yl)ethan-1-one

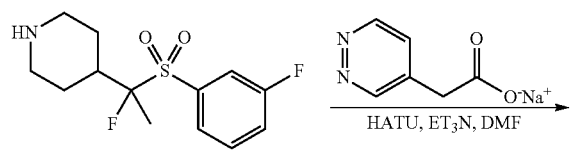

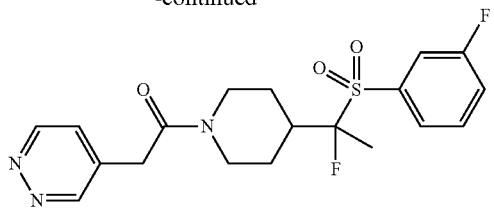

Compound 10. 1-(4-(1-Fluoro-1-((3-fluorophenyl)sulfonyl)ethyl)piperidin-1-yl)-2-(pyridazin-4-yl)ethan-1-one To a solution of 4-(1-fluoro-1-((3-fluorophenyl)sulfonyl)ethyl)piperidine (6.3, 0.025 g, 0.086 mmol) and sodium 2-(pyridazin-4-yl)acetate (0.014 g, 0.086 mmol) in DMF (1 mL) was added triethyl amine (0.024 mL, 0.172 mmol) and HATU (0.039 g, 0.103 mmol). The reaction mixture was stirred for 18 h at room temperature and the reaction mixture was diluted with EtOAc (5 mL) and H$_2$O (2 mL). The two layers were separated and the organic layer was dried with Na$_2$SO$_4$, filtered and concentrated. The resulting residue was purified using reverse phase high pressure liquid chromatography (0-90% CH$_3$CN in H$_2$O (both containing 0.1% TFA)) to provide the desired product as a white solid (0.015 g, 42%). LC-MS (ES, m/z): 410 [M+H]$^+$; $^1$H-NMR (400 MHz, CDCl$_3$): δ 9.28 (m, 2H), 7.73 (t, J=6.04 Hz, 1H), 7.66 (d, J=7.83 Hz, 1H), 7.60 (m, 3H), 7.41-7.32 (m, 1H), 4.73-4.61 (m, 1H), 4.00-3.86 (m, 1H), 3.80 (s, 2H), 3.04 (m, 1H), 2.39-2.15 (m, 2H), 1.79 (m, 1H), 1.52-1.27 (m, 5H) ppm.

Example 11. Preparation of 4-(1-fluoro-1-((3-fluorophenyl)sulfonyl)ethyl)-N-(isoxazol-5-yl)piperidine-1-carboxamide

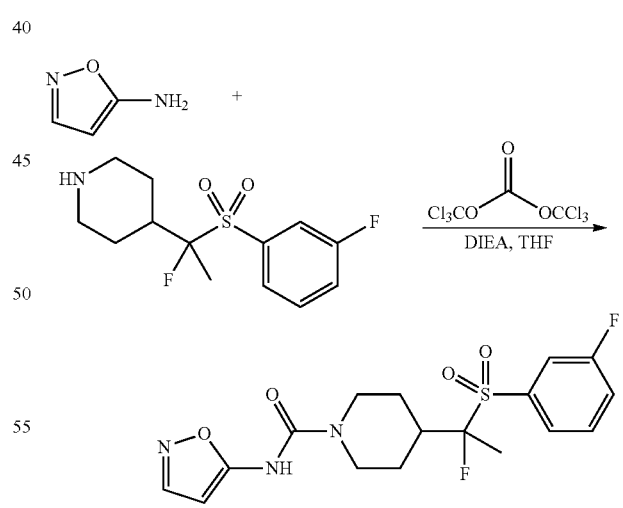

Compound 11. 4-(1-Fluoro-1-((3-fluorophenyl)sulfonyl)ethyl)-N-(isoxazol-5-yl)piperidine-1-carboxamide To a solution of 4-(1-fluoro-1-((3-fluorophenyl)sulfonyl)ethyl)piperidine (6.3, 0.050 g, 0.172 mmol) in THF (1 mL) at 0° C. was added DIEA (0.184 mL, 1.03 mmol) followed by triphosgene (0.017 g, 0.057 mmol). The reaction mixture was stirred for 15 minutes before the isoxazol-5-amine (0.014 g, 0.172 mmol) was added. The reaction mixture was stirred overnight at room temperature and then was diluted with EtOAc (5 mL) and was quenched with $H_2O$ (2 mL). The two layers were separated, and the organic layer was concentrated. The resulting residue was purified using reverse phase high pressure liquid chromatography (0-90% $CH_3CN$ in $H_2O$ (both containing 0.1% TFA)) to provide the desired product as a white solid (0.015 g, 42%). LC-MS (ES, m/z): 400 [M+H]$^+$; $^1$H NMR (400 MHz, CDCl$_3$): δ 8.06 (d, J=1.8 Hz, 1H), 7.70-7.62 (m, 1H), 7.60-7.48 (m, 2H), 7.30 (m, 2H), 6.14 (m, 1H), 4.18-4.00 (m, 2H), 2.99-2.83 (m, 2H), 2.62-2.49 (m, 1H), 2.30 (m, 1H), 1.94 (m, 1H), 1.51-1.33 (m, 5H) ppm.

Example 12. Preparation of 4-(1-fluoro-1-((3-fluorophenyl)sulfonyl)ethyl)-N-(6-methylpyridazin-4-yl)piperidine-1-carboxamide

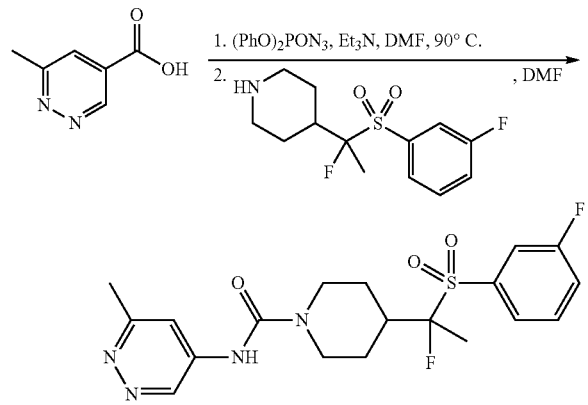

Compound 12. 4-(1-Fluoro-1-((3-fluorophenyl)sulfonyl)ethyl)-N-(6-methylpyridazin-4-yl)piperidine-1-carboxamide To a solution of 6-methylpyridazine-4-carboxylic acid (0.060 g, 0.345 mmol) and triethyl amine (0.058 mL, 0.414 mmol) in DMF (1 mL) was added DPPA (0.082 mL, 0.372 mmol). The reaction mixture was plunged into a preheated 90° C. oil bath and was stirred for 10 minutes. A solution of 4-(1-fluoro-1-((3-fluorophenyl)sulfonyl)ethyl)piperidine (6.3, 0.025 g, 0.086 mmol) in DMF (1 mL) was added slowly. The reaction mixture was stirred for 3.5 h while cooling to room temperature. The reaction mixture was diluted with EtOAc (5 mL) and $H_2O$ (2 mL) and the two layers were separated. The organic layer was concentrated and the resulting residue was purified using reverse phase high pressure liquid chromatography (0-90% $CH_3CN$ in $H_2O$ (both containing 0.1% TFA)) to provide the desired product as a white solid (0.047 g, 4%). LC-MS (ES, m/z): 425 [M+H]$^+$; $^1$H NMR (400 MHz, CDCl$_3$): δ 10.58 (br s, 1H), 9.44 (m, 1H), 8.53 (m, 1H), 7.76 (d, J=8.19 Hz, 1H), 7.65 (s, 1H), 7.45 (dt, J=1.83, 8.19 Hz, 1H), 7.15 (m, 1H), 4.57-4.38 (m, 2H), 2.94-2.78 (m, 2H), 2.71 (s, 3H), 2.43 (m, 1H), 2.37 (m, 1H), 1.96-1.84 (m, 1H), 1.58-1.37 (m, 5H) ppm.

Example 13. Preparation of 4-(1-fluoro-1-((3-fluorophenyl)sulfonyl)ethyl)-N-(1-methyl-1H-pyrazol-4-yl)piperidine-1-carboxamide

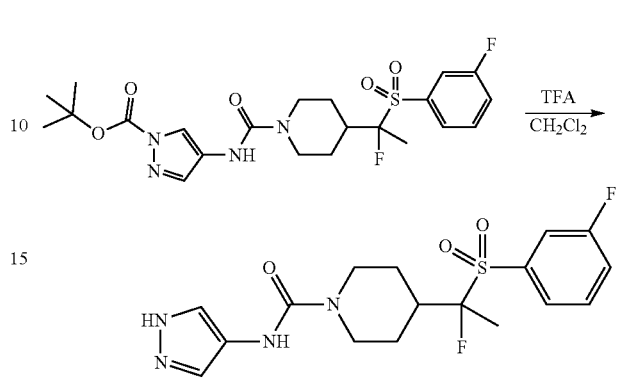

Compound 13.1. 4-(1-Fluoro-1-((3-fluorophenyl)sulfonyl)ethyl)-N-(1H-pyrazol-4-yl)piperidine-1-carboxamide To a solution of tert-butyl 4-(4-(1-fluoro-1-((3-fluorophenyl)sulfonyl)ethyl)piperidine-1-carboxamido)-1H-pyrazole-1-carboxylate (0.093 g, 0.185 mmol) was dissolved in DCM (2 mL) and trifluoroactetic acid (0.20 mL, 2.61 mmol) was added slowly. The reaction mixture was stirred at room temperature overnight. The reaction mixture was concentrated and the resulting residue was purified using reverse phase high pressure liquid chromatography (0-90% (v/v) $CH_3CN$ in $H_2O$ (both containing 0.1% TFA)) to provide the desired product as a white solid (0.032 g, 70%). LC-MS (ES, m/z): 499.1 [M+H]$^+$; $^1$H NMR (400 MHz, CDCl$_3$): δ 8.31 (s, 1H), 7.78 (m, 1H), 7.71 (s, 1H), 7.69 (m, 2H), 7.49 (m, 1H), 6.33 (br s, 1H), 4.29-4.06 (m, 2H), 3.05-2.88 (m, 2H), 2.54 (m, 1H), 2.27 (m, 1H), 2.02 (m, 1H), 1.72-1.40 (m, 14H) ppm.

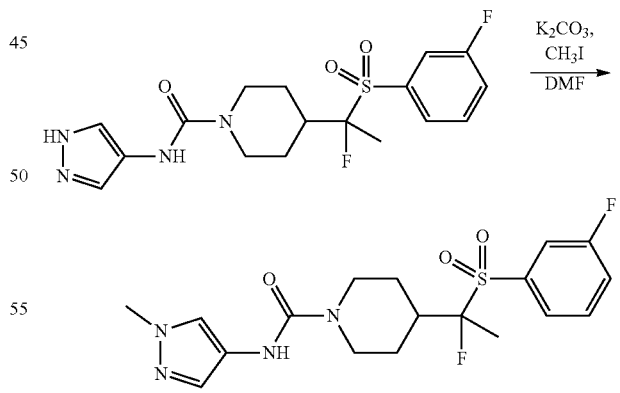

Compound 13. 4-(1-Fluoro-1-((3-fluorophenyl)sulfonyl)ethyl)-N-(1-methyl-1H-pyrazol-4-yl)piperidine-1-carboxamide To a solution of 4-(1-fluoro-1-((3-fluorophenyl)sulfonyl)ethyl)-N-(1H-pyrazol-4-yl)piperidine-1-carboxamide (13.1, 0.030 g, 0.075 mmol) and $K_2CO_3$ (0.026 g, 0.188 mmol) in DMF (1 mL) was added iodomethane (0.005 mL, 0.090 mmol). The reaction mixture was plunged into a preheated 60° C. oil bath and was stirred for 18 h. The reaction mixture was cooled to room temperature and filtered. The filtrate was concentrated the resulting residue was purified using reverse phase high pressure liquid chromatography (0-90% (v/v) $CH_3CN$ in $H_2O$ (both containing 0.1% TFA)) to provide the desired product as a white solid (0.032 g, 70%). LC-MS (ES, m/z): 399.1 [M+H]$^+$; $^1$H NMR (400 MHz, CDCl$_3$): δ 7.88 (br s, 2H), 7.68 (d, J=7.70 Hz, 1H), 7.62-7.51 (m, 2H), 7.49-7.32 (m, 2H), 4.28-4.02 (m, 2H), 2.95 (m, 2H), 2.59 (m, 2H), 2.20 (d, J=11.86 Hz, 1H), 1.85 (d, J=12.35 Hz, 1H), 1.54-1.31 (m, 5H) ppm.

Example 14. Preparation of 4-(1-((6-(difluoromethoxy)pyridin-3-yl)sulfonyl)-1-fluoroethyl)-N-(pyridazin-4-yl)piperidine-1-carboxamide Compound 14.2. tert-Butyl 4-(((6-hydroxypyridin-3-yl)sulfonyl)methyl)piperidine-1-carboxylate To a solution of tert-butyl 4-[[(6-hydroxypyridin-3-yl)sulfanyl]methyl]piperidine-1-carboxylate (14.1, 4.00 g, 12.33 mmol) and ruthenium (III) chloride (0.80 g, 3.85 mmol) in THF/$H_2O$ (1:1 (v/v), 60 mL) was added dropwise a solution of NaIO$_4$ (12.0 g, 49.3 mmol) in water (5 mL). The resulting solution was stirred for 1 h at room temperature. The reaction was then quenched by the addition of $H_2O$ (30 mL) and was extracted with EtOAc (3×20 mL), dried over anhydrous $Na_2SO_4$, filtered and concentrated. The resulting residue was purified by silica gel column with (EtOAc/petroleum ether (100:1)) to provide the desired product as a white solid (2.40 g, 55%). $^1$H NMR (400 MHz, DMSO-d6): δ 12.35 (s, 1H), 7.89-7.95 (d, J=2.8 Hz, 1H), 7.67-7.75 (m, 1H), 6.41-6.48 (d, J=9.7 Hz, 1H), 3.78-3.86 (d, J=13.3 Hz, 2H), 3.23-3.28 (d, J=6.3 Hz, 4H), 2.73 (s, 1H), 1.91-2.02 (m, 1H), 1.70-1.78 (m, 2H), 1.34-1.39 (s, 9H), 1.07-1.20 (m, 2H) ppm.

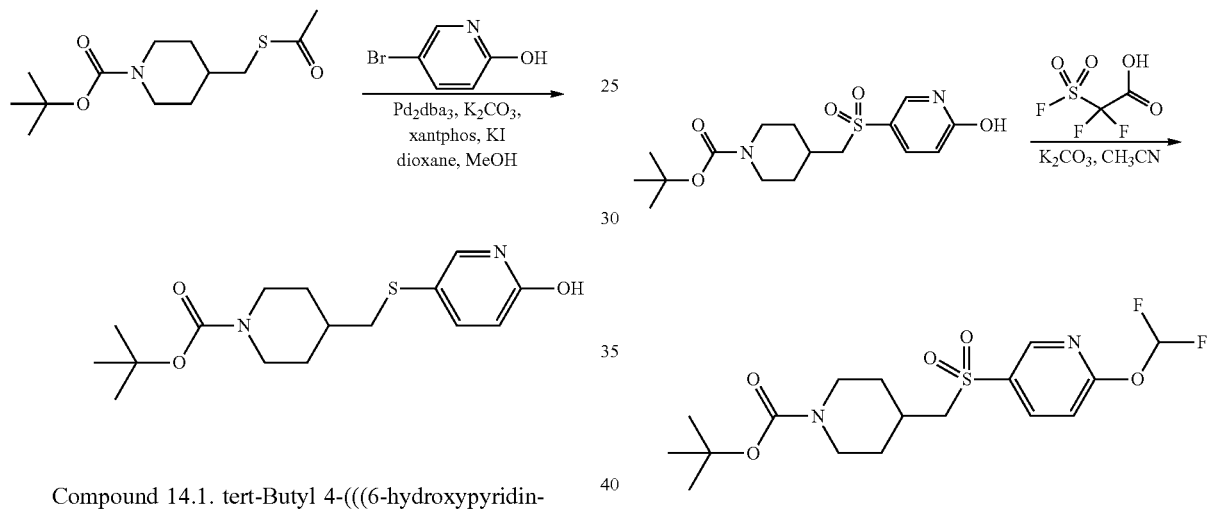

Compound 14.1. tert-Butyl 4-(((6-hydroxypyridin-3-yl)thio)methyl)piperidine-1-carboxylate Compound 14.1 was prepared in a similar manner to compound 4.2 to provide the desired product as a yellow solid (4.00 g, 72%). $^1$H NMR (400 MHz, CDCl$_3$) δ 7.50-7.65 (m, 3H), 6.62-6.70 (m, 1H), 6.53-6.60 (d, J=10.4 Hz, 1H), 2.60-2.73 (m, 4H), 1.76-1.84 (m, 2H), 1.50-1.63 (m, 1H), 1.41-1.46 (s, 9H), 1.22-1.32 (m, 3H), 1.06-1.20 (m, 2H) ppm.

Compound 14.3. tert-Butyl 4-(((6-(difluoromethoxy)pyridin-3-yl)sulfonyl)methyl)piperidine-1-carboxylate To a solution of tert-butyl 4-(((6-hydroxypyridin-3-yl)sulfonyl)methyl)piperidine-1-carboxylate (14.2, 1.00 g, 2.81 mmol) and $K_2CO_3$ (0.590 g, 5.57 mmol) in $CH_3CN$ (20 mL) was added 2,2-difluoro-2-(fluorosulfonyl)acetic acid (0.550 g, 3.09 mmol). The resulting solution was stirred for 2 h at room temperature. The reaction was then quenched by the addition of $H_2O$ (50 mL) and was extracted with EtOAc (3×30 mL). The combined organic layers were washed with brine (50 mL), dried over $Na_2SO_4$, filtered and concentrated. The resulting residue was purified by silica gel column with (EtOAc/petroleum ether (1:10-1:3 (v/v))) to provide the desired product as a white solid (1.00 g, 88%). $^1$H NMR (300 MHz, CDCl$_3$): δ 8.74 (d, J=2.4, 1H), 8.21 (dd, J=2.4 Hz, 8.7 Hz, 1H), 7.31-7.78 (t, J=71.7 Hz, 1H), 7.08 (d, J=8.4 Hz, 1H), 4.08 (d, J=13.5 Hz, 2H), 3.04 (d, J=6.3 Hz, 2H), 2.72-2.81 (m, 2H), 2.22 (m, 1H), 1.92 (d, J=12.9 Hz, 2H), 1.46 (s, 9H), 1.24-1.37 (m, 2H) ppm.

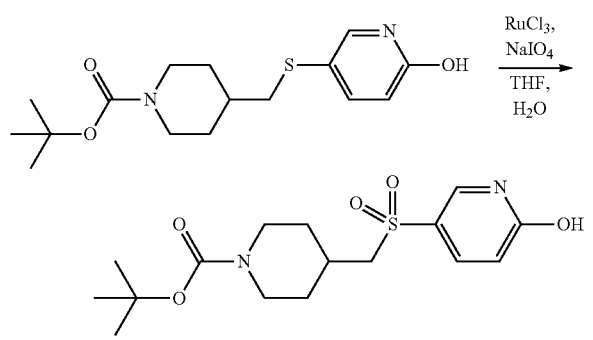

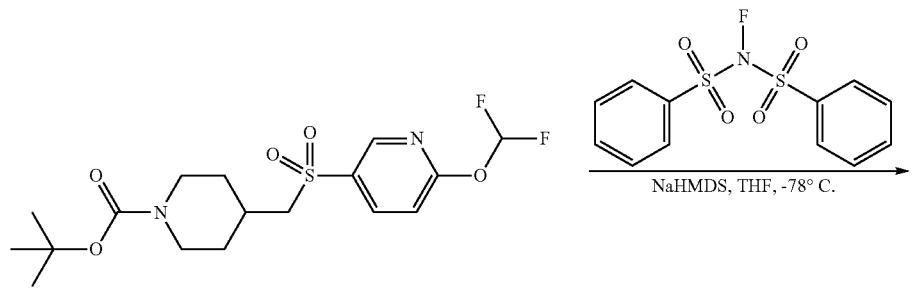

Compound 14.4. tert-Butyl 4-(((6-(difluoromethoxy)pyridin-3-yl)sulfonyl)fluoromethyl)piperidine-1-carboxylate Compound 14.4 was prepared in a similar manner to compound 9.3 to provide the desired product as a yellow oil (0.20 g, 34%). $^1$H NMR (300 MHz, CDCl$_3$) δ 8.74 (d, J=2.4, 1H), 8.22 (m, 1H), 7.31-7.80 (t, J=71.7 Hz, 1H), 7.15 (d, J=8.4 Hz, 1H), 4.77-4.95 (dd, J=6.0, 18.0 Hz, 1H), 4.19 (m, 2H), 2.79 (m, 2H), 2.40-2.60 (m, 1H), 2.00 (m, 1H), 1.50-1.60 (m, 3H), 1.47 (s, 9H) ppm.

Compound 14.5. tert-Butyl 4-(1-((6-(difluoromethoxy)pyridin-3-yl)sulfonyl)-1-fluoroethyl)piperidine-1-carboxylate Compound 14.5 was prepared in a similar manner to compound 9.4 to provide the desired product as a yellow oil (0.100 g, 48%). $^1$H NMR (300 MHz, CDCl$_3$) δ 8.70 (d, J=2.4, 1H), 8.20 (m, 1H), 7.37-7.73 (t, J=71.6 Hz, 1H), 7.08 (d, J=8.4 Hz, 1H), 4.24 (m, 2H), 2.69-2.77 (m, 2H), 2.43-2.59 (m, 1H), 2.18 (m, 1H), 1.81 (d, J=12.0 Hz, 1H), 1.55 (d, J=22 Hz, 3H), 1.50 (s, 9H), 1.31-1.40 (m, 2H) ppm.

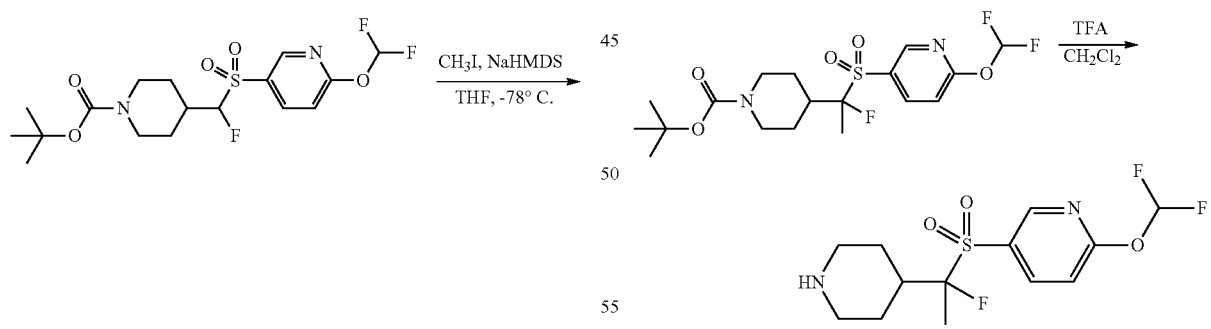

Compound 14.6. 2-(Difluoromethoxy)-5-((1-fluoro-1-(piperidin-4-yl)ethyl)sulfonyl)pyridine Compound 14.6 was prepared in a similar manner to compound 4.5 to provide the desired product as a yellow oil (0.300 g). The desired product was used as is in the next reaction without purification. LC-MS (ES, m/z): 339.0 [M+H]$^+$.

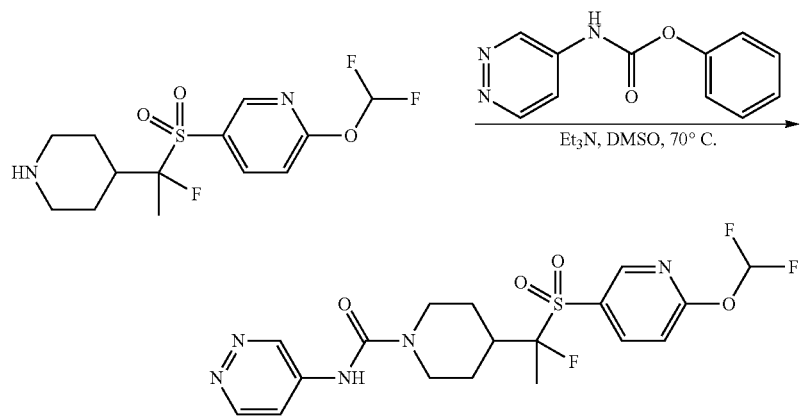

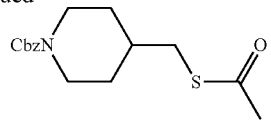

Compound 14. 4-(1-((6-(Difluoromethoxy)pyridin-3-yl)sulfonyl)-1-fluoroethyl)-N-(pyridazin-4-yl)piperidine-1-carboxamide Compound 14 was prepared in a similar manner to compound 9 to provide the desired product as a white solid (0.116 g, 29%). LC-MS (ES, m/z): 460.1 [M+H]+; 1H NMR (400 MHz, DMSO-d6): δ 9.28 (d, J=2.0 Hz, 1H), 9.21 (s, 1H), 8.88 (d, J=6.0 Hz, 1H), 8.77 (d, J=2.4 Hz, 1H), 8.37 (dd, J=8.4, 1.6 Hz, 1H), 7.83 (t, J=71.6 Hz, 1H), 7.77 (d, J=2.4 Hz, 1H), 7.41 (d, J=8.8 Hz, 1H), 4.23-4.31 (m, 2H), 2.89 (m, 2H), 2.47 (m, 1H), 2.10 (m, 1H), 1.73 (m, 1H), 1.57 (d, J=22.8 Hz, 3H), 1.40 (m, 2H) ppm.

Example 15. Preparation of 4-(1-((3-chloro-1-methyl-1H-pyrazol-5-yl)sulfonyl)-1-fluoroethyl)-N-(pyridazin-4-yl)piperidine-1-carboxamide

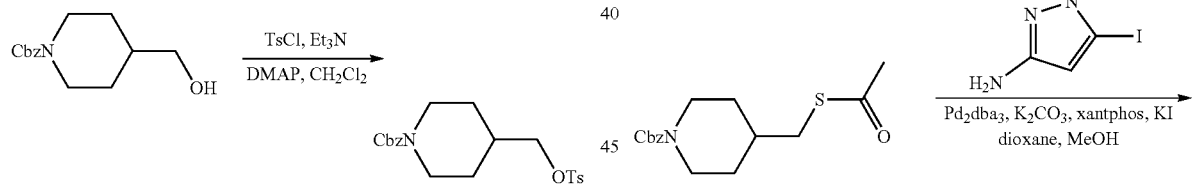

Compound 15.1. Benzyl 4-((tosyloxy)methyl)piperidine-1-carboxylate

Compound 15.1 was prepared in a similar manner to compound 1.1 to provide the desired product as a white solid (13.0 g, 80%). LC-MS (ES, m/z): 404.2 [M+H]+; 1H NMR (300 MHz, CDCl3): δ 7.78 (d, J=8.4 Hz, 2H), 7.38-7.78 (m, 7H), 5.10 (s, 2H), 4.20-4.15 (m, 2H), 3.85 (d, J=6.3 Hz, 2H), 2.77-2.69 (m, 2H), 2.41 (s, 3H), 1.89-1.79 (m, 1H), 1.69-1.64 (m, 2H), 1.19-1.15 (m, 2H) ppm.

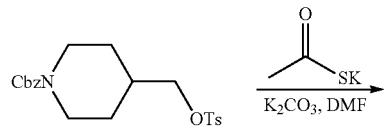

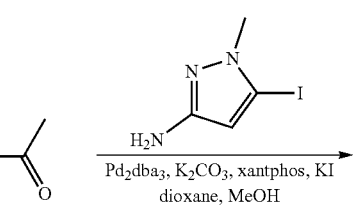

Compound 15.2. Benzyl 4-((carbamimidoylthio)methyl)piperidine-1-carboxylate

Compound 15.2 was prepared in a similar manner to compound 3.1 to provide the desired product as a brown oil (25.0 g). The material was used as is in the next reaction without further purification. LC-MS (ES, m/z): 308.1 [M+H]+.

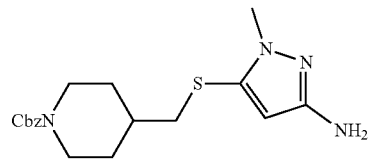

Compound 15.3. Benzyl 4-(((3-amino-1-methyl-1H-pyrazol-5-yl)thio)methyl)piperidine-1-carboxylate Compound 15.3 was prepared in a similar manner to compound 4.2 to provide the desired product as a yellow oil (8.3 g, 59%). 1H NMR (400 MHz, CDCl3) δ 7.29-7.39 (m, 5H), 5.65 (s, 1H), 5.12 (s, 2H), 4.05-4.19 (m, 2H), 3.71 (s, 3H), 2.66-2.79 (m, 2H), 2.64 (m, 2H), 1.73-1.85 (m, 2H), 1.60-1.72 (m, 1H), 1.10-1.35 (m, 2H) ppm.

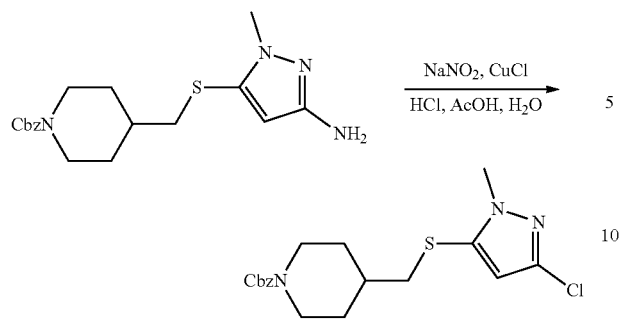

Compound 15.4. benzyl 4-(((3-chloro-1-methyl-1H-pyrazol-5-yl)thio)methyl)piperidine-1-carboxylate To a solution of benzyl 4-(((3-amino-1-methyl-1H-pyrazol-5-yl)thio)methyl)piperidine-1-carboxylate (1.9 g, 5.27 mmol) in concentrated HCl (9.5 mL) and AcOH (57 mL) at 0° C. was added dropwise a solution of sodium nitrate (0.551 g, 7.99 mmol) in H$_2$O (9.5 mL). The resulting solution was stirred for 30 minutes at 0° C. The temperature was increased to 80° C., and a solution of copper (I) chloride (2.09 g, 21.1 mmol) in concentrated HCl (9.5 mL) and AcOH (19 mL) was added dropwise. The resulting solution was stirred for an additional 10 min while the temperature was maintained at 70° C. The resulting solution was extracted with EtOAc (100 mL) and the organic layers combined. The resulting solution was washed with brine (50 mL), dried over anhydrous Na$_2$SO$_4$, filtered, and then concentrated. The resulting residue was purified by silica gel column with (EtOAc/petroleum ether (1:2 (v/v))) to provide the desired product as a white solid (0.700 g, 35%). $^1$H NMR (300 MHz, CDCl$_3$): δ 7.29-7.39 (m, 5H), 6.19 (s, 1H), 5.12 (s, 2H), 4.23-4.19 (m, 2H), 3.83 (s, 3H), 2.68-2.80 (m, 3H), 1.69-1.85 (m, 2H), 1.60 (m, 1H), 1.22 (m, 2H) ppm.

Compound 15.6. Benzyl 4-(1-((3-chloro-1-methyl-1H-pyrazol-5-yl)sulfonyl)-1-fluoroethyl)piperidine-1-carboxylate To a solution of benzyl 4-[(3-chloro-1-methyl-1H-pyrazole-5-sulfonyl)methyl]piperidine-1-carboxylate (15.5, 2.9 g, 7.04 mmol) in THF (120 mL) at −78° C. was added t-BuOK (7 mL, 7.04 mmol, 1M in THF) dropwise, followed by a solution of NFSI (1.33 g, 4.22 mmol) in THF (20 mL) dropwise. The resulting solution was stirred for 1 h at −78° C. before additional t-BuOK (21.1 mL, 21.12 mmol, 1M in THF) was added dropwise. The resulting solution was stirred for 30 min at −78° C. before iodomethane (3.00 g, 21.14 mmol) was added dropwise. The resulting solution was stirred for an additional 30 min at −78° C. before being quenched by the addition of n-hexane (50 mL). The reaction mixture was warmed to room temperature, the solids were removed by filtration, and the filtrate was concentrated. The resulting residue was purified by prep-HPLC (ACN/H$_2$O 10:90 (v/v) increasing to ACN/H$_2$O 80:20 (v/v) within 50 min; Detector, UV 254 nm) to provide the product as a white solid (1.5 g, 83%). $^1$H NMR (400 MHz, CDCl$_3$): δ 7.35 (m, 5H), 6.80 (s, 1H), 5.13 (s, 2H), 4.09-4.33 (m, 2H), 4.07 (s, 3H), 2.56-2.82 (m, 2H), 2.52 (m, 1H), 2.12 (m, 1H), 1.84 (m, 1H), 1.59 (d, J=24.0 Hz, 3H), 1.40 (m, 2H) ppm.

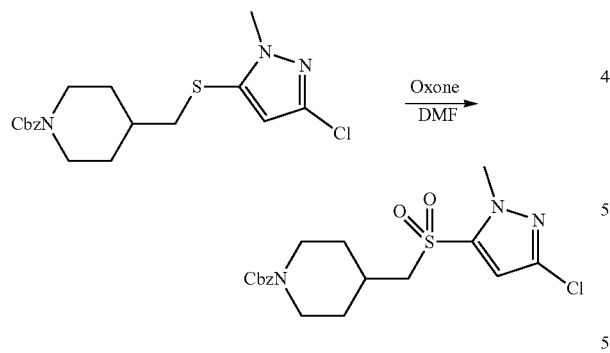

Compound 15.5. Benzyl 4-(((3-chloro-1-methyl-1H-pyrazol-5-yl)sulfonyl)methyl)piperidine-1-carboxylate Compound 15.5 was prepared in a similar manner to compound 5.3 to provide the desired product as a yellow oil (8.3 g, 59%). $^1$H NMR (400 MHz, CDCl$_3$): δ 7.26-7.39 (m, 5H), 6.14 (s, 1H), 5.12 (s, 2H), 4.17-4.28 (m, 2H), 4.09 (s, 3H), 3.09 (m, 2H), 2.84 (m, 2H), 2.19-2.29 (m, 1H), 1.91 (m, 2H), 1.27-1.40 (m, 2H) ppm.

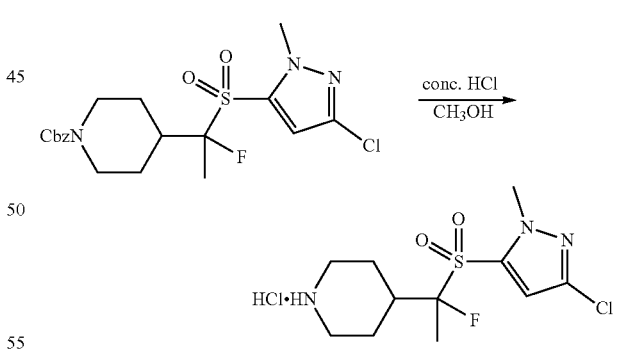

Compound 15.7. 4-(1-((3-Chloro-1-methyl-1H-pyrazol-5-yl)sulfonyl)-1-fluoroethyl)piperidine hydrochloride To a solution of benzyl 4-[1-(3-chloro-1-methyl-1H-pyrazole-5-sulfonyl)-1-fluoroethyl]piperidine-1-carboxylate (15.6, 1.00 g, 2.25 mmol, 1.00) in methanol (5 mL) was added concentrated HCl (15 mL). The resulting solution was stirred for 3 h at 70° C. in an oil bath, and then was concentrated. The resulting residue was precipitated with methanol (2 mL). The crude product was purified by recrystallization from ether to provide the desired product as a white solid (0.429 g, 55%). LC-MS (ES, m/z): 310.1 [M+H]⁺; ¹H NMR (400 MHz, CD₃OD): δ 7.05 (s, 1H), 4.09 (s, 3H), 3.50 (m, 2H), 3.03-3.13 (m, 2H), 2.64-2.73 (m, 1H), 2.35 (m, 1H), 2.10 (m, 2H), 1.70-1.85 (m, 2H), 1.65 (d, J=24.0 Hz, 3H) ppm; ¹⁹F NMR (376 MHz, CD₃OD): δ −146.30 ppm.

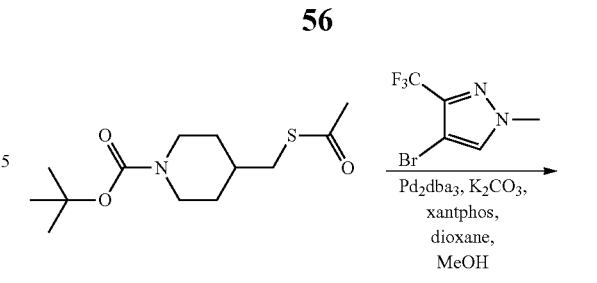

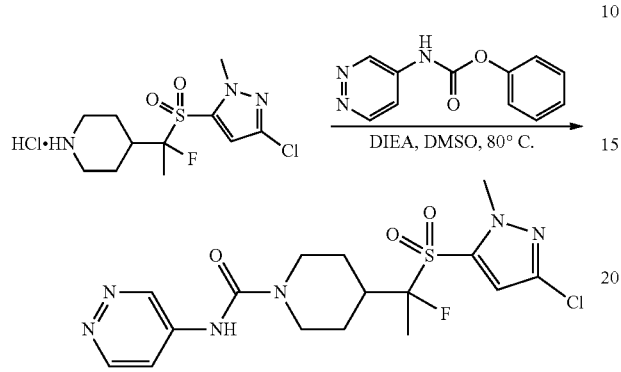

Compound 15. 4-(1-((3-Chloro-1-methyl-1H-pyrazol-5-yl)sulfonyl)-1-fluoroethyl)-N-(pyridazin-4-yl)piperidine-1-carboxamide Compound 15 was prepared in a similar manner to compound 6 to provide the desired product as an off-white solid (0.012 g, 8%). LC-MS (ES, m/z): 430.1 [M+H]⁺; ¹H NMR (300 MHz, CD₃OD): δ 9.20 (m, 1H), 8.84 (d, J=8.0 Hz, 1H), 7.83 (m, 1H), 6.99 (s, 1H), 4.33 (m, 2H), 4.03 (s, 3H), 2.99 (m, 2H), 2.56 (m, 1H), 2.17 (m, 1H), 1.90 (m, 1H), 1.66-1.42 (m, 5H) ppm; ¹⁹F NMR (376 MHz, CD₃OD): δ −77.12, −145.34 ppm.

Example 16. Preparation of 4-(1-fluoro-1-((1-methyl-3-(trifluoromethyl)-1H-pyrazol-4-yl)sulfonyl)ethyl)-N-(isoxazol-3-yl)piperidine-1-carboxamide Compound 16.2. tert-Butyl 4-(((1-methyl-3-(trifluoromethyl)-1H-pyrazol-4-yl)thio)methyl)piperidine-1-carboxylate Compound 16.2 was prepared in a similar manner to compound 4.2 to provide the desired product as a yellow solid (0.200 g, crude). The desired product was used as is in the next reaction without further purification. LC-MS (ES, m/z): 279.9 [M+H-Boc]⁺.

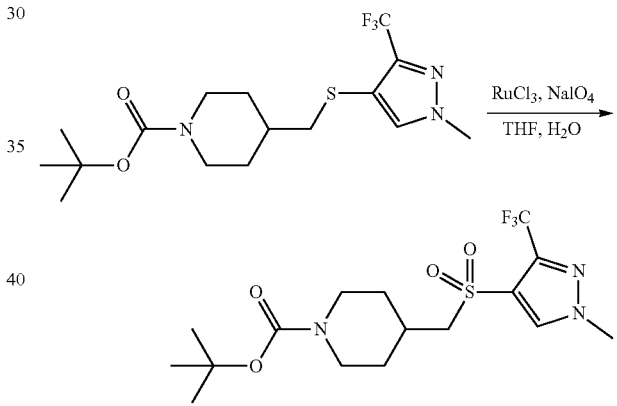

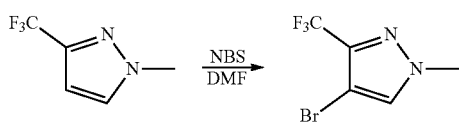

Compound 16.1. 4-Bromo-1-methyl-3-(trifluoromethyl)-1H-pyrazole

Into a 10-mL sealed tube purged and maintained with an inert atmosphere of argon, was placed a solution of 1-methyl-3-(trifluoromethyl)-1H-pyrazole (10.0 g, 66.62 mmol) and NBS (16.2 g, 66.62 mmol) in DMF (100 mL). The resulting solution was stirred overnight at 50° C. in an oil bath. The reaction was then quenched by the addition of ice water (1 L). The resulting solution was extracted with ether (3×200 mL), the organic layers combined and dried over anhydrous Na₂SO₄, filtered and then concentrated to provide the desired product as a yellow oil (12.0 g, crude), which was used as is without further purification. ¹H NMR (400 MHz, CDCl₃): δ 7.46 (s, 1H), 3.94 (s, 3H) ppm.

Compound 16.3. tert-Butyl 4-(((1-methyl-3-(trifluoromethyl)-1H-pyrazol-4-yl)sulfonyl)methyl)piperidine-1-carboxylate Compound 16.3 was prepared in a similar manner to compound 14.2 to provide the desired product as a yellow solid (0.200 g, 15%). The desired product was used as is in the next reaction without further purification. ¹H NMR (400 MHz, CDCl₃): δ 7.96 (s, 1H), 4.07 (m, 2H), 4.02 (s, 3H), 3.14 (d, J=6.4 Hz, 2H), 2.74 (m, 1H), 2.22 (m, 2H), 1.90 (m, 2H), 1.46 (s, 9H), 1.25-1.35 (m, 2H) ppm.

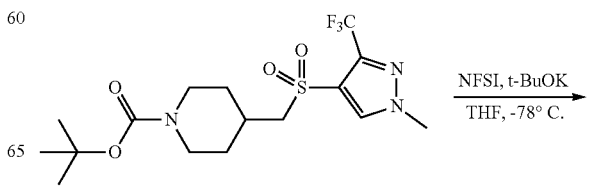

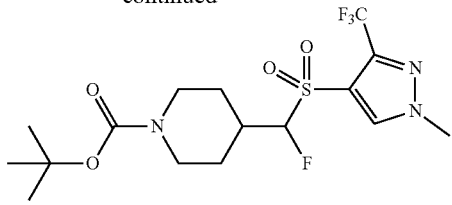

Compound 16.4. tert-Butyl 4-(fluoro((1-methyl-3-(trifluoromethyl)-1H-pyrazol-4-yl)sulfonyl)methyl)piperidine-1-carboxylate

To a solution of tert-butyl 4-[[1-methyl-3-(trifluoromethyl)-1H-pyrazole-4-sulfonyl]methyl]piperidine-1-carboxylate (16.3, 0.450 mg, 1.09 mmol) in THF (20 mL) at −78° C. was added dropwise a solution of t-BuOK (11 mL, 1.0M in THF, 5.54 mmol). The resulting solution was stirred for 0.5 h before a solution of NFSI (2.42 g, 7.63 mmol) in THF (2 mL) was added. The resulting solution was stirred for an additional 1 h at −78° C. before being quenched by the addition of ice water (50 mL). The resulting mixture was extracted with EtOAc (3×50 mL), and the organic layers combined, then dried over $Na_2SO_4$ and concentrated. The resulting residue was purified by prep-HPLC (ACN/$H_2O$ 0:100 (v/v) increasing to ACN/$H_2O$ 100:0 (v/v) within 50 min; Detector, UV 254 nm) to provide the product as a white solid (0.200 g, 43%). $^1$H NMR (400 MHz, CDCl$_3$): δ 7.99 (s, 1H), 4.87-5.00 (m, 1H), 4.18 (d, J=13.2 Hz, 2H), 4.03 (s, 3H), 2.71-2.82 (m, 2H), 2.42-2.54 (m, 1H), 1.93-2.01 (m, 2H), 1.40-1.60 (m, 11H) ppm.

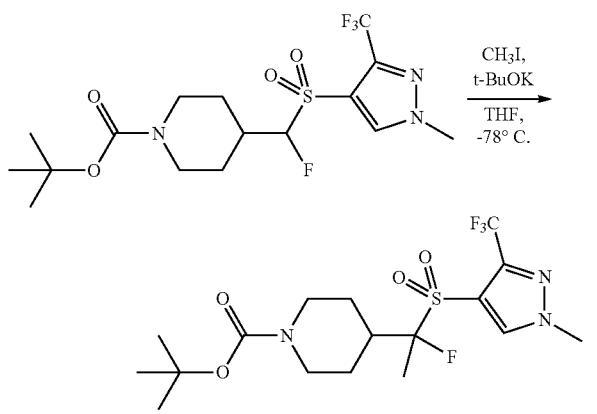

Compound 16.5. tert-Butyl 4-(1-fluoro-1-((1-methyl-3-(trifluoromethyl)-1H-pyrazol-4-yl)sulfonyl)ethyl)piperidine-1-carboxylate

To a solution of tert-butyl 4-[fluoro[1-methyl-3-(trifluoromethyl)-1H-pyrazole-4-sulfonyl]methyl]piperidine-1-carboxylate (16.4, 0.060 g, 0.14 mmol) in THF (3 mL) at −78° C. was added a solution of t-BuOK (0.45 mL, 1.0M in THF, 0.56 mmol). The reaction mixture was stirred for 0.5 h at −78° C. before iodomethane (0.052 g, 0.37 mmol) was added dropwise. The reaction mixture was stirred for an additional 4 hours at −78° C. before being quenched by the addition of ice water (30 mL). The resulting solution was extracted with EtOAc (3×30 mL). The combined organic layers were dried over $Na_2SO_4$, filtered and concentrated to provide the desired product as a solid (0.040 g, crude) which was used as is in the next reaction without further purification. LC-MS (ES, m/z): 344 [M+H-Boc]$^+$.

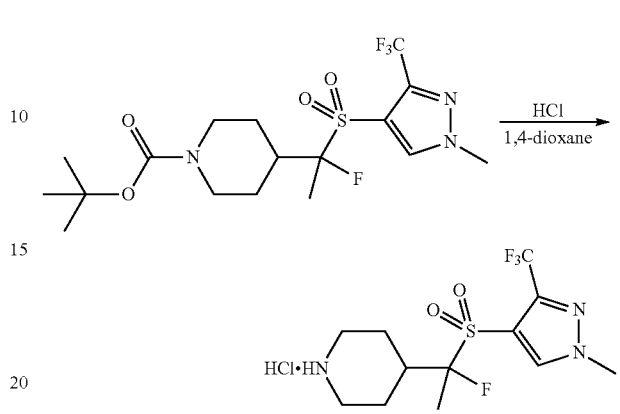

Compound 16.6. 4-(1-Fluoro-1-((1-methyl-3-(trifluoromethyl)-1H-pyrazol-4-yl)sulfonyl)ethyl)piperidine hydrochloride

Compound 16.4 was prepared in a similar manner to compound 9.5 to provide the desired product as a white (0.104 g, 93%). LC-MS (ES, m/z): 343.9 [M+H]$^+$; $^1$H NMR (400 MHz, $D_2O$): δ 8.39 (s, 1H), 3.93 (s, 3H), 3.38-3.50 (m, 2H), 2.88-3.02 (m, 2H), 2.53 (m, 1H), 2.21 (d, J=14.5 Hz, 1H), 2.01 (dt, J=14.4, 3.0 Hz, 1H), 1.58-1.77 (m, 4H), 1.55 (s, 2H) ppm.

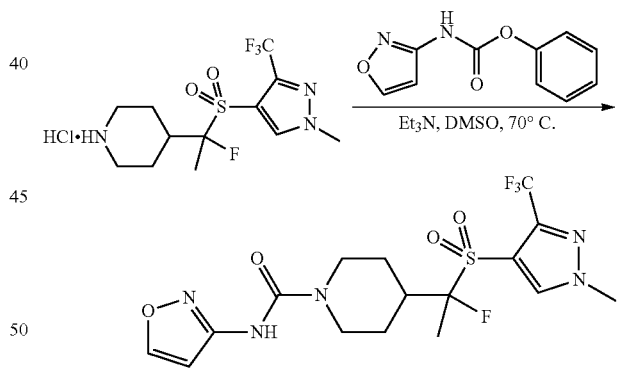

Compound 16. 4-(1-Fluoro-1-((1-methyl-3-(trifluoromethyl)-1H-pyrazol-4-yl)sulfonyl)ethyl)-N-(isoxazol-3-yl)piperidine-1-carboxamide

Compound 16 was prepared in a similar manner to compound 9 to provide the desired product as a white solid (0.09 g, 22%). LC-MS (ES, m/z): 454.1 [M+H]$^+$; $^1$H NMR (400 MHz, CD$_3$OD): δ 8.39 (d, J=1.5 Hz, 2H), 6.68 (d, J=1.8 Hz, 1H), 4.00-4.30 (m, 2H), 3.98 (s, 3H), 2.84-2.93 (m, 2H), 2.48-2.58 (m, 1H), 2.18 (d, J=1.5 Hz, 1H), 1.84 (d, J=12.6 Hz, 1H), 1.33-1.61 (m, 5H) ppm; $^{19}$F NMR (376 MHz, CD$_3$OD): δ −61.149, −61.182, −144.269, −144.300 ppm.

Example 17. Preparation of 4-(1-((3-(difluoromethyl)-1-methyl-1H-pyrazol-5-yl)sulfonyl)-1-fluoroethyl)-N-(pyridazin-4-yl)piperidine-1-carboxamide

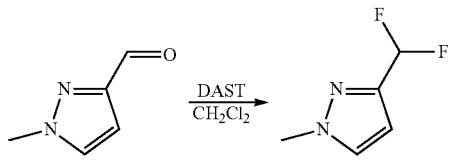

Compound 17.1. 3-(Difluoromethyl)-1-methyl-1H-pyrazole

To a solution of 1-methyl-1H-pyrazole-3-carbaldehyde (4.00 g, 36.33 mmol) in CH$_2$Cl$_2$ (50 mL) at 0° C. was added DAST (23.4 g, 145.17 mmol, 4.00 equiv) dropwise. The reaction mixture was stirred overnight at room temperature and then was quenched by the addition of saturated NaHCO$_3$ (100 mL), and extracted with CH$_2$Cl$_2$ (3×200 mL). The combined organic layers were dried over anhydrous MgSO$_4$, filtered and concentrated to provide the desired product as an oil (4.8 g, crude) which was used in the next reaction without further purification. $^1$H NMR (400 MHz, CDCl$_3$): δ 7.32-7.37 (m, 1H), 6.44-6.45 (t, 1H), 6.80 (m, 1H), 3.90 (s, 3H) ppm.

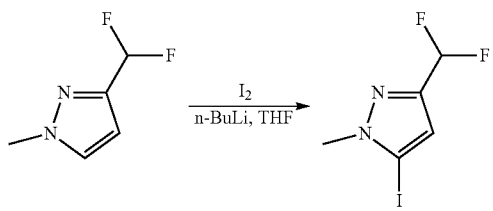

Compound 17.2. 3-(Difluoromethyl)-5-iodo-1-methyl-1H-pyrazole

To a solution of 3-(difluoromethyl)-1-methyl-1H-pyrazole (17.1, 4.8 g, 36.33 mmol) in THF (50 mL) at −78° C. was added n-BuLi (20.0 mL, 2.5 M in n-hexane) dropwise. The resulting solution was stirred for 30 min at −78° C. before a solution of I$_2$ (13.8 g, 54.49 mmol) in THF (50 mL) was added dropwise. The reaction mixture was stirred for 2 h at −78° C. before being quenched by the addition of NH$_4$Cl$_{(sat.)}$ (100 mL). The resulting solution was extracted Et$_2$O (2×200 mL) and the combined organic layers were washed with saturated Na$_2$S$_2$O$_{3(aq.)}$ (2×100 mL), dried over anhydrous MgSO$_4$, filtered and concentrated to provide the desired product (9.0 g, crude), which was used as is in the next reaction without further purification. $^1$H NMR (400 MHz, CDCl$_3$): δ 6.51-6.78 (m, 2H), 3.97 (s, 3H) ppm.

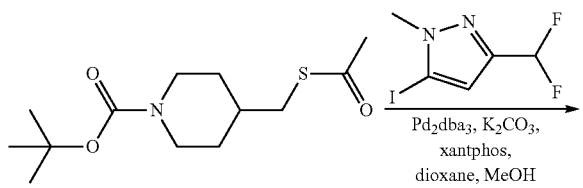

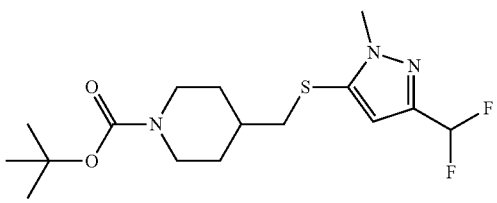

Compound 17.3. tert-Butyl 4-(((3-(difluoromethyl)-1-methyl-1H-pyrazol-5-yl)thio)methyl)piperidine-1-carboxylate Compound 17.3 was prepared in a similar manner to compound 4.2 to provide the desired product as a dark red oil (0.370 g, 38%). The desired product was used as is in the next reaction without further purification. $^1$H NMR (400 MHz, CDCl$_3$): δ 6.44-6.74 (m, 2H), 4.08-4.17 (m, 2H), 3.83-3.96 (m, 3H), 2.62-2.76 (m, 4H), 1.82 (d, J=13.2 Hz, 2H), 1.60 (m, 2H), 1.46 (s, 8H), 1.09-1.28 (m, 2H) ppm.

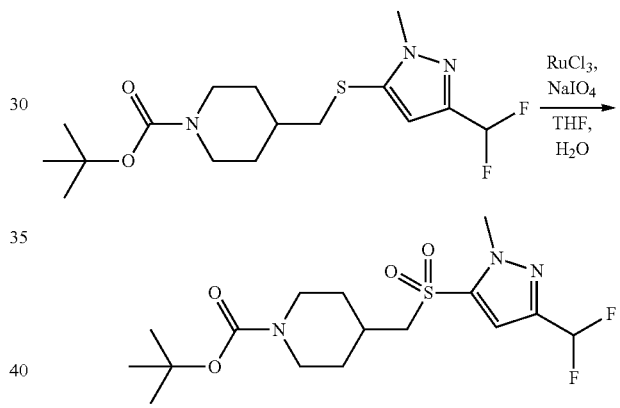

Compound 17.4. tert-Butyl 4-(((3-(difluoromethyl)-1-methyl-1H-pyrazol-5-yl)sulfonyl)methyl)piperidine-1-carboxylate Compound 17.4 was prepared in a similar manner to compound 14.2 to provide the desired product as a dark red oil (0.200 g, 68%). The desired product was used as is in the next reaction without further purification. $^1$H NMR (400 MHz, CDCl$_3$): δ 7.05 (s, 1H), 6.67 (t, J=54.7 Hz, 1H), 4.17 (m, 5H), 3.11 (d, J=6.4 Hz, 2H), 2.68-2.84 (m, 2H), 2.24 (m, 1H), 1.90 (d, J=13.5 Hz, 2H), 1.45 (s, 9H), 1.22-1.41 (m, 2H) ppm.

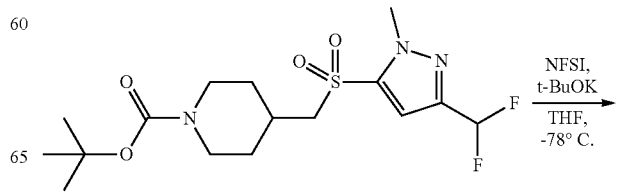

-continued

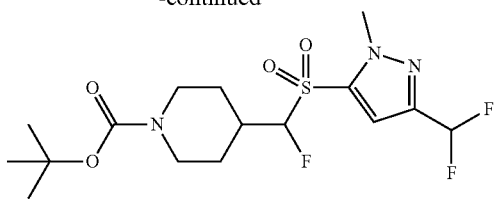

Compound 17.5. tert-Butyl 4-(((3-(difluoromethyl)-1-methyl-1H-pyrazol-5-yl)sulfonyl)fluoromethyl)piperidine-1-carboxylate Compound 17.5 was prepared in a similar manner to compound 16.4 to provide the desired product as a yellow oil (0.900 g, 29%). ¹H NMR (400 MHz, CDCl₃): δ 7.11 (s, 1H), 6.68 (t, J=54.7 Hz, 1H), 5.03 (d, J=6.4 Hz, 0.5H), 4.87 (d, J=6.4 Hz, 0.5H), 4.16 (s, 5H), 2.86-2.69 (m, 2H), 2.45 (s, 1H), 2.04-1.91 (m, 2H), 1.59-1.50 (m, 2H), 1.46 (s, 9H) ppm.

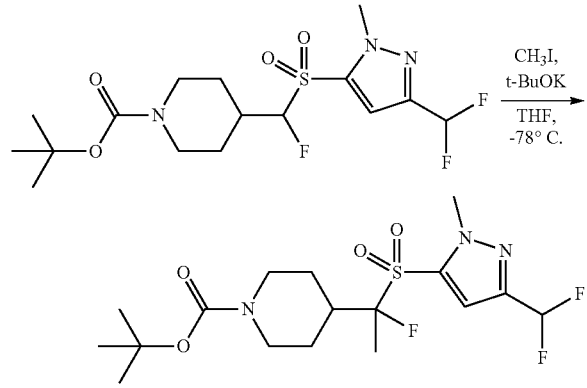

Compound 17.6. tert-Butyl 4-(1-((3-(difluoromethyl)-1-methyl-1H-pyrazol-5-yl)sulfonyl)-1-fluoroethyl)piperidine-1-carboxylate Compound 17.6 was prepared in a similar manner to compound 16.5 to provide the desired product as a clear oil (0.900 g, 29%). ¹H NMR (400 MHz, CDCl₃): δ 7.11 (s, 1H), 6.70 (t, J=54.7 Hz, 1H), 4.25 (m, 2H), 4.14 (s, 3H), 2.74 (m, 2H), 2.51 (m, 1H), 2.13 (d, J=12.2 Hz, 1H), 1.81 (m, 1H), 1.53-1.65 (m, 4H), 1.47 (s, 9H) ppm.

Compound 17.7. 4-[1-[3-(Difluoromethyl)-1-methyl-1H-pyrazole-5-sulfonyl]1-fluoroethyl]piperidine trifluoroacetic acid Compound 17.7 was prepared in a similar manner to compound 4.5 to provide the desired product as a white solid (0.496 g, 69%). The desired product was used as is in the next reaction without further purification. LC-MS (ES, m/z): 326.1 [M+H]⁺, 367.1 [M+H+CH₃CN]⁺; ¹H NMR (300 MHz, CD₃OD): δ 7.24 (s, 1H), 6.80 (t, J=54.5 Hz, 1H), 4.11 (s, 3H), 3.47 (m, 2H), 3.05 (m, 2H), 2.69 (m, 1H), 2.28-2.40 (m, 1H), 2.09 (m, 1H), 1.57-1.87 (m, 5H) ppm.

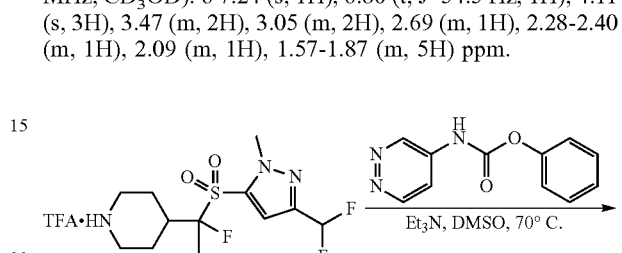

Compound 17. 4-(1-((3-(Difluoromethyl)-1-methyl-1H-pyrazol-5-yl)sulfonyl)-1-fluoroethyl)-N-(pyridazin-4-yl)piperidine-1-carboxamide fluoroethyl]piperidine trifluoroacetic acid Compound 17 was prepared in a similar manner to compound 9 to provide the desired product as a white solid (0.068 g, 60%). LC-MS (ES, m/z): 447.0 [M+H]⁺; ¹H NMR (300 MHz, CD₃OD): δ 9.20 (d, J=2.1 Hz, 1H), 8.84 (d, J=6.0 Hz, 1H), 7.84-7.81 (m, 1H), 7.21 (s, 1H), 6.79 (t, J=54.3 Hz, 1H), 4.34-4.26 (m, 2H), 4.11 (s, 3H), 3.03-2.94 (m, 2H), 2.64-2.53 (m, 1H), 2.19-2.15 (m, 1H), 1.90-1.86 (m, 1H), 1.65-1.48 (m, 5H) ppm.

Example 18. Preparation of (R)-4-(1-fluoro-1-((1-methyl-3-(trifluoromethyl)-1H-pyrazol-5-yl)sulfonyl)ethyl)-N-(isoxazol-3-yl)piperidine-1-carboxamide

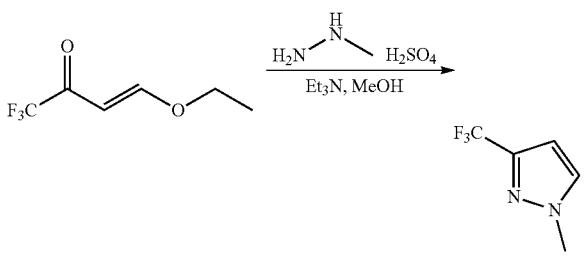

Compound 18.1. 1-Methyl-3-(trifluoromethyl)-1H-pyrazole

To a solution of (3E)-4-ethoxy-1,1,1-trifluorobut-3-en-2-one (29.0 g, 172.50 mmol) in methanol (300 mL) was added methylhydrazine sulfuric acid (39.8 g, 276.10 mmol) portionwise, followed by the addition of triethylamine (18.0 g, 177.88 mmol) portionwise. The resulting solution was stirred overnight at 40° C. The resulting mixture was then cooled to room temperature and concentrated under vacuum. The reaction was then quenched by the addition of ice water (200 mL) and was extracted with Et$_2$O (3×200 mL). The combined organic layers were washed with brine (2×200 mL), dried over anhydrous MgSO$_4$, filtered and concentrated to provide the desired product as a light brown oil (29.0 g, crude) which was used as is in the next reaction. LC-MS (ES, m/z): 151.0 [M+H]$^+$, 192.0 [M+H+CH$_3$CN]$^+$; $^1$H NMR (300 MHz, CDCl$_3$): δ 7.37 (m, 1H), 6.48 (d, J=2.2 Hz, 1H), 3.94 (s, 3H) ppm.

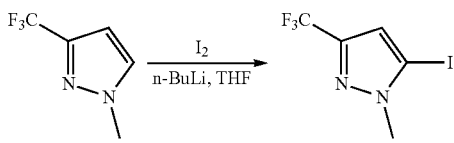

Compound 18.2.
5-Iodo-1-methyl-3-(trifluoromethyl)-1H-pyrazole

To a solution of 1-methyl-3-(trifluoromethyl)-1H-pyrazole (18.1, 3.7 g, 24.65 mmol) in THF (40 mL) at −78° C. was added n-BuLi (2.5M in n-hexane, 11.2 mL, 27.11 mmol) dropwise. The resulting solution was stirred for 10 min at −78° C. before a solution of solution of I2 (10.0 g, 39.44 mmol) in THF (10 mL) was added dropwise. The reaction mixture was stirred at −78° C. for 30 minutes before being quenched by the addition of saturated NH$_4$Cl$_{(aq)}$ (100 mL) and extracted with Et$_2$O (3×200 mL). The combined organic layers were washed with saturated Na$_2$S$_2$O$_{3(aq)}$ (2×100 mL) and brine (2×50 mL), dried over anhydrous MgSO$_4$, filtered and concentrated to provide the desired product as a yellow solid (8.0 g, crude) that was used as is in the next reaction. LC-MS (ES, m/z): 276.8 [M+H]$^+$, 317.8 [M+H+CH$_3$CN]$^+$; $^1$H NMR (300 MHz, CDCl$_3$): δ 6.67 (s, 1H), 3.96 (s, 3H) ppm.

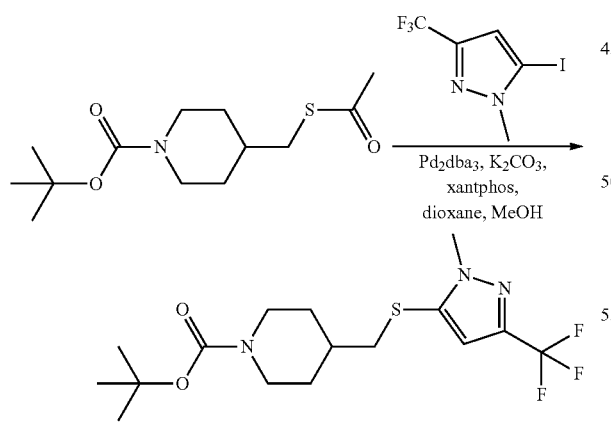

Compound 18.3. tert-Butyl 4-(((1-methyl-3-(trifluoromethyl)-1H-pyrazol-5-yl)thio)methyl)piperidine-1-carboxylate Compound 18.3 was prepared in a similar manner to compound 4.2 to provide the desired product as a dark red oil (2.20 g, 85%). The desired product was used as is in the next reaction without further purification. $^1$H NMR (300 MHz, CDCl$_3$): δ 6.53 (s, 1H), 4.13 (d, J=13.1 Hz, 2H), 3.94 (s, 3H), 2.60-2.78 (m, 4H), 1.82 (d, J=13.5 Hz, 2H), 1.53-1.70 (m, 1H), 1.46 (s, 9H), 1.07-1.29 (m, 2H) ppm.

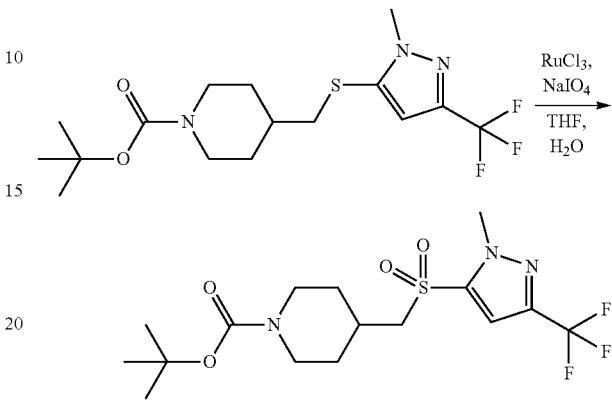

Compound 18.4. tert-Butyl 4-(((1-methyl-3-(trifluoromethyl)-1H-pyrazol-5-yl)sulfonyl)methyl)piperidine-1-carboxylate Compound 18.4 was prepared in a similar manner to compound 14.2 to provide the desired product as a dark red oil (3.5 g, 92%). The desired product was used as is in the next reaction without further purification. $^1$H NMR (400 MHz, CD$_3$OD): δ 7.09 (s, 1H), 4.20 (s, 3H), 4.12 (m, 2H), 3.12 (d, J=6.4 Hz, 2H), 2.71-2.83 (m, 2H), 2.27 (m, 1H), 1.90 (d, J=12.9 Hz, 2H), 1.45 (s, 9H), 1.30 (m, 2H) ppm.

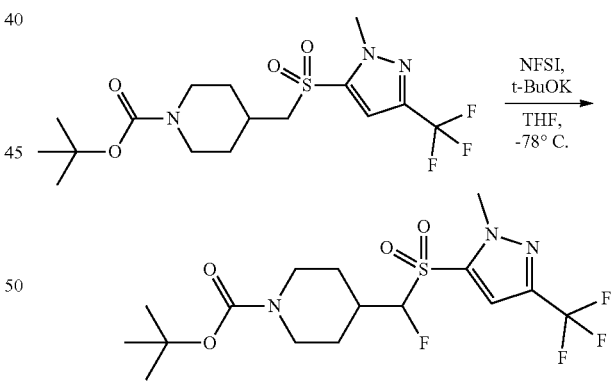

Compound 18.5. tert-Butyl 4-(fluoro((1-methyl-3-(trifluoromethyl)-1H-pyrazol-5-yl)sulfonyl)methyl)piperidine-1-carboxylate Compound 18.5 was prepared in a similar manner to compound 16.4 to provide the desired product as a yellow oil (0.100 g, 27%). $^1$H NMR (400 MHz, CDCl$_3$): δ 7.15 (s, 1H), 4.97 (dd, J=48.0, 6.5 Hz, 1H), 4.21 (m, 5H), 2.71-2.82 (m, 2H), 2.48 (m, 1H), 1.97 (t, J=12.8 Hz, 2H), 1.48 (m, 2H), 1.46 (s, 9H) ppm.

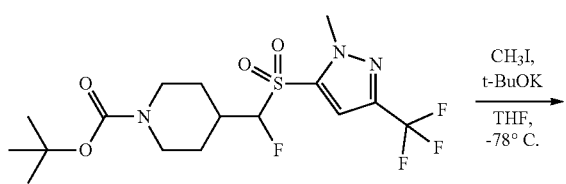

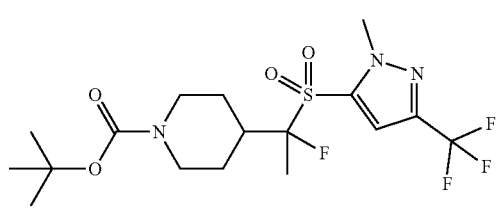

Compound 18.6. tert-Butyl 4-(1-fluoro-1-((1-methyl-3-(trifluoromethyl)-1H-pyrazol-5-yl)sulfonyl)ethyl)piperidine-1-carboxylate Compound 18.6 was prepared in a similar manner to compound 16.5 to provide the desired product as a clear oil (10.0 g, 86%). $^1$H NMR (400 MHz, CDCl$_3$): δ 7.12 (s, 1H), 4.25 (d, J=15.2 Hz, 2H), 4.15 (s, 3H), 2.70 (tt, J=12.9, 2.6 Hz, 2H), 2.48 (m, 1H), 2.08 (d, J=13.2 Hz, 1H), 1.79 (d, J=13.3 Hz, 1H), 1.58 (d, J=22.4 Hz, 3H), 1.44 (s, 9H), 1.19-1.40 (m, 2H) ppm.

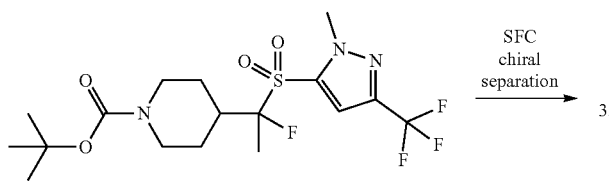

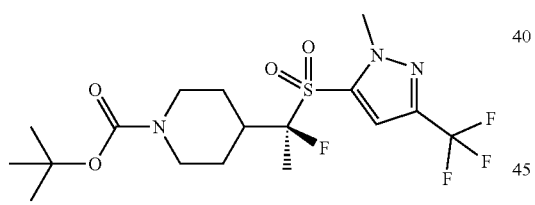

+

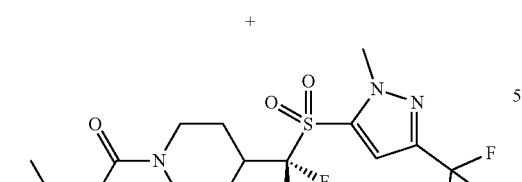

Compound 18.6a. tert-Butyl (R)-4-(1-fluoro-1-((1-methyl-3-(trifluoromethyl)-1H-pyrazol-5-yl)sulfonyl)ethyl)piperidine-1-carboxylate and Compound 18.6b. tert-Butyl (S)-4-(1-fluoro-1-((1-methyl-3-(trifluoromethyl)-1H-pyrazol-5-yl)sulfonyl)ethyl)piperidine-1-carboxylate The enantiomers of tert-butyl 4-(1-fluoro-1-((1-methyl-3-(trifluoromethyl)-1H-pyrazol-5-yl)sulfonyl)ethyl)piperidine-1-carboxylate (18.6, 3.3 g) were separated using by Prep-SFC (Column: Phenomenex Lux 5u Cellulose-4250*50 mm; Mobile Phase A: CO$_2$:80, Mobile Phase B: MeOH:20; Flow rate: 150 mL/min; 220 nm) to provide RT$_1$=3.04 min (18.6a, 1.3 g, 78%) as a white solid and RT$_2$=3.59 min (18.6b, 1.3 g, 78%) as a white solid.

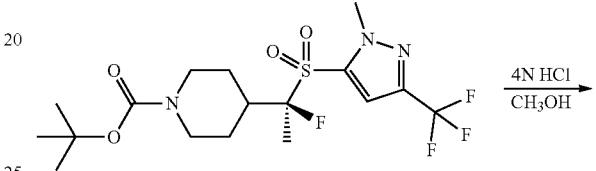

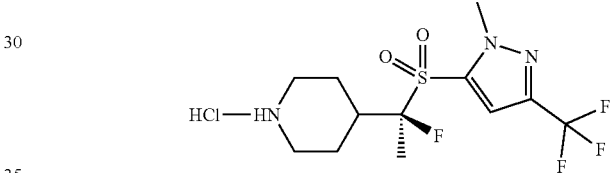

Compound 18.7. (R)-4-(1-Fluoro-1-((1-methyl-3-(trifluoromethyl)-1H-pyrazol-5-yl)sulfonyl)ethyl)piperidine hydrochloride To a solution of tert-butyl 4-[(1R)-1-fluoro-1-[1-methyl-3-(trifluoromethyl)-1H-pyrazole-5-sulfonyl]ethyl]piperidine-1-carboxylate (18.6a, 1.3 g, 2.93 mmol) in CH$_2$Cl$_2$ (10 mL) was added 4N HCl in CH$_3$OH (10 mL). The resulting solution was stirred for 1 h at room temperature and then was concentrated. The resulting residue was dissolved in CH$_3$OH (5 mL) and was precipitated by the addition of Et$_2$O (8 mL) to provide the desired product (1.03 g, 92%) as a white solid. LC-MS (ES, m/z): 344.0 [M+H]$^+$, 385.0 [M+H+CH$_3$CN]$^+$; $^1$H NMR (400 MHz, CD$_3$OD): δ 7.42 (s, 1H), 4.16 (s, 3H), 3.46 (d, J=8.9 Hz, 2H), 3.06 (dt, J=14.0, 10.5 Hz, 2H), 2.62-2.79 (m, 1H), 2.34 (d, J=14.6 Hz, 1H), 2.09 (d, J=14.5 Hz, 1H), 1.77 (t, J=12.8 Hz, 2H), 1.66 (d, J=22.9 Hz, 3H) ppm.

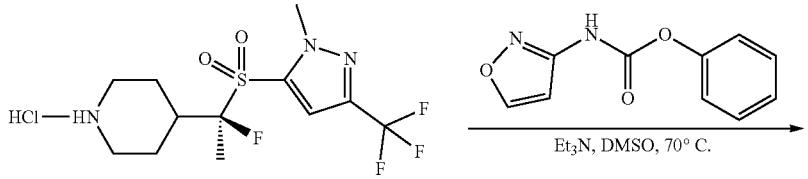

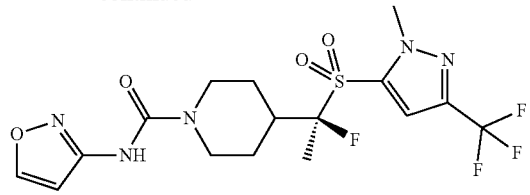

Compound 18. (R)-4-(1-Fluoro-1-((1-methyl-3-(trifluoromethyl)-1H-pyrazol-5-yl)sulfonyl)ethyl)-N-(isoxazol-3-yl)piperidine-1-carboxamide Compound 18 was prepared in a similar manner to compound 9 to provide the desired product as a white solid (0.09 g, 22%). LC-MS (ES, m/z): 454.1 [M+H]+; 1H NMR (400 MHz, CD3CN): δ 8.36 (s, 1H), 8.01-8.16 (m, 1H), 8.09 (br. s., 1H), 7.39 (s, 1H), 6.85 (s, 1H), 4.17 (s, 5H), 2.82-3.00 (m, 2H), 2.45-2.61 (m, 1H), 2.05-2.17 (m, 1H), 1.76-1.90 (m, 1H), 1.59-1.72 (m, 3H), 1.41-1.58 (m, 2H) ppm.

Example 19. Preparation of 4-(1-((3-chloro-1-methyl-1H-pyrazol-4-yl)sulfonyl)-1-fluoroethyl)-N-(isoxazol-3-yl)piperidine-1-carboxamide

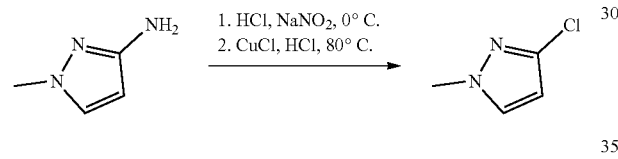

Compound 19.1. 3-Chloro-1-methyl-1H-pyrazole

To a solution of 1-methyl-1H-pyrazol-3-amine (5.0 g, 51.48 mmol) in concentrated HCl(aq) (50 mL) at 0° C. was added NaNO2 (3.56 g, 51.59 mmol). The resulting solution was stirred for 30 min at 0° C. before being added to a solution of CuCl (5.1 g, 51.48 mmol) in concentrated HCl(aq) (50 mL). The reaction mixture was stirred overnight at 80° C. and then was quenched by the addition of H2O (100 mL). The resulting solution was extracted with EtOAc (50 mL), washed with brine (3×50 mL), dried over anhydrous MgSO4, filtered and was concentrated. The resulting residue was purified by flash chromatography (CH2Cl2/petroleum ether=1:1 (v/v)) to provide the desired product as a solid (1.9 g, 32%). 1H NMR (400 MHz, CD3OD): δ 7.57 (d, J=2.3 Hz, 1H), 6.22 (d, J=2.3 Hz, 1H), 3.85 (s, 3H) ppm.

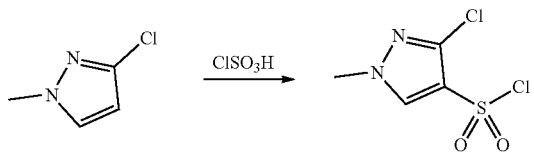

Compound 19.2. 3-Chloro-1-methyl-1H-pyrazole-4-sulfonyl chloride

3-Chloro-1-methyl-1H-pyrazole (19.1, 3.0 g, 25.74 mmol) was added to chlorosulfuric acid (20 mL) and the reaction mixture was stirred overnight at 100° C. The reaction was then quenched by the addition of water/ice (200 mL), extracted with EtOAc (3×200 mL), washed with brine (3×200 mL), dried over MgSO4, filtered and concentrated. The resulting residue was purified by flash chromatography (10% (v/v) CH3OH in CH2Cl2) to provide the desired product as a white solid (4.2 g, 76%). 1H NMR (400 MHz, CDCl3): δ 12.48 (d, J=6.1 Hz, 1H), 7.90 (d, J=3.0 Hz, 3H) ppm.

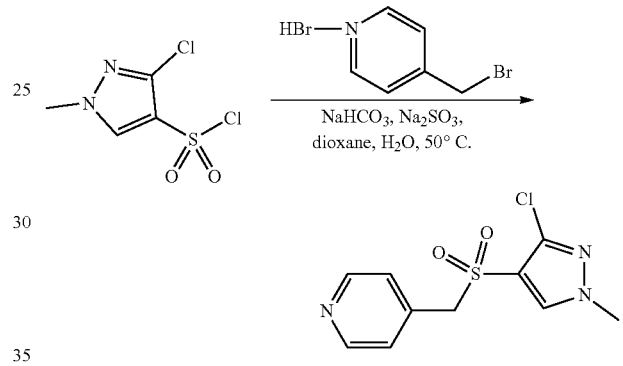

Compound 19.3. 4-(((3-Chloro-1-methyl-1H-pyrazol-4-yl)sulfonyl)methyl)pyridine To a solution of NaHCO3 (5.86 g, 69.75 mmol) and Na2SO3 (5.86 g, 69.75 mmol) in H2O (7.5 mL) at 50° C. was added a solution of 3-chloro-1-methyl-1H-pyrazole-4-sulfonyl chloride (19.2, 5.0 g, 23.25 mmol) in dioxane (2.5 mL). The reaction mixture was stirred for 1.5 h at 50° C. and then was concentrated. The resulting residue was then added to a solution of 4-(bromomethyl)pyridine hydrobromide (4.94 g, 19.53 mmol) in DMF (100 mL). The resulting solution was stirred for 15 min at room temperature and then was heated to 50° C. for an additional 2 h. The reaction was then quenched by the addition of H2O (200 mL), extracted with EtOAc (3×100 mL), washed with brine (100 mL), dried over NaSO4, filtered and concentrated to provide the desired product as a white solid (3.7 g, crude), which was used as is in the next reaction without purification. LC-MS (ES, m/z): 271.9 [M+H]+, 312.9 [M+CH3CN]+; 1H NMR (400 MHz, DMSO-d6): δ 8.56 (m, 2H), 8.31 (s, 1H), 7.24 (m, 2H), 4.72 (s, 2H), 3.84 (s, 3H) ppm.

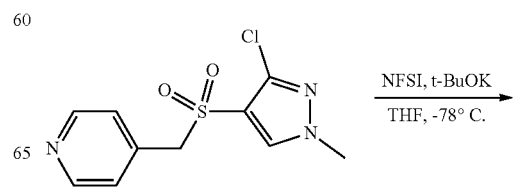

-continued

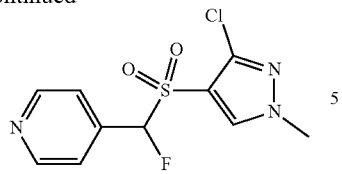

Compound 19.4. 4-(((3-Chloro-1-methyl-1H-pyrazol-4-yl)sulfonyl)fluoromethyl)pyridine To a solution of 4-[(3-chloro-1-methyl-1H-pyrazole-4-sulfonyl)methyl]pyridine (19.3, 200 mg, 0.74 mmol) in THF (5 mL) at −78° C. was added t-BuOK (0.44 mL, 0.44 mmol, 1M in THF) and NFSI (127 mg, 0.41 mmol). The reaction mixture was stirred for 2 h at −78° C., and then was quenched by the addition of H$_2$O (20 mL). The resulting solution was extracted with EtOAc (3×20 mL), washed with brine (3×20 mL), dried over anhydrous MgSO$_4$, filtered and concentrated to provide the desired product as a white solid (0.100 g, 47%). LC-MS (ES, m/z): 290.0 [M+H]$^+$, 331.2 [M+CH$_3$CN]$^+$.

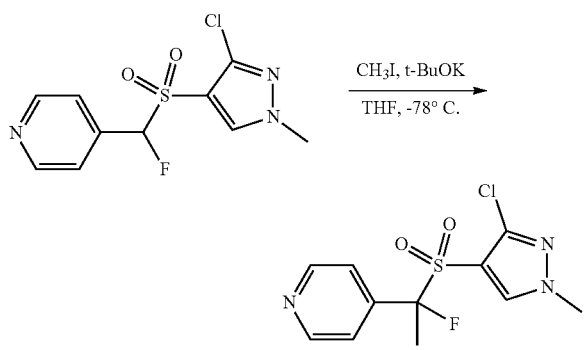

Compound 19.5. 4-(1-((3-Chloro-1-methyl-1H-pyrazol-4-yl)sulfonyl)-1-fluoroethyl)pyridine To a solution of 4-[(3-chloro-1-methyl-1H-pyrazole-4-sulfonyl)(fluoromethyl)]pyridine (19.4, 0.100 g, 0.35 mmol) in THF (5 mL) at −78° C. was added t-BuOK (0.42 mL, 0.42 mmol, 1M in THF) and iodomethane (0.58 g, 0.41 mmol). The reaction mixture was stirred for 2 h at −78° C., and then was quenched by the addition of H$_2$O (20 mL). The resulting solution was extracted with EtOAc (3×20 mL), washed with brine (3×20 mL), dried over anhydrous MgSO$_4$, filtered and concentrated. The resulting residue was purified by silica gel column chromatography (EtOAc/petroleum ether=4:1 (v/v)) to provide the desired product as a white solid (0.80 g, 76%). LC-MS (ES, m/z): 303.9 [M+H]$^+$; $^1$H NMR (400 MHz, CD$_3$OD): δ 8.70-8.59 (m, 2H), 8.15 (s, 1H), 7.59-7.48 (m, 2H), 3.89 (s, 3H), 2.14 (d, J=22.8 Hz, 3H) ppm.

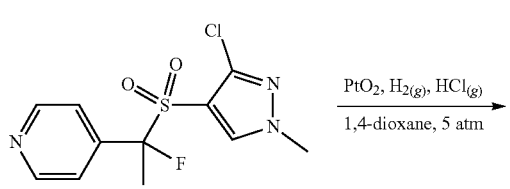

-continued

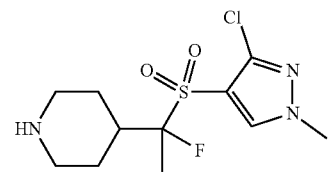

Compound 19.6. 4-(1-((3-Chloro-1-methyl-1H-pyrazol-4-yl)sulfonyl)-1-fluoroethyl)piperidine To a pressure tank reactor containing a solution of 4-(1-((3-chloro-1-methyl-1H-pyrazol-4-yl)sulfonyl)-1-fluoroethyl)pyridine (0.150 g, 0.49 mmol) in 4N HCl in dioxane (3 mL) was added PtO$_2$ (0.75 g, 0.245 mmol). The system was purged and then maintained with an atmosphere of H$_{2(g)}$ (5 atm), and stirred for 2 h at 35° C. The reaction mixture was then cooled to room temperature, evacuated and the purged with N$_{2(g)}$. The solids were removed by filtration and the reaction mixture was concentrated to provide the desired product as a yellow solid (0.120 g, crude). The material was used as is in the next reaction. LC-MS (ES, m/z): 310.0 [M+H]$^+$, 351.1 [M+CH$_3$CN]$^+$.

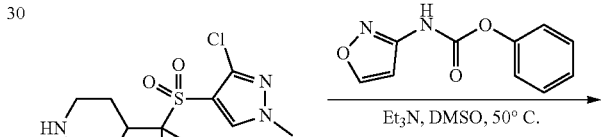

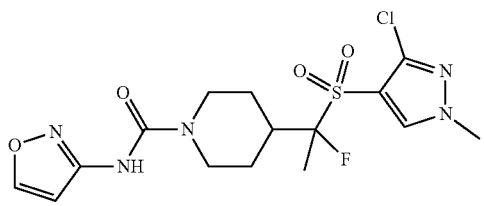

Compound 19. 4-(1-((3-Chloro-1-methyl-1H-pyrazol-4-yl)sulfonyl)-1-fluoroethyl)-N-(isoxazol-3-yl)piperidine-1-carboxamide Compound 19 was prepared in a similar manner to compound 9 to provide the desired product as a white solid (0.011 g, 7%). LC-MS (ES, m/z): 420.2 [M+H]$^+$, 465.3 [M+Na+CH$_3$CN]$^+$; $^1$H NMR (400 MHz, CD$_3$OD): δ 8.45 (d, J=1.8 Hz, 1H), 8.30 (s, 1H), 6.76 (d, J=1.8 Hz, 1H), 4.30 (t, J=16.4 Hz, 2H), 3.95 (s, 3H), 2.93 (m, 2H), 2.52 (m, 1H), 2.25 (d, J=13.4 Hz, 1H), 1.88 (d, J=13.0 Hz, 1H), 1.66 (d, J=23.0 Hz, 3H), 1.52 (m, 2H) ppm.

Example 20. Preparation of (R)-4-(1-((3-(difluoromethyl)-1-methyl-1H-pyrazol-4-yl)sulfonyl)-1-fluoroethyl)-N-(isoxazol-3-yl)piperidine-1-carboxamide desired product as a yellow solid (24 g, 60%). $^1$H NMR (400 MHz, CDCl$_3$): δ 10.02 (d, J=0.8 Hz, 1H), 7.35 (s, 1H), 4.11 (m, 2H), 4.00 (s, 3H), 2.77 (d, J=6.9 Hz, 2H), 2.68 (t, J=12.9 Hz, 2H), 1.89-1.79 (m, 2H), 1.70-1.58 (m, 1H), 1.47 (s, 9H), 1.32-1.11 (m, 2H) ppm.

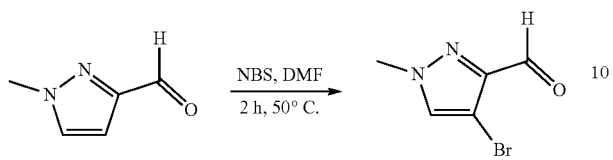

Compound 20.1.
4-Bromo-1-methyl-1H-pyrazole-3-carbaldehyde

To a solution of 1-methyl-1H-pyrazole-3-carbaldehyde (150 g, 1.36 mol) in DMF (1000 mL) was added NBS (240 g, 1.35 mol). The resulting solution was stirred for 2 h at 50° C. and then was quenched by the addition of ice water (2000 mL). The reaction mixture was cooled to –10° C. with an ice/salt bath, and the solids were collected by filtration to provide the desired product as a white solid (200 g, 78%). $^1$H NMR (300 MHz, CDCl$_3$): δ 9.90 (d, J=0.7 Hz, 1H), 7.46 (s, 1H), 3.96 (s, 3H) ppm.

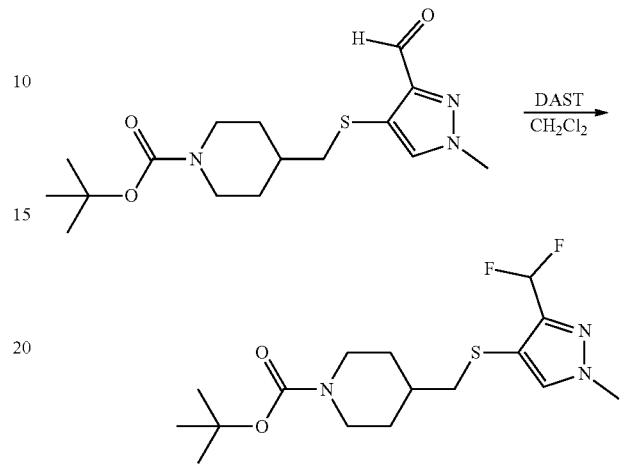

Compound 20.3. tert-Butyl 4-(((3-(difluoromethyl)-1-methyl-1H-pyrazol-4-yl)thio)methyl)piperidine-1-carboxylate To a solution of tert-butyl 4-(((3-formyl-1-methyl-1H-pyrazol-4-yl)thio)methyl)piperidine-1-carboxylate (20.2, 50 g, 147.30 mmol) in dichloromethane (500 mL) at 0° C. was added DAST (95 g, 589.37 mmol) dropwise. The reaction mixture was stirred overnight at 30° C. The temperature was decreased to 0° C. and the reaction mixture was quenched with saturated NaHCO$_{3(aq)}$. The resulting solution was extracted with EtOAc (3×1000 mL). The combined organic layers were washed with brine (500 mL), dried over anhydrous Na$_2$SO$_4$, filtered and concentrated. The resulting residue was purified by flash chromatography (EtOAc/petroleum ether=1/5 (v/v)) to provide the desired product as a yellow solid (35 g, 66%). $^1$H NMR (300 MHz, CD$_3$OD): δ 7.73 (s, 1H), 6.74 (t, J=53.9 Hz, 1H), 4.07-3.95 (m, 2H), 3.87 (d, J=1.1 Hz, 3H), 2.66 (d, J=12.6 Hz, 2H), 2.58 (d, J=6.9 Hz, 2H), 1.81 (d, J=13.0 Hz, 2H), 1.54 (m, 1H), 1.41 (s, 9H), 1.07 (m, 2H) ppm.

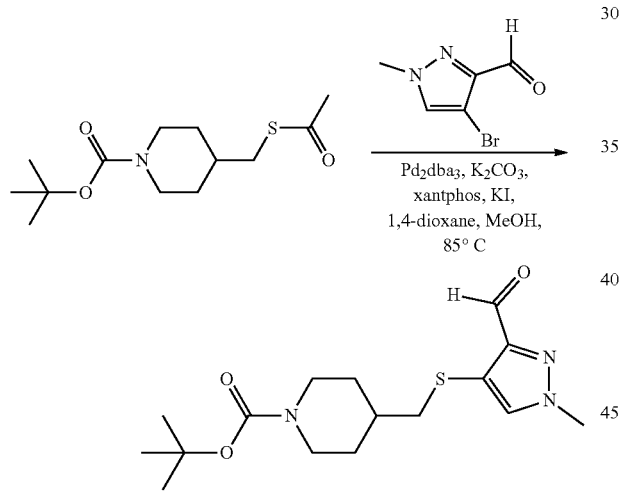

Compound 20.2. tert-Butyl 4-(((3-formyl-1-methyl-1H-pyrazol-4-yl)thio)methyl)piperidine-1-carboxylate To a solution of 4-bromo-1-methyl-1H-pyrazole-3-carbaldehyde (20.1, 20 g, 105.81 mmol), in 1,4-dioxane (300 mL) was added Pd$_2$(dba)$_3$·CHCl$_3$ (5.4 g, 5.22 mmol), K$_2$CO$_3$ (36 g, 260.47 mmol), Xantphos (6.1 g, 10.54 mmol), KI (1.7 g, 10.58 mmol) and tert-butyl 4-[(acetylsulfanyl)methyl]piperidine-1-carboxylate (34 g, 124.36 mmol). The reaction mixture was heated to 80° C. and MeOH (40 g, 1.25 mol) was added dropwise. The reaction mixture was stirred for 12 h at 85° C. The reaction mixture was cooled to room temperature with ice water bath, and the solids were removed by filtration. The filtrate was concentrated and the resulting residue was purified by flash column chromatography (EtOAc/petroleum ether=1/2 (v/v)) to provide the

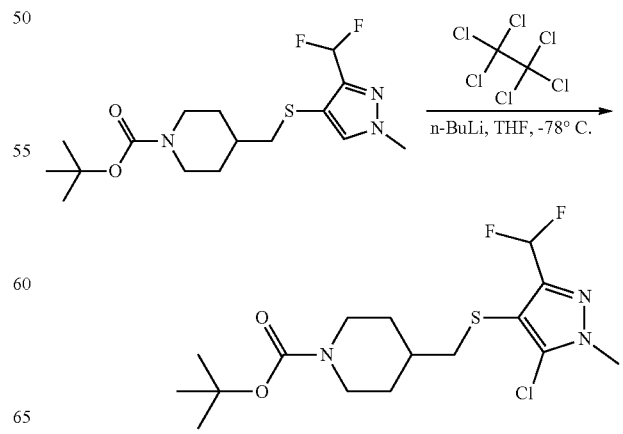

Compound 20.4. tert-Butyl 4-(((5-chloro-3-(difluoromethyl)-1-methyl-1H-pyrazol-4-yl)thio)methyl)piperidine-1-carboxylate To a solution of tert-butyl 4-(((3-(difluoromethyl)-1-methyl-1H-pyrazol-4-yl)thio)methyl)piperidine-1-carboxylate (20.3, 30 g, 83.00 mmol) in THF (400 mL) at –78° C. was added dropwise a solution of n-BuLi (50 mL, 124.5 mmol, 2.5M in n-hexane). The reaction mixture was stirred for 20 minutes before a solution of perchloroethane (23.6 g, 99.72 mmol) in THF (30 mL) was added dropwise. The reaction mixture was stirred for 30 min at –78° C. before being quenched by the addition of saturated NH$_4$Cl$_{(aq)}$ (100 mL). The resulting solution was extracted with EtOAc (3×500 mL), washed with brine (300 mL), dried over anhydrous Na$_2$SO$_4$, filtered and then concentrated to provide the desired product as a white solid (30 g, crude) which was used as is in the next reaction without further purification. $^1$H NMR (400 MHz, CDCl$_3$): δ 6.68 (t, J=53.8 Hz, 1H), 4.16-4.04 (m, 2H), 3.90 (t, J=0.9 Hz, 3H), 2.71-2.56 (m, 4H), 1.91-1.75 (m, 2H), 1.45 (m, 10H), 1.19-1.04 (m, 2H) ppm.

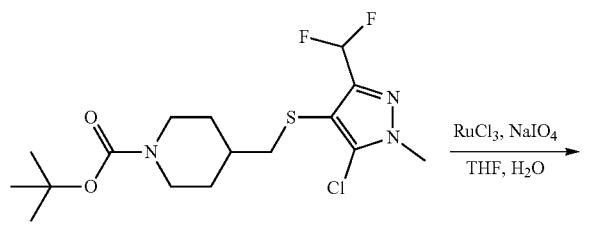

Compound 20.5. tert-Butyl 4-(((5-chloro-3-(difluoromethyl)-1-methyl-1H-pyrazol-4-yl)sulfonyl)methyl)piperidine-1-carboxylate Compound 20.5 was prepared in a similar manner to compound 14.2 to provide the desired product as a white solid (28 g, 86%). $^1$H NMR (400 MHz, CDCl$_3$): δ 7.03 (t, J=53.8 Hz, 1H), 4.12-4.03 (m, 2H), 3.96 (s, 3H), 3.10 (d, J=6.3 Hz, 2H), 2.74 (m, 2H), 1.90 (m, 2H), 1.44 (s, 9H), 1.36-1.18 (m, 3H) ppm.

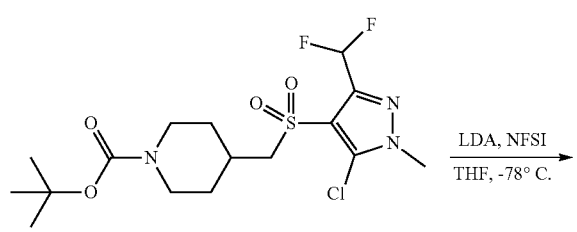

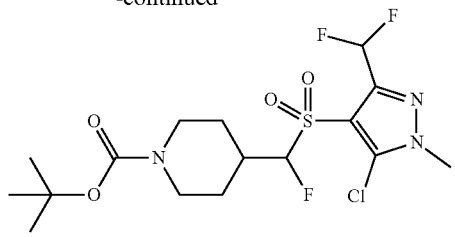

Compound 20.6. tert-Butyl 4-(((5-chloro-3-(difluoromethyl)-1-methyl-1H-pyrazol-4-yl)sulfonyl)fluoromethyl)piperidine-1-carboxylate To a solution of tert-butyl 4-(((5-chloro-3-(difluoromethyl)-1-methyl-1H-pyrazol-4-yl)sulfonyl)methyl)piperidine-1-carboxylate (20.5, 25 g, 58.43 mmol) in THF (300 mL) at –78° C. was added LDA (43 mL, 87.64 mmol, 2.0 M in THF) dropwise, followed by the dropwise addition of a solution of NFSI (22 g, 58.43 mmol) in THF (100 mL). The reaction mixture was stirred for 30 min at –78° C. and then was quenched by the addition of saturated NH$_4$Cl$_{(aq)}$ (500 mL). The reaction mixture was extracted with EtOAc (3×500 mL), washed with brine (500 mL), dried over anhydrous Na$_2$SO$_4$, filtered, and concentrated. The resulting residue was purified by flash chromatography (EtOAc/petroleum ether=1/4 (v/v)) to provide the desired product as a white solid (18 g, 69%). $^1$H NMR (300 MHz, CD$_3$OD): δ 6.96 (t, J=53.2 Hz, 1H), 5.27 (d, J=6.4 Hz, 1H), 5.11 (d, J=6.4 Hz, 1H), 4.16-4.02 (m, 2H), 3.94 (s, 3H), 2.80 (s, 2H), 2.42 (m, 1H), 1.92 (m, 2H), 1.43 (s, 9H), 0.95-0.74 (m, 2H) ppm.

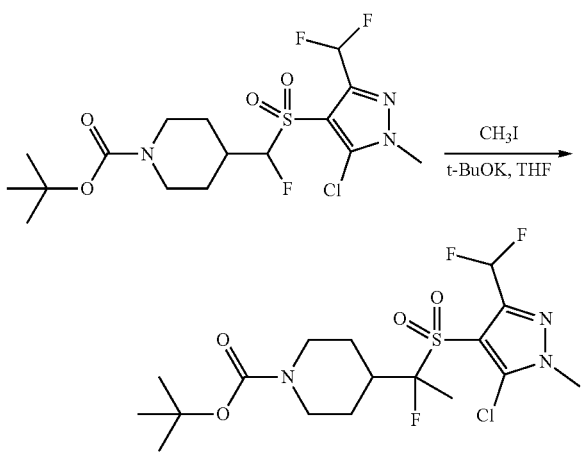

Compound 20.7. tert-Butyl 4-(1-((5-chloro-3-(difluoromethyl)-1-methyl-1H-pyrazol-4-yl)sulfonyl)-1-fluoroethyl)piperidine-1-carboxylate To a solution of tert-butyl 4-(((5-chloro-3-(difluoromethyl)-1-methyl-1H-pyrazol-4-yl)sulfonyl)fluoromethyl)piperidine-1-carboxylate (20.6, 15.6 g, 34.99 mmol) in THF (250 mL) at –78° C. was added dropwise a solution of t-BuOK (70 mL, 69.98 mmol, 1.0 M in THF). The reaction mixture was stirred for 5 minutes before iodomethane (7.4 g, 52.14 mmol) was added dropwise. The reaction mixture was stirred for 15 min at –78° C. before being quenched by the addition of saturated NH$_4$Cl$_{(aq)}$ (500 mL). The resulting solution was extracted with EtOAc (3×500 mL), washed with brine (300 mL), dried over anhydrous Na$_2$SO$_4$, filtered and then concentrated to provide the desired product as a white solid (15 g, crude), which was used directly to next step without purification.

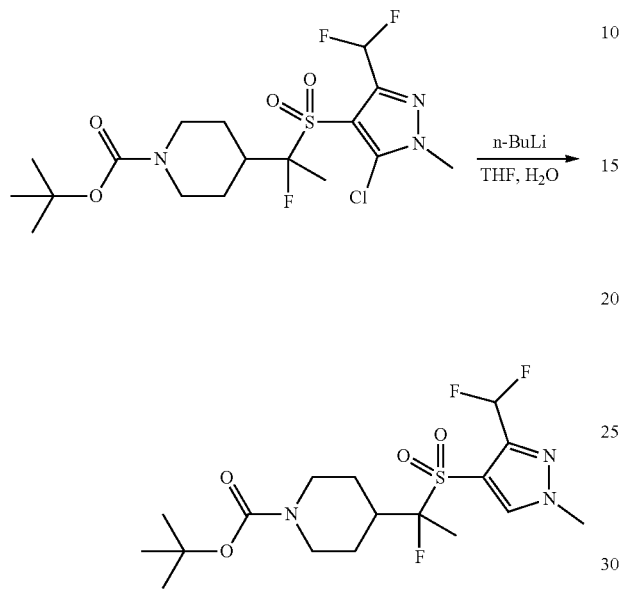

Compound 20.8. tert-Butyl 4-(1-((3-(difluoromethyl)-1-methyl-1H-pyrazol-4-yl)sulfonyl)-1-fluoroethyl)piperidine-1-carboxylate To a solution of tert-butyl 4-(1-((5-chloro-3-(difluoromethyl)-1-methyl-1H-pyrazol-4-yl)sulfonyl)-1-fluoroethyl)piperidine-1-carboxylate (20.7, 25 g, 54.36 mmol) in THF (400 mL) at −78° C. was added n-BuLi (28 mL, 70.66 mmol, 2.5 M in hexanes) dropwise. The reaction mixture was stirred for 30 min at −78° C. before being quenched by the addition of ice water (200 mL). The resulting mixture was extracted with EtOAc (3×500 mL), washed with brine (300 mL), dried over anhydrous Na$_2$SO$_4$, filtered, and then concentrated. The resulting residue was purified by Flash-Prep-HPLC (Column, C18 silica gel; mobile phase, ACN:H$_2$O=20:80 (v/v) increasing to ACN:H$_2$O=95:5 (v/v) within 60 min; Detector, UV 254 nm) to provide the desired product as a white solid (15 g, 65%). $^1$H NMR (300 MHz, CDCl$_3$): δ 7.85 (s, 1H), 6.95 (t, J=53.3 Hz, 1H), 4.18 (m, 2H), 4.01 (s, 3H), 2.79-2.59 (m, 2H), 2.43 (m, 1H), 2.16-2.05 (m, 1H), 1.77 (m, 1H), 1.53 (d, J=22.2 Hz, 3H), 1.43 (s, 9H), 1.32 (m, 2H) ppm.

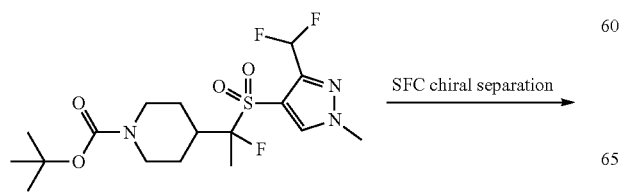

SFC chiral separation

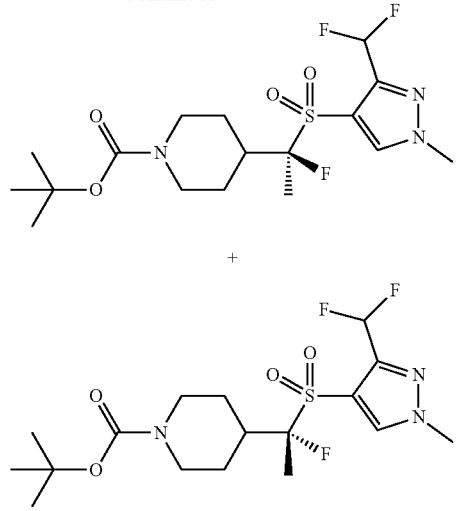

Compound 20.8a. tert-Butyl (R)-4-(1-((3-(difluoromethyl)-1-methyl-1H-pyrazol-4-yl)sulfonyl)-1-fluoroethyl)piperidine-1-carboxylate and Compound 20.8b. tert-Butyl (S)-4-(1-((3-(difluoromethyl)-1-methyl-1H-pyrazol-4-yl)sulfonyl)-1-fluoroethyl)piperidine-1-carboxylate The enantiomers of tert-butyl 4-(1-((3-(difluoromethyl)-1-methyl-1H-pyrazol-4-yl)sulfonyl)-1-fluoroethyl)piperidine-1-carboxylate (20.8, 63.6 g) were separated using by Prep-SFC (Column: Phenomenex Lux Cellulose-4 (5*25 cm, 5 μm); Mobile Phase A: CO$_2$: 70, Mobile Phase B: EtOH: 30; Flow rate: 150 mL/min; 220 nm) to provide RT$_1$=1.448 min (20.8a, 24.0 g, 91%, [α]=−26.9 (C=0.37 g/100 mL, T=23.6° C., MeOH)) as a white solid and RT$_2$=1.744 min (20.8b, 24.0 g, 91%, [α]=+23.4 (C=0.33 g/100 mL, T=24.6° C., MeOH)) as a white solid.

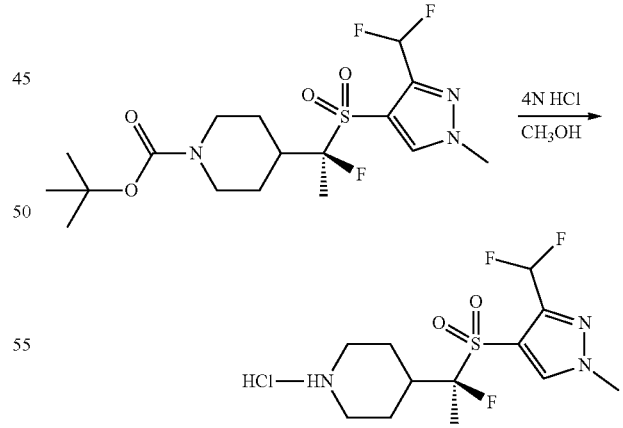

Compound 20.9. (R)-4-(1-((3-(Difluoromethyl)-1-methyl-1H-pyrazol-4-yl)sulfonyl)-1-fluoroethyl)piperidine hydrochloride Compound 20.9 was prepared in a similar manner to compound 18.7 to provide the desired product as a white solid (15.0 g, 85%). LC-MS (ES, m/z): 326.0 [M+H]$^+$; $^1$H NMR (300 MHz, CD$_3$OD): δ 8.29 (s, 1H), 6.92 (t, J=53.1 Hz, 1H), 4.01 (s, 3H), 3.19-3.07 (m, 2H), 2.62-2.52 (m, 1H), 2.41-2.38 (m, 1H), 2.10-2.03 (m, 1H), 1.76-1.73 (m, 1H), 1.56-1.38 (m, 5H) ppm.

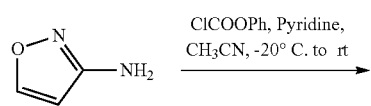

Compound 20.10. Phenyl isoxazol-3-ylcarbamate

To a solution of 3-amino-isoxazole (25 g, 0.297 mmol) and pyridine (29.0 mL, 0.356 mmol) in acetonitrile (600 mL) was added phenyl chloroformate (39.1 mL, 0.312 mmol) dropwise at −20° C. over 15 min. The reaction mixture was gradually warmed to rt and stirred at rt overnight. Subsequently, the reaction mixture was concentrated and the residue was added ice water (500 mL). The suspension was filtered and the solid was washed with water and dried in vacuo to give the desired product as a white solid (58.76 g, 97% yield).

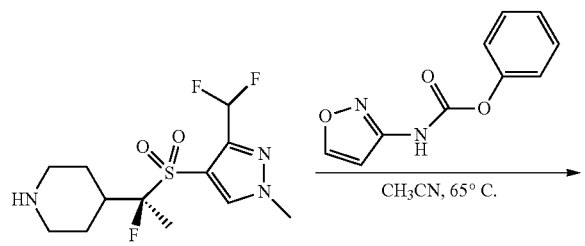

Compound 20. (R)-4-(1-((3-(Difluoromethyl)-1-methyl-1H-pyrazol-4-yl)sulfonyl)-1-fluoroethyl)-N-(isoxazol-3-yl)piperidine-1-carboxamide To a solution of (R)-4-(1-((3-(difluoromethyl)-1-methyl-1H-pyrazol-4-yl)sulfonyl)-1-fluoroethyl)piperidine (20.9, 20.0 g, 61.46 mmol) in acetonitrile (246 mL, 0.5 M) was added 3-aminoisoxazole phenyl carbamate (13.18 g, 64.54 mmol) portion-wise at 65° C. over 5 minutes. After stirring at 65° C. overnight, the reaction mixture was concentrated and the residue was purified by silica gel column chromatography (ISCO CombiFlash, 330 g column, CAT #69-2203-330) using MeOH/DCM=0% to 2% (v/v) as the eluent to give the desired product as a white solid (25.6 g, 96% yield). LC-MS− (ES, m/z): 436.0 [M+H]$^+$; $^1$H NMR (400 MHz, CDCl$_3$): δ 8.23 (s, 1H), 8.11 (s, 1H), 7.89 (s, 1H), 6.98 (t, J=53.1 Hz, 1H), 6.98 (s, 1H), 4.32-4.25 (m, 2H), 4.04 (s, 3H), 2.99-2.90 (m, 2H), 2.62-2.54 (m, 1H), 2.27-2.24 (m, 1H), 1.94-1.91 (m, 1H), 1.53-1.47 (m, 5H) ppm; $^{19}$F NMR (376 MHz, CDCl$_3$): δ −114.3 to −117.1 (m, 2F), −144.8 (s, 1F) ppm.

Example 21. Preparation of (S)-4-(1-((3-(difluoromethyl)-1-methyl-1H-pyrazol-4-yl)sulfonyl)-1-fluoroethyl)-N-(isoxazol-3-yl)piperidine-1-carboxamide

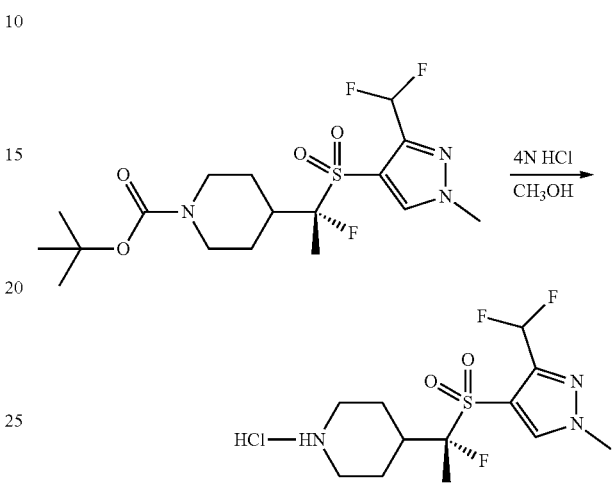

Compound 21.1. (S)-4-(1-((3-(Difluoromethyl)-1-methyl-1H-pyrazol-4-yl)sulfonyl)-1-fluoroethyl) piperidine hydrochloride Compound 21.1 was prepared in a similar manner to compound 18.7 to provide the desired product as a white solid (15.0 g, 85%). LC-MS (ES, m/z): 326.0 [M+H]$^+$; $^1$H NMR (300 MHz, CD$_3$OD): δ 8.29 (s, 1H), 6.92 (t, J=53.1 Hz, 1H), 4.01 (s, 3H), 3.19-3.07 (m, 2H), 2.62-2.52 (m, 1H), 2.41-2.38 (m, 1H), 2.10-2.03 (m, 1H), 1.76-1.73 (m, 1H), 1.56-1.38 (m, 5H) ppm.

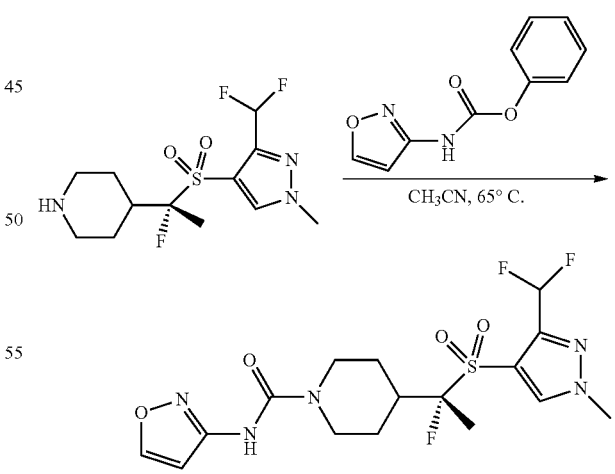

Compound 21. (S)-4-(1-((3-(Difluoromethyl)-1-methyl-1H-pyrazol-4-yl)sulfonyl)-1-fluoroethyl)-N-(isoxazol-3-yl)piperidine-1-carboxamide To a solution of (S)-4-(1-((3-(difluoromethyl)-1-methyl-1H-pyrazol-4-yl)sulfonyl)-1-fluoroethyl)piperidine (21.1, 0.20 g, 0.553 mmol) in acetonitrile (2 mL) was added 3-aminoisoxazole phenyl carbamate (0.118 g, 0.580 mmol) followed by trimethylamine (0.167 g, 1.65 mmol). After stirring at 65° C. overnight, the reaction mixture was concentrated and the residue was purified by reverse phase high pressure liquid chromatography (0-90% $CH_3CN$ in $H_2O$ (both containing 0.1% TFA)) to provide the desired product as a white solid (0.162 g, 67%). LC-MS (ES, m/z): 436.0 $[M+H]^+$; $^1H$ NMR (400 MHz, $CDCl_3$): δ 8.60 (s, 1H), 8.22 (s, 1H), 7.89 (s, 1H), 6.99 (t, J=52.0 Hz, 1H), 6.99 (s, 1H), 4.37-4.25 (m, 2H), 4.04 (s, 3H), 2.99-2.90 (m, 2H), 2.62-2.54 (m, 1H), 2.27-2.24 (m, 1H), 1.94-1.91 (m, 1H), 1.53-1.47 (m, 5H) ppm; $^{19}F$ NMR (376 MHz, $CDCl_3$): δ −114.3 to −117.1 (m, 2F), −144.8 (s, 1F) ppm.

Example 22. Preparation of 4-(difluoro(imidazo[1,2-a]pyridin-8-ylsulfonyl)methyl)-N-(pyridazin-4-yl)piperidine-1-carboxamide

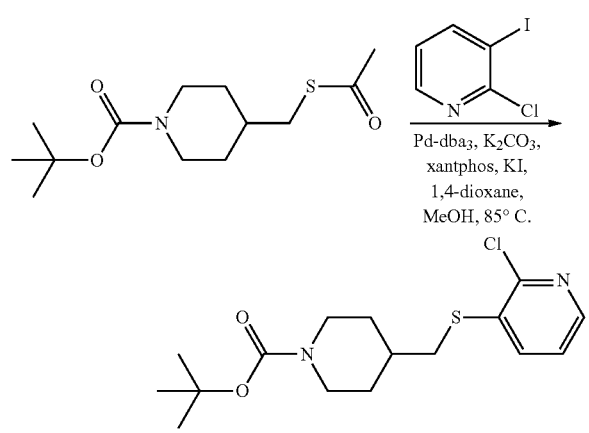

Compound 22.1 tert-Butyl 4-(((2-chloropyridin-3-yl)thio)methyl)piperidine-1-carboxylate Compound 22.1 was prepared in a similar manner to compound 4.2 to provide the desired product as a yellow solid (1.99 g, 55%). $^1H$ NMR (300 MHz, DMSO-d6): δ 8.16-8.18 (dd, J=4.4, 1.6 Hz, 1H), 7.827.85 (dd, J=8.0, 1.6 Hz, 1H), 7.39-7.42 (dd, J=8.0, 4.8 Hz, 1H), 3.92-3.95 (d, J=12.0 Hz, 2H), 2.99-3.00 (d, J=6.8 Hz, 2H), 2.70 (m, 2H), 1.79-1.82 (d, J=12.8 Hz, 2H), 1.68-1.75 (m, 1H), 1.39 (s, 9H), 1.10-1.14 (m, 2H) ppm.

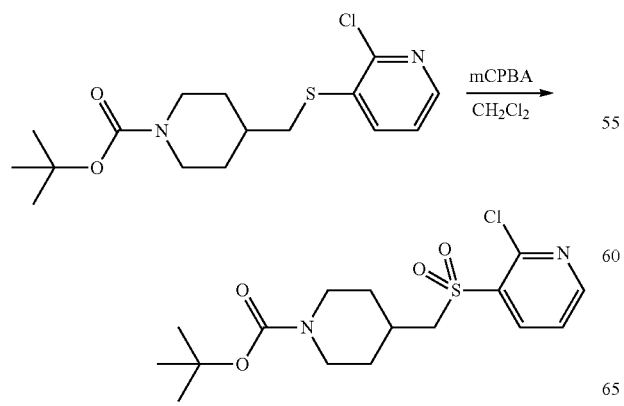

Compound 22.2 tert-Butyl 4-(((2-chloropyridin-3-yl)sulfonyl)methyl)piperidine-1-carboxylate Compound 22.2 was prepared in a similar manner to compound 4.3 to provide the desired product as a yellow solid (0.72 g, 53%). $^1H$ NMR (400 MHz, DMSO-d6): δ 8.74-8.76 (dd, J=4.8, 1.6 Hz, 1H), 8.44-8.46 (dd, J=8.0, 2.0 Hz, 1H), 7.73-7.76 (dd, J=7.6, 4.8 Hz, 1H), 3.84-3.87 (d, J=8.4 Hz, 2H), 3.56-3.57 (d, J=6.4 Hz, 2H), 2.65 (m, 2H), 2.07 (m, 1H), 1.72-1.75 (d, J=12.0 Hz, 2H), 1.38 (s, 9H), 1.17-1.26 (m, 2H) ppm.

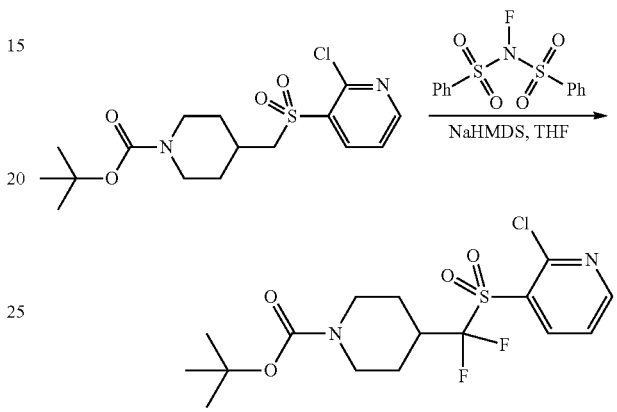

Compound 22.3. tert-Butyl 4-(((2-chloropyridin-3-yl)sulfonyl)difluoromethyl)piperidine-1-carboxylate Compound 22.3 was prepared in a similar manner to compound 4.4 to provide the desired product as a yellow solid (0.36 g, 66%). $^1H$ NMR (400 MHz, $CDCl_3$): δ 8.70-8.71 (dd, J=4.8, 2.0 Hz, 1H), 8.41-8.43 (dd, J=8.0, 2.0 Hz, 1H), 7.51-7.54 (dd, J=7.6, 4.8, 4.8 Hz, 1H), 4.27 (s, 2H), 2.74-2.77 (m, 3H), 2.06-2.09 (d, J=13.6 Hz, 2H), 1.60-1.64 (m, 2H), 1.47 (s, 9H) ppm.

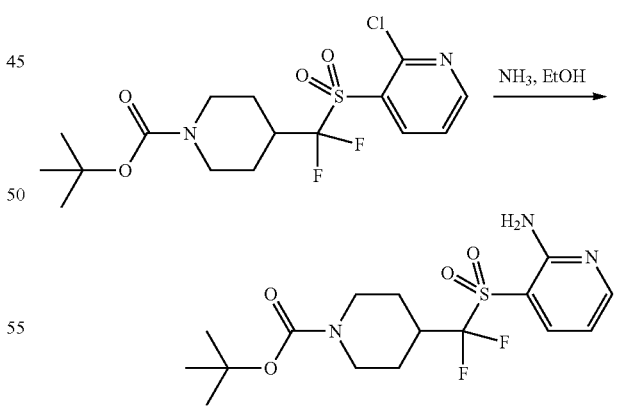

Compound 22.4. tert-Butyl 4-(((2-aminopyridin-3-yl)sulfonyl)difluoromethyl)piperidine-1-carboxylate To a solution of tert-butyl 4-(((2-chloropyridin-3-yl)sulfonyl)difluoromethyl)piperidine-1-carboxylate (22.3, 0.360 g, 0.88 mmol) in EtOH (2 mL) was added saturated $NH_3$ in EtOH (10 mL). The resulting solution was stirred for 2 h at room temperature and then was concentrated. The resulting residue was purified by flash chromatography (EtOAc/petroleum ether=1/1 (v/v)) to provide the desired product as a light yellow solid (0.100 g, 29%). ¹H NMR (400 MHz, CDCl₃): δ 8.31-8.33 (d, J=3.6 Hz, 1H), 7.94-7.96 (d, J=7.8 Hz, 1H), 6.76-6.80 (dd, J=7.5, 4.8 Hz, 1H), 6.15 (s, 2H), 4.22-4.25 (d, J=8.7 Hz, 2H), 2.62-2.78 (m, 3H), 2.04-2.08 (d, J=12.9 Hz, 2H), 1.61-1.66 (m, 2H), 1.46 (s, 9H) ppm.

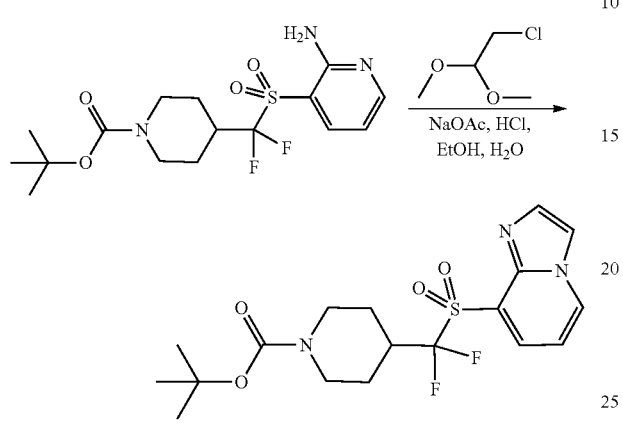

Compound 22.5. tert-Butyl 4-(difluoro(imidazo[1,2-a]pyridin-8-ylsulfonyl)methyl)-piperidine-1-carboxylate To a solution of tert-butyl 4-(((2-aminopyridin-3-yl)sulfonyl)difluoromethyl)-piperidine-1-carboxylate (22.4, 0.100 g, 0.26 mmol) in EtOH (1.2 mL) and H₂O (1.4 mL) was added NaOAc (0.526 g, 2.52 equiv), 2-chloro-1,1-dimethoxyethane (0.59 g, 0.47 mmol), and 6N HCl (0.1 mL). The resulting solution was stirred overnight at 75° C. The EtOH was removed under vacuum and the resulting solution was extracted with EtOAc (3×5 mL). The combined organic layers were washed with brine (2×5 mL), dried over anhydrous Na₂SO₄, filtered and concentrated. The resulting residue was purified by flash column chromatography (EtOAc/petroleum ether=1/1 (v/v)) to provide the desired product as a light yellow solid (0.75 g, 71%). LC-MS (ES, m/z): 316 [M+H]⁺.

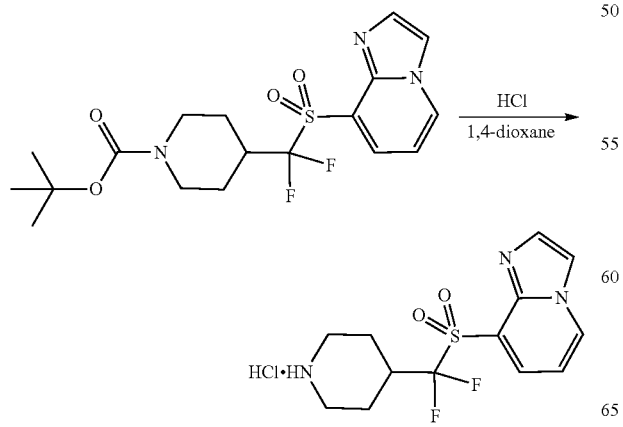

Compound 22.6. 8-((Difluoro(piperidin-4-yl)methyl)sulfonyl)imidazo[1,2-a]pyridine hydrochloride Compound 22.6 was prepared in a similar manner to compound 9.5 to provide the desired product as a yellow solid (0.51 g, crude). LC-MS (ES, m/z): 316 [M+H]⁺.

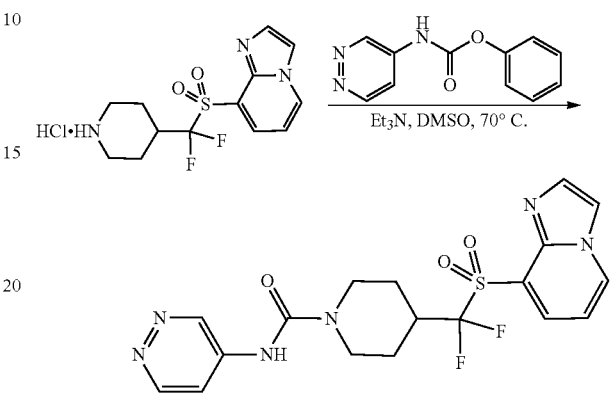

Compound 22. 4-(Difluoro(imidazo[1,2-a]pyridin-8-ylsulfonyl)methyl)-N-(pyridazin-4-yl)piperidine-1-carboxamide Compound 22 was prepared in a similar manner to compound 9 to provide the desired product as a yellow solid (0.33 g, 47%). LC-MS (ES, m/z): 437 [M+H]⁺; ¹H NMR (300 MHz, DMSO-d6): δ 9.25-9.26 (m, 1H), 9.23 (s, 1H), 9.04-9.06 (dd, J=6.9, 1.2 Hz, 1H), 8.84-8.86 (dd, J=6.0, 0.6 Hz, 1H), 8.22-8.23 (d, J=1.5 Hz, 1H), 8.03-8.05 (dd, J=7.2, 0.9 Hz, 1H), 7.77-7.78 (d, J=1.5 Hz, 1H), 7.73-7.76 (dd, J=6.0, 2.8 Hz, 1H), 7.18-7.20 (t, J=7.0 Hz, 1H), 4.22-4.27 (d, J=14.1 Hz, 2H), 2.89-2.97 (t, J=12.8 Hz, 3H), 2.08-2.10 (d, J=5.4 Hz, 2H), 1.48-1.54 (m, 2H) ppm.

Example 23. Preparation of 4-(((1,3-dimethyl-1H-pyrazol-5-yl)sulfonyl)difluoromethyl)-N-(pyridazin-4-yl)piperidine-1-carboxamide

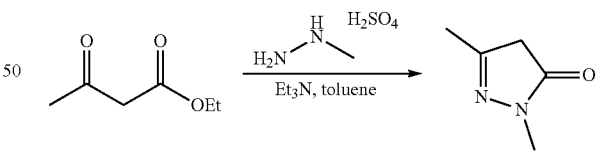

Compound 23.1.
2,5-Dimethyl-2,4-dihydro-3H-pyrazol-3-one

To a solution of methylhydrazine sulfuric acid (5.47 g, 37.95 mmol) in toluene (100 mL) at 0° C. was added triethylamine (30.7 g, 303.39 mmol) dropwise. The resulting solution was stirred for 30 min at 0° C. before ethyl 3-oxobutanoate (5 g, 38.42 mmol) was added dropwise followed by the portionwise addition of magnesium sulfate (9.12 g, 2.00 equiv.). The resulting solution was allowed to react, with stirring, for an additional 2 days at room temperature. The solids were removed by filtration and the filtrate was concentrated. The resulting residue was purified by flash column chromatography (6% (v/v) of CH$_3$OH in CH$_2$Cl$_2$) to provide the desired product as a yellow solid (8 g, crude). $^1$H NMR (300 MHz, CDCl$_3$): δ 3.28 (s, 3H), 3.19 (s, 2H), 2.10 (s, 3H) ppm.

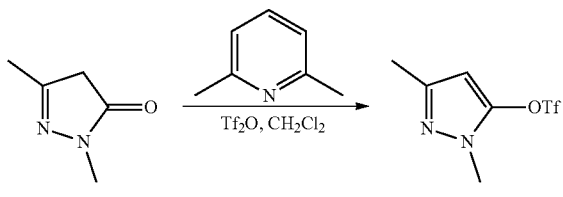

Compound 23.2.
1,3-Dimethyl-4,5-dihydro-1H-pyrazol-5-yl trifluoromethanesulfonate To a solution of 2,5-dimethyl-2,4-dihydro-3H-pyrazol-3-one (23.1, 2 g, 17.84 mmol) in dichloromethane (20 mL) at 0° C. was added 2,6-dimethylpyridine (2.86 g, 26.76 mmol) dropwise, followed by the dropwise addition of triflic anhydride (6.54 g, 23.18 mmol). The resulting solution was stirred for 2 h at room temperature and then was quenched by the addition of H$_2$O (20 mL). The resulting solution was extracted with dichloromethane (2×25 mL) and the combined organic layers were dried over anhydrous MgSO$_4$, filtered and concentrated. The resulting residue was purified by flash chromatography (9% (v/v) EtOAc in petroleum ether) to provide the desired product as a yellow oil (0.750 g, 17%). $^1$H NMR (300 MHz, CDCl$_3$): δ 5.93 (s, 1H), 3.75 (s, 3H), 2.24 (s, 3H) ppm.

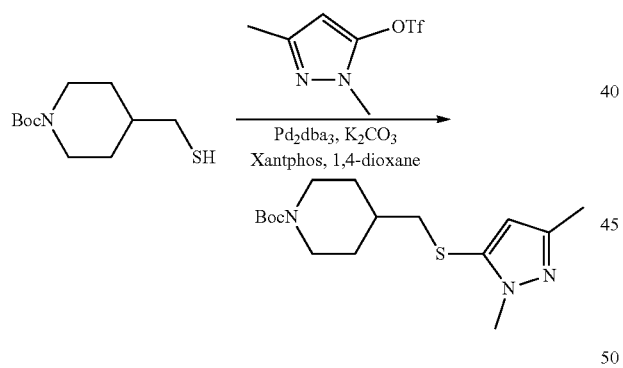

Compound 23.3. tert-Butyl 4-(((1,3-dimethyl-1H-pyrazol-5-yl)thio)methyl)piperidine-1-carboxylate To a solution of 1,3-dimethyl-4,5-dihydro-1H-pyrazol-5-yl trifluoromethanesulfonate (23.2, 1.9 g, 7.78 mmol) in 1,4-dioxane (50 mL) was added tert-butyl 4-(mercaptomethyl)piperidine-1-carboxylate (1.3, 1.8 g, 7.78 mmol), potassium carbonate (2.69 g, 19.46 mmol), Xantphos (0.450 g, 0.78 mmol), and Pd$_2$(dba)$_3$ (0.403 g, 0.44 mmol). The resulting solution was stirred for 4 h at 100° C. The reaction mixture was cooled to room temperature, the solids were removed by filtration, and the filtrate was concentrated. The resulting residue was purified by flash chromatography (22% EtOAc in petroleum ether) to provide the desired product as a yellow oil (1.95 g, 77%). $^1$H NMR (300 MHz, CDCl$_3$): δ 6.08 (s, 1H), 4.13-4.09 (m, 2H), 3.84 (s, 3H), 2.71-2.63 (m, 4H), 2.25 (s, 3H), 1.82 (d, J=12.9 Hz, 2H), 1.60-1.50 (m, 1H), 1.45 (s, 9H), 1.23-1.12 (m, 2H) ppm.

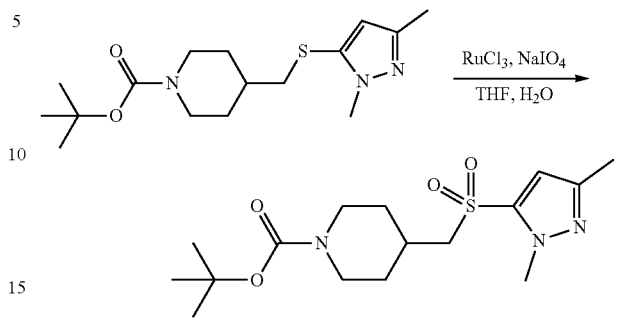

Compound 23.4. tert-Butyl 4-(((1,3-dimethyl-1H-pyrazol-5-yl)sulfonyl)methyl)piperidine-1-carboxylate Compound 23.4 was prepared in a similar manner to compound 14.2 to provide the desired product as a yellow oil (1.60 g, 7%). LC-MS (ES, m/z): 437 [M+H]$^+$; $^1$H NMR (300 MHz, DMSO-d6): δ 6.61 (s, 1H), 4.16-4.06 (m, 5H), 3.07 (d, J=6.3 Hz, 2H), 2.79-2.70 (m, 2H), 2.28 (s, 3H), 2.19-2.10 (m, 1H), 1.87 (d, J=13.5 Hz, 2H), 1.45 (s, 9H), 1.31-1.24 (m, 2H) ppm.

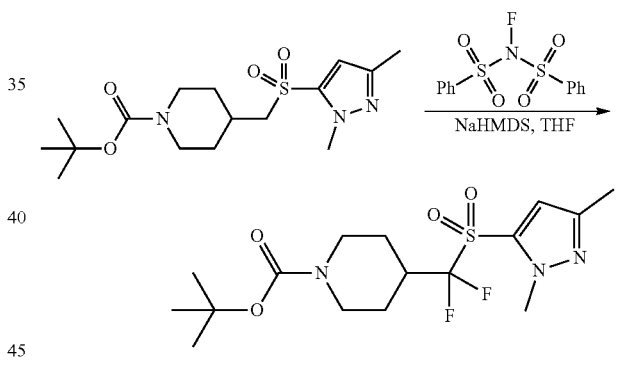

Compound 23.5. tert-Butyl 4-(((1,3-dimethyl-1H-pyrazol-5-yl)sulfonyl)difluoromethyl)-piperidine-1-carboxylate Compound 23.5 was prepared in a similar manner to compound 4.4 to provide the desired product as a yellow solid (0.66 g, crude), which was used as is in the next reaction without purification. $^1$H NMR (400 MHz, CDCl$_3$): δ 6.77 (s, 1H), 422-4.27 (d, J=13.2 Hz, 3H), 4.06 (s, 3H), 2.67-2.79 (m, 3H), 2.31 (s, 3H), 2.03-2.07 (d, J=12.9 Hz, 2H), 1.57-1.67 (m, 2H), 1.46 (s, 9H), 1.28 (m, 2H) ppm.

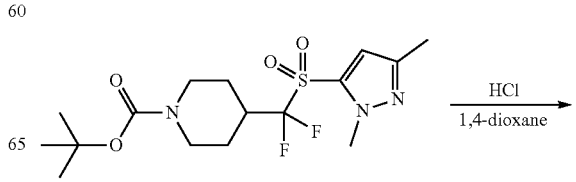

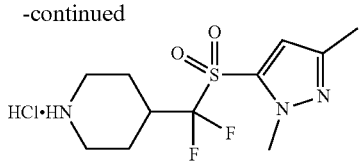

Compound 23.6. 4-(((1,3-Dimethyl-1H-pyrazol-5-yl)sulfonyl)difluoromethyl)piperidine hydrochloride Compound 23.6 was prepared in a similar manner to compound 9.5 to provide the desired product as a yellow solid (0.51 g, crude). LC-MS (ES, m/z): 294 [M+H]+.

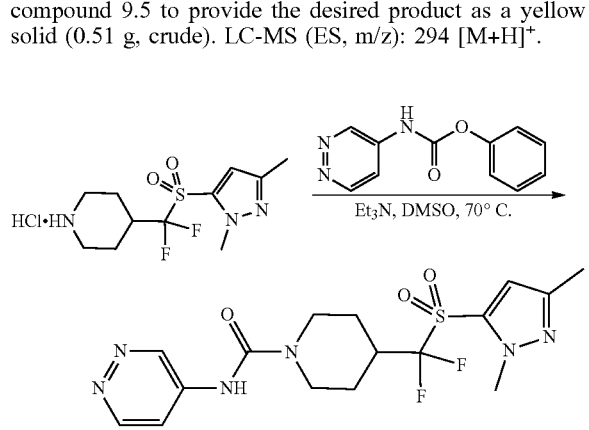

Compound 23. 4-(((1,3-Dimethyl-1H-pyrazol-5-yl)sulfonyl)difluoromethyl)-N-(pyridazin-4-yl)piperidine-1-carboxamide Compound 23 was prepared in a similar manner to compound 9 to provide the desired product as a yellow solid (0.33 g, 47%). LC-MS (ES, m/z): 415 [M+H]+; $^1$H NMR (300 MHz, DMSO-d6): δ 9.27-9.23 (m, 2H), 8.88 (m, 1H), 7.45 (m, 1H), 7.03 (s, 1H). 4.24 (d, J=13.2 Hz, 2H), 4.00 (s, 3H), 3.02-2.88 (m, 3H), 2.25 (s, 3H), 2.01 (d, J=12.0 Hz, 2H), 1.59-1.46 (m, 2H) ppm.

Example 24. Preparation of 4-(((3-cyclopropyl-1-methyl-1H-pyrazol-5-yl)sulfonyl)difluoromethyl)-N-(pyridazin-4-yl)piperidine-1-carboxamide

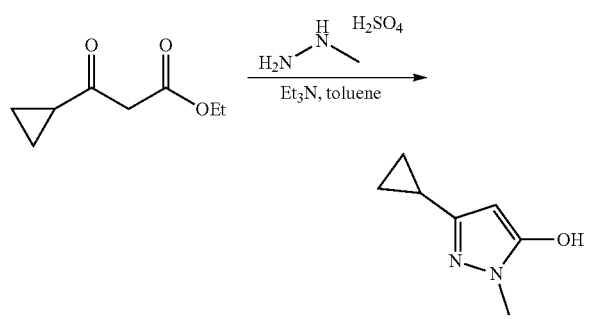

Compound 24.1.
3-Cyclopropyl-1-methyl-1H-pyrazol-5-ol

Compound 24.1 was prepared in a similar manner to compound 23.1 to provide the desired product as a yellow solid (1.60 g, 45%). LC-MS (ES, m/z): 139 [M+H]+; $^1$H NMR (300 MHz, DMSO-d6): δ 10.61 (s, 1H), 5.02 (s, 1H), 3.58 (s, 3H), 1.62-1.73 (m, 1H), 0.72-0.81 (m, 2H), 0.53-0.67 (m, 2H) ppm.

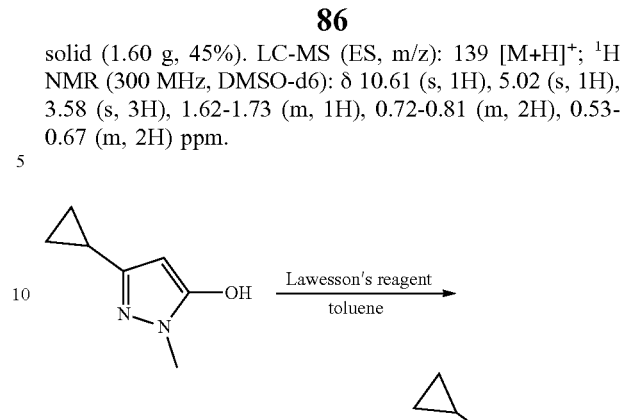

Compound 24.2.
3-Cyclopropyl-1-methyl-1H-pyrazole-5-thiol

To a solution of 3-cyclopropyl-1-methyl-1H-pyrazol-5-ol (1.6 g, 11.58 mmol) in toluene (30 mL) was added Lawesson's reagent (4.68 g, 11.58 mmol). The resulting solution was stirred overnight at 60° C., cooled to room temperature and then concentrated. The resulting residue was purified by flash chromatography (chloroform/methanol=20/1 (v/v)) to provide the desired product as a yellow oil (1.1 g, 62%). LC-MS (ES, m/z): 155 [M+H]+.

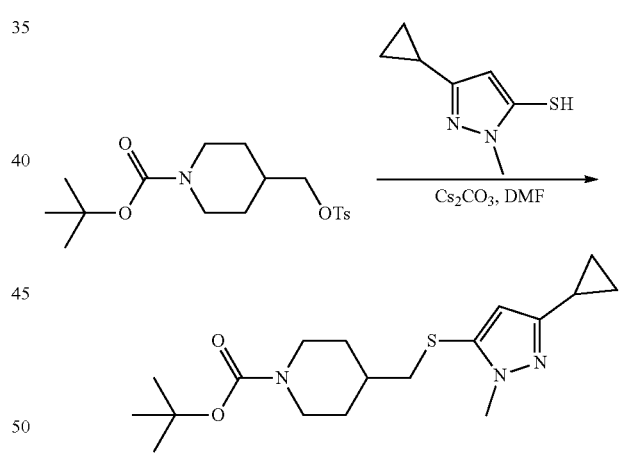

Compound 24.3. tert-Butyl 4-(((3-cyclopropyl-1-methyl-1H-pyrazol-5-yl)thio)methyl)-piperidine-1-carboxylate To a solution of 3-cyclopropyl-1-methyl-1H-pyrazole-5-thiol (24.2, 1.1 g, 7.13 mmol) in DMF (20 mL) was added tert-butyl 4-((tosyloxy)methyl)piperidine-1-carboxylate (1.1, 2.63 g, 7.12 mmol), and Cs$_2$CO$_3$ (4.6 g, 14.12 mmol). The reaction mixture was stirred for 3 h at room temperature, and then was quenched by the addition of H$_2$O (100 mL) and extracted with EtOAc (3×30 mL). The combined organic layers were dried over anhydrous Na$_2$SO$_4$, filtered and concentrated to provide the desired product as a yellow oil (1.5 g, 60%). LC-MS (ES, m/z): 352 [M+H]+

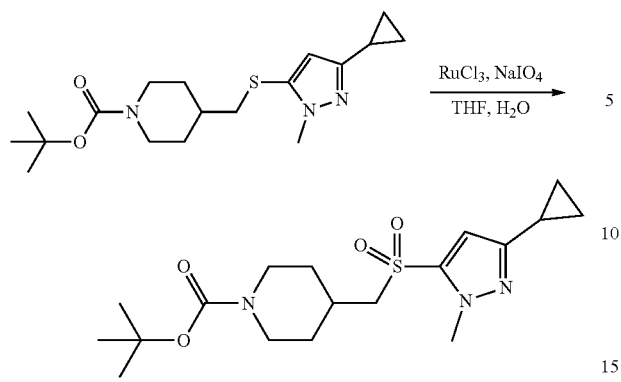

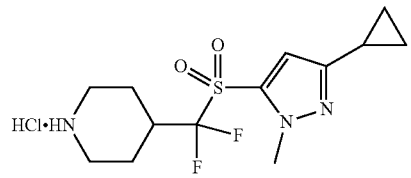

Compound 24.4. tert-Butyl 4-(((3-cyclopropyl-1-methyl-1H-pyrazol-5-yl)sulfonyl)methyl)piperidine-1-carboxylate Compound 24.4 was prepared in a similar manner to compound 14.2 to provide the desired product as a yellow oil (1.60 g, 7%). LC-MS (ES, m/z): 406 [M+Na]⁺; ¹H NMR (300 MHz, DMSO-d6): δ 6.66 (s, 1H), 3.96 (s, 3H), 3.83-3.87 (d, J=18.6 Hz, 2H), 3.40-3.42 (d, J=6.3 Hz, 2H), 2.74 (s, 1H), 1.99-2.03 (m, 1H), 1.87-1.93 (m, 1H), 1.72-1.75 (d, J=11.1 Hz, 2H), 1.38 (s, 9H), 1.15-1.25 (m, 2H), 0.80-0.90 (m, 2H), 0.65-0.70 (m, 2H) ppm.

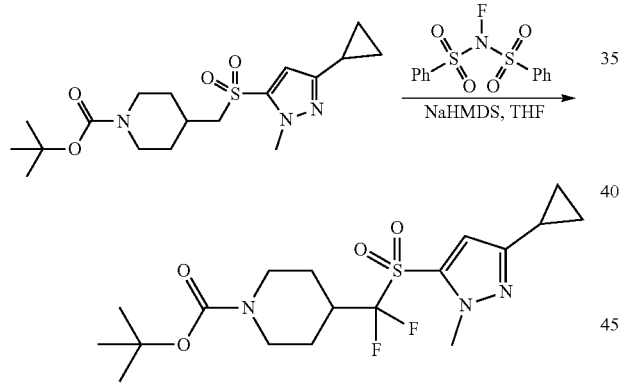

Compound 24.5. tert-Butyl 4-(((3-cyclopropyl-1-methyl-1H-pyrazol-5-yl)sulfonyl)difluoromethyl)piperidine-1-carboxylate Compound 24.5 was prepared in a similar manner to compound 4.4 to provide the desired product as a yellow solid (0.70 g, 64%). LC-MS (ES, m/z): 406 [M-CH₃+H]⁺.

Compound 24.6. 4-(((3-Cyclopropyl-1-methyl-1H-pyrazol-5-yl)sulfonyl)difluoromethyl)-piperidine hydrochloride Compound 24.6 was prepared in a similar manner to compound 9.5 to provide the desired product as a red solid (0.40 g, crude). LC-MS (ES, m/z): 320 [M+H]⁺.

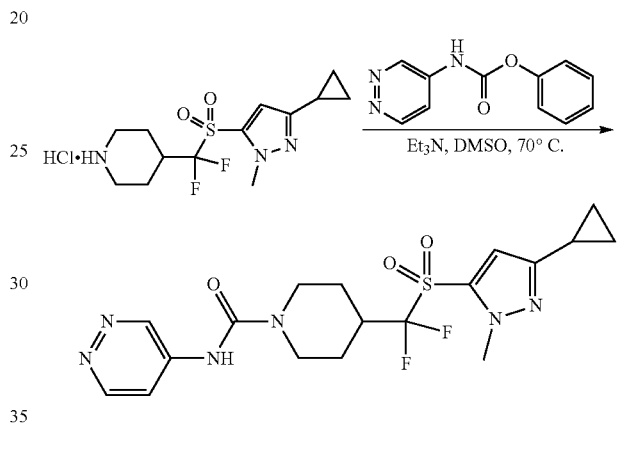

Compound 24. 4-(((3-Cyclopropyl-1-methyl-1H-pyrazol-5-yl)sulfonyl)difluoromethyl)-N-(pyridazin-4-yl)piperidine-1-carboxamide Compound 24 was prepared in a similar manner to compound 9 to provide the desired product as a yellow solid (0.33 g, 47%). LC-MS (ES, m/z): 441 [M+H]⁺; ¹H NMR (300 MHz, CDCl₃): δ 9.13-9.14 (d, J=2.4 Hz, 1H), 8.88-8.90 (d, J=6.3 Hz, 1H), 8.63 (s, 1H), 8.02-8.05 (m, 1H), 6.66 (s, 1H), 4.39-4.43 (d, J=13.5 Hz, 2H), 4.03 (s, 3H), 2.92-3.00 (m, 2H), 2.71-2.79 (m, 1H), 2.12-2.16 (d, J=2.4 Hz, 2H), 1.88-1.96 (m, 1H), 1.66-1.76 (m, 2H), 0.99 (m, 2H), 0.98 (m, 2H) ppm.

Example 25. Preparation of 4-(difluoro((2-(hydroxymethyl)phenyl)sulfonyl)methyl)-N-(pyridazin-4-yl)piperidine-1-carboxamide

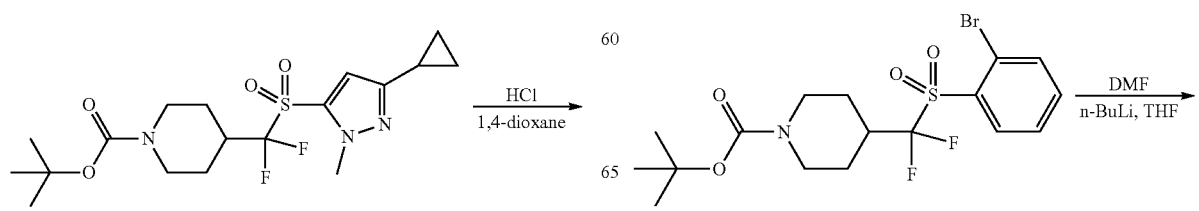

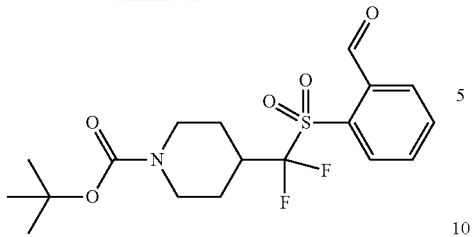

Compound 25.1. tert-Butyl 4-(difluoro((2-formylphenyl)sulfonyl)methyl)piperidine-1-carboxylate To a solution of tert-butyl 4-[[(2-bromobenzene)sulfonyl] difluoromethyl]piperidine-1-carboxylate (600 mg, 1.32 mmol) in THF (15 mL) at −78° C. was added n-BuLi (0.52 mL, 2.5M in n-hexane, 2.64 mmol) dropwise. The reaction mixture was stirred for 30 minutes at −78° C. before DMF (0.300 g, 4.10 mmol) was added. The resulting solution was allowed to react, with stirring, for an additional 5 min while the temperature was maintained at −78° C. The reaction was then quenched by the addition of NH$_4$Cl$_{(sat.)}$ (2 mL). The resulting solution was extracted with EtOAc (3×100 mL) and the organic layers combined and dried over anhydrous sodium sulfate and concentrated under vacuum to provide (0.600 g, crude) of the desired product as yellow oil which was used without further purification. LC-MS (ES, m/z): 425.9 [M+H]$^+$.

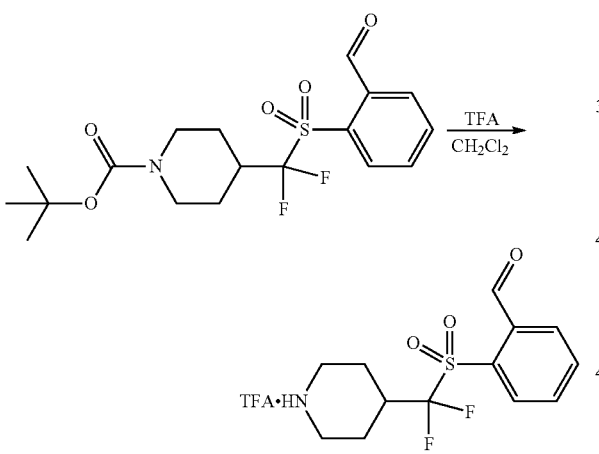

Compound 25.2. 2-((Difluoro(1-(2,2,2-trifluoroacetyl)-1l4-piperidin-4-yl)methyl)sulfonyl)benzaldehyde Compound 25.2 was prepared in a similar manner to compound 4.5 to provide the desired product as a yellow solid (0.40 g, crude) which was used as is without further purification. LC-MS (ES, m/z): 304 [M+H]$^+$.

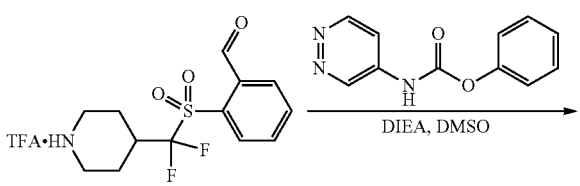

Compound 25.3. 4-(Difluoro((2-formylphenyl)sulfonyl)methyl)-N-(pyridazin-4-yl)piperidine-1-carboxamide Compound 25.2 was prepared in a similar manner to compound 4 to provide the desired product as a yellow solid (0.150 g, 27%). LC-MS (ES, m/z): 425 [M+H]$^+$; $^1$H NMR (300 MHz, DMSO-d6): δ 10.57 (s, 1H), 9.33-9.15 (m, 2H), 8.87 (m, 1H), 8.17-7.88 (m, 4H), 7.81-7.69 (m, 1H), 4.24 (d, J=13.2 Hz, 2H), 3.01 (m, 3H), 2.00 (d, J=19.3 Hz, 2H), 1.54 (m, 2H) ppm.

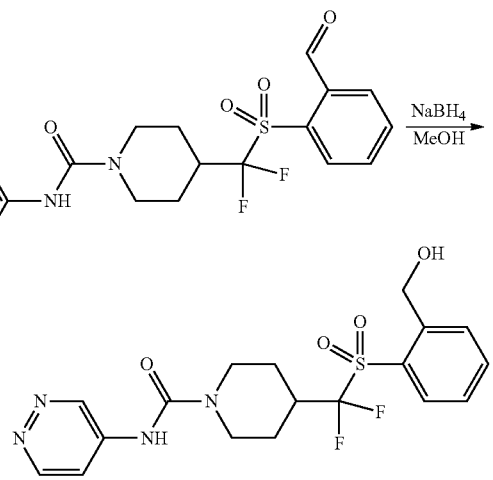

Compound 25. 4-(Difluoro((2-(hydroxymethyl)phenyl)sulfonyl)methyl)-N-(pyridazin-4-yl)piperidine-1-carboxamide To a solution of 4-(difluoro((2-formylphenyl)sulfonyl) methyl)-N-(pyridazin-4-yl)piperidine-1-carboxamide (25.3, 0.150 g, 0.35 mmol) in methanol (10.0 g, 312.09 mmol) at 0° C. was added NaBH$_4$ (0.017 g, 0.45 mmol). The resulting solution was stirred for 1 h at room temperature. The reaction was then quenched by the addition of NH$_4$Cl$_{(sat.)}$ (20 mL). The resulting solution was extracted with EtOAc (3×50 mL) and the organic layers were combined, dried over anhydrous sodium sulfate and concentrated. The resulting residue was purified by Prep-HPLC (Column: X Bridge C18, 19*250 mm, 10 um; Mobile Phase A: Water/10 mM NH$_4$HCO$_3$, Mobile Phase B: ACN; Flow rate: 30 mL/min; Gradient: 15-60% B in 6 min; 254 nm) to provide (0.0356 g, 24%) of the desired product as a white solid. LC-MS (ES, m/z): 427 [M+H]$^+$; $^1$H NMR (300 MHz, CD$_3$OD): δ 9.22-9.26 (m, 2H), 8.87-8.89 (m, 1H), 7.89-7.99 (m, 3H), 7.73-7.75 (m, 1H), 6.60-6.64 (m, 1H), 5.56-5.58 (t, J=5.6 Hz, 1H), 4.90-4.92 (d, J=5.6 Hz, 2H), 4.22-4.25 (m, 2H), 2.88-2.97 (m, 3H), 2.00-2.07 (m, 2H), 1.46-1.57 (m, 2H) ppm.

Example 26. N-(Isoxazol-3-yl)-4-(2-((1-methyl-3-(trifluoromethyl)-1H-pyrazol-4-yl)sulfonyl)propan-2-yl)piperidine-1-carboxamide

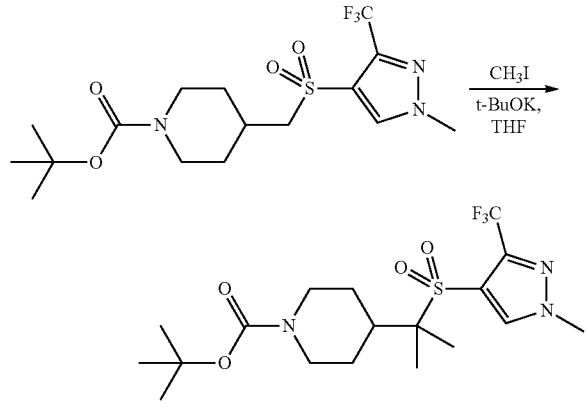

Compound 26.1. tert-Butyl 4-(2-((1-methyl-3-(trifluoromethyl)-1H-pyrazol-4-yl)sulfonyl)propan-2-yl)piperidine-1-carboxylate To a solution of tert-butyl 4-(((1-methyl-3-(trifluoromethyl)-1H-pyrazol-4-yl)sulfonyl)methyl)piperidine-1-carboxylate (16.3, 1.0 g, 2.43 mmol) in THF (20 mL) at −78° C. was added dropwise a solution of t-BuOK (1N in THF, 7.2 mL, 7.29 mmol). The resulting solution was stirred for 20 min at −78° C. before a solution of MeI (858 mg, 6.07 mmol) in THF (2 mL) was added dropwise. The resulting solution was allowed to react, with stirring, for an additional 1 h while the temperature was maintained at −60° C. in a liquid nitrogen bath. The reaction was then quenched by the addition of NH$_4$Cl$_{(sat.)}$ (50 mL). The resulting solution was extracted with EtOAc (3×100 mL), washed with brine (2×100 mL), dried over anhydrous sodium sulfate, filtered and concentrated. The resulting residue was purified by Flash-Prep-HPLC ((IntelFlash-1): Column, C18 silica gel; mobile phase, CH$_3$CN:H$_2$O=20:80 (v/v) increasing to CH$_3$CN:H$_2$O=95:5 (v/v) within 35 min; Detector, UV 254 nm) to provide the desired product as a white solid (0.150 g, 14%). LC-MS (ES, m/z): 462.1 [M+H]$^+$.

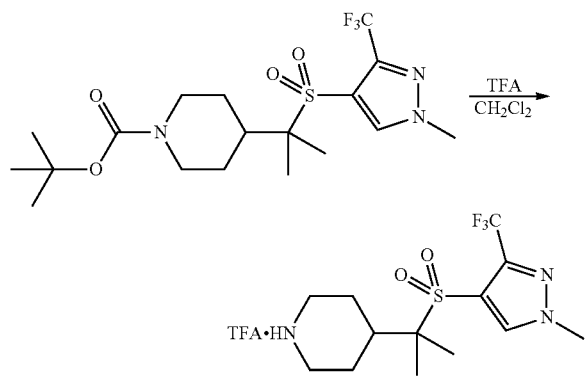

Compound 26.2. 4-(2-((1-Methyl-3-(trifluoromethyl)-1H-pyrazol-4-yl)sulfonyl)propan-2-yl)piperidine Compound 26.2 was prepared in a similar manner to compound 4.5 to provide the desired product as a yellow solid (0.25 g, crude) which was used as is without further purification. LC-MS (ES, m/z): 340.0 [M+H]$^+$.

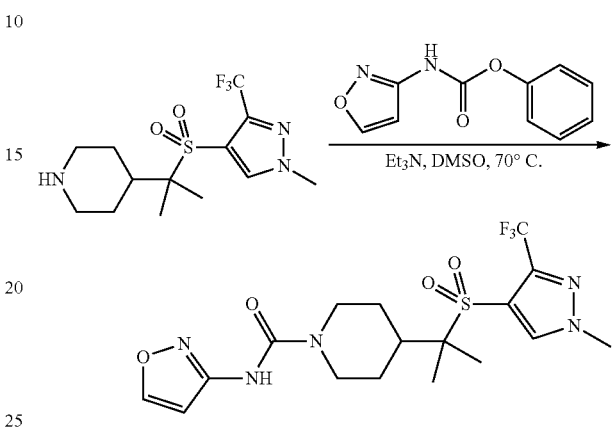

Compound 26. N-(Isoxazol-3-yl)-4-(2-((1-methyl-3-(trifluoromethyl)-1H-pyrazol-4-yl)sulfonyl)propan-2-yl)piperidine-1-carboxamide Compound 26 was prepared in a similar manner to compound 9 to provide the desired product as a yellow solid (0.024 g, 13%). LC-MS (ES, m/z): 448.0 [M+H]$^+$; $^1$H NMR (300 MHz, CD$_3$OD): δ 8.40 (s, 1H), 8.33 (s, 1H), 6.70 (s, 1H), 4.21 (d, J=13.8 Hz, 2H), 3.99 (s, 3H), 2.90-2.81 (m, 2H), 2.22-2.03 (m, 3H), 1.49-1.44 (m, 2H), 1.27 (s, 6H) ppm.

Example 27. Preparation of 4-(2-((3-chloro-1-methyl-1H-pyrazol-4-yl)sulfonyl)propan-2-yl)-N-(isoxazol-3-yl)piperidine-1-carboxamide

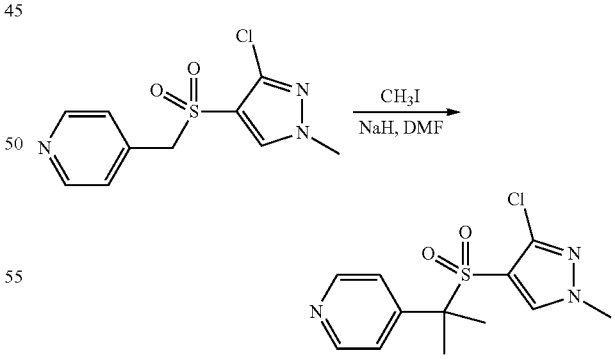

Compound 27.1. 4-(2-((3-Chloro-1-methyl-1H-pyrazol-4-yl)sulfonyl)propan-2-yl)pyridine To a solution of 4-[(3-chloro-1-methyl-1H-pyrazole-4-sulfonyl)methyl]pyridine (680 mg, 2.50 mmol) in DMF (10 mL) at 0° C. was added sodium hydride (200 mg, 8.33 mmol), followed by MeI (713 mg, 5.00 mmol). The resulting solution was stirred for 2 h at 0° C. in an ice/salt bath. The reaction was then quenched by the addition of water (20 mL). The resulting solution was extracted with EtOAc (3×20 mL), washed with brine (3×20 mL), dried over anhydrous magnesium sulfate, filtered and concentrated. The resulting residue was purified by flash chromatography (dichloromethane/methanol (20:1)) to provide the desired product as a yellow solid (0.650 g, 87%). LC-MS (ES, m/z): 299.9 [M+H]⁺; ¹H NMR (300 MHz, DMSO-d6): δ 8.60-8.53 (m, 2H), 8.25 (s, 1H), 7.47-7.40 (m, 2H), 3.84 (s, 3H), 1.73 (s, 6H) ppm.

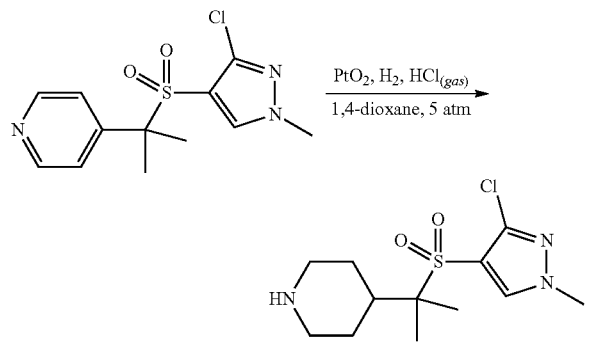

Compound 27.2. 4-(2-((3-Chloro-1-methyl-1H-pyrazol-4-yl)sulfonyl)propan-2-yl)piperidine To a solution of 4-(2-((3-chloro-1-methyl-1H-pyrazol-4-yl)sulfonyl)propan-2-yl)pyridine (27.1, 0.200 g, 0.67 mmol) in 4N HCl in 1, 4-dioxane (3 mL) was added PtO₂ (0.80 g, 0.27 mmol). Then H₂(g) was introduced in the mixture and a pressure of 5 atm was maintained while the reaction mixture was stirred at 35° C. for 48 h. The reaction mixture was cooled to room temperature and filtered. The filtrate was concentrated and the resulting residue was purified by Prep-HPLC (Column: XBridge Prep C18 OBD Column, Sum, 19*150 m; Mobile Phase A: H₂O (10 mmol/L NH₄HCO₃), Mobile Phase B: ACN; Flow rate: 20 mL/min; Gradient: 20% B to 40% B in 8 min; Detector, UV 254 nm) to provide the desired product as a white solid (0.20 g, 10%). LC-MS (ES, m/z): 306.0 [M+H]⁺.

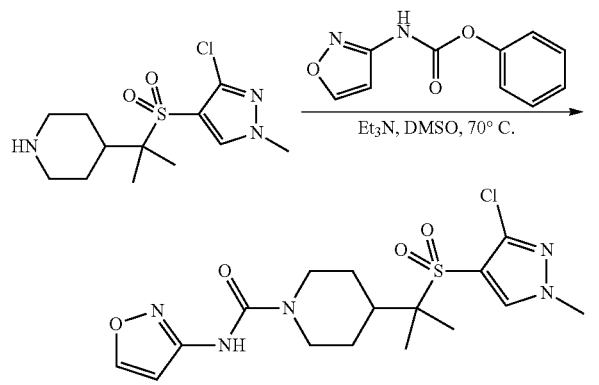

Compound 27. 4-(2-((3-Chloro-1-methyl-1H-pyrazol-4-yl)sulfonyl)propan-2-yl)-N-(isoxazol-3-yl)piperidine-1-carboxamide Compound 27 was prepared in a similar manner to compound 9 to provide the desired product as a yellow solid (0.038 g, 16%). LC-MS (ES, m/z): 416.1 [M+H]⁺; ¹H NMR (400 MHz, CD₃OD): δ 8.45 (d, J=1.8 Hz, 1H), 8.23 (s, 1H), 6.76 (d, J=1.8 Hz, 1H), 4.26 (m, 2H), 3.94 (s, 3H), 2.97-2.85 (m, 2H), 2.15 (m, 3H), 1.55-1.39 (m, 2H), 1.33 (s, 6H) ppm.

Example 28. Preparation of 4-(3,3-difluoro-1-((3-fluorophenyl)sulfonyl)cyclobutyl)-N-(pyridazin-4-yl)piperidine-1-carboxamide Compound 28.1. tert-Butyl 4-(1-((3-fluorophenyl)sulfonyl)-3-hydroxycyclobutyl)piperidine-1-carboxylate To a solution of tert-butyl 4-(((3-fluorophenyl)sulfonyl)methyl)piperidine-1-carboxylate (5.3, 2.0 g, 5.60 mmol) in THF (100 mL) at 10° C. was added n-BuLi (2.5M, 6.7 mL, 16.8 mmol) dropwise. The resulting solution was stirred for 30 min at −10° C. before 2-(chloromethyl)oxirane (1.04 g, 11.24 mmol) was added dropwise. The reaction mixture was stirred overnight while warming to room temperature, and then was quenched by the addition of water (30 mL). The resulting solution was extracted with EtOAc (2×50 mL), dried over anhydrous sodium sulfate, filtered and concentrated. The resulting residue was purified by Prep-HPLC ((IntelFlash-1): Column, C18 silica gel; Mobile Phase A: Water with 10 mmol NH₄HCO₃, Mobile Phase B: ACN; Flow rate: 50 mL/min; Gradient: 0% B to 100% B in 40 min; Detector, UV 254 nm) to provide the desired product as a yellow solid (1.1 g, 47%). LC-MS (ES, m/z): 414.1 [M+H]⁺.

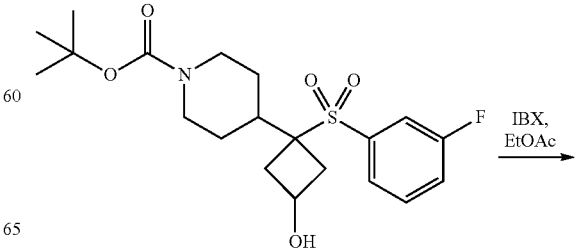

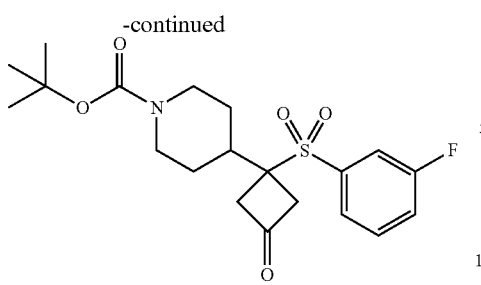

Compound 28.2. tert-Butyl 4-(1-((3-fluorophenyl)sulfonyl)-3-oxocyclobutyl)piperidine-1-carboxylate To a solution of tert-butyl 4-(1-((3-fluorophenyl)sulfonyl)-3-hydroxycyclobutyl)piperidine-1-carboxylate (28.1, 1.1 g, 2.66 mmol) in EtOAc (40 mL) was added IBX (1.49 g, 5.32 mmol). The resulting solution was stirred overnight at 75° C. The reaction mixture was cooled to room temperature and the solids were removed by filtration. The filtrate was washed with brine (2×30 mL), dried over anhydrous sodium sulfate, filtered and concentrated to provide the desired product as a yellow oil (1.0 g, crude), which was used as is without further purification. LC-MS (ES, m/z): 397.0 [M-CH$_3$+H]$^+$.

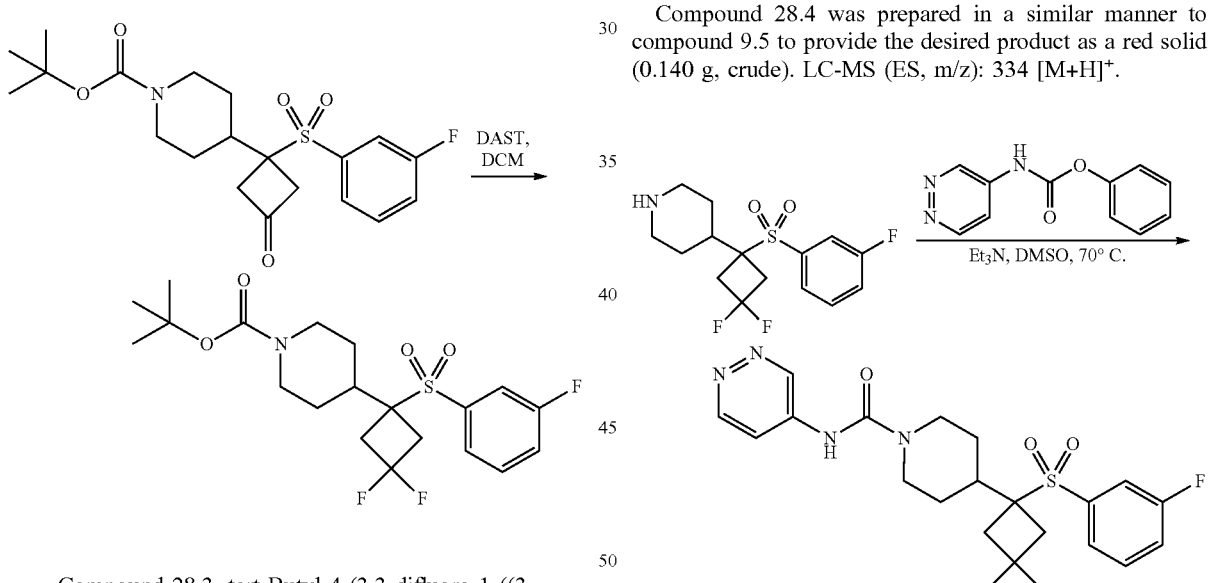

Compound 28.3. tert-Butyl 4-(3,3-difluoro-1-((3-fluorophenyl)sulfonyl)cyclobutyl)-piperidine-1-carboxylate To a solution of tert-butyl 4-(1-((3-fluorophenyl)sulfonyl)-3-oxocyclobutyl)piperidine-1-carboxylate (0.300 g, 0.73 mmol) in dichloromethane (10 mL) was added DAST (1.17 g, 7.26 mmol). The resulting solution was stirred for 3 days at room temperature. The reaction was then quenched by the addition of water (10 mL), and the pH of the solution was adjusted to 7 with the addition of sodium bicarbonate. The resulting solution was extracted with DCM (2×20 mL), dried over anhydrous magnesium sulfate, filtered and concentrated. The resulting residue was purified by preparative thin layer chromatography (petroleum ether/ethyl acetate=1/1 (v/v)) to provide the desired product as a yellow solid (0.150 g, 47%). $^1$H NMR (400 MHz, DMSO-d6): δ 7.72-7.86 (m, 4H), 3.92-4.02 (m, 2H), 3.22-3.32 (m, 4H), 3.08-3.15 (m, 2H), 1.75-1.79 (m, 3H), 1.36 (s, 9H), 1.18-1.20 (m, 2H) ppm.

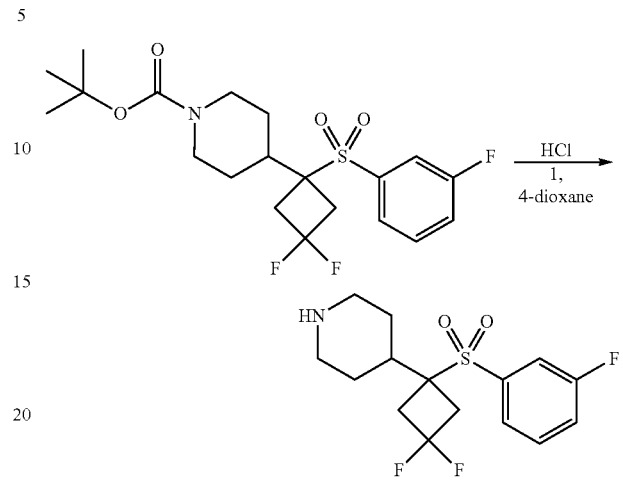

Compound 28.4. 4-(3,3-Difluoro-1-((3-fluorophenyl)sulfonyl)cyclobutyl)piperidine Compound 28.4 was prepared in a similar manner to compound 9.5 to provide the desired product as a red solid (0.140 g, crude). LC-MS (ES, m/z): 334 [M+H]$^+$.

Compound 28. 4-(3,3-Difluoro-1-((3-fluorophenyl)sulfonyl)cyclobutyl)-N-(pyridazin-4-yl)piperidine-1-carboxamide Compound 28 was prepared in a similar manner to compound 4 to provide the desired product as a white solid (0.027 g, 14%). LC-MS (ES, m/z): 455 [M+H]$^+$; $^1$H NMR (300 MHz, DMSO-d6): δ 9.18 (d, J=0.9 Hz, 1H), 8.83 (dd, J1=0.9 Hz, J2=6.0 Hz, 1H), 7.84-7.66 (m, 4H), 7.57-7.54 (m, 1H), 4.22 (d, J=13.8 Hz, 2H), 3.33-3.23 (m, 2H), 3.04-2.94 (m, 2H), 2.81-2.73 (m, 2H), 2.00-1.92 (m, 3H), 1.47-1.42 (m, 2H) ppm.

Example 29. Preparation of 4-((S)-1-((3-(difluoromethyl)-1-methyl-1H-pyrazol-4-yl)sulfonyl)-1-fluoroethyl)-N-(2-((S)-1-hydroxyethyl)pyridin-4-yl)piperidine-1-carboxamide

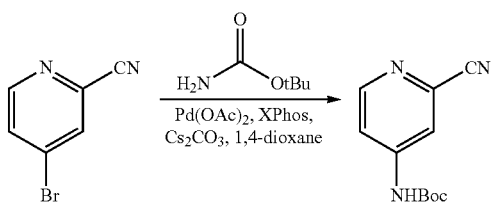 [SMILES: N#Cc1cc(Br)ccn1 ; CC(C)(C)OC(N)=O ; CC(C)(C)OC(=O)Nc1ccnc(C#N)c1]

Example 29.1. tert-Butyl (2-cyanopyridin-4-yl)carbamate

To a solution of 4-bromopyridine-2-carbonitrile (20 g, 109.29 mmol) in 1,4-dioxane (300 mL) was added Pd(OAc)$_2$ (2.98 g, 13.27 mmol), XPhos (18.9 g, 39.34), Cs$_2$CO$_3$ (50.3 g, 154.38 mmol). The resulting solution was stirred for 1 h at 100° C. The reaction was cooled to room temperature and the solids were removed by filtration. The filtrate was concentrated and the resulting residue was purified by flash column chromatography (EtOAc/petroleum ether=1/3 (v/v)) to provide the desired product as a yellow solid (23 g, 95%). LC-MS (ES, m/z): 220 [M+H]$^+$. $^1$H NMR (300 MHz, CDCl$_3$): δ 8.49 (d, J=5.6 Hz, 1H), 7.87 (d, J=2.2 Hz, 1H), 7.43 (dd, J=5.6, 2.2 Hz, 1H), 6.90 (s, 1H), 1.54 (s, 9H) ppm.

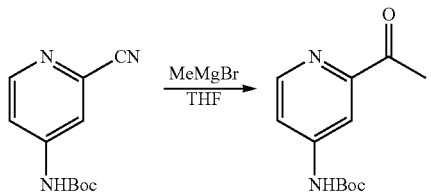 [SMILES: "MeMgBr" ; CC(C)(C)OC(=O)Nc1ccnc(C#N)c1 ; CC(=O)c1cc(NC(=O)OC(C)(C)C)ccn1 ; "THF"]

Example 29.2. tert-Butyl (2-acetylpyridin-4-yl)carbamate

To a solution of tert-butyl (2-cyanopyridin-4-yl)carbamate (29.1, 23.0 g, 104.91 mmol) in THF (200 mL) at 0° C. was added a solution of MeMgBr (1M in THF, 125.4 mmol, 125.4 mL) dropwise. The resulting solution was stirred for 1 h and then was quenched by the addition of ice water (1000 mL). The resulting solution was extracted with EtOAc (3×500 mL) and the organic layers combined, washed with brine (2×200 mL) of brine, dried over anhydrous sodium sulfate and concentrated. The resulting residue was purified by flash column chromatography (EtOAc/petroleum ether=1/4 (v/v)) to provide the desired product as a white solid (21 g, 85%). LC-MS (ES, m/z): 237 [M+H]$^+$. $^1$H NMR (300 MHz, CDCl$_3$): δ 8.49 (d, J=5.4 Hz, 1H), 7.81-7.71 (m, 2H), 6.89 (s, 1H), 2.68 (s, 3H), 1.51 (s, 9H) ppm.

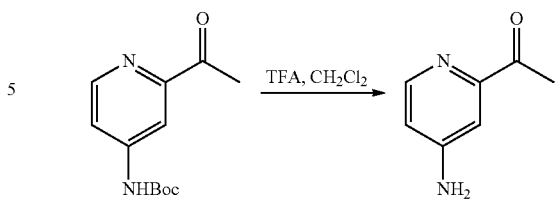

Example 29.3. 1-(4-Aminopyridin-2-yl)ethan-1-one

To a solution of tert-butyl N-(2-acetylpyridin-4-yl)carbamate (29.2, 2.3 g, 9.73 mmol) in dichloromethane (5 mL) was added trifluoroacetic acid (15 g, 132.70 mmol). The resulting solution was stirred overnight at room temperature and then was concentrated. The crude product was precipitated from ether, and the solids were collected by filtration to provide the desired product as a white solid (2.0 g, 82%). $^1$H NMR (300 MHz, DMSO-d6): δ 13.33 (s, 1H), 8.28 (s, 2H), 8.08 (d, J=6.8 Hz, 1H), 7.44 (d, J=2.4 Hz, 1H), 6.86 (dd, J=6.8, 2.4 Hz, 1H), 2.46 (m, 3H) ppm.

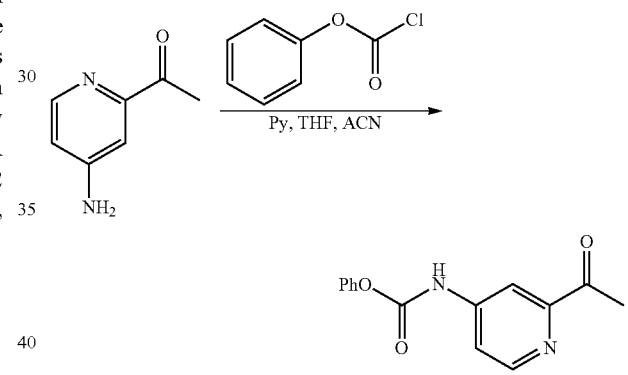

Example 29.4. Phenyl (2-acetylpyridin-4-yl)carbamate

To a solution of 1-(4-aminopyridin-2-yl)ethan-1-one (29.3, 5 g, 36.72 mmol) in ACN/THF (1:1 (v/v), 50 mL) and pyridine (4.74 g, 59.92 mmol) at 0° C. was added dropwise phenyl chloroformate (4.68 g, 29.89 mmol). The resulting solution was stirred for 2 h at room temperature. The resulting mixture was concentrated under vacuum and washed with ether (2×30 mL) to provide the desired product as a yellow solid (9 g, crude), which was used as is without further purification. LC-MS (ES, m/z): 257 [M+H]$^+$.

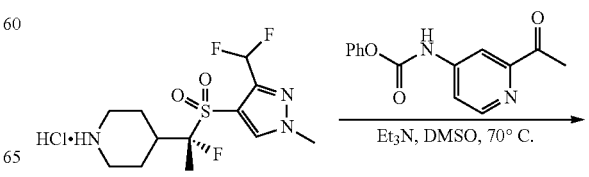

-continued

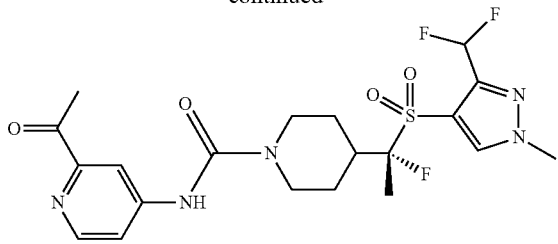

Example 29.5. (S)—N-(2-Acetylpyridin-4-yl)-4-(1-((3-(difluoromethyl)-1-methyl-1H-pyrazol-4-yl)sulfonyl)-1-fluoroethyl)piperidine-1-carboxamide Compound 29.5 was prepared in a similar manner to compound 4 to provide the desired product as a white solid (0.28 g, 37%). LC-MS (ES, m/z): 488 [M+H]$^+$; $^1$H NMR (300 MHz, DMSO-d6): δ 9.15 (s, 1H), 8.62 (s, 1H), 8.42 (d, J=5.6 Hz, 1H), 8.05 (d, J=2.1 Hz, 1H), 7.73 (dd, J=5.7, 2.2 Hz, 1H), 6.92 (d, J=53.0 Hz, 1H), 4.20 (d, J=12.6 Hz, 2H), 3.96 (s, 3H), 2.81 (m, 2H), 2.56 (s, 3H), 2.46 (m, 1H), 1.99 (d, J=13.2 Hz, 1H), 1.69 (d, J=12.5 Hz, 1H), 1.53 (d, J=22.8 Hz, 3H), 1.42-1.30 (m, 2H) ppm.

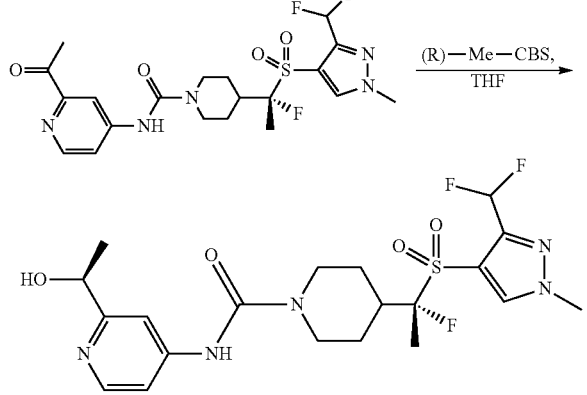

Example 29. 4-((S)-1-((3-(Difluoromethyl)-1-methyl-1H-pyrazol-4-yl)sulfonyl)-1-fluoroethyl)-N-(2-((S)-1-hydroxyethyl)pyridin-4-yl)piperidine-1-carboxamide To a solution of 4-((S)-1-((3-(difluoromethyl)-1-methyl-1H-pyrazol-4-yl)sulfonyl)-1-fluoroethyl)-N-(2-((S)-1-hydroxyethyl)pyridin-4-yl)piperidine-1-carboxamide (29.5, 0.120 g, 0.25 mmol) in THF (2 mL) at 0° C. was added (R)-Me-CBS (0.074 mL, 0.75 mmol) dropwise, followed by the dropwise addition of BH$_3$-THF (0.37 mL, 0.375 mmol). The resulting solution was stirred for 1 h at 0° C. in a water/ice bath and then was quenched by the addition of methanol (2 mL). The reaction mixture was concentrated and the resulting residue was purified by Prep-HPLC ((IntelFlash-1): Column, C18 silica gel; mobile phase, CH3 CN:H2O=5:95 increasing to CH3 CN:H2O=95:5 within 30 min; Detector, UV 254 nm) to provide the desired product as a racemate. The racemate (50 mg) was purified by Prep-SFC ((Prep SFC100): Column, CHIRALPAK-AD-H-SL002, 20*250 mm; Mobile Phase A: CO$_2$:50, Mobile Phase B: IPA:50; Flow rate: 40 mL/min; 220 nm; RT1=4.68 min; RT2=5.98 min) to provide the desired product as a white solid (0.029, 24%). LC-MS (ES, m/z): 490.2 [M+H]$^+$; $^1$H NMR (300 MHz, CD$_3$OD): δ 8.33 (s, 1H), 8.18 (d, J=5.8 Hz, 1H), 7.59 (d, J=2.1 Hz, 1H), 7.38 (dd, J=5.8, 2.2 Hz, 1H), 6.94 (t, J=53.1 Hz, 1H), 4.76 (m, 1H), 4.27 (m, 2H), 4.00 (s, 3H), 3.00-2.80 (m, 2H), 2.51 (s, 1H), 2.18 (d, J=13.2 Hz, 1H), 1.84 (d, J=13.3 Hz, 1H), 1.65-1.36 (m, 8H) ppm.

Example 30. Preparation of 4-fluoro-4-(2-((3-fluorophenyl)sulfonyl)propan-2-yl)-N-(pyridazin-4-yl)piperidine-1-carboxamide

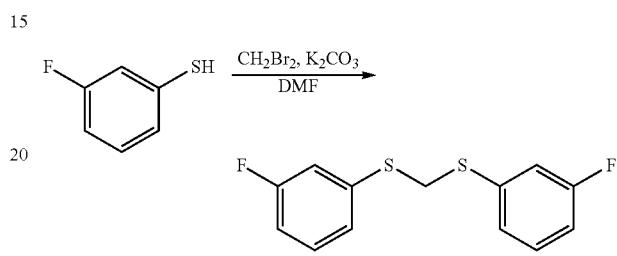

Example 30.1. Bis((3-fluorophenyl)thio)methane

To a solution of 3-fluorobenzene-1-thiol (2 g, 15.60 mmol) and potassium carbonate (3.23 g, 23.37 mmol) in DMF (10 mL) was added CH$_2$Br$_2$ (1.5 g, 8.58 mmol). The resulting solution was stirred overnight at 70° C., cooled to room temperature and then was concentrated. The resulting residue was purified by flash column chromatography (EtOAc/petroleum ether=1/10 (v/v)) to provide the desired product as a solid (2.1 g, 50%). $^1$H NMR (300 MHz, CD$_3$OD): δ 7.30-7.40 (m, 4H), 7.21-7.23 (m, 2H), 7.04-7.09 (m, 2H), 4.82 (s, 2H) ppm.

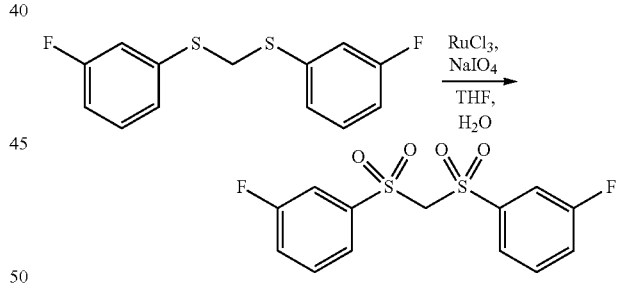

Example 30.2. Bis((3-fluorophenyl)sulfonyl)methane

To a solution of bis((3-fluorophenyl)sulfonyl)methane (30.1, 0.200 g, 0.75 mmol) in THF/H$_2$O (1:1 (v/v), 10 mL) was added NaIO$_4$ (1.6 g, 7.5 mmol) and RuCl$_3$ (0.15 g, 0.075 mmol). The resulting solution was stirred for 1 h at room temperature and then was quenched by the addition of water (20 mL). The resulting solution was extracted with EtOAc (3×20 mL), washed with brine (3×20 mL), dried over anhydrous magnesium sulfate, filtered and was concentrated to provide the desired product as a yellow solid (0.180 g, 73%), which was used without further purification. $^1$H NMR (400 MHz, DMSO-d6): δ 7.63-7.76 (m, 8H), 6.13 (s, 2H) ppm.

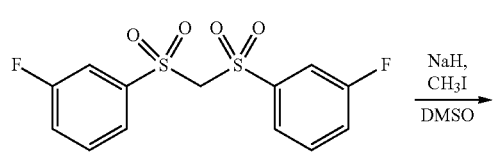

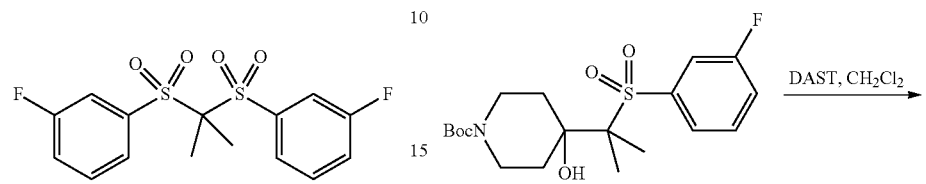

Example 30.3. 3,3'-(Propane-2,2-diyldisulfonyl)bis(fluorobenzene)

To a solution of bis((3-fluorophenyl)sulfonyl)methane (30.2, 2.0 g, 6.02 mmol) in DMSO (15 mL) was added sodium hydride (0.600 g, 15.00 mmol), followed by the addition of MeI (2.55 g, 17.96 mmol) over 30 minutes. The resulting solution was stirred for 2 h at room temperature and then was quenched by the addition of water (80 mL). The resulting solution was extracted with EtOAc (3×30 mL), washed with brine (2×30 mL), dried over anhydrous sodium sulfate, filtered and concentrated. The resulting residue was purified by flash column chromatography (EtOAc/petroleum ether=1/1 (v/v)) to provide the desired product as a white solid (1.8 g, 83%). $^1$H NMR (400 MHz, DMSO-d6): δ 7.72-7.88 (m, 8H), 1.65 (s, 6H) ppm.

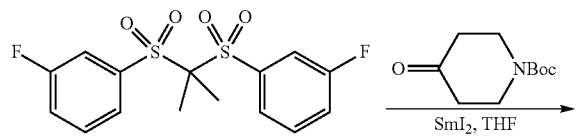

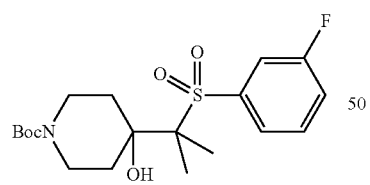

Example 30.4. tert-Butyl 4-(2-((3-fluorophenyl)sulfonyl)propan-2-yl)-4-hydroxypiperidine-1-carboxylate To a solution of 3,3'-(propane-2,2-diyldisulfonyl)bis(fluorobenzene) (30.3, 1.0 g, 2.77 mmol) and tert-butyl 4-oxopiperidine-1-carboxylate (1.6 g, 8.03 mmol) in THF (5 mL) was added SmI$_2$ (83 mL, 8.31 mmol). The resulting solution was stirred for 1 h at room temperature and then quenched by the addition of saturated NH$_4$Cl (400 mL) and water (10 mL). The resulting solution was extracted with EtOAc (3×150 mL), washed with brine (2×100 mL), dried over anhydrous sodium sulfate, filtered and concentrated. The resulting residue was purified by flash chromatography (EtOAc/petroleum ether=1/3 (v/v)) to provide the desired product as a white solid (0.830 g, 75%). $^1$H NMR (400 MHz, DMSO-d6): δ 7.57-7.70 (m, 4H), 4.97 (m, 1H), 3.77-3.79 (d, J=10.8, 2H), 2.95-2.97 (m, 2H), 1.76-1.97 (m, 4H), 1.41 (s, 9H), 1.22 (s, 6H) ppm.

Example 30.5. tert-Butyl 4-fluoro-4-(2-((3-fluorophenyl)sulfonyl)propan-2-yl)piperidine-1-carboxylate To a solution of tert-butyl 4-fluoro-4-(2-((3-fluorophenyl)sulfonyl)propan-2-yl)piperidine-1-carboxylate (30.4, 0.040 g, 0.10 mmol) in DCM (3 mL) at −30° C. was added DAST (0.024 g, 0.15 mmol). The resulting solution was stirred overnight while warming to 0° C. The reaction was then quenched by the addition of water (10 mL), extracted with EtOAc (3×10 mL), washed with brine (2×10 mL), dried over anhydrous sodium sulfate, filtered and was concentrated. The resulting residue was purified by flash column chromatography (ethyl acetate/petroleum ether=1/3 (v/v)) to provide the desired product as a white solid (0.025 g). LC-MS (ES, m/z): 389 [M-CH$_3$+H]$^+$.

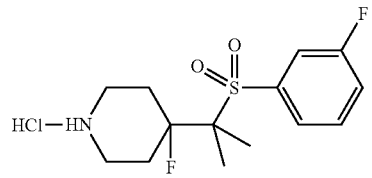

Example 30.6. 4-Fluoro-4-(2-((3-fluorophenyl)sulfonyl)propan-2-yl)piperidine hydrochloride Compound 30.6 was prepared in a similar manner to compound 9.5 to provide the desired product as a white solid (0.350 g, crude) which was used as is without further purification. LC-MS (ES, m/z): 304 [M+H]⁺.

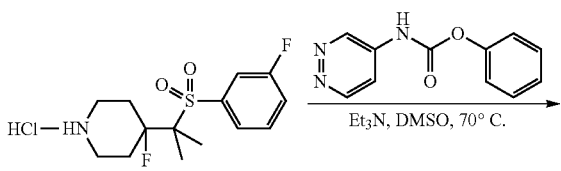

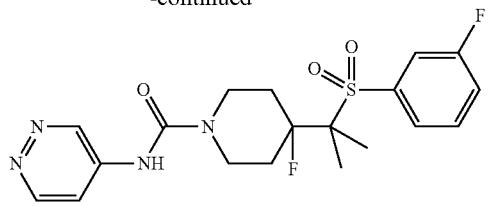

Example 30. 4-Fluoro-4-(2-((3-fluorophenyl)sulfonyl)propan-2-yl)-N-(pyridazin-4-yl)piperidine-1-carboxamide Compound 30 was prepared in a similar manner to compound 4 to provide the desired product as a white solid (0.070 g, 14%). LC-MS (ES, m/z): 425 [M+H]⁺; ¹H NMR (300 MHz, DMSO-d6): δ 9.26-9.28 (m, 2H), 8.87-8.89 (d, J=6.0 Hz, 1H), 7.62-7.77 (m, 5H), 4.10-4.15 (d, J=14.8 Hz, 2H), 2.96-3.32 (m, 2H), 2.22-2.52 (m, 2H), 1.359 (s, 6H) ppm.

The compounds in Table 1 were prepared according to the examples as described above.

TABLE 1

Representative compounds of the Invention and Analytical Data

| Structure | Name | Cmpd. No. | Ref. Example | Obs. Mass (M + H)+ | ¹H NMR |
|---|---|---|---|---|---|
| 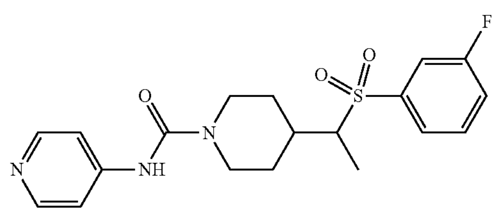 [SMILES: CC(C1CCN(C(=O)Nc2ccncc2)CC1)S(=O)(=O)c1cccc(F)c1] | 4-(1-((3-fluorophenyl)sulfonyl)ethyl)-N-(pyridin-4-yl)piperidine-1-carboxamide | 31 | 2 | 392 | 1H-NMR (400 MHz, DMSO-d6): δ 9.10 (s, 1H), 8.33 (d, J = 6.4 Hz, 2H), 7.76-7.72 (m, 3H), 7.68-7.64 (m, 1H), 7.53-7.52 (m, 2H), 4.19-4.18 (m, 2H), 3.50-3.47 (m, 1H), 2.86-2.76 (m, 2H), 2.28-2.24 (m, 1H), 1.84-1.80 (m, 1H), 1.65-1.62 (m, 1H), 1.40-1.32 (m, 2H), 1.10 (d, J = 7.2 Hz, 3H) ppm |
| 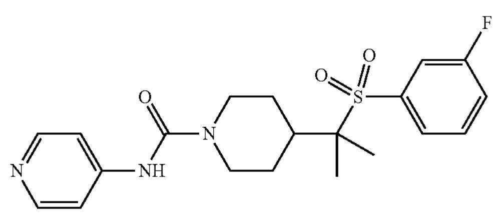 [SMILES: CC(C)(C1CCN(C(=O)Nc2ccncc2)CC1)S(=O)(=O)c1cccc(F)c1] | 4-(2-((3-fluorophenyl)sulfonyl)propan-2-yl)-N-(pyridin-4-yl)piperidine-1-carboxamide | 32 | 7 | 406 | 1H-NMR (400 MHz, DMSO-d6): δ 8.98 (s, 1H), 8.31 (d, J = 6.4 Hz, 2H), 7.78-7.65 (m, 4H), 7.50 (d, J = 6.4 Hz, 2H), 4.22-4.18 (m, 2H), 2.80-2.73 (m, 2H), 2.07-1.93 (m, 3H), 1.38-1.35 (m, 2H), 1.19 (s, 6H) ppm |
| 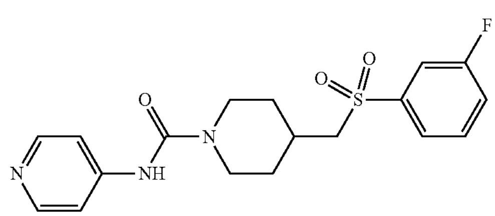 [SMILES: O=C(Nc1ccncc1)N1CCC(CS(=O)(=O)c2cccc(F)c2)CC1] | 4-(((3-fluorophenyl)sulfonyl)methyl)-N-(pyridin-4-yl)piperidine-1-carboxamide | 33 | 5 | 378 | 1H-NMR (400 MHz, DMSO-d6): δ 8.87 (s, 1H), 8.29-8.27 (m, 2H), 7.80-7.72 (m, 3H), 7.66-7.64 (m, 1H), 7.46-7.44 (m, 2H), 4.04-4.00 (m, 2H), 3.43-3.42 (m, 2H), 2.88-2.82 (m, 2H), 2.10-2.06 (m, 1H), 1.80-1.77 (m, 2H), 1.29-1.24 (m, 2H) ppm |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 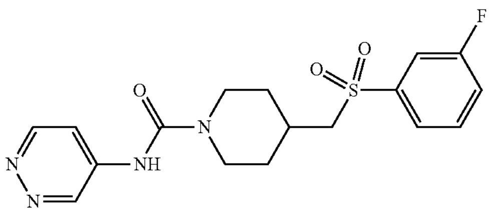 [SMILES: O=C(Nc1ccnnc1)N1CCC(CS(=O)(=O)c2cccc(F)c2)CC1] | 4-(((3-fluorophenyl)sulfonyl)methyl)-N-(pyridazin-4-yl)piperidine-1-carboxamide | 34 | 5 | 379 | 1H-NMR (400 MHz, DMSO-d6): δ 9.25 (d, J = 2.4 Hz, 1H), 9.13 (s, 1H), 8.86-8.85 (m, 1H), 7.80-7.71 (m, 4H), 7.66-7.62 (m, 1H), 4.04-4.01 (m, 2H), 3.43 (d, J = 6.4 Hz, 2H), 2.92-2.86 (m, 2H), 2.08-2.04 (m, 1H), 1.82-1.79 (m, 2H), 1.31-1.22 (m, 2H) ppm |
| 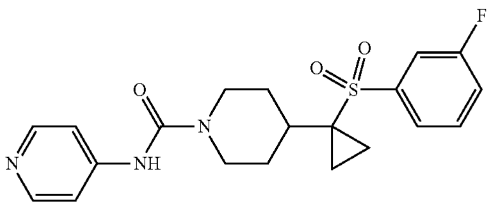 [SMILES: O=C(Nc1ccncc1)N1CCC(C2(S(=O)(=O)c3cccc(F)c3)CC2)CC1] | 4-(1-((3-fluorophenyl)sulfonyl)cyclopropyl)-N-(pyridin-4-yl)piperidine-1-carboxamide | 35 | 5 | 404 | 1H-NMR (300 MHz, CDCl3): δ 8.83-8.29 (m, 2H), 7.71-7.68 (m, 1H), 7.61-7.57 (m, 4H), 7.41-7.36 (m, 1H), 4.18-4.11 (m, 2H), 2.83-2.75 (m, 2H), 2.15-2.08 (m, 1H), 1.74-1.70 (m, 2H), 1.61-1.56 (m, 3H), 1.37-1.26 (m, 2H), 1.00-0.95 (m, 2H) ppm |
| 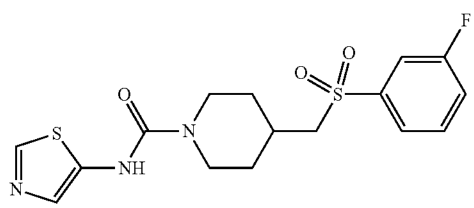 [SMILES: O=C(Nc1cncs1)N1CCC(CS(=O)(=O)c2cccc(F)c2)CC1] | 4-(((3-fluorophenyl)sulfonyl)methyl)-N-(thiazol-5-yl)piperidine-1-carboxamide | 36 | 5 | 384 | 1H-NMR (400 MHz, CD3OD): δ 8.44 (s, 1H), 7.82-7.80 (m, 1H), 7.75-7.68 (m, 2H), 7.54-7.50 (m, 2H), 4.14-4.10 (m, 2H), 3.15-3.00 (m, 2H), 2.97-2.94 (m, 2H), 2.26-2.20 (m, 1H), 1.98-1.95 (m, 2H), 1.40-1.37 (m, 2H) ppm |
| 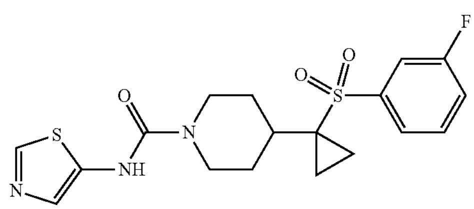 [SMILES: O=C(Nc1cncs1)N1CCC(C2(S(=O)(=O)c3cccc(F)c3)CC2)CC1] | 4-(1-((3-fluorophenyl)sulfonyl)cyclopropyl)-N-(thiazol-5-yl)piperidine-1-carboxamide | 37 | 5 | 410 | 1H-NMR (400 MHz, CDCl3): δ 8.14 (s, 1H), 7.72-7.70 (m, 1H), 7.62-7.57 (m, 4H), 7.42-7.40 (m, 1H), 4.10-4.07 (m, 2H), 2.85-2.79 (m, 2H), 2.13-2.05 (m, 1H), 1.62-1.35 (m, 4H), 1.00-0.93 (m, 2H), 0.89-0.85 (m, 2H) ppm |
| 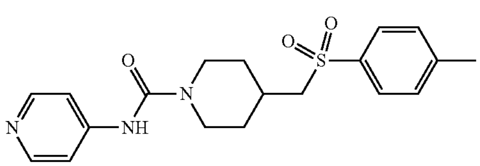 [SMILES: Cc1ccc(S(=O)(=O)CC2CCN(C(=O)Nc3ccncc3)CC2)cc1] | N-(pyridin-4-yl)-4-(tosylmethyl)piperidine-1-carboxamide | 38 | 2 | 374 | 1H-NMR (300 MHz, DMSO-d6): δ 8.86 (s, 1H), 8.28 (d, J = 4.8 Hz, 2H), 7.81 (d, J = 6.3 Hz, 2H), 7.48-7.44 (m, 4H), 4.02-3.99 (m, 2H), 3.31-3.29 (m, 2H), 2.82 (m, 2H), 2.52-2.49 (m, 3H), 2.00 (m, 1H), 1.78-1.75 (m, 2H), 1.23 (m, 2H) ppm |
| 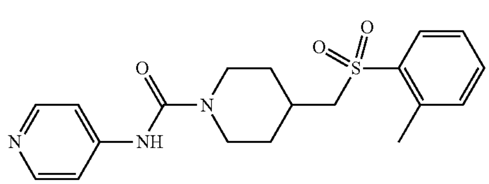 [SMILES: Cc1ccccc1S(=O)(=O)CC1CCN(C(=O)Nc2ccncc2)CC1] | N-(pyridin-4-yl)-4-((o-tolylsulfonyl)methyl)piperidine-1-carboxamide | 39 | 5 | 374 | 1H-NMR (300 MHz, DMSO-d6): δ 8.86 (s, 1H), 8.28-8.26 (m, 2H), 7.92-7.89 (m, 1H), 7.63-7.60 (m, 1H), 7.50-7.44 (m, 4H), 4.05-4.00 (m, 2H), 3.32-3.28 (m, 2H), 2.85-2.82 (m, 2H), 2.64 (s, 3H), 2.08-2.00 (m, 1H), 1.79-1.75 (m, 2H), 1.32-1.25 (m, 2H) ppm |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 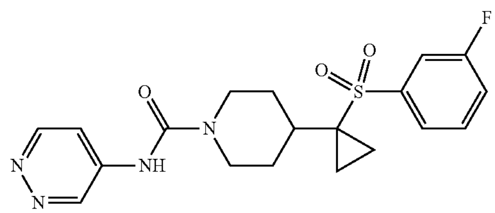 [SMILES: O=C(Nc1ccnnc1)N1CCC(C2(S(=O)(=O)c3cccc(F)c3)CC2)CC1] | 4-(1-((3-fluorophenyl)sulfonyl)cyclopropyl)-N-(pyridazin-4-yl)piperidine-1-carboxamide | 40 | 5 | 405 | 1H-NMR (400 MHz, DMSO-d6): δ 9.23 (s, 1H), 9.05 (s, 1H), 8.85 (d, J = 6.0 Hz, 1H), 7.80-7.65 (m, 5H), 4.08-4.05 (m, 2H), 2.74-2.68 (m, 2H), 2.08-2.05 (m, 1H), 1.48-1.41 (m, 4H), 1.10-1.08 (m, 2H), 1.05-1.01 (m, 2H) ppm |
| | 4-(((2-methoxyphenyl)sulfonyl)methyl)-N-(pyridin-4-yl)piperidine-1-carboxamide | 41 | 5 | 390 | 1H-NMR (400 MHz, CD3OD): δ 8.29-8.27 (m, 2H), 7.93-7.90 (m, 1H), 7.74-7.69 (m, 1H), 7.49-7.47 (m, 2H), 7.30-7.28 (m, 1H), 7.21-7.14 (m, 1H), 4.11-4.10 (m, 2H), 4.01 (s, 3H), 3.43-3.41 (m, 2H), 2.95-2.88 (m, 2H), 2.16-2.13 (m, 1H), 2.03-1.89 (m, 2H), 1.45-1.36 (m, 2H) ppm |
| 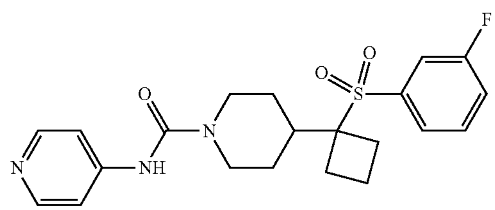 [SMILES: O=C(Nc1ccncc1)N1CCC(C2(S(=O)(=O)c3cccc(F)c3)CCC2)CC1] | 4-(1-((3-fluorophenyl)sulfonyl)cyclobutyl)-N-(pyridin-4-yl)piperidine-1-carboxamide | 42 | 5 | 418 | 1H-NMR (400 MHz, DMSO-d6): δ 10.21 (s, 1H), 8.55 (d, J = 7.2 Hz, 2H), 7.91 (d, J = 7.2 Hz, 2H), 7.79-7.65 (m, 4H), 4.21-4.17 (m, 2H), 2.81-2.74 (m, 2H), 2.62-2.54 (m, 2H), 2.29-2.22 (m, 2H), 1.91-1.88 (m, 3H), 1.77-1.362 (m, 2H), 1.45-1.39 (m, 2H) ppm |
| 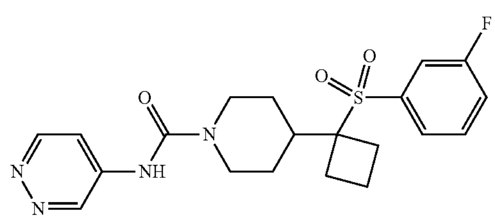 [SMILES: O=C(Nc1ccnnc1)N1CCC(C2(S(=O)(=O)c3cccc(F)c3)CCC2)CC1] | 4-(1-((3-fluorophenyl)sulfonyl)cyclobutyl)-N-(pyridazin-4-yl)piperidine-1-carboxamide | 43 | 5 | 419 | 1H-NMR (400 MHz, DMSO-d6): δ 9.27 (s, 1H), 9.14 (s, 1H), 8.88-8.86 (m, 1H), 7.79-7.66 (m, 5H), 4.20-4.17 (m, 2H), 2.75-2.69 (m, 2H), 2.63-2.60 (m, 2H), 2.31-2.23 (m, 2H), 1.88-1.85 (m, 3H), 1.78-1.71 (m, 2H), 1.69-1.66 (m, 2H) ppm |
| | 4-(difluoro((3-fluorophenyl)sulfonyl)methyl)-N-(1,2,3-thiadiazol-5-yl)piperidine-1-carboxamide | 44 | 5 | 421 | 1H NMR (400 MHz, DMSO-d6): δ 10.97 (s, 1H), 8.53 (s, 1H), 7.76-7.89 (m, 4H), 4.21 (d, J = 13.3 Hz, 2H), 2.78-3.15 (m, 3H), 1.94-2.11 (m, 2H), 1.40-1.65 (m, 2H) ppm |
| 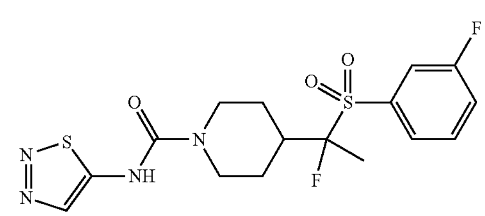 [SMILES: CC(F)(C1CCN(C(=O)Nc2cnns2)CC1)S(=O)(=O)c1cccc(F)c1] | 4-(1-fluoro-1-((3-fluorophenyl)sulfonyl)ethyl)-N-(1,2,3-thiadiazol-5-yl)piperidine-1-carboxamide | 45 | 6 | 417 | 1H NMR (400 MHz, CDCl3): δ 9.29 (s, 1H), 8.55 (s, 1 H), 7.73 (d, J = 7.83 Hz, 1 H), 7.56-7.67 (m, 2 H), 7.44 (td, J = 8.22, 1.96 Hz, 1 H), 4.24-4.44 (m, 2 H), 2.96-3.13 (m, 2 H), 2.55-2.84 (m, 3H), 2.35 (d, J = 13.30 Hz, 1 H), 1.99 (d, J = 12.13 Hz, 1 H), 1.43-1.59 (m, 3H) ppm |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 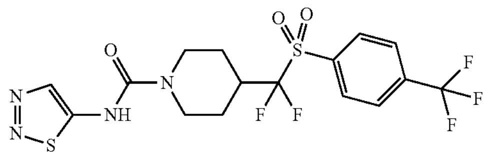 [SMILES: O=C(Nc1cnns1)N1CCC(C(F)(F)S(=O)(=O)c2ccc(C(F)(F)F)cc2)CC1] | 4-(difluoro((4-(trifluoromethyl)phenyl)sulfonyl)methyl)-N-(1,2,3-thiadiazol-5-yl)piperidine-1-carboxamide | 46 | 5 | 422 | 1H NMR (400 MHz, CD3OD): δ 8.49 (s, 1H), 8.20 (d, J = 8.22 Hz, 2H), 8.05 (d, J = 8.22 Hz, 2H), 4.31 (d, J = 13.69 Hz, 2H), 3.03-3.15 (m, 2H), 2.86-3.03 (m, 1H), 2.18 (d, J = 13.30 Hz, 2H), 1.68 (qd, J = 12.78, 4.30 Hz, 2H) ppm |
| 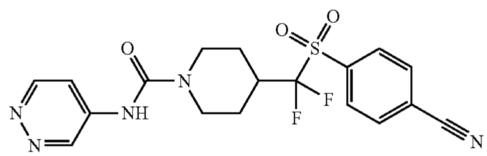 [SMILES: N#Cc1ccc(S(=O)(=O)C(F)(F)C2CCN(C(=O)Nc3ccnnc3)CC2)cc1] | 4-(((4-cyanophenyl)sulfonyl)difluoromethyl)-N-(pyridazin-4-yl)piperidine-1-carboxamide | 47 | 5 | 472 | 1H NMR (400 MHz, CD3CN): δ 9.19-9.22 (m, 1 H) 8.84-8.88 (m, 1 H) 8.12-8.17 (m, 2 H) 8.05-8.09 (m, 2 H) 7.77 (dd, J = 5.87, 2.74 Hz, 1 H) 7.69 (br. s., 1 H) 4.21-4.28 (m, 2 H) 2.94-3.03 (m, 2 H) 2.79-2.92 (m, 1 H) 2.08-2.14 (m, 2 H) 1.60-1.71 (m, 2 H) ppm |
| 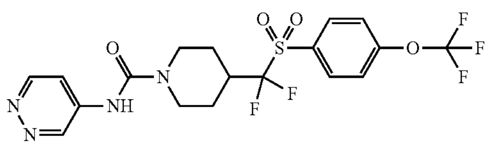 [SMILES: O=C(Nc1ccnnc1)N1CCC(C(F)(F)S(=O)(=O)c2ccc(OC(F)(F)F)cc2)CC1] | 4-(difluoro((4-(trifluoromethoxy)phenyl)sulfonyl)methyl)-N-(pyridazin-4-yl)piperidine-1-carboxamide | 48 | 5 | 481 | 1H NMR (400 MHz, CD3CN): δ 9.18-9.21 (m, 1 H) 8.84-8.88 (m, 1 H) 8.10 (d, J = 9.00 Hz, 2 H) 7.78 (dd, J = 5.87, 2.74 Hz, 1 H) 7.68 (br. s., 1 H) 7.61 (d, J = 7.83 Hz, 2 H) 4.20-4.28 (m, 2 H) 2.94-3.03 (m, 2 H) 2.79-2.93 (m, 1 H) 2.09-2.13 (m, 2 H) 1.59-1.71 (m, 2 H) ppm |
| 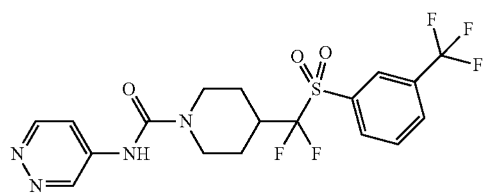 [SMILES: O=C(Nc1ccnnc1)N1CCC(C(F)(F)S(=O)(=O)c2cccc(C(F)(F)F)c2)CC1] | 4-(difluoro((3-(trifluoromethyl)phenyl)sulfonyl)methyl)-N-(pyridazin-4-yl)piperidine-1-carboxamide | 49 | 5 | 465 | 1H NMR (400 MHz, CD3OD): δ 9.21-9.26 (m, 1H), 8.83-8.89 (m, 1H), 8.27 (d, J = 7.83 Hz, 1H), 8.17-8.24 (m, 2H), 7.96 (t, J = 8.22 Hz, 1H), 7.87 (dd, J = 6.26, 2.74 Hz, 1H), 4.33 (d, J = 13.69 Hz, 2H), 2.88-3.10 (m, 3H), 2.17 (d, J = 12.13 Hz, 2H), 1.69 (qd, J = 12.72, 4.11 Hz, 2H) ppm |
| 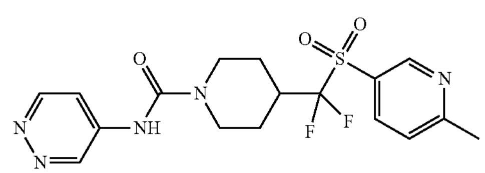 [SMILES: Cc1ccc(S(=O)(=O)C(F)(F)C2CCN(C(=O)Nc3ccnnc3)CC2)cn1] | 4-(difluoro((6-methylpyridin-3-yl)sulfonyl)methyl)-N-(pyridazin-4-yl)piperidine-1-carboxamide | 50 | 4 | 412 | 1H NMR (400 MHz, CD3OD): δ 9.27 (d, J = 2.35 Hz, 1 H) 9.10 (d, J = 7.04 Hz, 1 H) 8.91 (d, J = 2.35 Hz, 1 H) 8.36 (dd, J = 7.04, 2.74 Hz, 1 H) 8.23 (dd, J = 8.61, 2.35 Hz, 1 H) 7.62 (d, J = 8.22 Hz, 1 H) 4.31-4.39 (m, 2 H) 3.06-3.15 (m, 2 H) 2.92-3.03 (m, 1 H) 2.69 (s, 3 H) 2.16-2.24 (m, 2 H) 1.65-1.79 (m, 2 H) ppm |
| 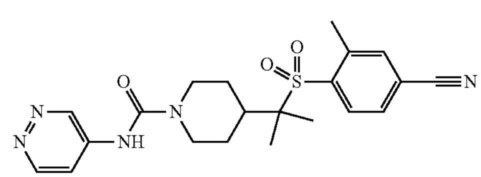 [SMILES: Cc1cc(C#N)ccc1S(=O)(=O)C(C)(C)C1CCN(C(=O)Nc2ccnnc2)CC1] | 4-(2-((4-cyano-2-methylphenyl)sulfonyl)propan-2-yl)-N-(pyridazin- | 51 | 4 | 428 | 1H NMR (400 MHz, CDCl3): δ 10.46 (s, 1 H), 9.56 (d, J = 2.35 Hz, 1H), 8.77 (d, J = 7.04 Hz, 1H), 8.65 (dd, J = 6.85, 2.54 Hz, 1H), 8.09 (d, J = 8.22 Hz, 1H), 7.63-7.75 |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | 4-yl) piperidine-1-carboxamide | | | | (m, 2H), 7.19-7.27 (m, 1H), 4.43 (d, J = 13.30 Hz, 2H), 3.07-3.24 (m, 1H), 2.86-3.09 (m, 3H), 2.54 (d, J = 3.13 Hz, 1H), 2.13 (d, J = 12.91 Hz, 1H), 1.74 (d, J = 12.91 Hz, 1H), 1.43-1.63 (m, 2H), 1.35 (t, J = 7.43 Hz, 3H), 1.15 (d, J = 7.04 Hz, 3H) ppm |
| 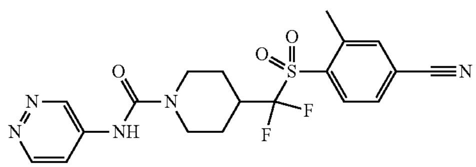 [SMILES: Cc1cc(C#N)ccc1S(=O)(=O)C(F)(F)C1CCN(C(=O)Nc2ccnnc2)CC1] | 4-(((4-cyano-2-methyl-phenyl) sulfonyl) difluoro-methyl)-N-(pyridazin-4-yl) piperidine-1-carboxamide | 52 | 3 | 436 | 1H NMR (400 MHz, CDCl3): δ 10.46 (s, 1H), 9.58 (d, J = 2.74 Hz, 1H), 8.81 (d, J = 6.65 Hz, 1H), 8.69 (dd, J = 6.85, 2.54 Hz, 1H), 8.11 (d, J = 8.22 Hz, 1H), 7.64-7.75 (m, 2H), 4.51 (d, J = 13.69 Hz, 2H), 3.02 (t, J = 12.91 Hz, 2H), 2.85 (t, J = 13.11 Hz, 1H), 2.75 (s, 3H), 2.21 (d, J = 12.13 Hz, 2H), 1.72 (qd, J = 12.78, 3.91 Hz, 2H) ppm |
| 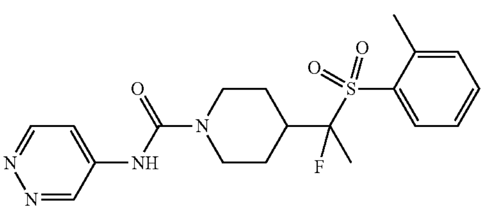 [SMILES: Cc1ccccc1S(=O)(=O)C(C)(F)C1CCN(C(=O)Nc2ccnnc2)CC1] | 4-(1-fluoro-1-(o-tolylsulfonyl) ethyl)-N-(pyridazin-4-yl) piperidine-1-carboxamide | 53 | 6 | 407 | 1H-NMR (300 MHz, CD3OD): δ 9.20 (dd, J = 0.9, 2.7 Hz, 1H), 8.83 (dd, J = 0.9, 3.0 Hz, 1H), 7.94 (d, J = 7.2 Hz, 1H), 7.83 (dd, J = 3.0, 6.0 Hz, 1H), 7.65-7.58 (m, 1H), 7.48-7.40 (m, 2H), 4.38-4.22 (m, 2H), 2.92 (t, J = 12.9 Hz, 2H), 2.66 (s, 3H), 2.62-2.45 (m, 1H), 2.25 (d, J = 13.5 Hz, 1H), 1.88 (d, J = 12.6 Hz, 1H), 1.60-1.40 (m, 2H), 1.50 (d, J = 22.5 Hz, 3H) ppm |
| 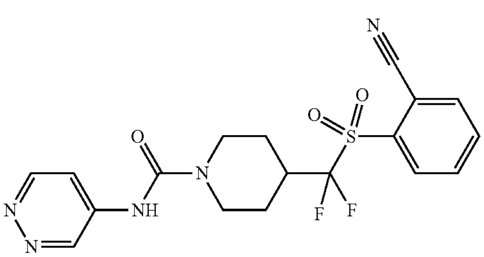 [SMILES: N#Cc1ccccc1S(=O)(=O)C(F)(F)C1CCN(C(=O)Nc2ccnnc2)CC1] | 4-(((2-cyanophenyl) sulfonyl) difluoro-methyl)-N-(pyridazin-4-yl) piperidine-1-carboxamide | 54 | 2, 3 | 422 | 1H-NMR (400 MHz, DMSO-d6): δ 10.20 (br.s, 1H), 9.29 (d, J = 2.4 Hz, 1H), 9.13 (d, J = 6.4 Hz, 1H), 8.38-8.30 (m, 1H), 8.28-8.20 (m, 1H), 8.16-8.08 (m, 3H), 4.25 (d, J = 13.6 Hz, 2H), 3.15-2.98 (m, 3H), 2.08 (d, J = 12.0 Hz, 2H), 1.66-1.50 (m, 2H) ppm |
| 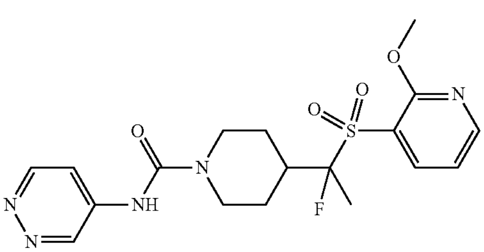 | 4-(1-fluoro-1-((2-methoxy-pyridin-3-yl)sulfonyl) ethyl)-N-(pyridazin-4-yl) piperidine-1-carboxamide | 55 | 9 | 424 | 1H-NMR (400 MHz, CD3OD): δ 9.27 (s, 1H), 9.10 (d, J = 6.8 Hz, 1H), 8.51 (dd, J = 1.8, 5.0 Hz, 1H), 8.36 (dd, J = 2.8, 7.2 Hz, 1H), 8.25 (dd, J = 1.6, 7.6 Hz, 1H), 7.22 (dd, J = 5.0, 7.8 Hz, 1H), 4.42-4.28 (m, 2H), 4.06 (s, 3H), 3.02 (t, J = 12.6 |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | | | | | Hz, 2H), 2.66-2.53 (m, 1H), 2.32 (d, J = 13.2 Hz, 1H), 1.93 (d, J = 13.2 Hz, 1H), 1.70-1.48 (m, 2H), 1.63 (d, J = 23.2 Hz, 3H) ppm |
| 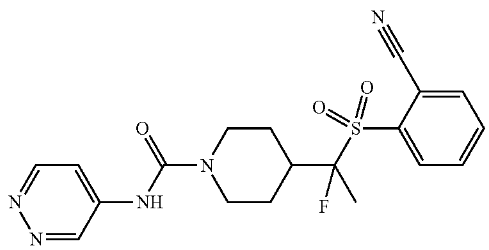 [SMILES: CC(F)(C1CCN(C(=O)Nc2ccnnc2)CC1)S(=O)(=O)c1ccccc1C#N] | 4-(1-((2-cyanophenyl)sulfonyl)-1-fluoroethyl)-N-(pyridazin-4-yl)piperidine-1-carboxamide | 56 | 6 | 418 | 1H-NMR (400 MHz, DMSO-d6): δ 10.26 (br. s, 1H), 9.31 (d, J = 2.4 Hz, 1H), 9.20-9.10 (m, 1H), 8.30-8.23 (m, 1H), 8.22-8.12 (m, 2H), 8.10-8.02 (m, 2H), 4.28 (d, J = 13.2 Hz, 2H), 3.00 (q, J = 11.2 Hz, 2H), 2.67-2.49 (m, 1H), 2.15 (d, J = 12.4 Hz, 1H), 1.80 (d, J = 12.4 Hz, 1H), 1.59 (d, J = 23.2 Hz, 3H), 1.57-1.43 (m, 2H) ppm |
| | 4-(1-fluoro-1-((2-(trifluoromethyl)phenyl)sulfonyl)ethyl)-N-(pyridazin-4-yl)piperidine-1-carboxamide | 57 | 2, 6 | 461 | 1H-NMR (300 MHz, CD3OD): δ 9.22-9.18 (m, 1H), 8.83 (dd, J = 0.9, 6.0 Hz, 1H), 8.27-8.20 (m, 1H), 8.08-8.00 (m, 1H), 7.97-7.88 (m, 2H), 7.85-7.81 (m, 1H), 4.35-4.23 (m, 2H), 3.02-2.88 (m, 2H), 2.72-2.55 (m, 1H), 2.20 (d, J = 12.9 Hz, 1H), 1.88 (d, J = 13.2 Hz, 1H), 1.56 (d, J = 22.5 Hz, 3H), 1.60-1.43 (m, 2H) ppm |
| 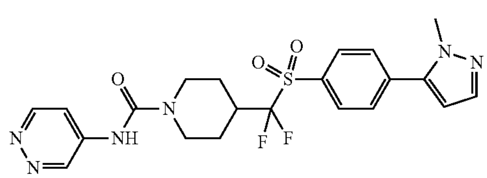 [SMILES: Cn1nccc1-c1ccc(S(=O)(=O)C(F)(F)C2CCN(C(=O)Nc3ccnnc3)CC2)cc1] | 4-(difluoro((4-(1-methyl-1H-pyrazol-5-yl)phenyl)sulfonyl)methyl)-N-(pyridazin-4-yl)piperidine-1-carboxamide | 58 | 5 | 477 | 1H-NMR (300 MHz, CDCl3): δ 9.27 (d, J = 2.4 Hz, 1H), 8.92 (d, J = 6 Hz, 1H), 8.11-8.08 (m, 1H), 8.05 (d, J = 8.4 Hz, 2H), 7.69 (d, J = 8.4 Hz, 2H), 7.56 (d, J = 1.8 Hz, 1H), 6.44 (d, J = 1.8 Hz, 1H), 4.42 (d, J = 14.4 Hz, 2H), 3.95 (s, 3H), 3.02 (t, J = 12 Hz, 2H), 2.89-2.81 (m, 1H), 2.37 (br. s, 1H), 2.26 (d, J = 12 Hz, 2H), 1.82-1.68 (m, 2H) ppm |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | N-(pyridazin-4-yl)-4-(2-((2-(trifluoromethyl)phenyl)sulfonyl)propan-2-yl)piperidine-1-carboxamide | 59 | 7 | 457 | 1H-NMR (300 MHz, CD3OD): δ 9.23 (d, J = 2.1 Hz, 1H), 8.84 (d, J = 6.0 Hz, 1H), 8.25-8.18 (m, 1H), 8.10-8.00 (m, 1H), 7.95-7.80 (m, 3H), 4.30 (d, J = 13.5 Hz, 2H), 2.95 (t, J = 12.6 Hz, 2H), 2.45-2.30 (m, 1H), 2.10 (d, J = 12.9 Hz, 2H), 1.60-1.40 (m, 2H), 1.30 (s, 6H) ppm |
| | 4-(((6-cyclopropyl-pyridin-3-yl)sulfonyl)difluoromethyl)-N-(pyridazin-4-yl)piperidine-1-carboxamide | 60 | 4 | 438 | 1H-NMR (300 MHz, DMSO-d6): δ 10.16 (br. s, 1H), 9.28 (d, J = 2.1 Hz, 1H), 9.12 (d, J = 6.3 Hz, 1H), 8.87 (d, J = 2.4 Hz, 1H), 8.20 (d, J = 2.4 Hz, 1H), 8.18-8.08 (m, 1H), 7.72 (d, J = 8.7 Hz, 1H), 4.25 (d, J = 13.5 Hz, 2H), 3.12-2.85 (m, 3H), 2.40-2.30 (m, 1H), 2.05 (d, J = 12.6 Hz, 2H), 1.65-1.45 (m, 2H), 1.20-1.07 (m, 4H) ppm |
| | 4-(difluoro((3-fluoro-2-methoxyphenyl)sulfonyl)methyl)-N-(pyridazin-4-yl)piperidine-1-carboxamide | 61 | 4 | 445 | 1H-NMR (400 MHz, CD3OD): δ 9.29 (d, J = 2.4 Hz, 1H), 9.09 (d, J = 7.2 Hz, 1H), 8.33 (dd, J = 2.8, 6.8 Hz, 1H), 7.75 (d, J = 8.0 Hz, 1H), 7.70-7.64 (m, 1H), 7.41-7.35 (m, 1H), 4.36 (d, J = 14 Hz, 2H), 4.05 (s, 3H), 3.10 (t, J = 12.4 Hz, 2H), 3.00-2.85 (m, 1H), 2.21 (d, J = 12.8 Hz, 2H), 1.80-1.60 (m, 2H) ppm |
| | 4-(difluoro((2-methoxyphenyl)sulfonyl)methyl)-N-(pyridazin-4-yl)piperidine-1-carboxamide | 62 | 2, 3 | 427 | 1H-NMR (300 MHz, DMSO-d6): δ 9.26 (dd, J = 0.9, 2.7 Hz, 1H), 9.22 (s, 1H), 8.88 (dd, J = 0.9, 6 Hz, 1H), 7.90-7.81 (m, 2H), 7.75 (dd, J = 2.7, 6.0 Hz, 1H), 7.37 (d, J = 8.1 Hz, 1H), 7.25 (t, J = 7.5 Hz, 1H), 4.25 (d, J = 13.2 Hz, 2H), 3.92 (s, 3H), 3.05-2.70 (m, 3H), 2.03 (d, J = 12.0 Hz, 2H), 1.57-1.40 (m, 2H) ppm |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(difluoro((5-fluoro-2-methylphenyl)sulfonyl)methyl)-N-(pyridazin-4-yl)piperidine-1-carboxamide | 63 | 4 | 429 | 1H NMR (400 MHz, DMSO-d6): δ 10.00 (br. s., 1 H) 9.26 (d, J = 2.74 Hz, 1 H) 9.07 (d, J = 6.65 Hz, 1 H) 8.03 (dd, J = 6.65, 2.74 Hz, 1 H) 7.60-7.73 (m, 3 H) 4.19-4.28 (m, 2 H) 2.89-3.08 (m, 3 H) 2.60 (s, 3 H) 1.99-2.08 (m, 2 H) 1.47-1.60 (m, 2 H) ppm |
| | 4-(((4-(1H-1,2,4-triazol-1-yl)phenyl)sulfonyl)difluoromethyl)-N-(pyridazin-4-yl)piperidine-1-carboxamide | 64 | 5 | 464 | 1H-NMR (400 MHz, DMSO-d6) δ ppm 9.56 (s, 1H), 9.25 (d, J = 13.2 Hz, 2H), 8.88 (d, J = 6.0 Hz, 1H), 8.38 (s, 1H), 8.29 (d, J = 8.8 Hz, 2H), 8.18 (d, J = 8.4 Hz, 2H), 7.75 (dd, J = 2.4, 6.0 Hz, 1H), 4.26 (d, J = 12.8 Hz, 2H), 3.05-2.85 (m, 3H), 2.05 (d, J = 11.2 Hz, 2H), 1.60-1.48 (m, 2H). |
| | 4-(difluoro((2-methyl-4-(trifluoromethyl)phenyl)sulfonyl)methyl)-N-(pyridazin-4-yl)piperidine-1-carboxamide | 65 | 4 | 479 | 1H-NMR (300 MHz, DMSO-d6): δ 10.20 (br. s, 1H), 9.29 (d, J = 1.8 Hz, 1H), 9.13 (d, J = 6.0 Hz, 1H), 8.17 (d, J = 8.4 Hz, 1H), 8.15-8.06 (m, 1H), 8.04 (s, 1H), 7.95 (d, J = 8.4 Hz, 1H), 4.27 (d, J = 13.2 Hz, 2H), 3.15-2.90 (m, 3H), 2.74 (s, 3H), 2.05 (d, J = 11.7 Hz, 2H), 1.68-1.48 (m, 2H) ppm |
| | 4-(difluoro((1-methyl-1H-indazol-4-yl)sulfonyl)methyl)-N-(pyridazin-4-yl)piperidine-1-carboxamide | 66 | 4 | 451 | 1H-NMR (400 MHz, CD3OD): δ 9.23 (d, J = 2.4 Hz, 1H), 8.86 (d, J = 6.0 Hz, 1H), 8.29 (s, 1H), 8.10 (d, J = 8.8 Hz, 1H), 7.90-7.85 (m, 2H), 7.69 (dd, J = 7.2, 8.4 Hz, 1H), 4.33 (d, J = 13.6 Hz, 2H), 4.17 (s, 3H), 3.10-2.85 (m, 3H), 2.20 (d, J = 11.6 Hz, 2H), 1.78-1.62 (m, 2H) ppm |
| | 4-(((6-(azetidin-1-yl)pyridin-3-yl)sulfonyl)difluoromethyl)-N-(pyridazin-4-yl)piperidine-1-carboxamide | 67 | 4 | 453 | 1H-NMR (300 MHz, DMSO-d6): δ 9.26 (d, J = 2.4 Hz, 1H), 9.22 (s, 1H), 8.88 (d, J = 5.7 Hz, 1H), 8.43 (d, J = 2.4 Hz, 1H), 7.85-7.72 (m, 2H), 6.47 (d, J = 8.7 Hz, 1H), 4.25 (d, J = 13.8 Hz, 2H), 4.14 (t, J = 7.7 Hz, 4H), 3.00-2.70 (m, 3H), 2.45-2.35 (m, 2H), 2.00 (d, J = 12.9 Hz, 2H), |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | | | | | 1.58-1.40 (m, 2H) ppm |
| 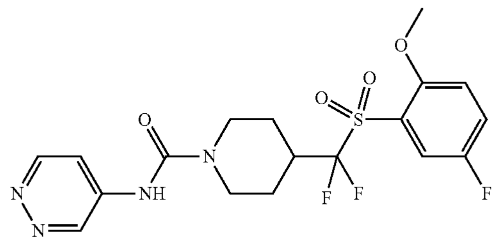 [SMILES: COc1ccc(F)cc1S(=O)(=O)C(F)(F)C1CCN(C(=O)Nc2ccnnc2)CC1] | 4-(difluoro ((5-fluoro-2-methoxy-phenyl) sulfonyl) methyl)-N-(pyridazin-4-yl) piperidine-1-carboxamide | 68 | 4 | 445 | 1H-NMR (300 MHz, DMSO-d6): δ 9.26 (dd, J = 0.9, 2.7 Hz, 1H), 9.22 (s, 1H), 8.88 (dd, J = 0.9, 6.0 Hz, 1H), 7.83-7.70 (m, 2H), 7.64 (dd, J = 3.3, 7.8 Hz, 1H), 7.44 (dd, J = 3.9, 9.3 Hz, 1H), 4.25 (d J = 13.5 Hz, 2H), 3.92 (s, 3H), 3.05-2.70 (m, 3H), 2.00 (d, J = 12.0 Hz, 2H), 1.60-1.40 (m, 2H) ppm |
| 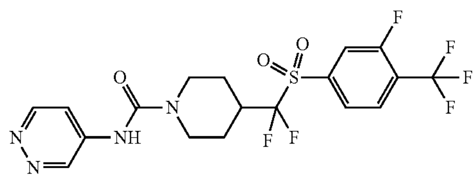 [SMILES: O=C(Nc1ccnnc1)N1CCC(C(F)(F)S(=O)(=O)c2ccc(C(F)(F)F)c(F)c2)CC1] | 4-(difluoro ((3-fluoro-4-(trifluoro-methyl) phenyl) sulfonyl) methyl)-N-(pyridazin-4-yl) piperidine-1-carboxamide | 69 | 4 | 483 | 1H-NMR (300 MHz, CD3OD): δ 9.20 (dd, J = 0.9, 2.7 Hz, 1H), 8.83 (dd, J = 0.9, 6.0 Hz, 1H), 8.12-8.05 (m, 1H), 7.98 (d, J = 8.4 Hz, 2H), 7.84 (dd, J = 2.9, 6.2 Hz, 1H), 4.30 (d, J = 13.5 Hz, 2H), 3.10-2.80 (m, 3H), 2.13 (d, J = 12.6 Hz, 2H), 1.66 (qd, J = 4.0, 8.9 Hz, 2H) ppm |
| 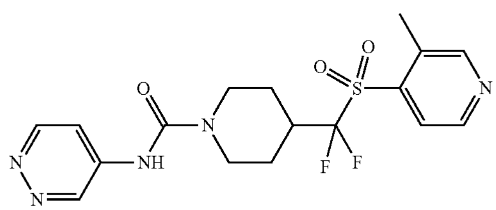 [SMILES: Cc1cnccc1S(=O)(=O)C(F)(F)C1CCN(C(=O)Nc2ccnnc2)CC1] | 4-(difluoro ((3-methyl-pyridin-4-yl)sulfonyl) methyl)-N-(pyridazin-4-yl) piperidine-1-carboxamide | 70 | 4 | 412 | 1H-NMR (300 MHz, CD3OD): δ 9.20 (dd, J = 0.9, 2.7 Hz, 1H), 8.83 (dd, J = 0.9, 6.0 Hz, 1H), 8.78-8.70 (m, 2H), 7.88-7.80 (m, 2H), 4.30 (d, J = 13.8 Hz, 2H), 3.10-2.80 (m, 3H), 2.67 (s, 3H), 2.13 (d, J = 12.3 Hz, 2H), 1.75-1.57 (m, 2H) ppm |
| 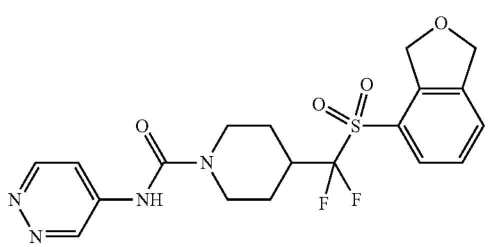 [SMILES: O=C(Nc1ccnnc1)N1CCC(C(F)(F)S(=O)(=O)c2cccc3c2COC3)CC1] | 4-(((1,3-dihydroiso-benzofuran-4-yl) sulfonyl) difluoro-methyl)-N-(pyridazin-4-yl) piperidine-1-carboxamide | 71 | 4 | 439 | 1H-NMR (400 MHz, DMSO-d6): δ 10.10 (br. s, 1H), 9.29 (d, J = 2.4 Hz, 1H), 9.10 (d, J = 6.8 Hz, 1H), 8.10-8.04 (m, 1H), 7.89 (d, J = 7.6 Hz, 1H), 7.83 (d, J = 7.6 Hz, 1H), 7.71 (t, J = 8.0 Hz, 1H), 5.24 (s, 2H), 5.11 (s, 2H), 4.25 (d, J = 13.2 Hz, 2H), 3.10-2.88 (m, 3H), 2.05 (d, J = 17.2 Hz, 2H), 1.64-1.47 (m, 2H) ppm |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(((2-chloro-5-methoxyphenyl)sulfonyl)difluoromethyl)-N-(pyridazin-4-yl)piperidine-1-carboxamide | 72 | 4 | 461 | 1H-NMR (400 MHz, CD3OD): δ 9.23 (dd, J = 1.0, 3.0 Hz, 1H), 8.86 (dd, J = 0.8, 6.0 Hz, 1H), 7.87 (dd, J = 2.8, 6.0 Hz, 1H), 7.63-7.55 (m, 2H), 3.35 (dd, J = 2.8, 8.8 Hz, 1H), 4.32 (d, J = 14.0 Hz, 2H), 3.89 (s, 3H), 3.08-2.85 (m, 3H), 2.16 (d, J = 12.8 Hz, 2H), 1.75-1.60 (m, 2H) ppm |
| | 4-(difluoro((2-methyl-4-(trifluoromethoxy)phenyl)sulfonyl)methyl)-N-(pyridazin-4-yl)piperidine-1-carboxamide | 73 | 3 | 495 | 1H NMR (400 MHz, CDCl3): δ 10.50 (s, 1H), 9.61 (d, J = 2.35 Hz, 1H), 8.79 (d, J = 7.04 Hz, 1H), 8.70 (dd, J = 6.85, 2.54 Hz, 1H), 8.04 (d, J = 9.00 Hz, 1H), 7.15-7.28 (m, 2H), 4.51 (d, J = 12.52 Hz, 2H), 3.01 (t, J = 11.54 Hz, 2H), 2.77-2.92 (m, 1H), 2.67-2.76 (m, 3H), 2.22 (d, J = 12.52 Hz, 2H), 1.64-1.82 (m, 2H) ppm |
| | 4-(((2-chloro-5-(trifluoromethoxy)phenyl)sulfonyl)difluoromethyl)-N-(pyridazin-4-yl)piperidine-1-carboxamide | 74 | 4 | 515 | 1H-NMR (300 MHz, DMSO-d6): δ 8.44 (br.s, 1H), 8.06 (d, J = 8.4 Hz, 1H), 7.19 (br. s, 1H), 7.10-7.02 (m, 2H), 6.98-6.90 (m, 1H), 3.53 (d, J = 21.2 Hz, 2H), 2.32-2.08 (m, 3H), 1.36 (d, J = 15.2 Hz, 2H), 0.98-0.75 (m, 2H) ppm |
| | 4-(((2-chloro-3-methoxyphenyl)sulfonyl)difluoromethyl)-N-(pyridazin-4-yl)piperidine-1-carboxamide | 75 | 4 | 460 | 1H-NMR (300 MHz, DMSO-d6): δ 9.25 (dd, J = 0.9, 2.7 Hz, 1H), 8.88 (dd, J = 0.9, 6.0 Hz, 1H), 7.74 (dd, J = 2.7, 6.0 Hz, 1H), 7.70-7.65 (m, 3H), 4.24 (d, J = 13.5 Hz, 2H), 3.97 (s, 3H), 3.05-2.80 (m, 3H), 2.02 (d, J = 10.8 Hz, 2H), 1.62-1.42 (m, 2H) ppm |
| | 4-(((2-chloro-4-cyanophenyl)sulfonyl)difluoromethyl)-N-(pyridazin-4-yl)piperidine-1-carboxamide | 76 | 4 | 456 | 1H-NMR (300 MHz, DMSO-d6): δ 9.27-9.20 (m, 2H), 8.88 (d, J = 6.0 Hz, 1H), 8.50 (d, J = 1.5 Hz, 1H), 8.30-8.25 (m, 1H), 8.20-8.15 (m, 1H), 7.74 (dd, J = 2.7, 6.0 Hz, 1H), 4.24 (d, J = 12.6 Hz, 2H), 2.98 (t, J = 11.8 Hz, 3H), 2.02 (d, J = 13.2 Hz, 2H), 1.64-1.45 (m, 2H) ppm |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(1-fluoro-1-((3-fluorophenyl)sulfonyl)propyl)-N-(pyridazin-4-yl)piperidine-1-carboxamide | 77 | 6 | 425 | 1H NMR (400 MHz, CDCl3): δ 10.45 (s, 1H), 9.53 (d, J = 2.35 Hz, 1H), 8.81 (d, J = 7.04 Hz, 1H), 8.63 (dd, J = 7.04, 2.35 Hz, 1H), 7.73 (d, J = 7.83 Hz, 1H), 7.55-7.66 (m, 2H), 7.42 (td, J = 8.22, 1.96 Hz, 1H), 4.46 (d, J = 13.30 Hz, 2H), 2.89 (t, J = 12.33 Hz, 2H), 2.44-2.59 (m, 1H), 2.19 (d, J = 13.69 Hz, 1H), 1.98 (td, J = 15.16, 8.41 Hz, 3H), 1.61-1.79 (m, 2H), 0.95 (t, J = 7.63 Hz, 3H) ppm |
| | N-(6-cyano-pyridin-3-yl)-4-(((3-(difluoromethyl)-1-methyl-1H-pyrazol-4-yl)sulfonyl)difluoromethyl)piperidine-1-carboxamide | 78 | 4, 20 | 475 | 1H NMR (400 MHz, MeOH-d4) δ ppm 8.90 (d, J = 2.45 Hz, 1 H), 8.38 (s, 1 H), 8.29 (dd, J1 = 8.80, J2 = 2.45 Hz, 1 H), 7.69 (d, J = 8.93 Hz, 1 H), 6.84 (t, J = 52.0 Hz, 1H), 4.24 (br d, J = 13.69 Hz, 2 H), 3.94 (s, 3 H), 2.92 (br t, J = 12.17 Hz, 2 H), 2.72-2.87 (m, 1 H), 2.61 (s, 3H), 2.05 (br d, J = 11.62 Hz, 2 H), 1.56 (qd, J1 = 12.76, J2 = 4.16 Hz, 2 H) ppm |
| | 4-(((3-(difluoromethyl)-1-methyl-1H-pyrazol-4-yl)sulfonyl)difluoromethyl)-N-(2-fluoropyridin-4-yl)piperidine-1-carboxamide | 79 | 4, 20 | 468 | 1H NMR (400 MHz, MeOH-d4) δ ppm 8.63 (d, J = 2.20 Hz, 1 H), 8.37 (s, 1 H), 7.99 (dd, J1 = 8.68, J2 = 2.57 Hz, 1 H), 7.66 (d, J = 8.68 Hz, 1 H), 6.67-7.04 (m, 1 H), 4.21 (br d, J = 13.69 Hz, 2 H), 3.90-3.96 (m, 3 H), 2.87-2.96 (m, 2 H), 2.64-2.85 (m, 1 H), 2.04 (br d, J = 11.74 Hz, 2 H), 1.56 (qd, J1 = 12.76, J2 = 4.16 Hz, 2 H) ppm |
| | 4-(((3-(difluoromethyl)-1-methyl-1H-pyrazol-4-yl)sulfonyl)difluoromethyl)-N-(6-methylpyridin-3-yl)piperidine-1-carboxamide | 80 | 4, 20 | 464 | 1H NMR (400 MHz, MeOH-d4) δ ppm 8.90 (d, J = 2.45 Hz, 1 H), 8.38 (s, 1 H), 8.29 (dd, J1 = 8.80, J2 = 2.45 Hz, 1 H), 7.69 (d, J = 8.93 Hz, 1 H), 6.84 (t, J = 52.0 Hz, 1H), 4.24 (br d, J = 13.69 Hz, 2 H), 3.94 (s, 3 H), 2.92 (br t, J = 12.17 Hz, 2 H), 2.71-2.87 (m, 1 H), 2.61 (s, 3 H), 2.05 (br d, J = 11.62 Hz, 2 H), 1.56 |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | | | | | (qd, J = 12.76, 4.16 Hz, 2 H) ppm |
| | 4-(((3-(difluoromethyl)-1-methyl-1H-pyrazol-4-yl)sulfonyl)difluoromethyl)-N-(6-fluoropyridin-3-yl)piperidine-1-carboxamide | 81 | 4, 20 | 468 | 1H NMR (400 MHz, MeOH-d4) δ ppm 8.37 (s, 1 H), 8.09 (dd, J1 = 2.63, J2 = 0.92 Hz, 1 H), 7.88 (ddd, J1 = 8.86, J2 = 7.03, J3 = 2.81 Hz, 1 H), 6.65-7.01 (m, 2 H), 4.19 (br d, J = 13.82 Hz, 2 H), 3.93 (s, 3 H), 2.84-2.96 (m, 2 H), 2.64-2.82 (m, 1 H), 1.98-2.08 (m, 2 H), 1.55 (qd, J1 = 12.76, J2 = 4.16 Hz, 2 H) ppm |
| | 4-(((3-(difluoromethyl)-1-methyl-1H-pyrazol-4-yl)sulfonyl)difluoromethyl)-N-(isoxazol-3-yl)piperidine-1-carboxamide | 82 | 4, 20 | 440 | 1H NMR (400 MHz, ACETONITRILE-d3) δ ppm 8.36 (s, 1 H), 8.26 (s, 1 H), 8.04 (s, 1 H), 7.00 (t, J = 52 Hz, 1 H), 6.84 (s, 1H), 4.21 (d, J = 13.69 Hz, 2 H), 4.00 (s, 3 H), 2.95 (t, J = 12.96 Hz, 2 H), 2.65-2.88 (m, 1 H), 2.08 (d, J = 12.72 Hz, 2 H), 1.62 (qd, J = 12.67, 3.79 Hz, 2 H) |
| | 4-(((3-(difluoromethyl)-1-methyl-1H-pyrazol-4-yl)sulfonyl)difluoromethyl)-N-(pyridazin-4-yl)piperidine-1-carboxamide | 83 | 4, 20 | 451.1 | 1H NMR (300 MHz, CD3OD) δ ppm 9.24-9.16 (m, 1H), 8.83 (d, J = 6.0 Hz, 1H), 8.43 (s, 1H), 7.84 (m, 1H), 6.91 (t, J = 53.1 Hz, 1H), 4.29 (d, J = 13.6 Hz, 2H), 4.00 (s, 3H), 3.07-2.91 (m, 2H), 2.84 (s, 1H), 2.12 (d, J = 13.4 Hz, 2H), 1.75-1.54 (m, 2H) |
| | 4-(difluoro((1-methyl-1H-imidazol-4-yl)sulfonyl)methyl)-N-(pyridazin-4-yl)piperidine-1-carboxamide | 84 | 3, 4 | 401 | 1H NMR (300 MHz, CD3OD) δ ppm 9.20-9.19 (m, 1H), 8.84-8.81 (m, 1H), 8.05 (d, J = 1.2 Hz, 1H), 7.87-7.82 (m, 2H), 4.29-4.25 (m, 2H), 3.81 (s, 3H), 3.00-2.92 (m, 2H), 2.81-2.73 (m, 1H), 2.14-2.10 (m, 2H), 1.68-1.53 (m, 2H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(((1-ethyl-1H-pyrazol-5-yl)sulfonyl)difluoromethyl)-N-(pyridazin-4-yl)piperidine-1-carboxamide | 85 | 3, 4 | 415 | 1H NMR (300 MHz, CDCl3) δ ppm 9.11 (d, J = 2.4 Hz, 1H), 8.83 (d, J = 6.3 Hz, 1H), 8.01-7.98 (m, 1H), 7.62 (d, J = 2.1 Hz, 1H), 6.95 (d, J = 2.1 Hz, 1H), 4.49-4.38 (m, 4H), 2.95-2.87 (m, 2H), 2.80-2.76 (m, 1H), 2.23-2.20 (m, 2H), 1.71-1.67 (m, 2H), 1.47 (t, J = 7.2 Hz, 3H) |
| | 4-(((2-(1H-1,2,4-triazol-1-yl)phenyl)sulfonyl)difluoromethyl)-N-(pyridazin-4-yl)piperidine-1-carboxamide | 86 | 5, 20 | 464.2 | 1H NMR (300 MHz, CD3OD) δ ppm 9.23 (dd, J = 2.7, 1.0 Hz, 1H), 8.87 (dd, J = 6.1, 1.0 Hz, 1H), 8.77 (s, 1H), 8.29 (dd, J = 7.9, 1.5 Hz, 1H), 8.19 (s, 1H), 8.07 (m, 1H), 7.84-8.00 (m, 2H), 7.73 (m, 1H), 4.28 (d, J = 13.8 Hz, 2H), 2.99 (m, 2H), 2.69-2.87 (m, 1H), 1.59 (m, 2H), δ1.99-2.09 (m, 2H) |
| | 4-(difluoro((1-isopropyl-3-methyl-1H-pyrazol-5-yl)sulfonyl)methyl)-N-(pyridazin-4-yl)piperidine-1-carboxamide | 87 | 23 | 443.2 | 1H NMR (400 MHz, CDCl3) δ ppm 10.48 (s, 1H), 9.58 (s, 1H), 8.86-8.85 (m, 1H), 8.70-8.69 (m, 1H), 6.74 (s, 1H), 5.12-5.05 (m, 1H), 4.53-4.49 (m, 2H), 3.05-2.99 (m, 2H), 2.84-2.78 (m, 1H), 2.35 (s, 3H), 2.23-2.20 (m, 2H), 1.78-1.69 (m, 2H), 1.51 (d, J = 6.4 Hz, 6H) |
| | 4-(difluoro((6-hydroxypyridin-3-yl)sulfonyl)methyl)-N-(pyridazin-4-yl)piperidine-1-carboxamide | 88 | 4 | 414 | 1H NMR (400 MHz, CD3OD) δ ppm 9.23-9.22 (m, 1H), 8.87-8.85 (m, 1H), 8.19-8.18 (m, 1H), 7.88-7.85 (m, 1H), 7.75-7.72 (m, 1H), 6.56 (d, J = 9.6 Hz, 1H), 4.33-4.29 (m, 2H), 3.04-3.01 (m, 2H), 2.92-2.82 (m, 1H), 2.20-2.16 (m, 2H), 1.71-1.60 (m, 2H) |
| | 4-(((3-(tert-butyl)-1-methyl-1H-pyrazol-5-yl)sulfonyl)difluoromethyl)-N-(pyridazin-4-yl)piperidine-1-carboxamide | 89 | 24 | 457.1 | 1H NMR (400 MHz, DMSO-d6) δ ppm 9.27-9.24 (m, 2H), 8.89-8.87 (m, 1H), 7.76-7.3 (m, 1H), 7.11 (m, 1H), 4.26-4.22 (m, 2H), 4.02 (m, 3H), 3.02-2.93 (m, 3H), 2.02-1.99 (m, 2H), 1.55-1.49 (m, 2H), 1.27 (s, 9H) |

TABLE 1-continued

Representative compounds of the Invention and Analytical Data

| Structure | Name | Cmpd. No. | Ref. Example | Obs. Mass (M + H)+ | $^1$H NMR |
|---|---|---|---|---|---|
| | 4-(((1-cyclopropyl-3-methyl-1H-pyrazol-5-yl)sulfonyl)difluoromethyl)-N-(pyridazin-4-yl)piperidine-1-carboxamide | 90 | 24 | 441.1 | 1H NMR (300 MHz, DMSO-d6) δ ppm 9.26-9.23 (m, 2H), 8.89-8.87 (m, 1H), 7.76-7.73 (m, 1H), 7.02 (s, 1H), 4.26-4.22 (m, 2H), 4.08-4.03 (m, 1H), 3.02-2.94 (m, 3H), 2.22 (s, 3H), 2.03-2.00 (m, 2H), 1.60-1.47 (m, 2H), 1.23-1.20 (m, 2H), 1.19-1.18 (m, 2H) |
| 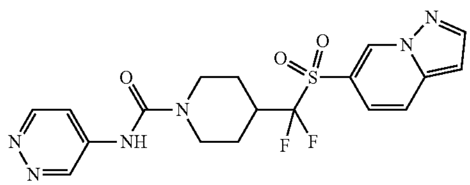 [SMILES: O=C(Nc1ccnnc1)N1CCC(C(F)(F)S(=O)(=O)c2ccc3ccnn3c2)CC1] | 4-(difluoro(pyrazolo[1,5-a]pyridin-6-ylsulfonyl)methyl)-N-(pyridazin-4-yl)piperidine-1-carboxamide | 91 | 4 | 437.1 | 1H NMR (300 MHz, DMSO-d6) δ ppm 9.44-9.43 (m, 1H), 9.26-9.23 (m, 2H), 8.89-8.86 (m, 1H), 8.41-8.40 (m, 1H), 8.00 (d, J = 9.0 Hz, 1H), 7.76-7.73 (m, 1H), 7.49-7.46 (m, 1H), 6.94-6.93 (m, 1H), 4.26-4.22 (m, 2H), 3.02-2.94 (m, 3H), 2.06-2.02 (m, 2H), 1.60-1.50 (m, 2H) |
| | 4-(((2-chloro-4-hydroxyphenyl)sulfonyl)difluoromethyl)-N-(pyridazin-4-yl)piperidine-1-carboxamide | 92 | 4 | 446.9 | 1H NMR (400 MHz, DMSO-d6) δ ppm 10.1-10.0 (m, 1H), 9.27 (s, 1H), 9.12-9.10 (m, 1H), 8.10-8.07 (m, 1H), 7.92-7.90 (m, 1H), 7.21 (s, 1H), 7.03-7.01 (m, 1H), 4.26-4.22 (m, 2H), 3.06-3.00 (m, 2H), 2.94-2.91 (m, 1H), 2.07-2.03 (m, 2H), 1.58-1.49 (m, 2H) |
| 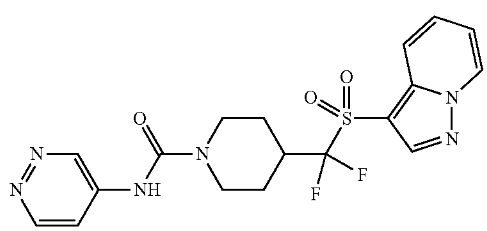 [SMILES: O=C(Nc1ccnnc1)N1CCC(C(F)(F)S(=O)(=O)c2cnn3ccccc23)CC1] | 4-(difluoro(pyrazolo[1,5-a]pyridin-3-ylsulfonyl)methyl)-N-(pyridazin-4-yl)piperidine-1-carboxamide | 93 | 4 | 437 | 1H NMR (300 MHz, DMSO-d6) δ ppm 9.26-9.23 (m, 2H), 9.08-9.06 (m, 1H), 8.89-8.87 (m, 1H), 8.65 (s, 1H), 7.94-7.92 (m, 1H), 7.84-7.81 (m, 1H), 7.76-7.73 (m, 1H), 7.40-7.35 (m, 1H), 4.25-4.21 (m, 2H), 3.00-2.82 (m, 3H), 2.07-2.02 (m, 2H), 1.58-1.44 (m, 2H) |
| 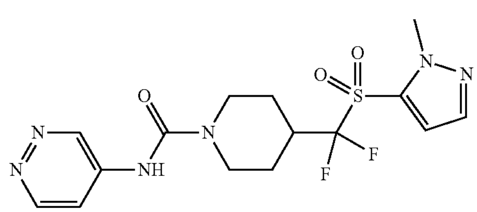 [SMILES: Cn1nccc1S(=O)(=O)C(F)(F)C1CCN(C(=O)Nc2ccnnc2)CC1] | 4-(difluoro((1-methyl-1H-pyrazol-5-yl)sulfonyl)methyl)-N-(pyridazin-4-yl)piperidine-1-carboxamide | 94 | 4 | 401.2 | 1H NMR (300 MHz, DMSO-d6) δ ppm 9.26-9.23 (m, 2H), 8.89-8.87 (m, 1H), 7.84-7.83 (m, 1H), 7.76-7.73 (m, 1H), 7.25-7.24 (m, 1H), 4.26-4.22 (m, 2H), 4.09 (s, 3H), 2.98-2.89 (m, 3H), 2.03-1.99 (m, 2H), 1.59-1.46 (m, 2H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(((2-(1H-pyrazol-1-yl)phenyl)sulfonyl)difluoromethyl)-N-(pyridazin-4-yl)piperidine-1-carboxamide | 95 | 4 | 463.1 | 1H NMR (300 MHz, CD3OD) δ ppm 9.23 (s, 1H), 8.92-8.86 (m, 1H), 8.25-8.23 (m, 1H), 8.02-8.00 (m, 2H), 7.99-7.94 (m, 2H), 7.75 (s, 1H), 7.63-7.60 (m, 1H), 6.51-6.49 (m, 1H), 4.29-4.25 (m, 2H), 3.00-2.94 (m, 2H), 2.81-2.78 (m, 1H), 2.08-2.01 (m, 2H), 1.62-1.52 (m, 2H) |
| | 4-(((2-(dimethylamino)pyridin-3-yl)sulfonyl)difluoromethyl)-N-(pyridazin-4-yl)piperidine-1-carboxamide | 96 | 4 | 441 | 1H NMR (300 MHz, DMSO-d6) δ ppm 9.25 (d, J = 1.8 Hz, 1H), 9.21 (s, 1H), 8.88 (m, 1H), 8.49 (m, 1H), 8.13 (d, J = 7.8 Hz, 1H), 7.74 (m, 1H), 7.07 (m, 1H), 4.22 (d, J = 12.9 Hz, 2H), 4.23 (d, J = 13.2 Hz, 2H), 3.02 (s, 6H), 2.72-2.96 (m, 3H), 1.97 (d, J = 12.9 Hz, 2H), 1.42-1.51 (m, 2H) |
| | (S)-4-(difluoro((3-fluorophenyl)sulfonyl)methyl)-N-(2-(1-hydroxyethyl)pyridin-4-yl)piperidine-1-carboxamide | 97 | 29 | 458.1 | 1H NMR (300 MHz, CD3OD) δ ppm 8.19-8.17 (m, 1H), 7.81-7.59 (m, 5H), 7.39-7.37 (m, 1H), 4.79-4.73 (m, 1H), 4.30-4.25 (m, 2H), 3.03-2.81 (m, 3H), 2.14 (m, 2H), 1.69-1.56 (m, 2H), 1.26-1.24 (m, 3H) |
| | (R)-4-(difluoro((3-fluorophenyl)sulfonyl)methyl)-N-(2-(1-hydroxyethyl)pyridin-4-yl)piperidine-1-carboxamide | 98 | 29 | 458.1 | 1H NMR (300 MHz, CD3OD) δ ppm 8.19-8.17 (m, 1H), 7.81-7.59 (m, 5H), 7.39-7.37 (m, 1H), 4.79-4.73 (m, 1H), 4.30-4.25 (m, 2H), 3.03-2.81 (m, 3H), 2.14 (m, 2H), 1.69-1.56 (m, 2H), 1.26-1.24 (m, 3H) |
| | (S)-4-(((3-(difluoromethyl)-1-methyl-1H-pyrazol-4-yl)sulfonyl)difluoromethyl)-N-(2-(1-hydroxyethyl) | 99 | 29 | 494.2 | 1H NMR (300 MHz, CD3OD) δ ppm 8.43 (s, 1H), 8.19-8.17 (m, 2H), 7.9-7.58 (m, 1H), 7.39-7.36 (m, 1H), 6.74 (t, J = 53.1 Hz, 1H), 4.79-4.72 (m, 1H), 4.29-4.25 (m, 2H), 4.03 (s, 3H), 3.04-2.74 (m, 3H), 2.13-2.08 (m, 2H), 1.69-1.55 (m, 2H), |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | pyridin-4-yl)piperidine-1-carboxamide | | | | 1.42 (d, J = 6.6 Hz, 3H) |
| | (R)-4-(((3-(difluoromethyl)-1-methyl-1H-pyrazol-4-yl)sulfonyl)difluoromethyl)-N-(2-(1-hydroxyethyl)pyridin-4-yl)piperidine-1-carboxamide | 100 | 29 | 494.2 | 1H NMR (300 MHz, CD3OD) δ ppm 8.43 (s, 1H), 8.19-8.17 (m, 2H), 7.9-7.58 (m, 1H), 7.39-7.36 (m, 1H), 6.74 (t, J = 53.1 Hz, 1H), 4.79-4.72 (m, 1H), 4.29-4.25 (m, 2H), 4.03 (s, 3H), 3.04-2.74 (m, 3H), 2.13-2.08 (m, 2H), 1.69-1.55 (m, 2H), 1.42 (d, J = 6.6 Hz, 3H) |
| | 4-(((3-(difluoromethyl)-1-methyl-1H-pyrazol-4-yl)sulfonyl)difluoromethyl)-N-(2-(hydroxymethyl)pyridin-4-yl)piperidine-1-carboxamide | 101 | 20 | 480 | 1H NMR (300 MHz, Acetonitrile-d3) δ ppm 8.69 (s, 1H), 8.18-8.14 (m, 2H), 7.77-7.76 (m, 1H), 7.67-7.64 (m, 1H), 6.88 (t, J = 56.1 Hz, 1H), 4.70 (s, 2H), 4.17-4.14 (m, 2H), 3.88 (s, 3H), 2.92-2.86 (m, 2H), 2.76-2.69 (m, 1H), 2.02-1.99 (m, 2H), 1.60-1.49 (m, 2H) |
| | 4-(2-((4-cyanophenyl)sulfonyl)propan-2-yl)-N-(isoxazol-3-yl)piperidine-1-carboxamide | 102 | 3, 26 | 403 | 1H NMR (400 MHz, DMSO-d6) δ ppm 9.64 (s, 1H), 8.61 (d, J = 1.5 Hz, 1H), 8.12 (d, J = 8.7 Hz, 2H), 7.99 (d, J = 8.7 Hz, 2H), 6.72 (s, 1H), 4.19-4.14 (m, 2H), 2.72-2.64 (m, 2H), 1.94-1.85 (m, 3H), 1.32-1.24 (m, 2H), 1.12 (s, 6H) |
| | 4-(2-((3-chloro-1-methyl-1H-pyrazol-4-yl)sulfonyl)propan-2-yl)-N-(pyridazin-4-yl)piperidine-1-carboxamide | 103 | 27 | 427.1 | 1H NMR (400 MHz, CD3OD) δ ppm 9.30 (br s, 1H), 9.12 (d, J = 6.8 Hz, 1H), 8.38-8.36 (m, 1H), 8.23 (s, 1H), 4.35-4.31 (m, 2H), 3.94 (s, 3H), 3.04-2.97 (m, 2H), 2.20-2.17 (m, 3H), 1.58-1.49 (m, 2H), 1.34 (s, 6H) |
| | N-(6-fluoropyridin-3-yl)-4-(2-((6-(trifluoromethyl)pyridin- | 104 | 4, 7 | 475 | 1H NMR (400 MHz, CDCl3) δ ppm 9.19 (s, 1H), 8.39 (d, J = 7.83 Hz, 1H), 8.11 (br. s., 2H), 7.95 (d, J = 8.31 Hz, 1H), 6.94 (br. s., 1H), 4.23-4.20 (m, 2H), |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 3-yl) sulfonyl) propan-2-yl) piperidine-1-carboxamide | | | | 3.11-3.00 (m, 2H), 2.38-2.33 (m, 1H), 2.20-2.18 (m, 2H), 1.31-1.28 (s, 8H) |
| | 4-(2-((3-(difluoromethyl)-1-methyl-1H-pyrazol-5-yl)sulfonyl)propan-2-yl)-N-(2-fluoropyridin-4-yl)piperidine-1-carboxamide | 105 | 17, 26 | 460 | 1H NMR (400 MHz, CD3OD) δ ppm 7.98-8.15 (m, 1H), 7.39-7.51 (m, 2H), 7.13 (s, 1H), 6.83 (t, J = 56.0 Hz, 1H), 4.26-4.39 (m, 2H), 4.20 (s, 3H), 2.87-3.06 (m, 2H), 2.21-2.37 (m, 1H), 2.04-2.18 (m, 2H), 1.43-1.66 (m, 2H), 1.34 (s, 6H) |
| | 4-(2-((3-(difluoromethyl)-1-methyl-1H-pyrazol-5-yl)sulfonyl)propan-2-yl)-N-(6-fluoropyridin-3-yl)piperidine-1-carboxamide | 106 | 17, 26 | 460 | 1H NMR (400 MHz, CD3OD) δ ppm 8.05-8.13 (m, 1H), 7.83-7.91 (m, 1H), 7.01 (s, 1H), 6.88-6.95 (m, 1H), 6.72 (t, J = 56.00 Hz, 1H), 4.12-4.23 (m, 2H), 4.09 (s, 3H), 2.74-2.88 (m, 2H), 2.10-2.23 (m, 1H), 1.93-2.03 (m, 2H), 1.34-1.51 (m, 2H), 1.23 (s, 6H) |
| | 4-(2-((3-(difluoromethyl)-1-methyl-1H-pyrazol-5-yl)sulfonyl)propan-2-yl)-N-(6-methylpyridin-3-yl)piperidine-1-carboxamide | 107 | 17, 26 | 456 | 1H NMR (400 MHz, CD3OD) δ ppm 9.01 (s, 1H), 8.34-8.43 (m, 1H), 7.76-7.85 (m, 1H), 7.08-7.16 (m, 1H), 6.82 (t, J = 56.00 Hz, 1H), 4.27-4.39 (m, 2H), 4.20 (s, 3H), 2.90-3.03 (m, 2H), 2.72 (s, 3H), 2.23-2.36 (m, 1H), 2.07-2.17 (m, 2H), 1.47-1.64 (m, 2H), 1.35 (s, 6H) |
| | 4-(2-((3-(difluoromethyl)-1-methyl-1H-pyrazol-5-yl)sulfonyl)propan-2-yl)-N-(isoxazol-3-yl)piperidine-1-carboxamide | 108 | 17, 26 | 432 | 1H NMR (400 MHz, DMSO-d6) δ ppm 9.74 (s, 1H), 8.67 (s, 1H), 7.24 (s, 1H), 7.18 (t, J = 53.0 Hz, 1H), 6.78 (s, 1H), 4.17-4.27 (m, 2H), 4.13 (s, 3H), 2.69-2.85 (m, 2H), 2.05-2.18 (m, 1H), 1.84-1.96 (m, 2H), 1.27-1.44 (m, 2H), 1.24 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(2-((4-cyanophenyl)sulfonyl)propan-2-yl)-N-(6-fluoropyridin-3-yl)piperidine-1-carboxamide | 109 | 3, 26 | 431 | 1H NMR (400 MHz, CHLOROFORM-d) δ ppm 8.06 (br. s., 2H), 7.93 (d, J = 8.07 Hz, 2H), 7.81 (d, J = 8.07 Hz, 2H), 6.81-6.95 (m, 2H), 4.12 (d, J = 13.20 Hz, 2H), 2.89 (t, J = 12.65 Hz, 2H), 2.21 (t, J = 11.80 Hz, 1H), 2.07 (d, J = 12.96 Hz, 2H), 1.44 (d, J = 12.10 Hz, 2H), 1.16 (s, 6H) |
| | 4-(2-((1-methyl-3-(trifluoromethyl)-1H-pyrazol-4-yl)sulfonyl)propan-2-yl)-N-(1H-pyrazol-4-yl)piperidine-1-carboxamide | 110 | 26 | 449 | 1H NMR (400 MHz, ACETONITRILE-d3) δ ppm 8.13 (s, 1 H) 7.62 (s, 2 H) 7.19 (br. s., 1 H) 4.11 (d, J = 13.33 Hz, 2 H) 3.97 (s, 3 H) 2.81 (t, J = 12.84 Hz, 2 H) 2.14 (t, J = 11.98 Hz, 1 H) 1.99-2.05 (m, 2 H) 1.39 (qd, J = 12.49, 3.36 Hz, 2 H) 1.27 (s, 6 H) |
| | N-(6-fluoropyridin-3-yl)-4-(2-((1-methyl-3-(trifluoromethyl)-1H-pyrazol-4-yl)sulfonyl)propan-2-yl)piperidine-1-carboxamide | 111 | 26 | 478 | 1H NMR (400 MHz, ACETONITRILE-d3) δ ppm 8.21 (br. s., 1 H) 8.13 (s, 1 H) 7.99 (t, J = 8.07 Hz, 1 H) 7.37 (br. s., 1 H) 6.95 (dd, J = 8.80, 2.69 Hz, 1 H) 4.17 (d, J = 13.45 Hz, 2 H) 3.98 (s, 3 H) 2.86 (t, J = 12.90 Hz, 2 H) 2.18 (t, J = 11.98 Hz, 1 H) 2.04 (d, J = 12.96 Hz, 2 H) 1.44 (qd, J = 12.55, 3.30 Hz, 2 H) 1.29 (s, 6 H) |
| | 4-(2-((3-cyanophenyl)sulfonyl)propan-2-yl)-N-(isoxazol-3-yl)piperidine-1-carboxamide | 112 | 3, 26 | 403.1 | 1H NMR (300 MHz, DMSO-d6) δ ppm 9.65 (s, 1H), 8.61 (s, 1H), 8.25-8.21 (m, 2H), 8.13-8.10 (m, 1H), 7.87-7.81 (m, 1H), 6.72 (d, J = 1.5 Hz, 1H), 4.19-4.15 (m, 2H), 2.73-2.65 (m, 2H), 2.00-1.86 (m, 3H), 1.33-1.22 (m, 2H), 1.13 (s, 6H) |
| | N-(isoxazol-3-yl)-4-(2-((6-(trifluoromethyl)pyridin-3-yl)sulfonyl)propan-2-yl)piperidine-1-carboxamide | 113 | 26 | 447 | 1H NMR (300 MHz, DMSO-d6) δ ppm 9.70 (br s, 1H), 9.17 (d, J = 1.2 Hz, 1H), 8.65 (d, J = 1.5 Hz, 1H), 8.57-8.53 (m, 1H), 8.22 (d, J = 8.4 Hz, 1H), 6.77 (d, J = 1.8 Hz, 1H), 4.24-4.20 (m, 2H), 2.80-2.71 (m, 2H), 2.08-1.92 (m, 3H), 1.40-1.27 (m, 2H), 1.22 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(2-((3-chloro-1-methyl-1H-pyrazol-5-yl)sulfonyl)propan-2-yl)-N-(6-fluoropyridin-3-yl)piperidine-1-carboxamide | 114 | 19, 26 | 444 | 1H NMR (400 MHz, CDCl3) δ ppm 8.03 (br. s., 1H), 7.18 (s, 1H), 6.89 (d, J = 8.31 Hz, 1H), 6.64 (s, 1H), 4.11 (d, J = 13.08 Hz, 2H), 4.03 (s, 3H), 2.82-2.95 (m, 2H), 2.16-2.29 (m, 1H), 1.99-2.12 (m, 2H), 1.36-1.53 (m, 2H), 1.23 (s, 6H) |
| | 4-(2-((3-chloro-1-methyl-1H-pyrazol-5-yl)sulfonyl)propan-2-yl)-N-(2-fluoropyridin-4-yl)piperidine-1-carboxamide | 115 | 19, 26 | 444 | 1H NMR (400 MHz, CDCl3) δ ppm 7.89-8.01 (m, 1H), 7.49-7.59 (m, 1H), 7.38-7.48 (m, 1H), 7.18 (s, 1H), 6.64 (s, 1H), 4.11-4.47 (m, 2H), 4.03 (s, 3H), 2.89 (t, J = 12.65 Hz, 2H), 2.17-2.32 (m, 1H), 2.05 (d, J = 12.84 Hz, 2H), 1.34-1.54 (m, 2H), 1.22 (s, 6H) |
| | 4-(2-((3-(difluoromethyl)-1-methyl-1H-pyrazol-4-yl)sulfonyl)propan-2-yl)-N-(2-fluoropyridin-4-yl)piperidine-1-carboxamide | 116 | 21, 26 | 478 | 1H NMR (400 MHz, CD3OD) δ ppm 8.31 (s, 1 H), 7.96 (d, J = 5.62 Hz, 1 H), 7.31 (d, J = 5.62 Hz, 1 H), 7.27 (s, 1H), 7.07 (t, J = 54 Hz, 1 H) 4.28 (d, J = 13.45 Hz, 2 H) 4.04 (s, 3 H) 2.92 (t, J = 12.84 Hz, 2 H) 2.21 (t, J = 12.10 Hz, 1 H) 2.12 (d, J = 13 Hz, 2 H) 1.40-1.61 (m, 2 H) 1.31 (s, 6 H) |
| | 4-(2-((3-(difluoromethyl)-1-methyl-1H-pyrazol-4-yl)sulfonyl)propan-2-yl)-N-(6-fluoropyridin-3-yl)piperidine-1-carboxamide | 117 | 21, 27 | 460 | 1H NMR (400 MHz, MeOH-d4) δ ppm 8.32 (s, 1 H), 8.20 (s, 1 H), 7.92-8.06 (m, 1 H), 6.91-7.26 (m, 2 H), 4.27 (br d, J = 13.20 Hz, 2 H), 4.04 (s, 3 H), 2.91 (br t, J = 12.90 Hz, 2 H), 2.06-2.27 (m, 3 H), 1.42-1.58 (m, 2 H), 1.25-1.38 (m, 7 H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 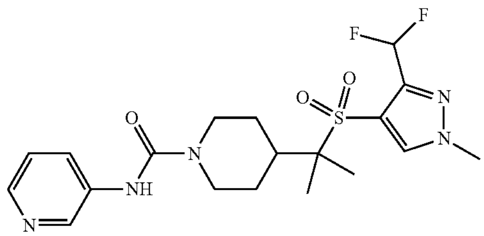 [SMILES: Cn1cc(S(=O)(=O)C(C)(C)C2CCN(C(=O)Nc3cccnc3)CC2)c(C(F)F)n1] | 4-(2-((3-(difluoromethyl)-1-methyl-1H-pyrazol-4-yl)sulfonyl)propan-2-yl)-N-(pyridin-3-yl)piperidine-1-carboxamide | 118 | 21, 26 | 442 | 1H NMR (400 MHz, CD3OD) δ ppm 8.62 (s, 1H), 8.29 (s, 1H), 8.18 (d, J = 4.65 Hz, 1H), 7.90-7.98 (m, 1H), 7.35-7.45 (m, 1H), 7.03 (t, J = 54.00 Hz, 1H), 4.21-4.32 (m, 2H), 4.01 (s, 3H), 2.83-2.95 (m, 2H), 2.13-2.24 (m, 1H), 2.03-2.13 (m, 2H), 1.40-1.58 (m, 2H), 1.29 (s, 6H) |
| 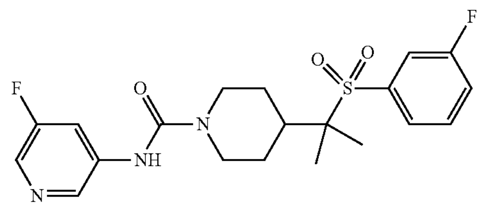 [SMILES: CC(C)(C1CCN(C(=O)Nc2cncc(F)c2)CC1)S(=O)(=O)c1cccc(F)c1] | 4-(2-((3-fluorophenyl)sulfonyl)propan-2-yl)-N-(5-fluoropyridin-3-yl)piperidine-1-carboxamide | 119 | 5, 26 | 424 | 1H NMR (400 MHz, CD3OD) δ ppm 8.37-8.43 (m, 1H), 8.03-8.09 (m, 1H), 7.82-7.90 (m, 1H), 7.60-7.76 (m, 3H), 7.48-7.58 (m, 1H), 4.20-4.31 (m, 2H), 2.82-2.95 (m, 2H), 2.04-2.22 (m, 3H), 1.41-1.58 (m, 2H), 1.26 (s, 6H) |
| 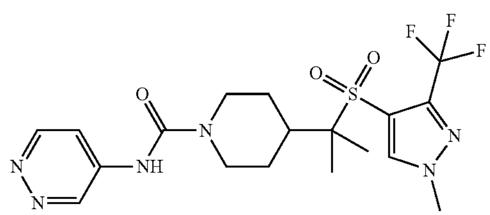 [SMILES: Cn1cc(S(=O)(=O)C(C)(C)C2CCN(C(=O)Nc3ccnnc3)CC2)c(C(F)(F)F)n1] | 4-(2-((1-methyl-3-(trifluoromethyl)-1H-pyrazol-4-yl)sulfonyl)propan-2-yl)-N-(pyridazin-4-yl)piperidine-1-carboxamide | 120 | 26 | 461 | 1H NMR (400 MHz, ACETONITRILE-d3) δ ppm 9.17 (s, 1H) 8.78-8.96 (m, 2 H) 8.17 (d, J = 6.72 Hz, 1 H) 8.02 (s, 1 H) 4.13 (d, J = 13.69 Hz, 2 H) 3.86 (s, 3 H) 2.84 (t, J = 12.65 Hz, 2 H) 2.11 (t, J = 11.98 Hz, 1 H) 1.98 (d, J = 12.84 Hz, 2 H) 1.30-1.43 (m, 2 H) 1.18 (s, 6 H) |
| 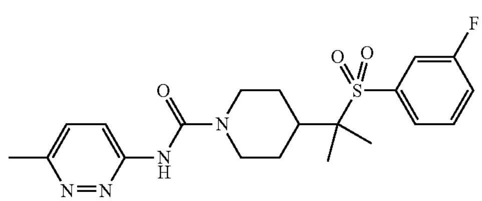 [SMILES: Cc1ccc(NC(=O)N2CCC(C(C)(C)S(=O)(=O)c3cccc(F)c3)CC2)nn1] | 4-(2-((3-fluorophenyl)sulfonyl)propan-2-yl)-N-(6-methylpyridazin-3-yl)piperidine-1-carboxamide | 121 | 5, 26 | 421 | 1H NMR (400 MHz, DMSO-d6) δ ppm 10.62 (br s, 1 H), 8.34 (d, J = 9.29 Hz, 1 H), 7.95 (d, J = 9.29 Hz, 1 H), 7.51-7.78 (m, 4 H), 4.22 (br d, J = 13.20 Hz, 2 H), 2.76 (br t, J = 12.53 Hz, 2 H), 2.59 (s, 2 H), 2.56-2.64 (m, 1 H), 1.83-2.06 (m, 3 H), 1.24-1.40 (m, 2 H), 1.11 (s, 6 H) |
| 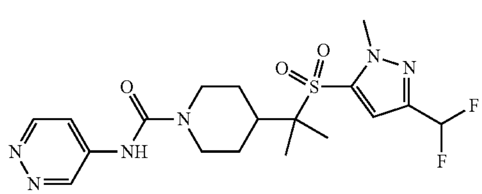 [SMILES: Cn1nc(C(F)F)cc1S(=O)(=O)C(C)(C)C1CCN(C(=O)Nc2ccnnc2)CC1] | 4-(2-((3-(difluoromethyl)-1-methyl-1H-pyrazol-5-yl)sulfonyl)propan-2-yl)-N-(pyridazin-4-yl)piperidine-1-carboxamide | 122 | 21, 26 | 443.1 | 1H NMR (400 MHz, CD3OD) δ ppm 9.20 (d, J = 2.4 Hz, 1H), 8.83 (d, J = 6.0 Hz, 1H), 7.84-7.81 (m, 1H), 7.07 (s, 1H), 6.77 (t, J = 54.6 Hz, 1H), 4.29-4.24 (m, 2H), 4.15 (s, 3H), 2.96-2.87 (m, 2H), 2.28-2.20 (m, 1H), 2.09-2.05 (m, 2H), 1.56-1.44 (m, 2H), 1.29 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 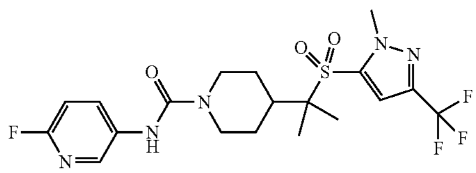 [SMILES: Cn1nc(C(F)(F)F)cc1S(=O)(=O)C(C)(C)C1CCN(C(=O)Nc2ccc(F)nc2)CC1] | N-(6-fluoro-pyridin-3-yl)-4-(2-((1-methyl-3-(trifluoro-methyl)-1H-pyrazol-5-yl)sulfonyl)propan-2-yl)piperidine-1-carboxamide | 123 | 18, 26 | 478 | 1H NMR (400 MHz, DMSO-d6) δ ppm 8.78 (s, 1H), 8.21 (s, 1H), 7.97 (t, J = 7.5 Hz, 1H), 7.51 (s, 1H), 4.17 (d, J = 13.1 Hx, 2), 4.11 (s, 3H), 2.73 (t, J = 12.5 Hz, 2H), 2.07 (t, J = 11.9 Hz, 1H), 1.86 (d, J = 12.4 Hz, 2H), 1.33 (m, 2H), 1.20 (s, 6H) |
| 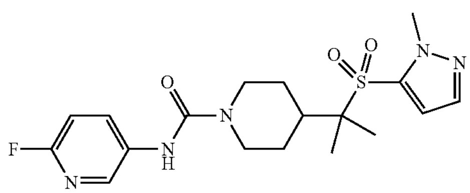 [SMILES: Cn1nccc1S(=O)(=O)C(C)(C)C1CCN(C(=O)Nc2ccc(F)nc2)CC1] | N-(6-fluoro-pyridin-3-yl)-4-(2-((1-methyl-1H-pyrazol-5-yl)sulfonyl)propan-2-yl)piperidine-1-carboxamide | 124 | 4, 26 | 410 | 1H NMR (400 MHz, DMSO-d6) δ ppm 8.56 (s, 1H), 8.28 (s, 1H), 8.04 (t, J = 7.6 Hz, 1H), 7.72 (d, J = 1.2 Hz, 1H), 7.06 (dd, J1 = 8.8 Hz, J2 = 3.1 Hz, 1H), 6.96 (s, 1H), 4.23 (d, J = 13.2 Hz, 2H), 4.08 (s, 3H), 2.78 (t, J = 12.6 Hz, 2H), 2.09 (t, J = 11.9 Hz, 1H), 1.91 (d, J = 12.6 Hz, 2H), 1.35 (m, 2H), 1.22 (s, 6H) |
| 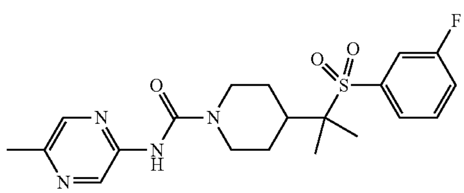 | 4-(2-((3-fluoro-phenyl)sulfonyl)propan-2-yl)-N-(5-methyl-pyrazin-2-yl)piperidine-1-carboxamide | 125 | 5, 26 | 421 | 1H NMR (400 MHz, DMSO-d6) δ ppm 9.53 (s, 1H), 8.92 (s, 1H), 8.26 (s, 1H), 7.76-7.65 (m, 4H), 4.25 (d, J = 13.1 Hz, 2H), 2.75 (t, J = 12.8 Hz, 2H), 2.43 (s, 3H), 2.04-1.91 (m, 3H), 1.33 (m, 2H), 1.17 (s, 6H) |
| 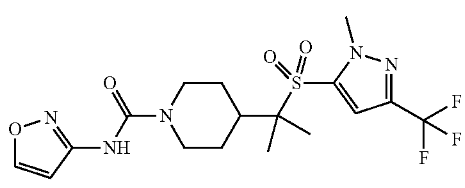 [SMILES: Cn1nc(C(F)(F)F)cc1S(=O)(=O)C(C)(C)C1CCN(C(=O)Nc2ccon2)CC1] | N-(isoxazol-3-yl)-4-(2-((1-methyl-3-(trifluoro-methyl)-1H-pyrazol-5-yl)sulfonyl)propan-2-yl)piperidine-1-carboxamide | 126 | 18, 26 | 450 | 1H NMR (400 MHz, DMSO-d6): 9.75 (s, 1H), 8.67 (s, 1H), 7.57 (s, 1H), 6.78 (s, 1H), 4.23 (d, J = 13.2 Hz, 2H), 4.17 (s, 3H), 2.78 (t, J = 12.4 Hz, 2H), 2.12 (t, J = 12.0 Hz, 1H), 1.90 (d, J = 12.8 Hz, 2H), 1.34 (m, 2H), 1.25 (s, 6H) |
| | N-(2-fluoro-pyridin-4-yl)-4-(2-((1-methyl-3-(trifluoro-methyl)-1H-pyrazol-5-yl)sulfonyl | 127 | 18, 26 | 478 | 1H NMR (400 MHz, MeOH-d4) δ ppm 8.08 (br d, J = 5.99 Hz, 1 H), 7.42-7.55 (m, 2 H), 7.30 (s, 1 H), 4.32 (br d, J = 13.20 Hz, 2 H), 4.24 (s, 3 H), 2.97 (br t, J = 12.78 Hz, 2 H), 2.30 (br t, J = 11.86 Hz, 1 H), 2.12 (br d, J = 12.84 Hz, 2 H), |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | propan-2-yl) piperidine-1-carboxamide | | | | 1.46-1.64 (m, 2 H), 1.35 (s, 6 H) |
| 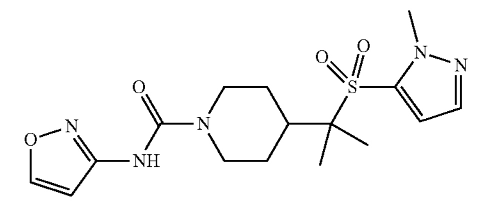 [SMILES: Cn1nccc1S(=O)(=O)C(C)(C)C1CCN(C(=O)Nc2ccon2)CC1] | N-(isoxazol-3-yl)-4-(2-((1-methyl-1H-pyrazol-5-yl)sulfonyl)propan-2-yl)piperidine-1-carboxamide | 128 | 4, 26 | 382 | 1H NMR (400 MHz, DMSO-d6) δ ppm 9.66 (s, 1 H), 8.60 (s, 1 H), 7.65 (d, J = 1.96 Hz, 1 H), 6.88 (d, J = 1.83 Hz, 1H), 6.70 (s, 1 H), 4.16 (br d, J = 13.33 Hz, 2 H), 4.00 (s, 3 H), 2.69 (br t, J = 12.65 Hz, 2 H), 2.01 (br t, J = 11.92 Hz, 1 H), 1.83 (br d, J = 12.59 Hz, 2 H), 1.20-1.37 (m, 2 H), 1.14 (s, 6 H) |
| 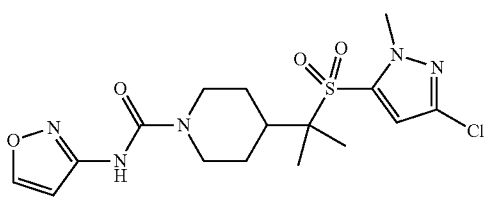 [SMILES: Cn1nc(Cl)cc1S(=O)(=O)C(C)(C)C1CCN(C(=O)Nc2ccon2)CC1] | 4-(2-((3-chloro-1-methyl-1H-pyrazol-5-yl)sulfonyl)propan-2-yl)-N-(isoxazol-3-yl)piperidine-1-carboxamide | 129 | 15, 26 | 416 | 1H NMR (400 MHz, DMSO-d6) δ ppm 9.65 (s, 1 H), 8.59 (s, 1 H), 7.07 (s, 1 H), 6.70 (s, 1 H), 4.15 (br d, J = 13.20 Hz, 2 H), 3.97 (s, 3 H), 2.70 (br t, J = 12.53 Hz, 2 H), 1.97-2.11 (m, 2 H), 1.82 (br d, J = 12.47 Hz, 2 H), 1.20-1.34 (m, 2 H), 1.17 (s, 7 H) |
| | 4-(2-((1-methyl-3-(trifluoromethyl)-1H-pyrazol-5-yl)sulfonyl)propan-2-yl)-N-(6-methylpyridin-3-yl)piperidine-1-carboxamide | 130 | 26 | 474 | 1H NMR (400 MHz, MeOH-d4) δ ppm 8.93 (d, J = 2.20 Hz, 1 H), 8.31 (dd, J = 8.80, 2.32 Hz, 1 H), 7.73 (d, J = 8.80 Hz, 1 H), 7.22 (s, 1 H), 4.26 (br d, J = 13.45 Hz, 2 H), 4.16 (s, 3 H), 2.90 (br t, J = 12.65 Hz, 2 H), 2.64 (s, 3 H), 2.22 (br t, J = 12.04 Hz, 1 H), 2.05 (br d, J = 12.84 Hz, 2 H), 1.48 (qd, J = 12.57, 3.61 Hz, 2 H), 1.27 (s, 6 H) |
| | 4-(2-((3-fluorophenyl)sulfonyl)propan-2-yl)-N-(pyrazin-2-yl)piperidine-1-carboxamide | 131 | 5, 26 | 407 | 1H NMR (400 MHz, CD3OD) δ ppm 9.02 (s, 1H), 8.24-8.33 (m, 1H), 8.12-8.18 (m, 1H), 7.59-7.78 (m, 3H), 7.44-7.58 (m, 1H), 4.20-4.39 (m, 2H), 2.81-2.98 (m, 2H), 2.02-2.22 (m, 3H), 1.40-1.60 (m, 2H), 1.27 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(2-((3-fluoro-phenyl)sulfonyl)propan-2-yl)-N-(pyrimidin-5-yl)piperidine-1-carboxamide | 132 | 5, 26 | 407 | 1H NMR (400 MHz, CD3OD) δ ppm 8.88 (s, 1H), 8.76 (s, 1H), 7.59-7.78 (m, 5H), 7.46-7.58 (m, 1H), 4.18-4.32 (m, 2H), 2.83-2.97 (m, 2H), 2.02-2.24 (m, 3H), 1.42-1.57 (m, 2H), 1.27 (s, 6H) |
| | 4-(2-((3-fluoro-phenyl)sulfonyl)propan-2-yl)-N-(pyridin-3-yl)piperidine-1-carboxamide | 133 | 5, 26 | 406 | 1H NMR (400 MHz, CD3OD) δ ppm 8.60-8.66 (m, 1H), 8.15-8.21 (m, 1H), 7.91-8.01 (m, 1H), 7.60-7.79 (m, 3H), 7.47-7.59 (m, 1H), 7.36-7.46 (m, 1H), 4.21-4.32 (m, 2H), 2.79-2.96 (m, 2H), 2.03-2.22 (m, 3H), 1.39-1.58 (m, 2H), 1.27 (s, 6H) |
| | N-(2-fluoro-pyridin-4-yl)-4-(2-((1-methyl-1H-pyrazol-5-yl)sulfonyl)propan-2-yl)piperidine-1-carboxamide | 134 | 26 | 410 | 1H NMR (400 MHz, MeOH-d4) δ ppm 8.01 (br d, J = 6.24 Hz, 1 H), 7.54 (d, J = 1.96 Hz, 1 H), 7.40-7.50 (m, 2 H), 6.80 (d, J = 1.96 Hz, 1 H), 4.21 (br d, J = 13.20 Hz, 2 H), 4.04 (s, 3 H), 2.85 (br t, J = 12.78 Hz, 2 H), 2.11-2.22 (m, 1 H), 2.00 (br d, J = 13.08 Hz, 2 H), 1.37-1.55 (m, 2 H), 1.20 (s, 6 H) |
| | 4-(2-((1-methyl-1H-pyrazol-5-yl)sulfonyl)propan-2-yl)-N-(6-methyl-pyridin-3-yl)piperidine-1-carboxamide | 135 | 26 | 406 | 1H NMR (400 MHz, MeOH-d4) δ ppm 9.02 (d, J = 2.20 Hz, 1 H), 8.41 (dd, J1 = 8.93, J2 = 2.32 Hz, 1 H), 7.81 (d, J = 8.93 Hz, 1 H), 7.66 (d, J = 2.08 Hz, 1 H), 6.92 (d, J = 1.96 Hz, 1 H), 4.34 (br d, J = 13.45 Hz, 2 H), 4.16 (s, 3 H), 2.96 (br t, J = 12.84 Hz, 2 H), 2.73 (s, 3 H), 2.27 (br t, J = 12.10 Hz, 1 H), 2.12 (br d, J = 13.08 Hz, 2 H), 1.54 (qd, J1 = 12.70, J2 = 3.85 Hz, 2 H), 1.28 (m, 6 H) |
| | 4-(2-((3-fluoro-phenyl)sulfonyl)propan-2-yl)-N-(1-methyl-1H-pyrazol-5-yl)piperidine-1- | 136 | 5, 26 | 409 | 1H NMR (400 MHz, MeOH-d4) δ ppm 9.02 (d, J = 2.20 Hz, 1 H), 8.41 (dd, J1 = 8.93, J2 = 2.32 Hz, 1 H), 7.81 (d, J = 8.93 Hz, 1 H), 7.66 (d, J = 2.08 Hz, 1 H), 6.92 (d, J = 1.96 Hz, 1 H), 4.34 (br d, J = 13.45 Hz, 2 H), 4.16 |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | carboxamide | | | | (s, 3 H), 2.96 (br t, J = 12.84 Hz, 2 H), 2.73 (s, 3 H), 2.27 (br t, J = 12.10 Hz, 1 H), 2.12 (br d, J = 13.08 Hz, 2 H), 1.54 (qd, J1 = 12.70, J2 = 3.85 Hz, 2 H), 1.28-1.37 (m, 6 H) |
| | 4-(2-((1-methyl-3-(trifluoromethyl)-1H-pyrazol-5-yl)sulfonyl)propan-2-yl)-N-(pyridazin-4-yl)piperidine-1-carboxamide | 137 | 26 | 461.1 | 1H NMR (400 MHz, CD3OD) δ ppm 9.23 (d, J = 1.5 Hz, 1H), 8.86 (d, J = 4.5 Hz, 1H), 7.87-7.85 (m, 1H), 7.27 (s, 1H), 4.31-4.28 (m, 2H), 4.22 (s, 3H), 2.98-2.92 (m, 2H), 2.31-2.24 (m, 1H), 2.11-2.03 (m, 2H), 1.58-1.48 (m, 2H), 1.33 (s, 6H) |
| | 4-(2-((3-fluorophenyl)sulfonyl)propan-2-yl)-N-(1-methyl-1H-pyrazol-3-yl)piperidine-1-carboxamide | 138 | 5, 26 | 409 | 1H NMR (400 MHz, DMSO-d6) δ ppm 9.20 (br s, 1 H), 7.55-7.84 (m, 5 H), 4.21 (br d, J = 12.84 Hz, 2 H), 3.73 (s, 3 H), 2.68 (br t, J = 12.41 Hz, 2 H), 1.83-2.06 (m, 3 H), 1.22-1.38 (m, 2 H), 1.17 (s, 6 H) |
| | 4-(2-((3-fluorophenyl)sulfonyl)propan-2-yl)-N-(1-methyl-1H-pyrazol-4-yl)piperidine-1-carboxamide | 139 | 5, 26 | 409 | 1H NMR (400 MHz, DMSO-d6) δ ppm 7.53-7.74 (m, 5 H), 7.34 (s, 1 H), 4.08 (br d, J = 13.20 Hz, 2 H), 3.70 (s, 3 H), 2.61 (br t, J = 12.23 Hz, 2 H), 1.78-1.99 (m, 3 H), 1.22 (qd, J1 = 12.37, J2 = 3.24 Hz, 2 H), 1.11 (s, 6 H) |
| | 4-(2-((3-chloro-1-methyl-1H-pyrazol-5-yl)sulfonyl)propan-2-yl)-N-(pyridazin-4-yl)piperidine-1-carboxamide | 140 | 15, 26 | 428.9 | 1H NMR (300 MHz, DMSO-d6) δ ppm 9.96 (br s, 1H), 9.29 (d, J = 2.4 Hz, 1H), 9.08 (d, J = 6.6 Hz, 1H), 8.06-8.03 (m, 1H), 7.14 (s, 1H), 4.25-4.21 (m, 2H), 4.05 (s, 3H), 2.94-2.86 (m, 2H), 2.19-2.11 (m, 1H), 2.07-1.98 (m, 2H), 1.45-1.34 (m, 2H), 1.25 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 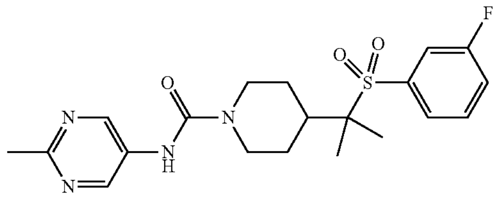 [SMILES: Cc1ncc(NC(=O)N2CCC(C(C)(C)S(=O)(=O)c3cccc(F)c3)CC2)cn1] | 4-(2-((3-fluorophenyl)sulfonyl)propan-2-yl)-N-(2-methylpyrimidin-5-yl)piperidine-1-carboxamide | 141 | 5, 26 | 421 | 1H NMR (400 MHz, DMSO-d6) δ ppm 8.82-8.90 (m, 2 H), 7.53-7.77 (m, 5 H), 4.17 (br d, J = 13.08 Hz, 2 H), 2.71 (br t, J = 12.41 Hz, 2 H), 2.52 (s, 3 H), 1.83-2.03 (m, 3 H), 1.22-1.38 (m, 2 H), 1.12 (s, 6 H) |
| 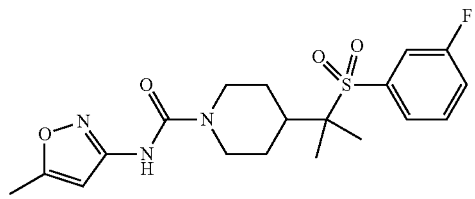 [SMILES: Cc1cc(NC(=O)N2CCC(C(C)(C)S(=O)(=O)c3cccc(F)c3)CC2)no1] | 4-(2-((3-fluorophenyl)sulfonyl)propan-2-yl)-N-(5-methylisoxazol-3-yl)piperidine-1-carboxamide | 142 | 5, 27 | 410 | 1H NMR (400 MHz, DMSO-d6) δ ppm 9.50 (s, 1 H), 7.50-7.77 (m, 4 H), 6.40 (s, 1 H), 4.13 (br d, J = 13.20 Hz, 2 H), 2.64 (br t, J = 12.53 Hz, 2 H), 2.26 (s, 3 H), 1.77-2.01 (m, 3 H), 1.15-1.36 (m, 2 H), 1.10 (s, 6 H) |
| 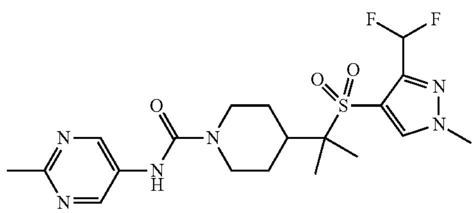 | 4-(2-((3-(difluoromethyl)-1-methyl-1H-pyrazol-4-yl)sulfonyl)propan-2-yl)-N-(2-methylpyrimidin-5-yl)piperidine-1-carboxamide | 143 | 21, 26 | 457 | 1H NMR (400 MHz, DMSO-d6) δ 9.06 (s, 1 H), 8.89 (s, 2 H), 8.56 (s, 1 H), 7.12 (t, J = 52.0 Hz, 1H), 4.23 (br d, J = 13.20 Hz, 2 H), 3.99 (s, 3 H), 2.73-2.89 (m, 2 H), 2.58 (s, 3 H), 2.03-2.13 (m, 1 H), 1.96 (br d, J = 12.47 Hz, 2 H), 1.27-1.45 (m, 2 H), 1.20 (s, 6 H) |
| 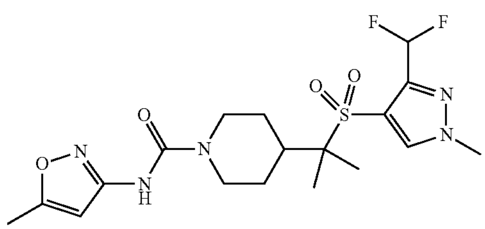 | 4-(2-((3-(difluoromethyl)-1-methyl-1H-pyrazol-4-yl)sulfonyl)propan-2-yl)-N-(5-methylisoxazol-3-yl)piperidine-1-carboxamide | 144 | 21, 26 | 446 | 1H NMR (400 MHz, DMSO-d6) δ ppm 9.57 (s, 1 H), 8.55 (s, 1 H), 7.11 (t, J = 65.0 Hz, 1H), 7.29 (m, 1 H), 6.47 (s, 1 H), 4.20 (br d, J = 13.20 Hz, 2 H), 3.98 (s, 3 H), 2.72 (br t, J = 12.41 Hz, 2 H), 2.33 (s, 3 H), 2.02 (br t, J = 11.80 Hz, 1 H), 1.91 (br d, J = 12.10 Hz, 2 H), 1.25-1.38 (m, 2 H), 1.18 (s, 6 H) |
| 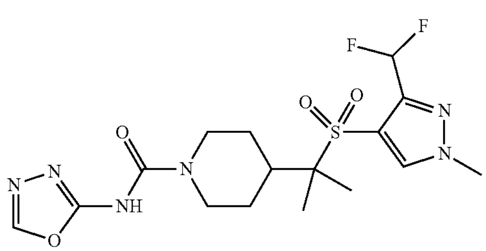 [SMILES: Cn1cc(S(=O)(=O)C(C)(C)C2CCN(C(=O)Nc3nnco3)CC2)c(C(F)F)n1] | 4-(2-((3-(difluoromethyl)-1-methyl-1H-pyrazol-4-yl)sulfonyl)propan-2-yl)-N-(1,3,4-oxadiazol-2-yl)piperidine-1-carboxamide | 145 | 21, 26 | 433 | 1H NMR (400 MHz, CD3OD) δ ppm 8.47-8.71 (m, 1H), 8.29 (s, 1H), 7.04 (t, J = 56.00 Hz, 1H), 4.16-4.41 (m, 2H), 4.01 (s, 3H), 2.75-3.00 (m, 2H), 2.01-2.23 (m, 3H), 1.37-1.54 (m, 2H), 1.28 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 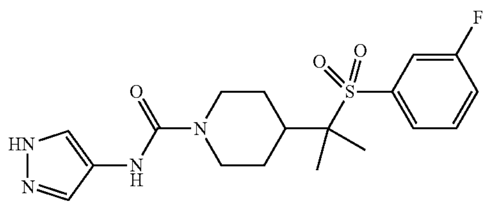 [SMILES: CC(C)(C1CCN(C(=O)Nc2cn[nH]c2)CC1)S(=O)(=O)c1cccc(F)c1] | 4-(2-((3-fluorophenyl)sulfonyl)propan-2-yl)-N-(1H-pyrazol-4-yl)piperidine-1-carboxamide | 146 | 5, 26 | 395 | 1H NMR (400 MHz, DMSO-d6) δ ppm 8.46 (s, 1 H), 7.56-7.73 (m, 4 H), 7.53 (s, 2 H), 4.07 (br d, J = 13.33 Hz, 2 H), 2.61 (br t, J = 12.17 Hz, 2 H), 1.77-2.01 (m, 3 H), 1.15-1.31 (m, 2 H), 1.11 (s, 6 H) |
| 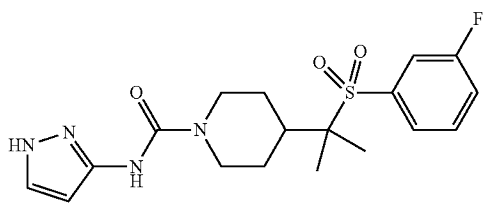 [SMILES: CC(C)(C1CCN(C(=O)Nc2cc[nH]n2)CC1)S(=O)(=O)c1cccc(F)c1] | 4-(2-((3-fluorophenyl)sulfonyl)propan-2-yl)-N-(1H-pyrazol-3-yl)piperidine-1-carboxamide | 147 | 5, 26 | 395 | 1H NMR (400 MHz, MeOH-d4) δ ppm 7.94 (br s, 1 H), 7.40-7.69 (m, 4 H), 6.21 (br s, 1 H), 4.18 (br d, J = 12.59 Hz, 2 H), 2.82 (br t, J = 12.53 Hz, 2 H), 1.96-2.16 (m, 3 H), 1.40 (q, J = 10.88 Hz, 2 H), 1.17 (s, 6 H) |
| 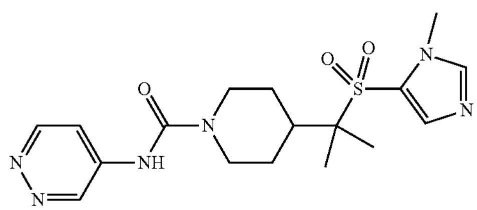 [SMILES: Cn1cncc1S(=O)(=O)C(C)(C)C1CCN(C(=O)Nc2ccnnc2)CC1] | 4-(2-((1-methyl-1H-imidazol-5-yl)sulfonyl)propan-2-yl)-N-(pyridazin-4-yl)piperidine-1-carboxamide | 148 | 4, 26 | 393 | 1H NMR (400 MHz, ACETONITRILE-d3) δ ppm 9.28 (d, J = 2.69 Hz, 1 H) 8.96 (d, J = 6.97 Hz, 1 H) 8.40 (br. s., 1 H) 8.34 (dd, J = 6.97, 2.81 Hz, 1H) 7.91 (br. s., 1 H) 4.26 (d, J = 12.23 Hz, 2 H) 3.96 (s, 3 H) 2.98 (t, J = 12.35 Hz, 2 H) 2.24 (tt, J = 12.03, 3.07 Hz, 1 H) 2.08 (d, J = 13.20 Hz, 2 H) 1.52 (qd, J = 12.70, 3.73 Hz, 2 H) 1.32 (s, 6 H) |
| 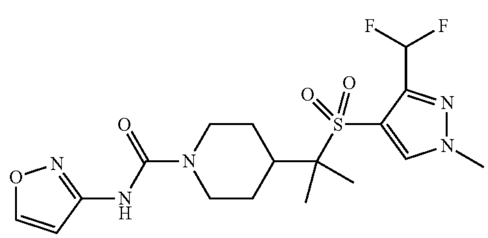 [SMILES: Cn1cc(S(=O)(=O)C(C)(C)C2CCN(C(=O)Nc3ccon3)CC2)c(C(F)F)n1] | 4-(2-((3-(difluoromethyl)-1-methyl-1H-pyrazol-4-yl)sulfonyl)propan-2-yl)-N-(isoxazol-3-yl)piperidine-1-carboxamide | 149 | 21, 26 | 432 | 1H NMR (400 MHz, CD3OD) δ ppm 8.43 (s, 1H), 8.29 (s, 1H), 7.05 (t, J = 56.00 Hz, 1H), 6.73 (s, 1H), 4.22 (br. s., 2H), 4.01 (s, 3H), 2.80-2.96 (m, 3H), 2.12-2.24 (m, 1H), 2.02-2.11 (m, 2H), 1.38-1.54 (m, 2H), 1.28 (s, 6H) |
| 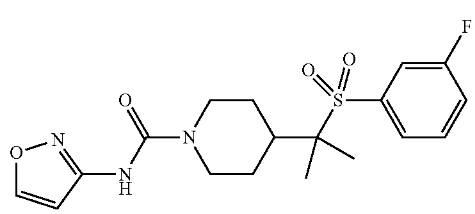 [SMILES: CC(C)(C1CCN(C(=O)Nc2ccon2)CC1)S(=O)(=O)c1cccc(F)c1] | 4-(2-((3-fluorophenyl)sulfonyl)propan-2-yl)-N-(isoxazol-3-yl)piperidine-1-carboxamide | 150 | 5, 26 | 393 | 1H NMR (400 MHz, MeOH-d4) δ ppm 8.36 (br s, 1 H), 7.58-7.67 (m, 2 H), 7.50-7.56 (m, 1 H), 7.38-7.49 (m, 1 H), 6.65 (s, 1 H), 4.15 (br d, J = 13.33 Hz, 2 H), 2.77 (br t, J = 12.59 Hz, 2 H), 1.93-2.11 (m, 3 H), 1.37 (qd, J1 = 12.51, J2 = 2.93 Hz, 2 H), 1.16 (s, 6 H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(2-((3-fluorophenyl)sulfonyl)propan-2-yl)-N-(2-fluoropyridin-4-yl)piperidine-1-carboxamide | 151 | 5, 26 | 424 | 1H NMR (400 MHz, MeOH-d4) δ ppm 8.10 (dd, J1 = 6.30, J2 = 1.16 Hz, 1 H), 7.69-7.78 (m, 2 H), 7.63-7.67 (m, 1 H), 7.46-7.59 (m, 3 H), 4.30 (br d, J = 13.57 Hz, 2 H), 2.94 (br t, J = 12.35 Hz, 2 H), 2.08-2.22 (m, 3 H), 1.48-1.60 (m, 2 H), 1.29 (s, 6 H) |
| | 4-(2-((3-fluorophenyl)sulfonyl)propan-2-yl)-N-(6-fluoropyridin-3-yl)piperidine-1-carboxamide | 152 | 5, 26 | 424 | 1H NMR (400 MHz, MeOH-d4) δ ppm 8.19 (d, J = 1.47 Hz, 1 H), 7.94-8.04 (m, 1 H), 7.63-7.79 (m, 3 H), 7.50-7.61 (m, 1 H), 7.02 (dd, J1 = 8.86, J2 = 2.87 Hz, 1 H), 4.27 (br d, J = 13.45 Hz, 2 H), 2.89 (br t, J = 12.17 Hz, 2 H), 2.05-2.23 (m, 3 H), 1.43-1.60 (m, 2 H), 1.29 (s, 6 H) |
| | 4-(2-((3-fluorophenyl)sulfonyl)propan-2-yl)-N-(1,3,4-oxadiazol-2-yl)piperidine-1-carboxamide | 153 | 5, 26 | 397 | 1H NMR (400 MHz, CD3OD) δ ppm 8.60-8.64 (m, 1H), 7.61-7.75 (m, 3H), 7.47-7.56 (m, 1H), 4.21-4.38 (m, 2H), 2.78-2.94 (m, 2H), 2.02-2.19 (m, 3H), 1.38-1.54 (m, 2H), 1.26 (s, 6H) |
| | 4-(2-((3-(difluoromethyl)-1-methyl-1H-pyrazol-4-yl)sulfonyl)propan-2-yl)-N-(6-methylpyridazin-4-yl)piperidine-1-carboxamide | 154 | 21, 26 | 457 | 1H NMR (400 MHz, CDCl3) δ ppm 8.18-8.30 (m, 1H), 7.68 (s, 1H), 6.79-7.29 (m, 3H), 4.21-4.35 (m, 1H), 3.94 (s, 3H), 2.46-2.64 (m, 3H), 2.41 (s, 3H), 1.92-2.12 (m, 3H), 1.13-1.31 (m, 1H), 1.08 (s, 6H) |
| | 4-(2-((3-(difluoromethyl)-1-methyl-1H-pyrazol-4-yl)sulfonyl)propan-2-yl)-N-(6-methylpyridin-3-yl)piperidine-1-carboxamide | 155 | 21, 26 | 456 | 1H NMR (400 MHz, MeOH-d4) δ ppm 9.01 (d, J = 2.45 Hz, 1 H), 8.37 (dd, J1 = 8.86, J2 = 2.51 Hz, 1 H), 8.32 (s, 1 H), 7.81 (d, J = 8.93 Hz, 1 H), 7.07 (t, J = 52.0 Hz, 1H), 4.31 (br d, J = 13.45 Hz, 2 H), 4.04 (s, 3 H), 2.88-3.03 (m, 2 H), 2.06-2.28 (m, 3 H) 2.72 (s, 3 H), 1.52 (qd, J = 12.53, 3.97 Hz, 2 H), 1.32 (s, 6 H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 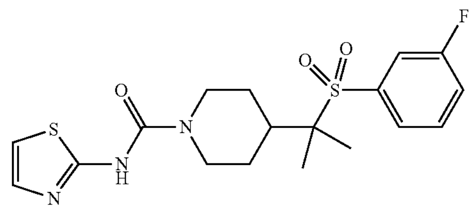 [SMILES: CC(C)(C1CCN(C(=O)Nc2nccs2)CC1)S(=O)(=O)c1cccc(F)c1] | 4-(2-((3-fluoro-phenyl)sulfonyl)propan-2-yl)-N-(thiazol-2-yl)piperidine-1-carboxamide | 156 | 5, 26 | 412 | 1H NMR (400 MHz, MeOH-d4) δ ppm 7.51-7.81 (m, 5 H), 7.37 (br s, 1 H), 4.31 (br d, J = 12.84 Hz, 2 H), 3.03 (br t, J = 12.59 Hz, 2 H), 2.11-2.28 (m, 3 H), 1.56 (qd, J1 = 12.70, J2 = 3.00 Hz, 2 H), 1.29 (s, 6 H) |
| 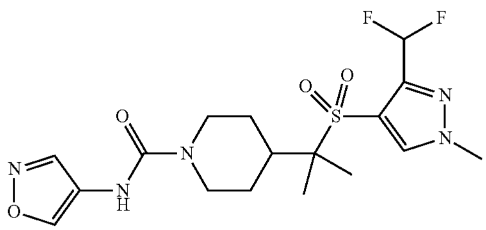 [SMILES: Cn1cc(S(=O)(=O)C(C)(C)C2CCN(C(=O)Nc3cnoc3)CC2)c(C(F)F)n1] | 4-(2-((3-(difluoro-methyl)-1-methyl-1H-pyrazol-4-yl)sulfonyl)propan-2-yl)-N-(isoxazol-4-yl)piperidine-1-carboxamide | 157 | 21, 26 | 432 | 1H NMR (400 MHz, MeOH-d4) δ ppm 8.63 (s, 1 H), 8.34 (s, 1 H), 8.19 (s, 1 H), 6.95 (t, J = 54.0 Hz, 1H), 4.09 (br d, J = 13.57 Hz, 2 H), 3.92-3.96 (m, 1 H), 2.78 (br t, J = 12.17 Hz, 2 H), 1.91-2.17 (m, 3 H), 1.35 (qd, J = 12.59, 3.91 Hz, 2 H), 1.16-1.24 (m, 8 H) |
| 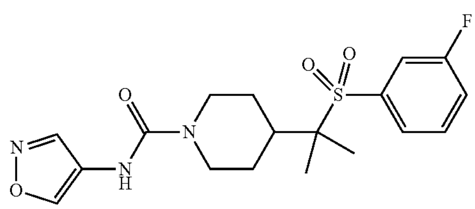 [SMILES: CC(C)(C1CCN(C(=O)Nc2cnoc2)CC1)S(=O)(=O)c1cccc(F)c1] | 4-(2-((3-fluoro-phenyl)sulfonyl)propan-2-yl)-N-(isoxazol-4-yl)piperidine-1-carboxamide | 158 | 5, 26 | 396 | 1H NMR (400 MHz, MeOH-d4) δ ppm 8.70-8.82 (m, 1 H), 8.45 (s, 1 H), 7.49-7.80 (m, 4 H), 4.21 (br d, J = 13.45 Hz, 2 H), 2.81-2.97 (m, 2 H), 2.01-2.24 (m, 3 H), 1.36-1.56 (m, 2 H), 1.28 (s, 6 H) |
| 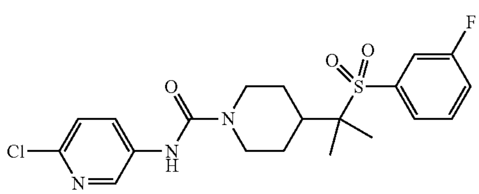 [SMILES: CC(C)(C1CCN(C(=O)Nc2ccc(Cl)nc2)CC1)S(=O)(=O)c1cccc(F)c1] | N-(6-chloro-pyridin-3-yl)-4-(2-((3-fluoro-phenyl)sulfonyl)propan-2-yl)piperidine-1-carboxamide | 159 | 5, 26 | 440 | 1H NMR (400 MHz, MeOH-d4) δ ppm 8.55 (d, J = 2.45 Hz, 1 H), 8.01 (dd, J1 = 8.80, J2 = 2.81 Hz, 1 H), 7.62-7.80 (m, 3 H), 7.51-7.61 (m, 1 H), 7.48 (d, J = 8.68 Hz, 1 H), 4.28 (br d, J = 13.57 Hz, 2 H), 2.90 (br t, J = 12.29 Hz, 2 H), 2.07-2.23 (m, 3 H), 1.42-1.61 (m, 2 H), 1.29 (s, 6 H) |
| 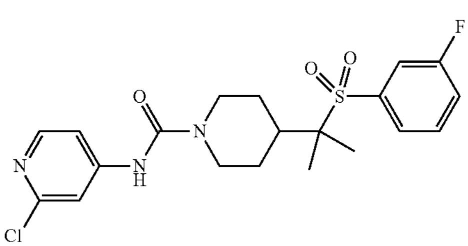 [SMILES: CC(C)(C1CCN(C(=O)Nc2ccnc(Cl)c2)CC1)S(=O)(=O)c1cccc(F)c1] | N-(2-chloro-pyridin-4-yl)-4-(2-((3-fluoro-phenyl)sulfonyl)propan-2-yl)piperidine-1-carboxamide | 160 | 5, 26 | 440 | 1H NMR (400 MHz, MeOH-d4) δ ppm 8.35 (d, J = 6.72 Hz, 1 H), 8.02 (d, J = 2.08 Hz, 1 H), 7.51-7.81 (m, 5 H), 4.32 (br d, J = 13.45 Hz, 2 H), 2.96 (br t, J = 12.65 Hz, 2 H), 2.09-2.27 (m, 3 H), 1.54 (qd, J1 = 12.72, J2 = 2.93 Hz, 2 H), 1.29 (s, 6 H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 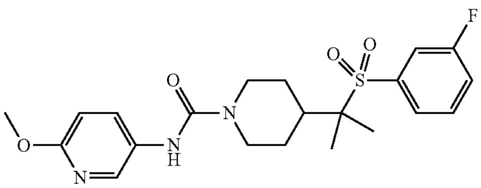 [SMILES: COc1ccc(NC(=O)N2CCC(C(C)(C)S(=O)(=O)c3cccc(F)c3)CC2)cn1] | 4-(2-((3-fluorophenyl)sulfonyl)propan-2-yl)-N-(6-methoxypyridin-3-yl)piperidine-1-carboxamide | 161 | 5, 26 | 436 | 1H NMR (400 MHz, MeOH-d4) δ ppm 7.93 (d, J = 7.09 Hz, 1 H), 7.50-7.66 (m, 4 H), 7.40-7.49 (m, 1 H), 7.33 (dd, J1 = 7.09, J2 = 1.83 Hz, 1 H), 4.22 (br d, J = 13.45 Hz, 2 H), 4.03 (s, 3 H), 2.84 (br t, J = 12.90 Hz, 2 H), 2.01-2.16 (m, 3 H), 1.36-1.51 (m, 2 H), 1.17 (s, 6 H) |
| 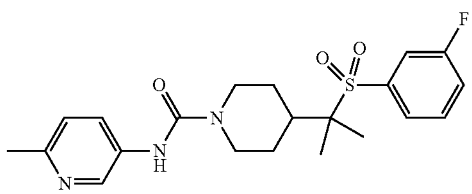 | 4-(2-((3-fluorophenyl)sulfonyl)propan-2-yl)-N-(6-methylpyridin-3-yl)piperidine-1-carboxamide | 162 | 5, 26 | 420 | 1H NMR (400 MHz, CD3OD) δ ppm 9.01 (d, J = 2.20 Hz, 1 H), 8.38 (dd, J1 = 8.93, J2 = 2.45 Hz, 1 H), 7.69-7.85 (m, 3 H), 7.62-7.68 (m, 1 H), 7.50-7.61 (m, 1 H), 4.32 (br d, J = 13.45 Hz, 2 H), 2.94 (br t, J = 12.41 Hz, 2 H), 2.72 (s, 3 H), 2.09-2.27 (m, 3 H), 1.44-1.61 (m, 2 H), 1.29 (s, 6 H) |
| 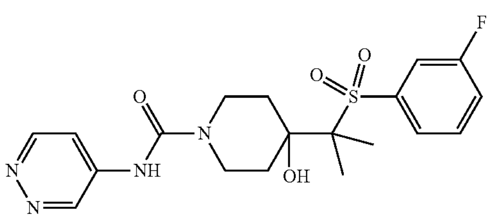 [SMILES: CC(C)(C1(O)CCN(C(=O)Nc2ccnnc2)CC1)S(=O)(=O)c1cccc(F)c1] | 4-(2-((3-fluorophenyl)sulfonyl)propan-2-yl)-4-hydroxy-N-(pyridazin-4-yl)piperidine-1-carboxamide | 163 | 30 | 423 | 1H NMR (400 MHz, DMSO-d6) δ ppm 9.27-9.28 (s, 1H), 9.18-9.27 (s, 1H), 8.86-8.88 (d, J = 6.9 Hz, 1H), 7.58-7.77 (m, 5H), 5.07 (s, 1H), 4.00-4.04 (d, J = 13.2 Hz, 2H), 3.06-3.13 (m, 2H), 1.85-1.99 (m, 4H), 1.26 (s, 6H) |
| 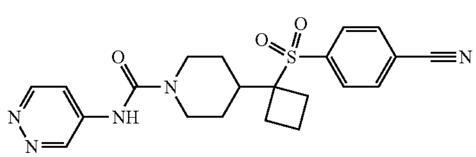 [SMILES: N#Cc1ccc(S(=O)(=O)C2(C3CCN(C(=O)Nc4ccnnc4)CC3)CCC2)cc1] | 4-(1-((4-cyanophenyl)sulfonyl)cyclobutyl)-N-(pyridazin-4-yl)piperidine-1-carboxamide | 164 | 2 | 426 | 1H NMR (400 MHz, CD3OD) δ ppm 9.25 (d, J = 0.8 Hz, 1H), 8.88-8.87 (m, 1H), 8.15-8.13 (m, 2H), 8.06-8.04 (m, 2H), 7.88-7.86 (m, 1H), 4.29-4.26 (m, 2H), 2.87-2.81 (m, 2H), 2.77-2.69 (m, 2H), 2.38-2.31 (m, 2H), 2.05-1.81 (m, 5H), 1.61-1.55 (m, 2H) |
| 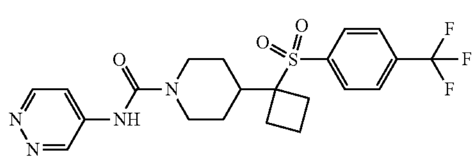 [SMILES: O=C(Nc1ccnnc1)N1CCC(C2(S(=O)(=O)c3ccc(C(F)(F)F)cc3)CCC2)CC1] | N-(pyridazin-4-yl)-4-(1-((4-(trifluoromethyl)phenyl)sulfonyl)cyclobutyl)piperidine-1-carboxamide | 165 | 2 | 469.2 | 1H NMR (300 MHz, DMSO-d6) δ ppm 9.27-9.26 (m, 1H), 9.15 (s, 1H), 8.88-8.86 (m, 1H), 8.17-8.14 (m, 2H), 8.07-8.04 (m, 2H), 7.76-7.73 (m, 1H), 4.21-4.16 (m, 2H), 3.33-3.16 (m, 2H), 2.77-2.72 (m, 2H), 2.60-2.57 (m, 2H), 1.91-1.62 (m, 5H), 1.46-1.34 (m, 2H) |

TABLE 1-continued

Representative compounds of the Invention and Analytical Data

| Structure | Name | Cmpd. No. | Ref. Example | Obs. Mass (M + H)+ | $^1$H NMR |
|---|---|---|---|---|---|
| | 4-fluoro-4-(1-((3-fluorophenyl)sulfonyl)cyclobutyl)-N-(pyridazin-4-yl)piperidine-1-carboxamide | 166 | 2, 30 | 437.1 | 1H NMR (400 MHz, DMSO-d6) δ ppm 9.26-9.25 (m, 1H), 8.88-8.86 (m, 1H), 7.83-7.65 (m, 5H), 4.12-4.10 (m, 2H), 3.00-2.94 (m, 2H), 2.71-2.63 (m, 2H), 2.52-2.48 (m, 2H), 2.16-2.10 (m, 2H), 1.98-1.75 (m, 3H), 1.57-1.55 (m, 2H) |
| | 4-(1-((3,5-difluorophenyl)sulfonyl)cyclobutyl)-N-(pyridazin-4-yl)piperidine-1-carboxamide | 167 | 2 | 437.2 | 1H NMR (400 MHz, DMSO-d6) δ ppm 9.27-9.26 (m, 1H), 9.15 (s, 1H), 8.87-8.86 (m, 1H), 7.84-7.68 (m, 4H), 4.20-4.16 (m, 2H), 2.76-2.70 (m, 2H), 2.65-2.62 (m, 2H), 2.32-2.24 (m, 2H), 1.88-1.69 (m, 5H), 1.58-1.55 (m, 2H) |
| | 4-(2-((3-(difluoromethyl)-1-methyl-1H-pyrazol-4-yl)sulfonyl)propan-2-yl)-N-(pyridazin-4-yl)piperidine-1-carboxamide | 168 | 21 | 443 | 1H NMR (400 MHz, CD3OD) δ ppm 9.23-9.22 (m, 1H), 8.86-8.84 (m, 1H), 8.29 (s, 1H), 7.87-7.84 (m, 1H), 7.05 (t, J = 53.2 Hz, 1H), 4.29-4.26 (m, 2H), 4.01 (s, 3H), 2.95-2.89 (m, 2H), 2.22-2.03 (m, 3H), 1.54-1.147 (m, 2H), 1.43 (s, 6H) |
| | 4-(2-((3,5-difluorophenyl)sulfonyl)propan-2-yl)-N-(pyridazin-4-yl)piperidine-1-carboxamide | 169 | 4, 26 | 425.2 | 1H NMR (400 MHz, DMSO-d6) δ ppm 9.28 (d, J = 2.0 Hz, 1H), 9.17 (s, 1H), 8.88 (d, J = 6.0 Hz, 1H), 7.83-7.74 (m, 2H), 7.62-7.59 (m, 2H), 4.23-4.19 (m, 2H), 2.84-2.78 (m, 2H), 2.09-2.06 (m, 1H), 1.97-1.94 (m, 2H), 1.41-1.32 (m, 2H), 1.21 (s, 6H) |
| | 4-(1-((3-(difluoromethyl)-1-methyl-1H-pyrazol-4-yl)sulfonyl)cyclobutyl)-N-(pyridazin-4-yl)piperidine-1-carboxamide | 170 | 2 | 455.2 | 1H NMR (400 MHz, CDCl3) δ ppm 9.38 (s, 1H), 8.94-8.92 (m, 1H), 8.16-8.14 (m, 1H), 7.94 (s, 1H), 7.02 (t, J = 53.6 Hz, 1H), 4.40-4.36 (m, 2H), 4.06 (s, 3H), 2.95-2.91 (m, 2H), 2.79-2.68 (m, 2H), 2.63-2.57 (m, 2H), 2.31-2.24 (m, 3H), 2.11-2.05 (2H), 1.93-1.82 (m, 2H), .68-1.62 (m, 2H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | N-(pyridazin-4-yl)-4-(2-((6-(trifluoromethyl)pyridin-3-yl)sulfonyl)propan-2-yl)piperidine-1-carboxamide | 171 | 26 | 458.1 | 1H NMR (300 MHz, DMSO-d6) δ ppm 9.28-9.27 (m, 1H), 9.19-9.17 (m, 2H), 8.88-8.86 (m, 1H), 8.58-8.54 (m, 1H), 8.23-8.20 (m, 1H), 7.77-7.74 (m, 1H), 4.24-4.20 (m, 2H), 2.87-2.79 (m, 2H), 2.13-1.97 (m, 3H), 1.44-1.40 (m, 2H), 1.23 (s, 6H) |
| 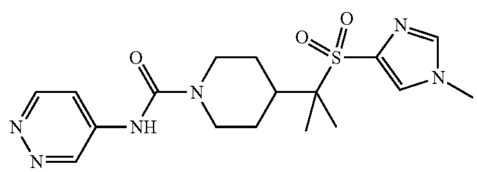 [SMILES: Cn1cnc(S(=O)(=O)C(C)(C)C2CCN(C(=O)Nc3ccnnc3)CC2)c1] | 4-(2-((1-methyl-1H-imidazol-4-yl)sulfonyl)propan-2-yl)-N-(pyridazin-4-yl)piperidine-1-carboxamide | 172 | 4, 26 | 393 | 1H NMR (300 MHz, CD3OD) δ ppm 9.23-9.22 (m, 1H), 8.86-8.84 (m, 1H), 7.86-7.82 (m, 3H), 4.28-4.24 (m, 2H), 3.82 (s, 3H), 2.92-2.86 (m, 2H), 2.17-2.09 (m, 3H), 1.50-1.46 (m, 2H), 1.30 (s, 6H) |
| 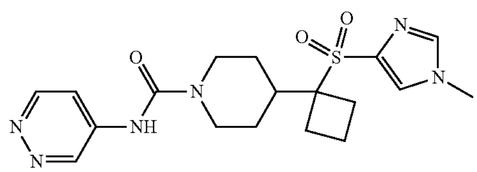 [SMILES: Cn1cnc(S(=O)(=O)C2(C3CCN(C(=O)Nc4ccnnc4)CC3)CCC2)c1] | 4-(1-((1-methyl-1H-imidazol-4-yl)sulfonyl)cyclobutyl)-N-(pyridazin-4-yl)piperidine-1-carboxamide | 173 | 2 | 405 | 1H NMR (300 MHz, CDCl3) δ ppm 9.23-9.22 (m, 1H), 8.89 (d, J = 6.3 Hz, 1H), 8.30 (br s, 1H), 8.00-7.97 (m, 1H), 7.60-7.56 (m, 2H), 4.32-4.27 (m, 2H), 3.80 (s, 3H), 2.87-2.70 (m, 4H), 2.24-2.18 (m, 3H), 2.16-2.11 (m, 2H), 1.90-1.82 (m, 2H), 1.79-1.59 (m, 2H) |
| 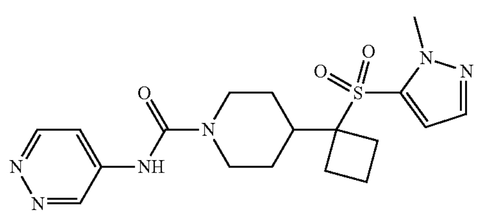 [SMILES: Cn1nccc1S(=O)(=O)C1(C2CCN(C(=O)Nc3ccnnc3)CC2)CCC1] | 4-(1-((1-methyl-1H-pyrazol-5-yl)sulfonyl)cyclobutyl)-N-(pyridazin-4-yl)piperidine-1-carboxamide | 174 | 2 | 405 | 1H NMR (400 MHz, CDCl3) δ ppm 9.21 (d, J = 2.4 Hz, 1H), 8.92-8.90 (m, 1H), 8.05-8.03 (m, 1H), 7.60 (s, 1H), 6.87 (s, 1H), 4.36-4.32 (m, 2H), 4.17 (s, 3H), 2.91-2.85 (m, 2H), 2.59-2.53 (m, 2H), 2.31-2.26 (m, 2H), 2.11-2.02 (m, 3H), 1.83-1.81 (m, 2H), 1.79-1.74 (m, 2H) |
| 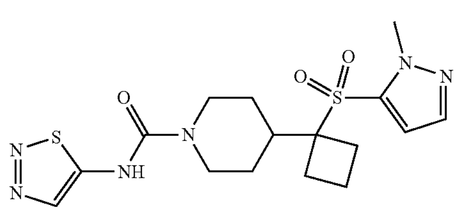 [SMILES: Cn1nccc1S(=O)(=O)C1(C2CCN(C(=O)Nc3cnns3)CC2)CCC1] | 4-(1-((1-methyl-1H-pyrazol-5-yl)sulfonyl)cyclobutyl)-N-(1,2,3-thiadiazol-5-yl)piperidine-1-carboxamide | 175 | 2 | 411 | 1H NMR (300 MHz, CDCl3) δ ppm 8.70 (br s, 1H), 7.69 (s, 1H), 6.89-6.82 (m, 2H), 4.37-4.33 (m, 2H), 4.18 (s, 3H), 2.96-2.84 (m, 2H), 2.63-2.53 (m, 2H), 2.30-2.23 (m, 2H), 2.10-2.02 (m, 3H), 1.79-1.63 (m, 4H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 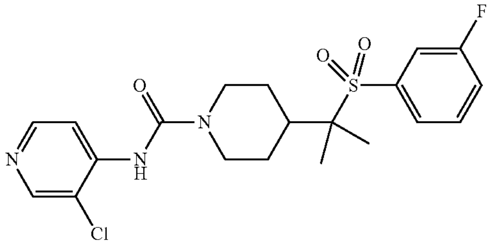 [SMILES: CC(C)(C1CCN(C(=O)Nc2ccncc2Cl)CC1)S(=O)(=O)c1cccc(F)c1] | N-(3-chloro-pyridin-4-yl)-4-(2-((3-fluoro-phenyl)sulfonyl)propan-2-yl)piperidine-1-carboxamide | 176 | 5, 26 | 440 | 1H NMR (400 MHz, MeOH-d4) δ ppm 8.82 (s, 1 H), 8.44-8.52 (m, 1 H), 8.37-8.43 (m, 1 H), 7.48-7.78 (m, 4 H), 4.26 (br d, J = 12.91 Hz, 2 H), 2.93-3.13 (m, 2 H), 2.07-2.26 (m, 3 H), 1.49-1.70 (m, 2 H), 1.27 (s, 5 H) |
| 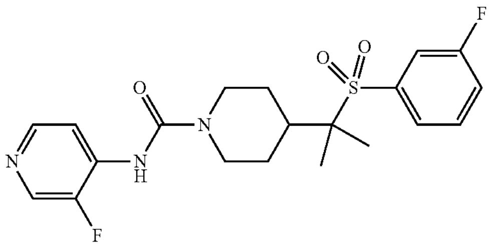 [SMILES: CC(C)(C1CCN(C(=O)Nc2ccncc2F)CC1)S(=O)(=O)c1cccc(F)c1] | 4-(2-((3-fluoro-phenyl)sulfonyl)propan-2-yl)-N-(3-fluoro-pyridin-4-yl)piperidine-1-carboxamide | 177 | 5, 26 | 424 | 1H NMR (400 MHz, MeOH-d4) δ ppm 8.74 (br s, 1 H), 8.33-8.48 (m, 2 H), 7.49-7.79 (m, 4 H), 4.27 (br d, J = 12.91 Hz, 2 H), 2.97 (br t, J = 12.91 Hz, 2 H), 2.08-2.24 (m, 3 H), 1.50-1.65 (m, 2 H), 1.33 (s, 1 H) 1.27 (s, 6 H) |
| 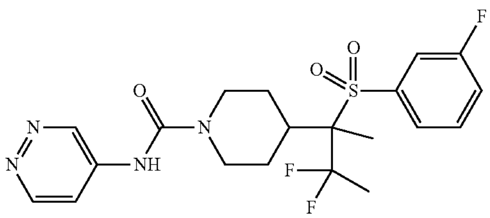 [SMILES: CC(F)(F)C(C)(C1CCN(C(=O)Nc2ccnnc2)CC1)S(=O)(=O)c1cccc(F)c1] | 4-(3,3-difluoro-2-((3-fluoro-phenyl)sulfonyl)butan-2-yl)-N-(pyridazin-4-yl)piperidine-1-carboxamide | 178 | 5, 26 | 457 | 1H NMR (400 MHz, CDCl3) δ ppm 10.41 (br. s., 1H), 9.56 (s, 1H), 8.74-8.82 (m, 1H), 8.60-8.72 (m, 1H), 7.61-7.95 (m, 3H), 7.52 (t, J = 9.20 Hz, 1H), 4.36-4.53 (m, 2H), 2.87-3.05 (m, 2H), 2.27-2.41 (m, 1H), 2.06-2.19 (m, 2H), 1.42-1.60 (m, 2H), 1.24 (s, 6H) |
| 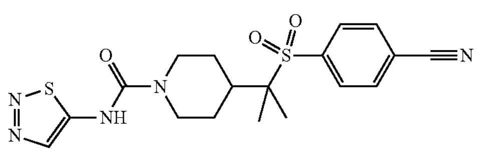 [SMILES: CC(C)(C1CCN(C(=O)Nc2cnns2)CC1)S(=O)(=O)c1ccc(C#N)cc1] | 4-(2-((4-cyano-phenyl)sulfonyl)propan-2-yl)-N-(1,2,3-thiadiazol-5-yl)piperidine-1-carboxamide | 179 | 3, 26 | 420.1 | 1H NMR (300 MHz, CD3OD) δ ppm 8.46 (s, 1H), 8.05-7.9 (m, 4H), 4.25-4.21 (m, 2H), 2.97-2.89 (m, 2H), 2.18-2.08 (m, 3H), 1.53-1.44 (m, 2H), 1.23 (s, 6H) |
| 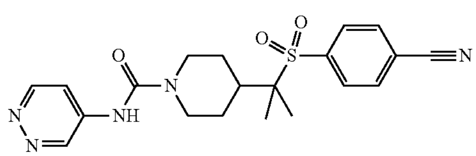 | 4-(2-((4-cyano-phenyl)sulfonyl)propan-2-yl)-N-(pyridazin-4-yl)piperidine-1-carboxamide | 180 | 3, 26 | 414.1 | 1H NMR (400 MHz, CD3OD) δ ppm 9.23-9.22 (m, 1H), 8.86-8.84 (m, 1H), 8.07-8.01 (m, 4H), 7.87-7.84 (m, 1H), 4.29-4.26 (m, 2H), 2.94-2.88 (m, 2H), 2.19-2.09 (m, 3H), 1.56-1.45 (m, 2H), 1.26 (s, 6H) |
| 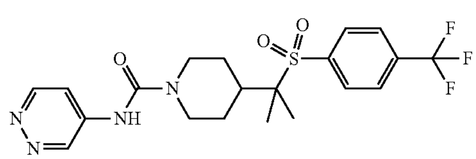 | N-(pyridazin-4-yl)-4-(2-((4-(trifluoro-methyl)phenyl)sulfonyl)propan- | 181 | 4, 26 | 457.2 | 1H NMR (400 MHz, DMSO-d6) δ ppm 9.28-9.27 (m, 1H), 9.17 (s, 1H), 8.88-8.86 (m, 1H), 8.09-8.04 (m, 4H), 7.76-7.74 (m, 1H), 4.23-4.20 (m, 2H), 2.84-2.78 (m, 2H), 2.08- |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 2-yl) piperidine-1-carboxamide | | | | 1.96 (m, 3H), 1.41-1.33 (m, 2H), 1.19 (s, 6H) |
| 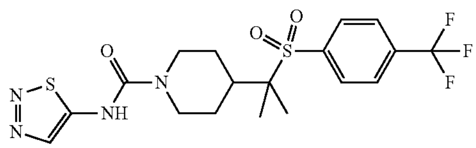 | N-(1,2,3-thiadiazol-5-yl)-4-(2-((4-(trifluoromethyl)phenyl)sulfonyl)propan-2-yl)piperidine-1-carboxamide | 182 | 4, 26 | 463 | 1H NMR (400 MHz, DMSO-d6) δ ppm 10.9 (m, 1H), 8.53 (s, 1H), 8.09-8.04 (m, 4H), 4.22-4.18 (m, 2H), 2.92-2.85 (m, 2H), 2.09-2.01 (m, 3H), 1.42-1.35 (m, 2H), 1.18 (6H) |
| 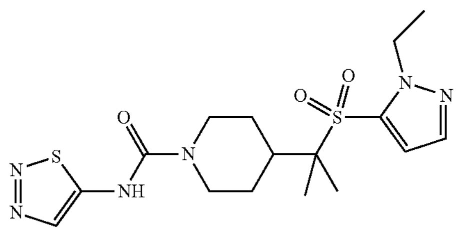 [SMILES: CCn1nccc1S(=O)(=O)C(C)(C)C1CCN(C(=O)Nc2cnns2)CC1] | 4-(2-((1-ethyl-1H-pyrazol-5-yl)sulfonyl)propan-2-yl)-N-(1,2,3-thiadiazol-5-yl)piperidine-1-carboxamide | 183 | 4, 26 | 412.9 | 1H NMR (400 MHz, DMSO-d6) δ ppm 10.8 (br s, 1H), 8.53 (s, 1H), 7.77-7.76 (m, 1H), 6.94-6.93 (m, 1H), 4.47-4.41 (m, 2H), 4.23-4.20 (m, 2H), 2.93-2.87 (m, 2H), 2.17-2.08 (m, 1H), 1.96-1.93 (m, 2H), 1.41-1.33 (m, 5H), 1.20 (6H) |
| 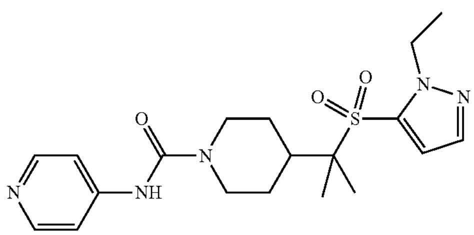 [SMILES: CCn1nccc1S(=O)(=O)C(C)(C)C1CCN(C(=O)Nc2ccncc2)CC1] | 4-(2-((1-ethyl-1H-pyrazol-5-yl)sulfonyl)propan-2-yl)-N-(pyridin-4-yl)piperidine-1-carboxamide | 184 | 4, 26 | 406 | 1H NMR (400 MHz, DMSO-d6) δ ppm 8.92 (m, 1H), 8.30-8.29 (m, 2H), 7.76 (s, 1H), 7.48-7.46 (m, 2H), 6.93 (s, 1H), 4.47-4.42 (m, 2H), 4.23-4.20 (m, 2H), 2.82-2.76 (m, 2H), 2.13-2.08 (m, 2H), 1.93-1.89 (m, 2H), 1.41-1.30 (m, 5H), 1.18 (s, 6H) |
| 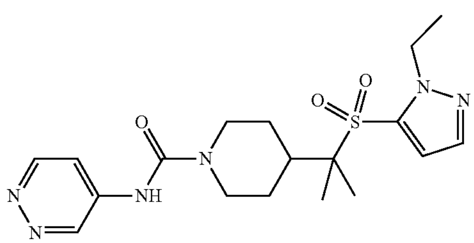 [SMILES: CCn1nccc1S(=O)(=O)C(C)(C)C1CCN(C(=O)Nc2ccnnc2)CC1] | 4-(2-((1-ethyl-1H-pyrazol-5-yl)sulfonyl)propan-2-yl)-N-(pyridazin-4-yl)piperidine-1-carboxamide | 185 | 4, 26 | 407 | 1H NMR (300 MHz, DMSO-d6) δ ppm 9.27 (s, 1H), 9.17 (s, 1H), 8.88 (d, J = 5.7 Hz, 1H), 7.76-7.73 (m, 2H), 6.93-6.92 (m, 1H), 4.47-4.40 (m, 2H), 4.24-4.19 (m, 2H), 2.86-2.78 (m, 2H), 2.16-2.08 (m, 1H), 1.94-1.90 (m, 2H), 1.41-1.35 (m, 5H), 1.21 (s, 6H) |
| 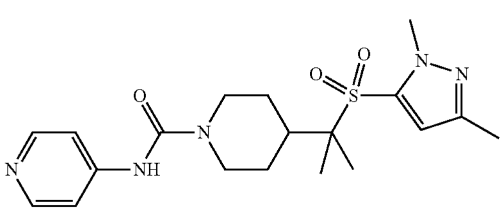 [SMILES: Cc1cc(S(=O)(=O)C(C)(C)C2CCN(C(=O)Nc3ccncc3)CC2)n(C)n1] | 4-(2-((1,3-dimethyl-1H-pyrazol-5-yl)sulfonyl)propan-2-yl)-N-(pyridin-4-yl)piperidine-1-carboxamide | 186 | 23, 26 | 406.1 | 1H NMR (300 MHz, DMSO-d6) δ ppm 8.87 (s, 1H), 8.25-8.23 (m, 2H), 7.43-7.41 (m, 2H), 6.67 (s, 1H), 4.18-4.14 (m, 2H), 3.94 (s, 3H), 2.79-2.70 (m, 2H), 2.17 (s, 3H), 2.09-2.01 (m, 1H), 1.89-1.84 (m, 2H), 1.35-1.27 (m, 2H), 1.23 (s, 6H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 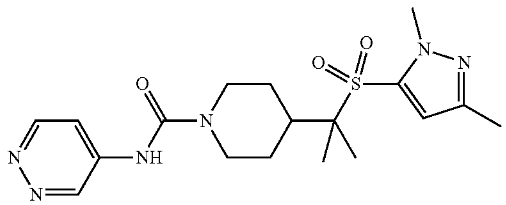 [SMILES: Cc1cc(S(=O)(=O)C(C)(C)C2CCN(C(=O)Nc3ccnnc3)CC2)n(C)n1] | 4-(2-((1,3-dimethyl-1H-pyrazol-5-yl)sulfonyl)propan-2-yl)-N-(pyridazin-4-yl)piperidine-1-carboxamide | 187 | 23, 26 | 407.1 | 1H NMR (300 MHz, DMSO-d6) δ ppm 9.23-9.22 (m, 1H), 9.12 (br s, 1H), 8.83-8.81 (m, 1H), 7.72-7.69 (m, 1H), 6.68 (s, 1H), 4.19-4.15 (m, 2H), 3.94 (s, 3H), 2.83-2.75 (m, 2H), 2.17 (s, 3H), 2.11-2.03 (m, 1H), 1.90-1.86 (m, 2H), 1.38-1.29 (m, 2H), 1.17 (s, 6H) |
| 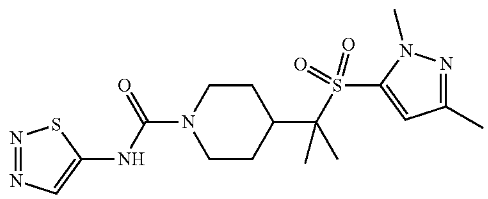 [SMILES: Cc1cc(S(=O)(=O)C(C)(C)C2CCN(C(=O)Nc3cnns3)CC2)n(C)n1] | 4-(2-((1,3-dimethyl-1H-pyrazol-5-yl)sulfonyl)propan-2-yl)-N-(1,2,3-thiadiazol-5-yl)piperidine-1-carboxamide | 188 | 23, 26 | 413 | 1H NMR (300 MHz, DMSO-d6) δ ppm 10.8 (br s, 1H), 8.49 (s, 1H), 6.68 (s, 1H), 4.18-4.14 (m, 2H), 3.94 (s, 3H), 2.90-2.82 (m, 2H), 2.17 (s, 3H), 2.12-2.03 (m, 1H), 1.92-1.88 (m, 2H), 1.38-1.30 (m, 2H), 1.16 (s, 6H) |
| 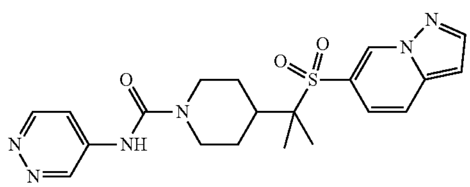 | 4-(2-(pyrazolo[1,5-a]pyridin-6-ylsulfonyl)propan-2-yl)-N-(pyridazin-4-yl)piperidine-1-carboxamide | 189 | 4, 26 | 429.1 | 1H NMR (300 MHz, DMSO-d6) δ ppm 9.27 (s, 1H) 9.16-9.14 (m, 2H), 8.88-8.86 (m, 1H), 8.31-8.30 (M, 1H), 7.92-7.89 (m, 1H), 7.76-7.73 (m, 1H), 7.46-7.43 (m, 1H), 6.86 (s, 1H), 4.23-4.19 (m, 2H), 2.86-2.78 (m, 2H), 2.10-1.98 (m, 3H), 1.38-1.30 (m, 2H), 1.25 (s, 6H) |
| | 4-(2-((2-methoxypyridin-3-yl)sulfonyl)propan-2-yl)-N-(pyridazin-4-yl)piperidine-1-carboxamide | 190 | 4, 26 | 420 | 1H NMR (300 MHz, CD3OD) δ ppm 9.23-9.22 (m, 1H), 8.86-8.84 (m, 1H), 8.48-8.46 (m, 1H), 8.22-8.20 (m, 1H), 7.87-7.84 (m, 1H), 7.21-7.18 (m, 1H), 4.30-4.26 (m, 2H), 4.05 (s, 3H), 2.93-2.87 (m, 2H), 2.22-2.11 (m, 3H), 1.53-1.42 (m, 2H), 1.30 (s, 6H) |
| 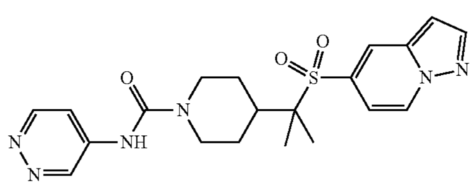 [SMILES: CC(C)(C1CCN(C(=O)Nc2ccnnc2)CC1)S(=O)(=O)c1ccn2nccc2c1] | 4-(2-(pyrazolo[1,5-a]pyridin-5-ylsulfonyl)propan-2-yl)-N-(pyridazin-4-yl)piperidine-1-carboxamide | 191 | 4, 26 | 429.1 | 1H NMR (300 MHz, DMSO-d6) δ ppm 9.27-9.26 (m, 1H), 9.16 (br s, 1H), 8.91-8.85 (m, 2H), 8.35 (s, 1H), 8.24-8.23 (m, 1H), 7.76-7.73 (m, 1H), 7.16-7.13 (m, 1H), 7.05-7.04 (m, 1H), 4.23-4.19 (m, 2H), 2.85-2.77 (m, 2H), 2.12-1.97 (m, 3H), 1.42-1.30 (m, 2H), .24 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 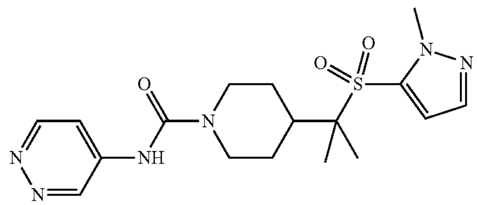 [SMILES: Cn1nccc1S(=O)(=O)C(C)(C)C1CCN(C(=O)Nc2ccnnc2)CC1] | 4-(2-((1-methyl-1H-pyrazol-5-yl)sulfonyl)propan-2-yl)-N-(pyridazin-4-yl)piperidine-1-carboxamide | 192 | 4, 26 | 393.1 | 1H NMR (300 MHz, DMSO-d6) δ ppm 9.27-9.26 (m, 1H), 9.17 (s, 1H), 8.88-8.85 (m, 1H), 7.76-7.71 (m, 2H), 6.96-6.95 (m, 1H), 4.24-4.19 (m, 2H), 4.07 (s, 3H), 2.87-2.72 (m, 2H), 2.15-2.08 (m, 1H), 1.95-1.91 (m, 2H), 1.43-1.30 (m, 2H), 1.22 (s, 6H) |
| 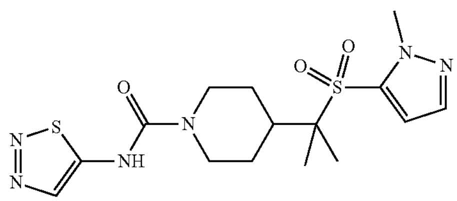 [SMILES: Cn1nccc1S(=O)(=O)C(C)(C)C1CCN(C(=O)Nc2cnns2)CC1] | 4-(2-((1-methyl-1H-pyrazol-5-yl)sulfonyl)propan-2-yl)-N-(1,2,3-thiadiazol-5-yl)piperidine-1-carboxamide | 193 | 4, 26 | 399 | 1H NMR (300 MHz, DMSO-d6) δ ppm 10.9 (br s, 1H), 8.53 (s, 1H), 7.71 (d, J = 1.8 Hz, 1H), 6.96 (d, J = 2.1 Hz, 1H), 4.23-4.18 (m, 2H), 4.07 (s, 3H), 2.95-2.86 (m, 2H), 2.17-2.09 (m, 1H), 1.97-1.92 (m, 2H), 1.43-1.32 (m, 2H), 1.21 (s, 6H) |
| 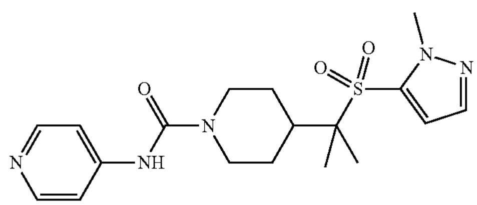 [SMILES: Cn1nccc1S(=O)(=O)C(C)(C)C1CCN(C(=O)Nc2ccncc2)CC1] | 4-(2-((1-methyl-1H-pyrazol-5-yl)sulfonyl)propan-2-yl)-N-(pyridin-4-yl)piperidine-1-carboxamide | 194 | 4, 26 | 392 | 1H NMR (300 MHz, DMSO-d6) δ ppm 8.91 (s, 1H), 8.30-8.28 (m, 2H), 7.72-7.71 (m, 1H), 7.47-7.45 (m, 2H), 6.95 (s, 1H), 4.23-4.18 (m, 2H), 4.07 (s, 3H), 2.83-2.75 (m, 2H), 2.14-2.07 (m, 1H), 1.93-1.89 (m, 2H), 1.40-1.29 (m, 2H), 1.21 (s, 6H) |
| | N-(pyridazin-4-yl)-4-(2-((2-(trifluoromethyl)phenyl)sulfonyl)propan-2-yl)piperidine-1-carboxamide | 195 | 4, 26 | 457.1 | 1H NMR (300 MHz, CD3OD) δ ppm 9.23-9.22 (m, 1H), 8.85-8.83 (m, 1H), 8.20-8.17 (m, 1H), 8.06-8.02 (m, 1H), 7.93-7.83 (m, 3H), 4.30-4.26 (m, 2H), 2.98-2.90 (m, 2H), 2.41-2.34 (m, 1H), 2.10-2.00 (m, 2H), 1.56-1.46 (m, 2H), 1.23 (s, 6H) |
| | 4-(2-((4-cyano-2-methylphenyl)sulfonyl)propan-2-yl)-N-(pyridazin-4-yl)piperidine-1-carboxamide | 196 | 4, 26 | 428 | 1H NMR (400 MHz, CDCl3) δ ppm 9.56 (d, J = 2.35 Hz, 1H), 8.77 (d, J = 7.04 Hz, 1H), 8.65 (dd, J = 2.54, 6.85 Hz, 1H), 8.09 (d, J = 8.22 Hz, 1H), 7.63-7.75 (m, 2H), 7.19-7.27 (m, 1H), 6.77-6.87 (m, 1H), 4.37-4.54 (m, 2H), 3.07-3.24 (m, 1H), 2.86-3.09 (m, 3H), 2.48-2.62 (m, 1H), 2.06-2.20 (m, 1H), 1.69-1.80 (m, 1H), 1.43-1.63 (m, 2H), 1.35 (t, J = 7.43 |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | | | | | Hz, 3H), 1.15 (d, J = 7.04 Hz, 3H) |
| | 4-(2-((2-chloro-phenyl)sulfonyl)propan-2-yl)-N-(pyridazin-4-yl)piperidine-1-carboxamide | 197 | 4, 26 | 423 | 1H NMR (300 MHz, CD3OD) δ ppm 9.20-9.19 (m, 1H), 8.83-8.81 (m, 1H), 8.04-8.01 (m, 1H), 7.84-7.81 (m, 1H), 7.69-7.52 (m, 3H), 4.27-4.23 (m, 2H), 2.94-2.86 (m, 2H), 2.29-2.21 (m, 1H), 2.12-2.08 (m, 2H), 1.53-1.40 (m, 2H), 1.20 (s, 6H) |
| | 4-(2-((1-methyl-1H-pyrazol-4-yl)sulfonyl)propan-2-yl)-N-(pyridin-4-yl)piperidine-1-carboxamide | 198 | 4, 26 | 392.1 | 1H NMR (300 MHz, CD3OD) δ ppm 8.43 (d, J = 7.5 Hz, 2H), 8.16 (s, 1H), 7.93 (d, J = 7.5 Hz, 2H), 7.75 (s, 1H), 4.28-4.23 (m, 2H), 3.94 (s, 3H), 2.96-2.88 (m, 2H), 2.12-2.05 (m, 3H), 1.54-1.41 (m, 2H), 1.25 (s, 6H) |
| | 4-(2-((1-methyl-1H-pyrazol-4-yl)sulfonyl)propan-2-yl)-N-(pyridazin-4-yl)piperidine-1-carboxamide | 199 | 4, 26 | 393 | 1H NMR (400 MHz, CD3OD) δ ppm 9.25 (d, J = 2.8 Hz, 1H), 8.87 (d, J = 6.0 Hz, 1H), 8.21 (s, 1H), 7.88-7.86 (m, 1H), 7.80 (s, 1H), 4.30-4.27 (m, 2H), 3.99 (s, 3H), 2.96-2.89 (m, 2H), 2.14-2.09 (m, 3H), 1.54-1.44 (m, 2H), 1.30 (s, 6H) |
| | 4-(1-((2-cyano-phenyl)sulfonyl)cyclo-propyl)-N-(pyridazin-4-yl)piperidine-1-carboxamide | 200 | 3, 2 | 412.1 | 1H NMR (400 MHz, CD3OD) δ ppm 9.27 (s, 1H), 9.11-9.09 (m, 1H), 8.35-8.33 (m, 1H), 8.22-8.20 (m, 1H), 8.11-8.09 (m, 1H), 7.99-7.91 (m, 2H), 4.23-4.19 (m, 2H), 2.94-2.88 (m, 2H), 2.28-2.22 (m, 1H), 1.81-1.78 (m, 2H), 1.70-1.67 (m, 2H), 1.26-1.16 (m, 4H) |
| | 4-(2-((2-cyano-phenyl)sulfonyl)propan-2-yl)-N-(isothiazol-5-yl)piperidine-1-carboxamide | 201 | 3, 26 | 419.1 | 1H NMR (400 MHz, DMSO-d6) δ ppm 8.21-8.18 (m, 1H), 8.11-8.07 (m, 2H), 8.01-7.95 (m, 2H), 6.80 (s, 1H), 4.23-4.19 (m, 2H), 2.90-2.82 (2H), 2.17-2.13 (m, 1H), 2.02-1.98 (m, 2H), 1.45-1.30 (m, 2H), 1.24 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | N-(pyridin-4-yl)-4-(1-(o-tolyl-sulfonyl)cyclopropyl)piperidine-1-carboxamide | 202 | 2 | 400.1 | 1H NMR (400 MHz, CD3OD) δ ppm 8.28 (d, J = 6.4 Hz, 2H), 8.03-8.01 (m, 1H), 7.62-7.58 (m, 1H), 7.46-7.44 (m, 4H), 4.13-4.10 (m, 2H), 2.73-2.67 (m, 5H), 2.01-1.98 (m, 1H), 1.68-1.65 (m, 2H), 1.50-1.47 (m, 2H), 1.19-1.09 (4H) |
| | 4-(1-((3,5-difluoro-phenyl)sulfonyl)cyclopropyl)-N-(isothiazol-5-yl)piperidine-1-carboxamide | 203 | 2 | 427.9 | 1H NMR (300 MHz, CD3OD) δ ppm 8.06 (s, 1H), 7.60-7.53 (m, 2H), 7.42-7.35 (m, 1H), 6.78 (s, 1H), 4.12-4.08 (m, 2H), 2.87-2.78 (m, 2H), 2.14-2.04 (m, 1H), 1.69-1.65 (m, 2H), 1.53-1.49 (m, 2H), 1.18-1.04 (m, 4H) |
| | 4-(2-((2-cyano-phenyl)sulfonyl)propan-2-yl)-N-(pyridazin-4-yl)piperidine-1-carboxamide | 204 | 3, 26 | 414.2 | 1H NMR (300 MHz, CD3OD) δ ppm 9.25 (d, J = 2.1 Hz, 1H), 8.87-8.85 (m, 1H), 8.15-8.07 (m, 2H), 7.99-7.85 (m, 3H), 4.32-4.28 (m, 2H), 3.08-2.92 (m, 2H), 2.31-2.15 (m, 3H), 1.60-1.47 (m, 2H), 1.29 (s, 6H) |
| | N-(pyridazin-4-yl)-4-(1-((4-(trifluoro-methoxy)phenyl)sulfonyl)cyclopropyl)piperidine-1-carboxamide | 205 | 2 | 471 | 1H NMR (300 MHz, DMSO-d6) δ ppm 9.23 (d, J = 1.8 Hz, 1H), 9.09 (br s, 1H), 8.85-8.83 (m, 1H), 8.09-8.06 (m, 2H), 7.72-7.64 (m, 3H), 4.20-4.18 (m, 2H), 3.71-2.58 (m, 2H), 2.10-2.08 (m, 1H), 1.41-1.37 (m, 4H), 1.11-1.06 (m, 4H) |
| | N-(pyridin-4-yl)-4-(1-((4-(trifluoro-methoxy)phenyl)sulfonyl)cyclopropyl)piperidine-1-carboxamide | 206 | 2 | 470.1 | 1H NMR (300 MHz, DMSO-d6) δ ppm 8.80 (s, 1H), 8.28-8.26 (m, 2H), 8.09-8.06 (m, 2H), 7.66-7.63 (m, 2H), 7.44-7.42 (m, 2H), 4.20-4.16 (m, 2H), 2.70-2.66 (m, 2H), 2.11-2.06 (m, 1H), 1.43-1.40 (m, 4H), 1.11-0.98 (m, 4H) |
| | N-(isothiazol-5-yl)-4-(1-((4-(trifluoro-methoxy)phenyl)sulfonyl)cyclo- | 207 | 2 | 476 | 1H NMR (300 MHz, DMSO-d6) δ ppm 10.4 (br s, 1H), 8.09-8.05 (m, 3H), 7.66-7.63 (m, 2H), 6.78 (s, 1H), 4.08-4.04 (m, 2H), 2.77-2.69 (m, 2H), 2.10-2.02 (m, 1H), 1.50-1.38 |

TABLE 1-continued

Representative compounds of the Invention and Analytical Data

| Structure | Name | Cmpd. No. | Ref. Example | Obs. Mass (M + H)+ | $^1$H NMR |
|---|---|---|---|---|---|
| | propyl)piperidine-1-carboxamide | | | | (m, 4H), 1.14-1.07 (m, 4H) |
| 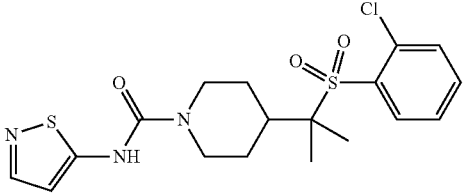 [SMILES: CC(C)(C1CCN(C(=O)Nc2ccns2)CC1)S(=O)(=O)c1ccccc1Cl] | 4-(2-((2-chlorophenyl)sulfonyl)propan-2-yl)-N-(isothiazol-5-yl)piperidine-1-carboxamide | 208 | 3, 26 | 428.1 | 1H NMR (400 MHz, CD3OD) δ ppm 8.21-8.20 (m, 1H), 8.08-8.06 (m, 1H), 7.73-7.67 (m, 2H), 7.61-7.57 (m, 1H), 6.89 (s, 1H), 4.29-4.6 = 26 (m, 2H), 3.02-2.95 (m, 2H), 2.34-2.28 (m, 1H), 2.17-2.14 (m, 2H), 1.56-1.45 (m, 2H), 2.28 (s, 6H) |
| 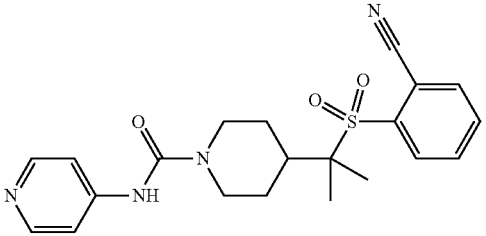 [SMILES: CC(C)(C1CCN(C(=O)Nc2ccncc2)CC1)S(=O)(=O)c1ccccc1C#N] | 4-(2-((2-cyanophenyl)sulfonyl)propan-2-yl)-N-(pyridin-4-yl)piperidine-1-carboxamide | 209 | 3, 26 | 413.2 | 1H NMR (400 MHz, DMSO-d6) δ ppm 8.90 (s, 1H), 8.29-8.28 (m, 2H), 8.21-8.19 (m, 1H), 8.10-8.08 (m, 1H), 8.02-7.98 (m, 2H), 7.47-7.46 (m, 2H), 4.23-4.19 (m, 2H), 2.83-2.76 (m, 2H), 2.12-2.10 (m, 1H), 1.99-1.96 (m, 2H), 1.40-1.35 (m, 2H), 1.24 (s, 6H) |
| 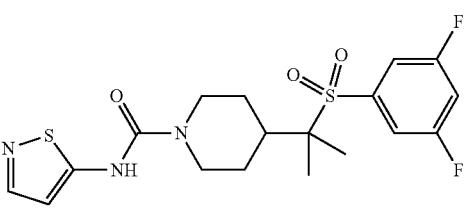 [SMILES: CC(C)(C1CCN(C(=O)Nc2ccns2)CC1)S(=O)(=O)c1cc(F)cc(F)c1] | 4-(2-((3,5-difluorophenyl)sulfonyl)propan-2-yl)-N-(isothiazol-5-yl)piperidine-1-carboxamide | 210 | 4, 26 | 430 | 1H NMR (400 MHz, CD3OD) δ ppm 8.13 (s, 1H), 7.55-7.54 (m, 2H), 7.48-7.43 (m, 1H), 6.86 (s, 1H), 4.29-4.26 (m, 2H), 2.99-2.93 (m, 2H), 2.24-2.11 (m, 3H), 1.55-1.46 (m, 2H), 1.28 (s, 6H) |
| 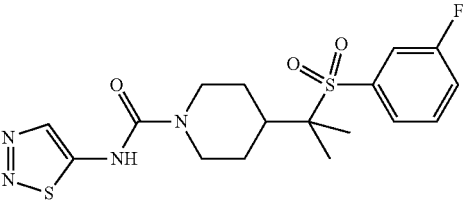 | 4-(2-((3-fluorophenyl)sulfonyl)propan-2-yl)-N-(1,2,3-thiadiazol-5-yl)piperidine-1-carboxamide | 211 | 5, 26 | 413 | 1H NMR (400 MHz, CD3OD) δ ppm 8.55 (s, 1H), 7.62-7.78 (m, 3H), 7.49-7.60 (m, 1H), 4.23-4.35 (m, 2H), 2.92-3.06 (m, 2H), 2.10-2.27 (m, 3H), 1.45-1.60 (m, 2H), 1.28 (s, 6H) |
| 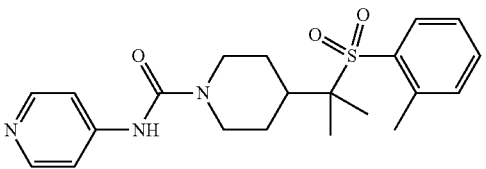 [SMILES: Cc1ccccc1S(=O)(=O)C(C)(C)C1CCN(C(=O)Nc2ccncc2)CC1] | N-(pyridin-4-yl)-4-(2-(o-tolylsulfonyl)propan-2-yl)piperidine-1-carboxamide | 212 | 4, 26 | 402.1 | 1H NMR (300 MHz, DMSO-d6) δ ppm 8.90 (s, 1H), 8.30-8.27 (m, 2H), 7.83-7.80 (m, 1H), 7.64-7.61 (m, 1H), 7.50-7.45 (m, 4H), 4.22-4.18 (m, 2H), 2.77-2.73 (m, 2H), 2.65 (s, 3H), 2.20-2.18 (m, 1H), 1.96-1.92 (m, 2H), 1.36-1.30 (m, 2H), 1.14 (s, 6H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 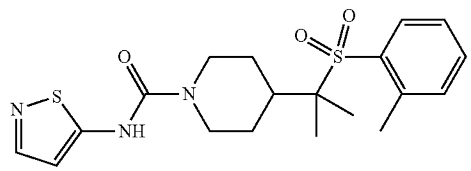 [SMILES: Cc1ccccc1S(=O)(=O)C(C)(C)C1CCN(C(=O)Nc2ccns2)CC1] | N-(isothiazol-5-yl)-4-(2-(o-tolyl-sulfonyl)propan-2-yl)piperidine-1-carboxamide | 213 | 4, 26 | 408.1 | 1H NMR (300 MHz, DMSO-d6) δ ppm 10.5 (s, 1H), 8.12-8.11 (m, 1H), 7.83-7.80 (m, 1H), 7.66-7.61 (m, 1H), 7.50-7.45 (m, 2H), 6.82 (s, 1H), 4.21-4.17 (m, 2H), 2.89-2.80 (m, 2H), 2.58 (s, 3H), 2.20-2.17 (m, 1H), 1.98-1.94 (m, 2H), 1.39-1.35 (m, 2H), 1.15 (s, 6H) |
| 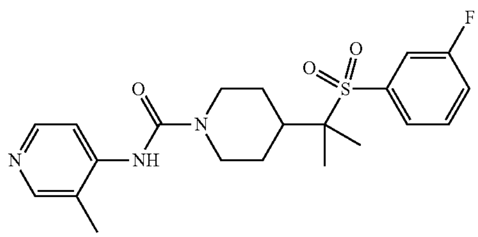 [SMILES: Cc1cnccc1NC(=O)N1CCC(C(C)(C)S(=O)(=O)c2cccc(F)c2)CC1] | 4-(2-((3-fluoro-phenyl)sulfonyl)propan-2-yl)-N-(3-methyl-pyridin-4-yl)piperidine-1-carboxamide | 214 | 5, 26 | 420.1 | 1H NMR (400 MHz, DMSO-d6) δ ppm 8.25-8.20 (m, 2H), 8.06 (s, 1H), 7.77-7.65 (m, 4H), 7.43-7.42 (m, 1H), 4.17-4.13 (m, 2H), 2.80-2.74 (m, 2H), 2.16 (s, 3H), 2.07-1.92 (m, 3H), 1.41-1.30 (m, 2H), 1.18 (s, 6H) |
| 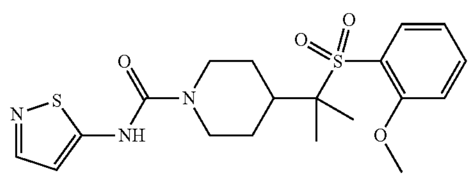 [SMILES: COc1ccccc1S(=O)(=O)C(C)(C)C1CCN(C(=O)Nc2ccns2)CC1] | N-(isothiazol-5-yl)-4-(2-((2-methoxy-phenyl)sulfonyl)propan-2-yl)piperidine-1-carboxamide | 215 | 4, 26 | 424 | 1H NMR (300 MHz, CD3OD) δ ppm 8.12 (s, 1H), 7.86-7.83 (m, 1H), 7.73-7.68 (m, 1H), 7.28-7.26 (m, 1H), 7.19-7.14 (m, 1H), 6.85-6.84 (m, 1H), 4.27-4.22 (m, 2H), 3.94 (s, 3H), 2.95-2.87 (m, 2H), 2.24-2.0 (m, 3H), 1.51-1.40 (m, 2H), 1.23 (s, 6H) |
| 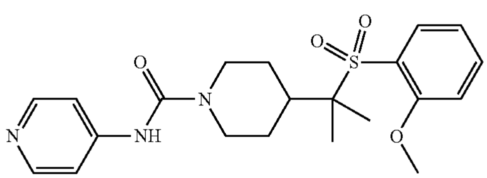 [SMILES: COc1ccccc1S(=O)(=O)C(C)(C)C1CCN(C(=O)Nc2ccncc2)CC1] | 4-(2-((2-methoxy-phenyl)sulfonyl)propan-2-yl)-N-(pyridin-4-yl)piperidine-1-carboxamide | 216 | 4, 26 | 418.1 | 1H NMR (300 MHz, CD3OD) δ ppm 8.29-8.27 (m, 2H), 7.87-7.84 (m, 1H), 7.74-7.69 (m, 1H), 7.50-7.48 (m, 2H), 7.28-7.26 (m, 1H), 7.19-7.14 (m, 1H), 4.29-4.24 (m, 2H), 3.94 (s, 3H), 2.91-2.82 (m, 2H), 2.22-2.09 (m, 3H), 1.51-1.40 (m, 2H), 1.29 (s, 6H) |
| 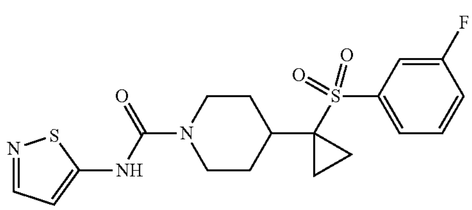 [SMILES: O=C(Nc1ccns1)N1CCC(C2(S(=O)(=O)c3cccc(F)c3)CC2)CC1] | 4-(1-((3-fluoro-phenyl)sulfonyl)cyclo-propyl)-N-(isothiazol-5-yl)piperidine-1-carboxamide | 217 | 2 | 410 | 1H NMR (400 MHz, CD3OD) δ ppm 8.18 (s, 1H), 7.81-7.79 (m, 1H), 7.73-7.68 (m, 2H), 7.55-7.51 (m, 1H), 6.86 (s, 1H), 4.15-4.12 (m, 2H), 2.89-2.83 (m, 2H), 2.16-2.09 (m, 1H), 1.70-1.67 (m, 2H), 1.56-1.55 (m, 2H), 1.20-1.10 (m, 4H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(2-((3-fluoro-phenyl)sulfonyl)propan-2-yl)-N-(isothiazol-5-yl)piperidine-1-carboxamide | 218 | 5, 26 | 412.1 | 1H NMR (400 MHz, DMSO-d6) δ ppm 10.5 (s, 1H), 8.11 (s, 1H), 7.75-7.65 (m, 4H), 6.82 (s, 1H), 4.20-4.16 (m, 2H), 2.85-2.79 (m, 2H), 2.03-1.93 (m, 3H), 1.35-1.31 (m, 2H), 1.17 (s, 6H) |
| | 4-(2-((3-fluoro-phenyl)sulfonyl)propan-2-yl)-N-methyl-N-(pyridin-4-yl)piperidine-1-carboxamide | 219 | 5, 26 | 420.2 | 1H NMR (300 MHz, DMSO-d6) δ ppm 8.33-8.31 (m, 2H), 7.77-7.63 (m, 4H), 6.92-6.90 (m, 2H), 3.85-3.80 (m, 2H), 3.11 (s, 3H), 2.82-2.74 (m, 2H), 1.99-1.87 (m, 3H), 1.38-1.23 (m, 2H), 1.16 (s, 6H) |
| | N-(isoxazol-3-yl)-4-(2-((6-(trifluoro-methyl)pyridin-3-yl)sulfonyl)propan-2-yl)piperidine-1-carboxamide | 220 | 4, 7 | 447 | 1H NMR (300 MHz, DMSO-d6) δ ppm 9.70 (s, 1H), 9.18-9.17 (m, 1H), 8.65 (s, 1H), 8.57-8.56 (m, 1H), 8.22-8.19 (m, 1H), 6.77 (s, 1H), 4.24-4.20 (m, 2H), 2.80-2.71 (m, 2H), 2.08-1.92 (m, 3H), 1.40-1.27 (m, 2H), 1.22 (s, 6H) |
| | N-(pyridazin-4-yl)-4-(2-((6-(trifluoro-methyl)pyridin-3-yl)sulfonyl)propan-2-yl)piperidine-1-carboxamide | 221 | 4, 7 | 458.1 | 1H NMR (300 MHz, DMSO-d6) δ ppm 9.28-9.27 (m, 1H), 9.19-9.17 (m, 2H), 8.88-8.86 (m, 1H), 8.58-8.54 (m, 1H), 8.23-8.20 (m, 1H), 7.77-7.74 (m, 1H), 4.24-4.20 (m, 2H), 2.87-2.79 (m, 2H), 2.13-1.97 (m, 3H), 1.44-1.32 (m, 2H), 1.23 (s, 6H) |
| | 4-(1-fluoro-1-((3-fluoro-phenyl)sulfonyl)ethyl)-N-(1,3,4-oxadiazol-2-yl)piperidine-1-carboxamide | 222 | 5, 6 | 401 | 1H NMR (400 MHz, CD3OD) δ ppm 8.45-8.58 (m, 1H), 7.77 (s, 3H), 7.52-7.62 (m, 1H), 4.25-4.45 (m, 2H), 2.79-2.95 (m, 2H), 2.44-2.56 (m, 1H), 2.16-2.28 (m, 1H), 1.76-1.90 (m, 1H), 1.40-1.64 (m, 5H) |
| | 4-(1-fluoro-1-((3-fluoro-phenyl)sulfonyl)ethyl)-N-(5-fluoro-pyridin-3-yl)piperidine-1- | 223 | 5, 6 | 427.6 | 1H NMR (400 MHz, CD3OD) δ ppm 8.40 (s, 1H), 8.05-8.10 (m, 1H), 7.83-7.90 (m, 1H), 7.64-7.81 (m, 3H), 7.53-7.62 (m, 1H), 4.23-4.35 (m, 2H), 2.85-2.97 (m, 2H), 2.46-2.59 (m, 1H), 2.20-2.29 (m, 1H), 1.81- |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | carboxamide | | | | 1.91 (m, 1H), 1.43-1.63 (m, 5H) |
| | 4-(1-fluoro-1-((3-fluorophenyl)sulfonyl)ethyl)-N-(pyridin-3-yl)piperidine-1-carboxamide | 224 | 5, 6 | 410.1 | 1H NMR (400 MHz, CD3OD) δ ppm 8.54-8.61 (m, 1H), 8.16 (d, J = 4.77 Hz, 1H), 7.86-7.94 (m, 1H), 7.77 (m, 3H), 7.52-7.63 (m, 1H), 7.30-7.40 (m, 1H), 4.22-4.36 (m, 2H), 2.84-2.97 (m, 2H), 2.45-2.60 (m, 1H), 2.19-2.30 (m, 1H), 1.81-1.92 (m, 1H), 1.41-1.65 (m, 5H) |
| | 4-(1-fluoro-1-((1-methyl-1H-pyrazol-5-yl)sulfonyl)ethyl)-N-(6-methylpyridin-3-yl)piperidine-1-carboxamide | 225 | 5, 6 | 409.9 | 1H NMR (400 MHz, CD3OD) δ ppm 8.97 (s, 1H), 8.30 (d, J = 9.06 Hz, 1H), 7.76 (d, J = 8.80 Hz, 1H), 7.66 (s, 1H), 7.01 (s, 1H), 4.31 (t, J = 14.31 Hz, 2H), 4.10 (s, 3H), 2.96 (t, J = 12.96 Hz, 2H), 2.68 (s, 3H), 2.59 (d, J = 7.95 Hz, 1H), 2.21 (d, J = 12.84 Hz, 1H), 1.90 (d, J = 12.96 Hz, 1H), 1.45-1.67 (m, 5H) |
| | 4-(1-fluoro-1-((1-methyl-1H-pyrazol-5-yl)sulfonyl)ethyl)-N-(2-fluoropyridin-4-yl)piperidine-1-carboxamide | 226 | 5, 6 | 414 | 1H NMR (400 MHz, CD3OD) δ ppm 7.91-7.97 (m, 1H), 7.63-7.68 (m, 1H), 7.27-7.31 (m, 1H), 7.23-7.27 (m, 1H), 6.98-7.03 (m, 1H), 4.22-4.36 (m, 2H), 4.10 (s, 3H), 2.88-2.99 (m, 2H), 2.50-2.64 (m, 1H), 2.14-2.25 (m, 1H), 1.84-1.92 (m, 1H), 1.42-1.67 (m, 5H) |
| | 4-(1-fluoro-1-((1-methyl-1H-pyrazol-5-yl)sulfonyl)ethyl)-N-(pyridin-3-yl)piperidine-1-carboxamide | 227 | 5, 6 | 396.1 | 1H NMR (400 MHz, CD3OD) δ ppm 9.13-9.20 (m, 1H), 8.37-8.47 (m, 2H), 7.89-7.98 (m, 1H), 7.66 (s, 1H), 6.97-7.05 (m, 1H), 4.26-4.41 (m, 2H), 4.10 (s, 3H), 2.90-3.04 (m, 2H), 2.53-2.67 (m, 1H), 2.15-2.26 (m, 1H), 1.85-1.96 (m, 1H), 1.45-1.70 (m 5H) |
| | 4-(1-fluoro-1-((1-methyl-1H-pyrazol-5-yl)sulfonyl)ethyl)-N-(6-fluoropyridin- | 228 | 5, 6 | 413.8 | 1H NMR (400 MHz, CD3OD) δ ppm 8.15-8.20 (m, 1H), 7.92-8.00 (m, 1H), 7.60-7.71 (m, 1H), 6.97-7.05 (m, 2H), 4.22-4.37 (m, 2H), 4.10 (s, 3H), 2.86-2.98 (m, 2H), 2.48- |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 3-yl)piperidine-1-carboxamide | | | | 2.62 (m, 1H), 2.14-2.23 (m, 1H), 1.82-1.93 (m, 1H), 1.59 (s, 5H) |
| | (S)-4-(1-fluoro-1-((1-methyl-3-(trifluoromethyl)-1H-pyrazol-5-yl)sulfonyl)ethyl)-N-(isoxazol-3-yl)piperidine-1-carboxamide | 229 | 18 | 453.8 | 1H NMR (400 MHz, CD3OD) δ ppm 8.43 (s, 1H), 7.43 (s, 1H), 6.73 (s, 1H), 4.22-4.39 (m, 2H), 4.18 (s, 3H), 2.85-3.05 (m, 2H), 2.54-2.70 (m, 1H), 2.10-2.23 (m, 1H), 1.84-1.94 (m, 1H), 1.38-1.73 (m, 5H) |
| | (S)-4-(1-fluoro-1-((1-methyl-3-(trifluoromethyl)-1H-pyrazol-5-yl)sulfonyl)ethyl)-N-(2-fluoropyridin-4-yl)piperidine-1-carboxamide | 230 | 18 | 481.8 | 1H NMR (400 MHz, CD3OD) δ ppm 7.94 (d, J = 5.87 Hz, 1H), 7.43 (s, 1H), 7.26-7.30 (m, 1H), 7.24 (s, 1H), 4.23-4.43 (m, 2H), 4.18 (s, 3H), 2.88-3.04 (m, 2H), 2.55-2.71 (m, 1H), 2.11-2.23 (m, 1H), 1.84-1.97 (m, 1H), 1.39-1.72 (m, 5H) |
| | (S)-4-(1-((3-(difluoromethyl)-1-methyl-1H-pyrazol-4-yl)sulfonyl)-1-fluoroethyl)-N-(2-fluoropyridin-4-yl)piperidine-1-carboxamide | 231 | 20 | 464 | 1H NMR (400 MHz, CD3OD) δ ppm 8.36 (s, 1H), 7.93 (d, J = 5.75 Hz, 1H), 7.26-7.30 (m, 1H), 7.24 (s, 1H), 6.97 (t, J = 52.0 Hz, 1H), 4.17-4.41 (m, 2H), 4.02 (s, 3H), 2.92 (br. s., 2H), 2.42-2.63 (m, 1H), 2.12-2.29 (m, 1H), 1.79-1.92 (m, 1H), 1.37-1.68 (m, 5H) |
| | (R)-4-(1-fluoro-1-((1-methyl-3-(trifluoromethyl)-1H-pyrazol-5-yl)sulfonyl)ethyl)-N-(2-methylpyridin-4-yl)piperidine-1-carboxamide | 232 | 18 | 477.8 | 1H NMR (400 MHz, CD3OD) δ ppm 8.31 (d, J = 7.21 Hz, 1H), 7.77 (s, 2H), 7.42 (s, 1H), 4.25-4.42 (m, 2H), 4.18 (s, 3H), 2.92-3.10 (m, 2H), 2.58-2.72 (m, 4H), 2.15-2.27 (m, 1H), 1.87-2.00 (m, 1H), 1.46-1.73 (m, 5H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 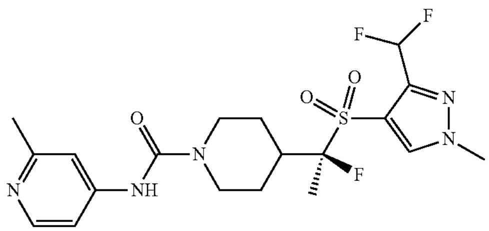 [SMILES: Cc1cc(NC(=O)N2CCC([C@](C)(F)S(=O)(=O)c3cn(C)nc3C(F)F)CC2)ccn1] | (R)-4-(1-((3-(difluoro-methyl)-1-methyl-1H-pyrazol-4-yl)sulfonyl)-1-fluoro-ethyl)-N-(2-methyl-pyridin-4-yl)piperidine-1-carboxamide | 233 | 20 | 460 | 1H NMR (400 MHz, CD3OD) δ ppm 8.36 (s, 1H), 8.31 (d, J = 7.34 Hz, 1H), 7.73-7.80 (m, 2H), 6.80-7.12 (t, J = 52.4 Hz, 1H), 4.23-4.38 (m, 2H), 4.02 (s, 3H), 2.91-3.05 (m, 2H), 2.50-2.67 (m, 4H), 2.19-2.30 (m, 1H), 1.85-1.95 (m, 1H), 1.43-1.67 (m, 5H) |
| 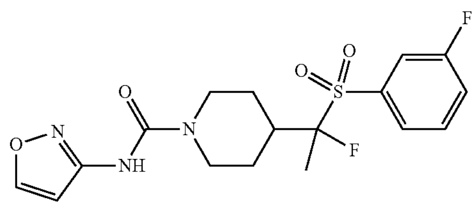 [SMILES: CC(F)(C1CCN(C(=O)Nc2ccon2)CC1)S(=O)(=O)c1cccc(F)c1] | 4-(1-fluoro-1-((3-fluoro-phenyl)sulfonyl)ethyl)-N-(isoxazol-3-yl)piperidine-1-carboxamide | 234 | 6 | 400 | 1H NMR (400 MHz, CDCl3) δ ppm 7.93 (s, 1H), 7.13-7.31 (m, 3H), 7.08 (t, J = 8.41 Hz, 1H), 6.23 (s, 1H), 3.78 (t, J = 10.96 Hz, 2H), 2.81 (s, 3H), 2.40 (t, J = 13.11 Hz, 2H), 1.91-2.13 (m, 1H), 1.73 (d, J = 13.30 Hz, 1H), 1.35 (d, J = 13.30 Hz, 1H), 0.87-1.16 (m, 3H) |
| 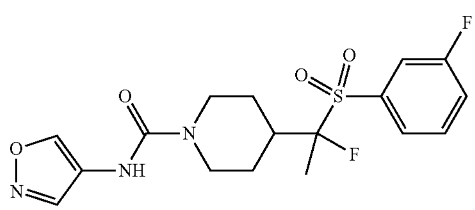 [SMILES: CC(F)(C1CCN(C(=O)Nc2cnoc2)CC1)S(=O)(=O)c1cccc(F)c1] | 4-(1-fluoro-1-((3-fluoro-phenyl)sulfonyl)ethyl)-N-(isoxazol-4-yl)piperidine-1-carboxamide | 235 | 6 | 400 | 1H NMR (400 MHz, CD3OD) δ ppm 8.73 (s, 1H), 8.43 (s, 1H), 7.77 (s, 3H), 7.58 (s, 1H), 4.23 (t, J = 12.13 Hz, 2H), 2.90 (t, J = 12.91 Hz, 2H), 2.44-2.60 (m, 1H), 2.23 (d, J = 12.91 Hz, 1H), 1.85 (d, J = 12.91 Hz, 1H), 1.37-1.66 (m, 5H) |
| 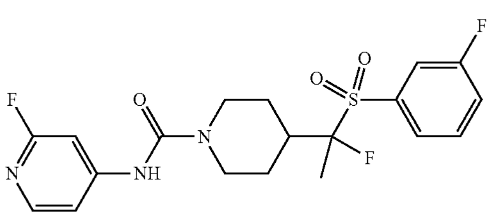 [SMILES: CC(F)(C1CCN(C(=O)Nc2ccnc(F)c2)CC1)S(=O)(=O)c1cccc(F)c1] | 4-(1-fluoro-1-((3-fluoro-phenyl)sulfonyl)ethyl)-N-(2-fluoro-pyridin-4-yl)piperidine-1-carboxamide | 236 | 6 | 428 | 1H NMR (400 MHz, CDCl3) δ ppm 8.06 (d, J = 5.8 Hz, 1H), 7.76 (dd, J = 1.16, 7.89 Hz, 1H), 7.70-7.59 (m, 2H), 7.47 (ddt, J = 0.86, 2.57, 8.25 Hz, 1H), 7.33 (d, J = 15.16 Hz, 2H), 7.19 (d, J = 5.62 Hz, 1H), 4.35-4.16 (m, 2H), 3.06-2.93 (m, 2H), 2.60-2.72 (m, 1H), 2.35 (d, J = 13.33 Hz, 1H), 1.99 (d, J = 13.20 Hz, 1H), 1.62-1.42 (m, 5H) |
| | tert-butyl 4-(4-(1-fluoro-1-((3-fluoro-phenyl)sulfonyl)ethyl)piperidine-1-carboxamido)-1H- | 237 | 6 | 499.1 | 1H NMR (400 MHz, CDCl3) δ ppm 8.31 (s, 1H), 7.78 (m, 1H), 7.71 (s, 1H), 7.69 (m, 2H), 7.49 (m, 1H), 6.33 (br s, 1H), 4.29-4.06 (m, 2H), 3.05-2.88 (m, 2H), 2.54 (m, 1H), 2.27 (m, 1H), 2.02 |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | pyrazole-1-carboxylate | | | | (m, 1H), 1.72-1.40 (m, 14H) |
| | 4-(1-fluoro-1-((3-fluoro-phenyl)sulfonyl)ethyl)-N-(3-methyl-isoxazol-4-yl)piperidine-1-carboxamide | 238 | 12 | 414 | 1H NMR (400 MHz, CDCl3) δ ppm 8.63 (s, 1H), 7.66 (d, J = 7.70 Hz, 1H), 7.60-7.48 (m, 2H), 7.32-7.41 (m, 1H), 5.78 (s, 1H), 3.94-4.18 (m, 2H), 2.81-2.99 (m, 2H), 2.47-2.61 (m, 1H), 2.16-2.30 (m, 3H), 1.80-2.08 (m, 2H), 1.34-1.52 (m, 5H) |
| | 4-(1-fluoro-1-((3-fluoro-phenyl)sulfonyl)ethyl)-N-(6-fluoro-pyridin-3-yl)piperidine-1-carboxamide | 239 | 6 | 428.1 | 1H NMR (400 MHz, CD3OD) δ ppm 8.19 (d, J = 1.47 Hz, 1H), 7.95-8.03 (m, 1H), 7.67-7.84 (m, 3H), 7.56-7.66 (m, 1H), 7.02 (dd, J = 2.93, 8.80 Hz, 1H), 4.25-4.37 (m, 2H), 2.87-3.00 (m, 2H), 2.48-2.61 (m, 1H), 2.22-2.31 (m, 1H), 1.83-1.93 (m, 1H), 1.46-1.65 (m, 5H) |
| | 4-(1-((4-cyano-phenyl)sulfonyl)-1-fluoro-ethyl)-N-(6-fluoro-pyridin-3-yl)piperidine-1-carboxamide | 240 | 3, 5, 9 | 435.1 | 1H NMR (400 MHz, CDCl3) δ ppm 8.05 (br s, 2H), 7.99 (d, J = 8.07 Hz, 2H), 7.84 (d, J = 8.19 Hz, 2H), 6.91 (d, J = 8.44 Hz, 1H), 6.75 (br s, 1H), 4.09 (m, 2H), 2.91 (m, 2H), 2.58 (m, 1H), 2.24 (m, 1H), 1.88 (m, 1H), 1.34-1.55 (m, 5H) |
| | 4-(1-((3-cyano-phenyl)sulfonyl)-1-fluoro-ethyl)-N-(6-fluoro-pyridin-3-yl)piperidine-1-carboxamide | 241 | 3, 5, 9 | 435.1 | 1H NMR (400 MHz, CDCl3) δ ppm 8.25 (s, 1H), 8.09-8.22 (m, 3H), 8.03 (d, J = 7.58 Hz, 1H), 6.96 (d, J = 8.31 Hz, 1H), 6.74 (s, 1H), 4.17-4.37 (m, 2H), 2.90-3.08 (m, 2H), 2.61-2.75 (m, 1H), 2.33 (d, J = 13.08 Hz, 1H), 1.81-2.09 (m, 2H), 1.45-1.62 (m, 5H) |
| | 4-(1-fluoro-1-((4-(trifluoro-methyl)phenyl)sulfonyl)ethyl)-N-(6-fluoro-pyridin-3-yl)piperidine-1-carboxamide | 242 | 8 | 478.1 | 1H NMR (400 MHz, CDCl3) δ ppm 7.97-8.08 (m, 4H), 7.81 (d, J = 8.19 Hz, 2H), 6.89 (d, J = 9.29 Hz, 1H), 6.77 (br. s., 1H), 4.06-4.26 (m, 2H), 2.83-2.99 (m, 2H), 2.51-2.65 (m, 1H), 2.20-2.31 (m, 1H), 1.83-1.93 (m, 1H), 1.36-1.53 (m, 5H) |

TABLE 1-continued

Representative compounds of the Invention and Analytical Data

| Structure | Name | Cmpd. No. | Ref. Example | Obs. Mass (M + H)+ | $^1$H NMR |
|---|---|---|---|---|---|
| | 4-(1-fluoro-1-((4-(trifluoromethyl)phenyl)sulfonyl)ethyl)-N-(2-fluoropyridin-4-yl)piperidine-1-carboxamide | 243 | 8 | 478.1 | 1H NMR (400 MHz, CDCl3) δ ppm 8.76 (br. s., 1H), 7.90-8.04 (m, 3H), 7.80 (d, J = 7.95 Hz, 2H), 7.64 (br. s., 1H), 7.58 (br. s., 1H), 4.25-4.39 (m, 2H), 2.84-3.00 (m, 2H), 2.52-2.66 (m, 1H), 2.21-2.32 (m, 1H), 1.84-1.94 (m, 1H), 1.36-1.52 (m, 5H) |
| | 4-(1-fluoro-1-((1-methyl-3-(trifluoromethyl)-1H-pyrazol-4-yl)sulfonyl)ethyl)-N-(6-fluoropyridin-3-yl)piperidine-1-carboxamide | 244 | 16 | 482.1 | 1H NMR (400 MHz, CDCl3) δ ppm 8.04 (br. s., 2H), 7.88 (s, 1H), 6.88 (d, J = 8.19 Hz, 1H), 6.69 (br. s., 1H), 4.00-4.28 (m, 2H), 3.97 (s, 3H), 2.79-2.97 (m, 2H), 2.51 (d, J = 10.51 Hz, 1H), 2.21 (d, J = 12.96 Hz, 1H), 1.87 (d, J = 11.98 Hz, 1H), 1.31-1.59 (m, 5H) |
| | 4-(1-fluoro-1-((1-methyl-3-(trifluoromethyl)-1H-pyrazol-4-yl)sulfonyl)ethyl)-N-(2-fluoropyridin-4-yl)piperidine-1-carboxamide | 245 | 16 | 482.1 | 1H NMR (400 MHz, CDCl3) δ ppm 8.44 (br. s., 1H), 7.88-8.01 (m, 2H), 7.45-7.63 (m, 2H), 4.35 (d, J = 13.08 Hz, 1H), 4.23 (d, J = 12.35 Hz, 1H), 3.97 (s, 3H), 2.81-2.99 (m, 2H), 2.54 (br. s., 1H), 2.20 (d, J = 13.45 Hz, 1H), 1.89 (d, J = 12.35 Hz, 1H), 1.32-1.58 (m, 5H) |
| | 4-(1-fluoro-1-((6-methoxypyridin-3-yl)sulfonyl)ethyl)-N-(isoxazol-3-yl)piperidine-1-carboxamide | 246 | 9 | 413.1 | 1H NMR (400 MHz, CDCl3) δ ppm 8.60 (s, 1H), 8.55 (s, 1H), 8.15 (s, 1H), 7.92 (d, J = 8.68 Hz, 1H), 6.97 (s, 1H), 6.82 (d, J = 8.80 Hz, 1H), 4.12-4.29 (m, 2H), 3.97 (s, 3H), 2.89 (q, J = 11.70 Hz, 2H), 2.46-2.61 (m, 1H), 2.26 (d, J = 13.20 Hz, 1H), 1.87 (d, J = 13.20 Hz, 1H), 1.29-1.54 (m, 5H) |
| | 4-(1-fluoro-1-((1-methyl-3-(trifluoromethyl)-1H-pyrazol-4-yl)sulfonyl)ethyl)-N-(6-methylpyridin- | 247 | 16 | 478.1 | 1H NMR (400 MHz, CDCl3) δ ppm 9.14 (br. s., 1H), 9.05 (br. s., 1H), 8.92 (d, J = 8.56 Hz, 1H), 7.93 (s, 1H), 7.42 (d, J = 8.80 Hz, 1H), 4.30-4.47 (m, 2H), 3.96 (s, 3H), 2.75-2.94 (m, 2H), 2.67 (s, 3H), 2.46-2.59 |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 3-yl) piperidine-1-carboxamide | | | | (m, 1H), 2.10-2.21 (m, 1H), 1.79-1.91 (m, 1H), 1.29-1.57 (m, 5H) |
| | (R)-4-(1-((3-(difluoromethyl)-1-methyl-1H-pyrazol-4-yl)sulfonyl)-1-fluoroethyl)-N-(oxazol-4-yl)piperidine-1-carboxamide | 248 | 20 | 436.1 | 1H NMR (400 MHz, CDCl3) δ ppm 8.17 (s, 1H), 7.82 (m, 3H), 6.75-7.06 (m, 1H), 4.61-5.07 (m, 2H), 3.97 (s, 3H), 2.87 (m, 3H), 2.21 (d, J = 12.84 Hz, 1H), 1.88 (d, J = 12.35 Hz, 1H), 1.32-1.58 (m, 5H) |
| | 4-(1-fluoro-1-((1-methyl-3-(trifluoromethyl)-1H-pyrazol-5-yl)sulfonyl)ethyl)-N-(isoxazol-3-yl)piperidine-1-carboxamide | 249 | 18 | 454 | 1H NMR (400 MHz, DMSO-d6) δ ppm 9.78 (s, 1H), 8.67 (s, 1H), 7.75 (s, 1H), 6.77 (s, 1H), 4.29-4.26 (m, 2H), 4.14 (s, 3H), 2.87-2.81 (m, 2H), 1.99-1.96 (m, 1H), 1.75-1.60 (m, 4H), 1.47-1.35 (m, 2H) |
| | 4-(1-fluoro-1-((1-methyl-3-(trifluoromethyl)-1H-pyrazol-5-yl)sulfonyl)ethyl)-N-(6-methylpyridin-3-yl)piperidine-1-carboxamide | 250 | 18 | 478.1 | 1H NMR (400 MHz, DMSO-d6) δ ppm 9.77 (s, 1H), 8.98 (s, 1H), 8.54 (d, J = 8.8 Hz, 1H), 7.80-7.75 (m, 2H), 4.37-4.34 (m, 2H), 4.15 (s, 3H), 2.95-2.84 (m, 2H), 2.64 (s, 3H), 2.58-2.50 (m, 1H), 2.07-2.00 (m, 1H), 1.77-1.74 (m, 1H), 1.61 (d, J = 23.2 Hz, 3H), 1.48-1.39 (m, 2H) |
| | 4-(1-fluoro-1-((1-methyl-3-(trifluoromethyl)-1H-pyrazol-5-yl)sulfonyl)ethyl)-N-(2-fluoropyridin-4-yl)piperidine-1-carboxamide | 251 | 18 | 482.1 | 1H NMR (400 MHz, DMSO-d6) δ ppm 9.41 (s, 1H), 7.97 (d, J = 5.7 Hz, 1H), 7.75 (s, 1H), 7.40-7.38 (m, 1H), 7.31 (s, 1H), 4.31-4.26 (m, 2H), 4.41 (s, 3H), 2.92-2.82 (m, 2H), 2.56-2.50 (m, 1H), 2.02-1.99 (m, 1H), 1.76-1.73 (m, 1H), 1.61 (d, J = 23.2 Hz, 3H), 1.47-1.39 (m, 2H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | 4-(1-fluoro-1-((1-methyl-3-(trifluoromethyl)-1H-pyrazol-5-yl)sulfonyl)ethyl)-N-(6-fluoropyridin-3-yl)piperidine-1-carboxamide | 252 | 18 | 482.1 | 1H NMR (400 MHz, DMSO-d6) δ ppm 8.80 (s, 1H), 8.26 (s, 1H), 8.04-7.99 (m, 1H), 7.76 (s, 1H), 7.09-7.06 (m, 1H), 4.27-4.21 (m, 2H), 4.15 (s, 3H), 2.91-2.80 (m, 2H), 2.52-2.50 (m, 1H), 2.02-1.99 (m, 1H), 1.76-1.72 (m, 1H), 1.62 (d, J = 23.1 Hz, 3H), 1.49-1.38 (m, 2H) |
| | 4-(1-((3-(difluoromethyl)-1-methyl-1H-pyrazol-5-yl)sulfonyl)-1-fluoroethyl)-N-(isoxazol-3-yl)piperidine-1-carboxamide | 253 | 17 | 434 | 1H NMR (400 MHz, CD3OD) δ ppm 9.77 (s, 1H), 8.66 (s, 1H), 7.42 (s, 1H), 7.12 (t, J = 54.1 Hz, 1H), 6.77 (s, 1H), 4.29-4.23 (m, 2H), 4.10 (s, 3H), 2.87-2.77 (m, 2H), 2.50-2.47 (m, 1H), 1.99-1.96 (m, 1H), 1.72-1.69 (m, 1H), 1.58 (d, J = 23.2 Hz, 3H), 1.49-1.35 (m, 2H) |
| | 4-(1-((3-(difluoromethyl)-1-methyl-1H-pyrazol-5-yl)sulfonyl)-1-fluoroethyl)-N-(6-fluoropyridin-3-yl)piperidine-1-carboxamide | 254 | 17 | 462 | 1H NMR (400 MHz, CD3OD) δ ppm 8.21 (s, 1H), 8.02-7.97 (m, 1H), 7.26 (s, 1H), 7.04-7.01 (m, 1H), 6.84 (t, J = 54.5 Hz, 1H), 4.36-4.29 (m, 2H), 4.16 (s, 3H), 2.98-2.92 (m, 2H), 2.63-2.61 (m, 1H), 2.22-2.18 (m, 1H), 1.92-1.89 (m, 1H), 1.69-1.52 (m, 5H) |
| | 4-(1-((3-(difluoromethyl)-1-methyl-1H-pyrazol-5-yl)sulfonyl)-1-fluoroethyl)-N-(2-fluoropyridin-4-yl)piperidine-1-carboxamide | 255 | 17 | 462 | 1H NMR (400 MHz, CD3OD) δ ppm 8.03 (d, J = 6.4 Hz, 1H), 7.48-7.41 (m, 2H), 7.14 (s, 1H), 6.72 (t, J = 54.3 Hz, 1H), 4.27-4.20 (m, 2H), 3.21 (s, 3H), 2.92-2.85 (m, 2H), 2.53-2.48 (m, 1H), 2.12-2.09 (m, 1H), 1.84-1.80 (m, 1H), 1.57-1.42 (m, 5H) |
| | 4-(1-((3-(difluoromethyl)-1-methyl-1H-pyrazol-5-yl)sulfonyl)-1-fluoroethyl)-N-(6-methylpyridin-3-yl) | 256 | 17 | 458 | 1H NMR (400 MHz, CD3OD) δ ppm 9.02 (s, 1H), 8.42 (d, J = 8.8 Hz, 1H), 7.82 (d, J = 8.8 Hz, 1H), 7.26 (s, 1H), 6.85 (t, J = 54.5 Hz, 1H), 4.41-4.34 (m, 2H), 4.16 (s, 3H), 3.02-2.96 (m, 2H), 2.72 (s, 3H), 2.68-2.60 (m, 1H), 2.23-2.20 (m, |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | piperidine-1-carboxamide | | | | 1H), 1.95-1.92 (m, 1H), 1.69-1.51 (m, 5H) |
| | (S)-4-(1-((3-(difluoro-methyl)-1-methyl-1H-pyrazol-4-yl)sulfonyl)-1-fluoro-ethyl)-N-(6-fluoro-pyridin-3-yl)piperidine-1-carboxamide | 257 | 21 | 464 | 1H NMR (400 MHz, CD3OD) δ ppm 8.77 (s, 1H), 8.60 (s, 1H), 8.20 (s, 1H), 7.98-7.94 (m, 1H), 711-6.84 (m, 2H), 4.21-4.13 (m, 2H), 3.93 (s, 3H), 2.80-2.70 (m, 2H), 2.43-2.35 (m, 1H), 1.97-1.94 (1H), 1.66-1.63 (m, 1H), 1.47 (d, J = 23.0 Hz, 3H), 1.39-1.26 (m, 2H) |
| | (S)-4-(1-((3-(difluoro-methyl)-1-methyl-1H-pyrazol-4-yl)sulfonyl)-1-fluoro-ethyl)-N-(6-methyl-pyridin-3-yl)piperidine-1-carboxamide | 258 | 21 | 460 | 1H NMR (400 MHz, DMSO-d6) δ ppm 9.01 (s, 1H), 8.41-8.39 (m, 2H), 7.82-7.80 (m, 2H), 6.98 (t, J = 53.1 Hz, 1H), 4.39-4.31 (m, 2H), 4.05 (s, 3H), 3.00-2.94 (m, 2H), 2.72 (s, 3H), 2.57-2.56 (m, 1H), 1.92-1.89 (m, 1H), 1.65-1.61 (m, 1H), 1.59-1.50 (m, 5H) |
| | (R)-4-(1-((3-(difluoro-methyl)-1-methyl-1H-pyrazol-4-yl)sulfonyl)-1-fluoro-ethyl)-N-(6-fluoro-pyridin-3-yl)piperidine-1-carboxamide | 259 | 20 | 464.1 | 1H NMR (400 MHz, DMSO-d6) δ ppm 8.26 (s, 1H), 8.07-8.06 (m, 1H), 7.89-7.84 (m, 1H), 7.00-6.74 (m, 2H), 4.23-4.17 (m, 2H), 3.92 (s, 3H), 2.85-2.74 (m, 2H), 2.45-2.41 (m, 1H), 2.12-1.93 (m, 1H), 1.78-1.75 (m, 1H), 1.53-1.36 (m, 5H) |
| | (R)-4-(1-((3-(difluoro-methyl)-1-methyl-1H-pyrazol-4-yl)sulfonyl)-1-fluoro-ethyl)-N-(6-methyl-pyridin-3-yl)piperidine-1-carboxamide | 260 | 20 | 460 | 1H NMR (400 MHz, CD3OD) δ ppm 8.38 (s, 1H), 8.21 (s, 1H), 8.02-7.97 (m, 2H), 7.12-6.86 (m, 2H), 4.34-4.26 (m, 2H), 4.04 (s, 3H), 2.97-2.90 (m, 2H), 2.55-2.52 (m, 1H), 2.24-2.20 (m, 1H), 1.90-1.87 (m, 1H), 1.65-1.46 (m, 5H) |
| | (R)-4-(1-((3-(difluoro-methyl)-1-methyl-1H-pyrazol-4-yl)sulfonyl)-1-fluoro-ethyl)-N-(6- | 261 | 20 | 514.1 | 1H NMR (400 MHz, CD3OD) δ ppm 8.63 (d, J = 2.4 Hz, 1H), 8.26 (s, 1H), 8.02-7.99 (m, 1H), 7.61 (d, J = 8.64 Hz, 1H), 6.87 (t, J = 53.1 Hz, 1H), 4.26-4.21 (m, 2H), 3.92 (s, 3H), 2.87-2.80 (m, 2H), |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | (trifluoro-methyl)pyridin-3-yl)piperidine-1-carboxamide | | | | 2.46-2.41 (m, 1H), 2.13-2.10 (m, 1H), 1.79-1.76 (m, 1H), 1.53-1.38 (m, 5H) |
| | 4-(1-fluoro-1-((6-(trifluoro-methyl)pyridin-3-yl)sulfonyl)ethyl)-N-(pyridazin-4-yl)piperidine-1-carboxamide | 262 | 5, 9 | 462 | 1H-NMR (300 MHz, DMSO-d6) δ ppm 9.28-9.20 (m, 3H), 8.88 (m, 1H), 8.62 (m, 1H), 8.29 (m, 1H), 7.75 (m, 1H), 4.23 (m, 2H), 2.90 (m, 2H), 2.50 (m, 1H), 2.11 (m, 1H), 1.76 (m, 1H), 1.64 (d, J = 23.1 Hz, 3H), 1.54-1.43 (m, 2H) |
| | 4-(1-((2-chloro-phenyl)sulfonyl)-1-fluoro-ethyl)-N-(pyridazin-4-yl)piperidine-1-carboxamide | 263 | 5, 9 | 427.2 | 1H NMR (400 MHz, CD3OD) δ ppm 9.23 (d, J = 2.0 Hz, 1H), 8.86 (d, J = 6.0 Hz, 1H), 8.10 (d, J = 1.2 Hz, 1H), 7.86 (m, 1H), 7.71-7.69 (m, 2H), 7.62-7.57 (m, 2H), 4.32 (m, 2H), 2.95 (m, 2H), 2.62 (m, 1H), 2.28 (m, 1H), 1.92 (m, 1H), 1.63-1.50 (m, 5H) |
| | 4-(1-((3-chloro-phenyl)sulfonyl)-1-fluoro-ethyl)-N-(pyridazin-4-yl)piperidine-1-carboxamide | 264 | 5, 9 | 427.2 | 1H NMR (400 MHz, DMSO-d6) δ ppm 9.27 (d, J = 2 Hz, 1H), 9.20 (s, 1H), 8.87 (d, J = 6 Hz, 1H), 7.97 (d, J = 0.8 Hz, 1H), 7.89 (m, 2H), 7.77 (m, 2H), 4.24 (d, J = 13.2 Hz, 2H), 2.87 (m, 2H), 2.43 (m, 1H), 2.07 (m, 1H), 1.73 (m, 1H), 1.53 (d, J = 21 Hz, 3H), 1.41 (m, 2H) |
| | 4-(1-((3-cyano-phenyl)sulfonyl)-1-fluoro-ethyl)-N-(pyridazin-4-yl)piperidine-1-carboxamide | 265 | 3, 5, 9 | 418 | 1H NMR (2300 MHz, DMSO-d6) δ ppm 9.22 (d, J = 2.7 Hz, 1H), 9.16 (br. S., 1H), 8.82 (d, J = 6.0 Hz, 1H), 8.32-8.28 (m, 2H), 8.18 (m, 1H), 7.89 (m, 1H), 7.70 (m, 1H), 4.23 (m, 2H), 2.83 (m, 2H), 2.45 (m, 1H), 2.03 (m, 1H), 1.69 (m, 1H), 1.47-1.32 (m, 5H) |
| | 4-(1-fluoro-1-((4-(trifluoro-methyl)phenyl)sulfonyl)ethyl)-N-(pyridazin-4-yl) | 266 | 8 | 461.2 | 1H-NMR (400 MHz, DMSO-d6) δ ppm 9.28 (m, 1H), 9.19 (br s, 1H), 8.88 (m, 1H), 8.15-8.10 (m, 4H), 7.76 (M, 1H), 4.26 (m, 2H), 2.91-2.83 (m, 2H), 2.47 (m, 1H), 2.10 (m, |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | piperidine-1-carboxamide | | | | 1H), 1.74 (m, 1H), 1.58 (d, J = 23.2 Hz, 3H), 1.49 (m, 2H) |
| 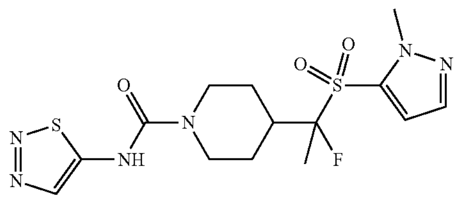 [SMILES: Cn1nccc1S(=O)(=O)C(C)(F)C1CCN(C(=O)Nc2cnns2)CC1] | 4-(1-fluoro-1-((1-methyl-1H-pyrazol-5-yl)sulfonyl)ethyl)-N-(1,2,3-thiadiazol-5-yl)piperidine-1-carboxamide | 267 | 5, 9 | 402.9 | 1H-NMR (400 MHz, DMSO-d6) δ ppm 10.96 (br s, 1H), 8.54 (s, 1H), 7.78 (d, J = 2.4 Hz, 1H), 7.12 (d, J = 2.4 Hz, 1H), 4.23 (m, 2H), 4.08 (s, 3H), 2.93 (m, 2H), 2.49 (m, 1H), 2.06 (m, 1H), 1.77 (m, 1H), 1.61 (d, J = 23.2 Hz, 3H), 1.54-1.46 (m, 2H) |
| | 4-(1-fluoro-1-((4-(trifluoromethyl)phenyl)sulfonyl)ethyl)-N-(1,2,3-thiadiazol-5-yl)piperidine-1-carboxamide | 268 | 8 | 467.2 | 1H-NMR (400 MHz, DMSO-d6) δ ppm 10.97 (br s, 1H), 8.54 (s, 1H), 8.13 (m, 4H), 4.25 (m, 2H), 2.94 (m, 2H), 2.44 (m, 1H), 2.09 (m, 1H), 1.75 (m, 1H), 1.58 (d, J = 22.8 Hz, 3H), 1.50-1.41 (m, 2H) |
| | 4-(1-((1-ethyl-1H-pyrazol-5-yl)sulfonyl)-1-fluoroethyl)-N-(pyridazin-4-yl)piperidine-1-carboxamide | 269 | 5, 9 | 411 | 1H-NMR (300 MHz, DMSO-d6) δ ppm 9.27 (m, 2H), 8.89 (d, J = 6.0 Hz, 1H), 7.82 (d, J = 1.5 Hz, 1H), 7.76 (m, 1H), 7.10 (d, J = 1.5 Hz, 1H), 4.43 (m, 2H), 4.27 (m, 2H), 2.90 (m, 2H), 2.46 (m, 1H), 2.05 (m, 1H), 1.76 (m, 1H), 1.63 (d, J = 23.1 Hz, 3H), 1.39-1.17 (m, 5H) |
| | 4-(1-((4-cyanophenyl)sulfonyl)-1-fluoroethyl)-N-(pyridazin-4-yl)piperidine-1-carboxamide | 270 | 3, 5, 9 | 418 | 1H-NMR (400 MHz, CD3OD) δ ppm 9.25 (d, J = 2.4 Hz, 1H), 8.88 (m, 1H), 8.14 (m, 2H), 8.08 (m, 2H), 7.88 (m, 1H), 4.33 (m, 2H), 2.94 (m, 2H), 2.59 (m, 1H), 2.29 (m, 1H), 1.90 (m, 1H), 1.62-1.57 (m, 5H) |
| 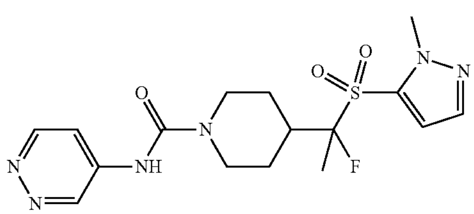 | 4-(1-fluoro-1-((1-methyl-1H-pyrazol-5-yl)sulfonyl)ethyl)-N-(pyridazin-4-yl)piperidine-1-carboxamide | 271 | 5, 9 | 396.9 | 1H-NMR (400 MHz, DMSO-d6) δ ppm 9.28 (d, J = 2.4 Hz, 1H), 9.20 (s, 1H), 8.88 (d, J = 6.0 Hz, 1H), 7.77 (m, 2H), 7.12 (d, J = 2.4 Hz, 1H), 4.27 (m, 2H), 4.07 (s, 3H), 2.86 (m, 2H), 2.46 (m, 1H), 2.05 (m, 1H), 1.79 (m, 1H), 1.62 (d, J = 23.2 Hz, 3H), 1.53-1.46 (m, 2H) |

TABLE 1-continued

Representative compounds of the Invention and Analytical Data

| Structure | Name | Cmpd. No. | Ref. Example | Obs. Mass (M + H)+ | $^1$H NMR |
|---|---|---|---|---|---|
| | 4-(1-fluoro-1-((1-methyl-1H-imidazol-4-yl)sulfonyl)ethyl)-N-(pyridazin-4-yl)piperidine-1-carboxamide | 272 | 16 | 396.9 | 1H-NMR (400 MHz, CD3OD) δ ppm 9.25 (d, J = 2.4 Hz, 1H), 8.88 (m, 1H), 7.96 (d, J = 1.2 Hz, 1H), 7.88 (m, 2H), 4.36 (m, 2H), 3.86 (s, 3H), 2.94 (m, 2H), 2.54 (m, 1H), 2.32 (m, 1H), 1.90 (m, 1H), 1.69 (d, J = 22.4 Hz, 3H), 1.56-1.48 (m, 2H) |
| | 4-(1-fluoro-1-((2-methoxyphenyl)sulfonyl)ethyl)-N-(pyridazin-4-yl)piperidine-1-carboxamide | 273 | 5, 9 | 423 | 1H-NMR (400 MHz, DMSO-d6) δ ppm 9.26 (d, J = 2.0 Hz, 1H), 9.19 (br s, 1H), 8.85 (m, 1H), 7.81-7.74 (m, 3H), 7.34 (d, J = 10.8 Hz, 1H), 7.17 (m, 1H), 4.27 (m, 2H), 3.90 (s, 3H), 2.85 (m, 2H), 2.38 (m, 1H), 2.10 (m, 1H), 1.73 (m, 1H), 1.49 (d, J = 23.2 Hz, 3H), 1.42-1.34 (m, 2H) |
| | 4-(1-((4-cyanophenyl)sulfonyl)-1-fluoroethyl)-N-(1,2,3-thiadiazol-5-yl)piperidine-1-carboxamide | 274 | 3, 5, 9 | 424 | 1H-NMR (400 MHz, DMSO-d6) δ ppm 10.93 (br s, 1H), 8.54 (s, 1H), 8.22 (d, J = 8.4 Hz, 2H), 8.10 (d, J = 8.4 Hz, 2H), 4.24 (m, 2H), 2.92 (m, 2H), 2.44 (m, 1H), 2.10 (m, 1H), 1.73 (m, 1H), 1.57 (d, J = 22.8 Hz, 3H), 1.49-1.36 (m, 2H) |
| | 4-(1-((3,5-difluorophenyl)sulfonyl)-1-fluoroethyl)-N-(pyridazin-4-yl)piperidine-1-carboxamide | 275 | 6 | 429 | 1H-NMR (400 MHz, DMSO-d6) δ ppm 9.28 (d, J = 2.0 Hz, 1H), 8.87 (m, 1H), 7.90 (m, 1H), 7.77 (m, 1H), 7.67 (m, 2H), 4.27 (m, 2H), 2.90 (m, 2H), 2.47 (m, 1H), 2.08 (m, 1H), 1.75 (m, 1H), 1.61 (d, J = 22.8 Hz, 3H), 1.49-1.40 (m, 2H) |
| | 4-(1-((3-(difluoromethyl)-1-methyl-1H-pyrazol-4-yl)sulfonyl)-1-fluoroethyl)-N-(pyridazin-4-yl)piperidine-1-carboxamide | 276 | 20 | 447 | 1H-NMR (400 MHz, CD3OD) δ ppm 9.23 (d, J = 2.0 Hz, 1H), 8.86 (d, J = 6.4 Hz, 1H), 8.36 (s, 1H), 7.85 (m, 1H), 6.97 (t, J = 53.2 Hz, 1H), 4.31 (m, 2H), 4.02 (s, 3H), 2.94 (m, 2H), 2.56 (m, 1H), 2.23 (m, 1H), 1.90 (m, 1H), 1.63-1.53 (m, 5H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 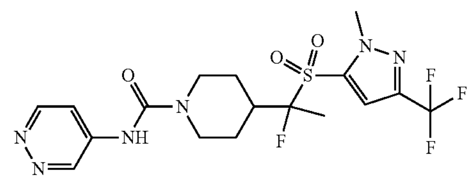 [SMILES: Cn1nc(C(F)(F)F)cc1S(=O)(=O)C(C)(F)C1CCN(C(=O)Nc2ccnnc2)CC1] | 4-(1-fluoro-1-((1-methyl-3-(trifluoro-methyl)-1H-pyrazol-5-yl)sulfonyl)ethyl)-N-(pyridazin-4-yl)piperidine-1-carboxamide | 277 | 18 | 465.4 | 1H-NMR (400 MHz, CD3OD) δ ppm 9.20 (d, J = 2.0 Hz, 1H), 8.84 (d, J = 8.0 Hz, 1H), 7.84 (m, 1H), 7.39 (s, 1H), 4.34 (m, 2H), 3.91 (s, 3H), 2.99 (m, 2H), 2.62 (m, 1H), 2.19 (m, 1H), 1.91 (m, 1H), 1.67-1.45 (m, 5H) |
| 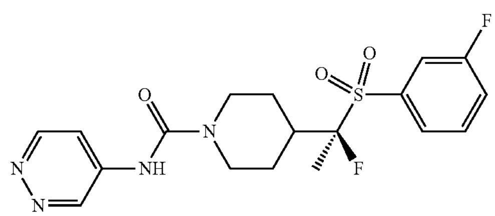 [SMILES: C[C@](F)(C1CCN(C(=O)Nc2ccnnc2)CC1)S(=O)(=O)c1cccc(F)c1] | (R)-4-(1-fluoro-1-((3-fluoro-phenyl)sulfonyl)ethyl)-N-(pyridazin-4-yl)piperidine-1-carboxamide | 278 | 6 | 411 | 1H-NMR (400 MHz, CD3OD) δ ppm 9.23 (d, J = 2 Hz, 1H), 8.86 (d, J = 6 Hz, 1H), 7.87 (m, 1H), 7.79-7.66 (m, 3H), 7.60 (m, 1H), 4.33 (m, 2H), 2.94 (m, 2H), 2.52 (m, 1H), 2.27 (m, 1H), 1.89 (m, 1H), 1.59-1.49 (m, 5H) |
| 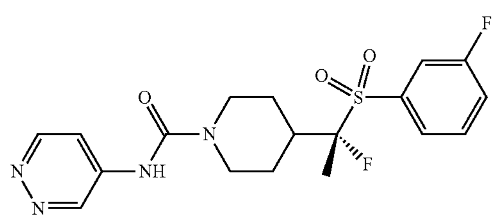 [SMILES: C[C@@](F)(C1CCN(C(=O)Nc2ccnnc2)CC1)S(=O)(=O)c1cccc(F)c1] | (S)-4-(1-fluoro-1-((3-fluoro-phenyl)sulfonyl)ethyl)-N-(pyridazin-4-yl)piperidine-1-carboxamide | 279 | 6 | 411.2 | 1H-NMR (400 MHz, CD3OD) δ ppm 9.23 (d, J = 2 Hz, 1H), 8.86 (d, J = 6 Hz, 1H), 7.87 (m, 1H), 7.79-7.66 (m, 3H), 7.60 (m, 1H), 4.33 (m, 2H), 2.94 (m, 2H), 2.52 (m, 1H), 2.27 (m, 1H), 1.89 (m, 1H), 1.59-1.49 (m, 5H) |
| 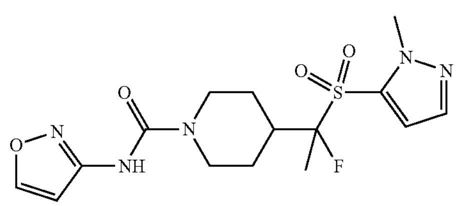 [SMILES: Cn1nccc1S(=O)(=O)C(C)(F)C1CCN(C(=O)Nc2ccon2)CC1] | 4-(1-fluoro-1-((1-methyl-1H-pyrazol-5-yl)sulfonyl)ethyl)-N-(isoxazol-3-yl)piperidine-1-carboxamide | 280 | 5, 9 | 386 | 1H-NMR (400 MHz, CD3OD) δ ppm 8.45 (d, J = 1.6 Hz, 1H), 7.68 (d, J = 2.0 Hz, 1H), 7.03 (d, J = 2.0 Hz, 1H), 6.75 (d, J = 1.4 Hz, 1H), 4.31 (m, 2H), 4.12 (s, 3H), 2.93 (m, 2H), 2.56 (m, 1H), 2.22 (m, 1H), 1.95 (m, 1H), 1.67 (d, J = 22.8 Hz, 3H), 1.58 (m, 2H) |
| 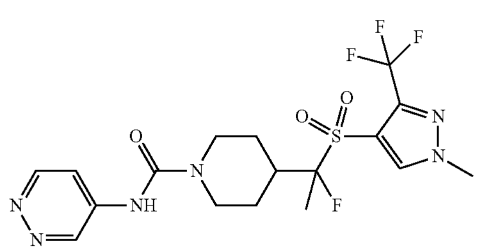 [SMILES: Cn1cc(S(=O)(=O)C(C)(F)C2CCN(C(=O)Nc3ccnnc3)CC2)c(C(F)(F)F)n1] | 4-(1-fluoro-1-((1-methyl-3-(trifluoro-methyl)-1H-pyrazol-4-yl)sulfonyl)ethyl)-N-(pyridazin-4-yl)piperidine-1-carboxamide | 281 | 16 | 465 | 1H-NMR (400 MHz, CD3OD) δ ppm 9.23 (d, J = 2.0 Hz, 1H), 8.86 (d, J = 6.0 Hz, 1H), 8.43 (s, 1H), 7.86 (m, 1H), 4.31 (m, 2H), 3.91 (s, 3H), 2.95 (m, 2H), 2.57 (m, 1H), 2.22 (m, 1H), 1.91 (m, 1H), 1.63-1.55 (m, 5H) |

| Structure | Name | Cmpd. No. | Ref. Example | Obs. Mass (M + H)+ | $^1$H NMR |
|---|---|---|---|---|---|
| 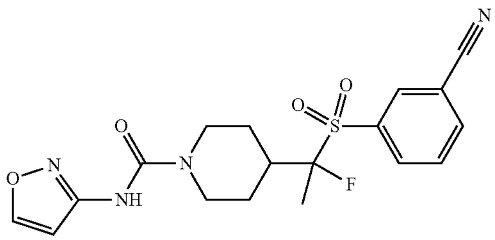 [SMILES: CC(F)(C1CCN(C(=O)Nc2ccon2)CC1)S(=O)(=O)c1cccc(C#N)c1] | 4-(1-((3-cyano-phenyl)sulfonyl)-1-fluoro-ethyl)-N-(isoxazol-3-yl)piperidine-1-carboxamide | 282 | 3, 5, 9 | 407 | 1H-NMR (300 MHz, DMSO-d6) δ ppm 9.69 (s, 1H), 8.61 (d, J = 1.8 Hz, 1H), 8.31-8.28 (m, 2H), 8.18-8.15 (m, 1H), 7.92-7.86 (m, 1H), 6.73 (s, 1H), 4.22-4.18 (m, 1H), 2.80-2.72 (m, 2H), 2.46-2.45 (m, 1H), 2.03-1.97 (m, 1H), 1.61-1.54 (m, 1H), 1.40-1.32 (m, 5H) |
| 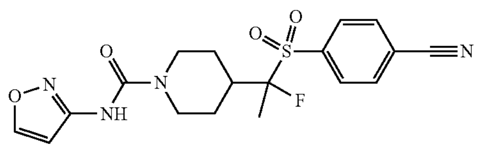 | 4-(1-((4-cyano-phenyl)sulfonyl)-1-fluoro-ethyl)-N-(isoxazol-3-yl)piperidine-1-carboxamide | 283 | 3, 5, 9 | 407.1 | 1H-NMR (400 MHz, DMSO-d6) δ ppm 9.74 (s, 1H), 8.66 (d, J = 1.8 Hz, 1H), 8.22 (d, J = 8.4 Hz, 2H), 8.10 (d, J = 8.1 Hz, 2H), 6.77 (d, J = 1.5 Hz, 1H), 4.30 (m, 2H), 2.79 (m, 2H), 2.50 (m, 1H), 2.19 (m, 1H), 1.63 (m, 1H), 1.58 (d, J = 22.8 Hz, 3H), 1.47 (m, 2H) |
| 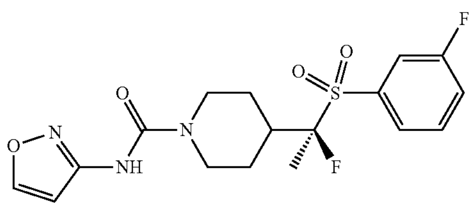 [SMILES: C[C@](F)(C1CCN(C(=O)Nc2ccon2)CC1)S(=O)(=O)c1cccc(F)c1] | (R)-4-(1-fluoro-1-((3-fluoro-phenyl)sulfonyl)ethyl)-N-(isoxazol-3-yl)piperidine-1-carboxamide | 284 | 6 | 400 | 1H-NMR (400 MHz, DMSO-d6) δ ppm 9.74 (s, 1H), 8.66 (d, J = 2.0 Hz, 1H), 7.83-7.70 (m, 4H), 6.77 (d, J = 1.6 Hz, 1H), 4.25 (m, 2H), 2.78 (m, 2H), 2.40 (m, 1H), 2.05 (m, 1H), 1.69 (m, 1H), 1.56 (d, J = 22.8 Hz, 3H), 1.45-1.34 (m, 2H) |
| 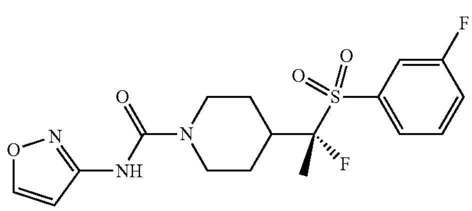 [SMILES: C[C@@](F)(C1CCN(C(=O)Nc2ccon2)CC1)S(=O)(=O)c1cccc(F)c1] | (S)-4-(1-fluoro-1-((3-fluoro-phenyl)sulfonyl)ethyl)-N-(isoxazol-3-yl)piperidine-1-carboxamide | 285 | 6 | 400 | 1H-NMR (400 MHz, DMSO-d6) δ ppm 9.74 (s, 1H), 8.66 (d, J = 2.0 Hz, 1H), 7.83-7.70 (m, 4H), 6.77 (d, J = 1.6 Hz, 1H), 4.25 (m, 2H), 2.78 (m, 2H), 2.40 (m, 1H), 2.05 (m, 1H), 1.69 (m, 1H), 1.56 (d, J = 22.8 Hz, 3H), 1.45-1.34 (m, 2H) |
| 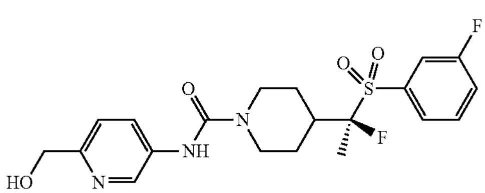 [SMILES: C[C@](F)(C1CCN(C(=O)Nc2ccc(CO)nc2)CC1)S(=O)(=O)c1cccc(F)c1] | (R)-4-(1-fluoro-1-((3-fluoro-phenyl)sulfonyl)ethyl)-N-(6-(hydroxy-methyl)pyridin-3-yl)piperidine-1-carboxamide | 286 | 6 | 440 | 1H-NMR (400 MHz, DMSO-d6) δ ppm 8.65 (s, 1H), 8.52 (d, J = 2.4 Hz, 1H), 7.86-7.71 (m, 5H), 7.30 (m, 1H), 5.26 (m, 1H), 4.48 (m, 2H), 4.25 (m, 2H), 2.84 (m, 2H), 2.49 (m, 1H), 2.07 (m, 1H), 1.68 (m, 1H), 1.52 (d, J = 22.8 Hz, 3H), 1.14-1.02 (m, 2H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | (R)-4-(1-fluoro-1-((3-fluorophenyl)sulfonyl)ethyl)-N-(2-(hydroxymethyl)pyridin-4-yl)piperidine-1-carboxamide | 287 | 6 | 440.2 | 1H-NMR (400 MHz, DMSO-d6) δ ppm 8.95 (s, 1H), 8.19 (d, J = 5.6 Hz, 1H), 7.82-7.71 (m, 4H), 7.56 (d, J = 2.0 Hz, 1H), 7.39 (m, 1H), 5.32 (m, 1H), 4.45 (d, J = 6.0 Hz, 2H), 4.26 (m, 2H), 2.81 (m, 2H), 2.46 (m, 1H), 2.07 (m, 1H), 1.71 (m, 1H), 1.57 (d, J = 23.0 Hz, 3H), 1.47-1.35 (m, 2H) |
| | (R)-4-(1-((3-(difluoromethyl)-1-methyl-1H-pyrazol-4-yl)sulfonyl)-1-fluoroethyl)-N-(pyridin-3-yl)piperidine-1-carboxamide | 288 | 20 | 446 | 1H NMR (400 MHz, DMSO-d6) δ ppm 9.24 (s, 1H), 8.92 (d, J = 2.45 Hz, 1H), 8.59 (s, 1H), 8.32-8.38 (m, 1H), 8.22-8.29 (m, 1H), 7.72 (dd, J = 5.32, 8.62 Hz, 1H), 6.98 (t, J = 52.00 Hz, 1H), 4.12-4.27 (m, 2H), 2.74-2.94 (m, 2H), 2.47 (s, 3H), 2.33-2.41 (m, 1H), 1.91-2.04 (m, 1H), 1.64-1.74 (m, 1H), 1.50 (d, J = 23.00 Hz, 3H), 1.25-1.45 (m, 2H) |
| | (R)-4-(1-((3-(difluoromethyl)-1-methyl-1H-pyrazol-4-yl)sulfonyl)-1-fluoroethyl)-N-(1H-pyrazol-4-yl)piperidine-1-carboxamide | 289 | 20 | 435 | 1H NMR (400 MHz, DMSO-d6) δ ppm 8.59 (s, 1H), 8.47 (s, 1H), 7.51 (s, 2H), 6.97 (t, J = 52.00 Hz, 1H), 4.04-4.18 (m, 23H), 3.93 (s, 3H), 2.59-2.76 (m, 2H), 2.23-2.39 (m, 1H), 1.87-1.98 (m, 1H), 1.57-1.66 (m, 1H), 1.49 (d, J = 23.00 Hz, 3H), 1.18-1.39 (m, 2H) |
| | (R)-4-(1-((3-(difluoromethyl)-1-methyl-1H-pyrazol-4-yl)sulfonyl)-1-fluoroethyl)-N-(1H-pyrazol-3-yl)piperidine-1-carboxamide | 290 | 20 | 435 | 1H NMR (400 MHz, DMSO-d6) δ ppm 8.59 (s, 1H), 8.47 (s, 1H), 7.51 (s, 2H), 6.97 (t, J = 52.00 Hz, 1H), 4.04-4.18 (m, 23H), 3.93 (s, 3H), 2.59-2.76 (m, 2H), 2.23-2.39 (m, 1H), 1.87-1.98 (m, 1H), 1.57-1.66 (m, 1H), 1.49 (d, J = 23.00 Hz, 3H), 1.18-1.39 (m, 2H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 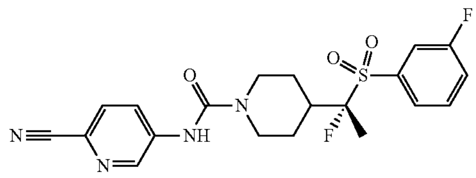 | (S)-N-(6-cyano-pyridin-3-yl)-4-(1-fluoro-1-((3-fluoro-phenyl)sulfonyl)ethyl)piperidine-1-carboxamide | 291 | 6 | 435 | 1H NMR (400 MHz, DMSO-d6) δ ppm 9.24 (s, 1H), 8.81 (d, J = 2.45 Hz, 1H), 8.11 (dd, J = 2.57, 8.68 Hz, 1H), 7.89 (d, J = 8.68 Hz, 1H), 7.68-7.85 (m, 4H), 4.18-4.31 (m, 2H), 2.79-2.95 (m, 2H), 2.38-2.48 (m, 1H), 2.03-2.13 (m, 1H), 1.68-1.77 (m, 1H), 1.34-1.62 (m, 5H) |
| 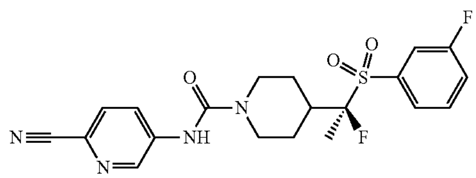 [SMILES: C[C@](F)(C1CCN(C(=O)Nc2ccc(C#N)nc2)CC1)S(=O)(=O)c1cccc(F)c1] | (R)-N-(6-cyano-pyridin-3-yl)-4-(1-fluoro-1-((3-fluoro-phenyl)sulfonyl)ethyl)piperidine-1-carboxamide | 292 | 6 | 435 | 1H NMR (400 MHz, DMSO-d6) δ ppm 9.24 (s, 1H), 8.81 (d, J = 2.45 Hz, 1H), 8.11 (dd, J = 2.57, 8.68 Hz, 1H), 7.89 (d, J = 8.68 Hz, 1H), 7.69-7.85 (m, 4H), 4.19-4.32 (m, 2H), 2.79-2.94 (m, 2H), 2.37-2.49 (m, 1H), 2.03-2.14 (m, 1H), 1.67-1.77 (m, 1H), 1.35-1.62 (m, 5H) |
| 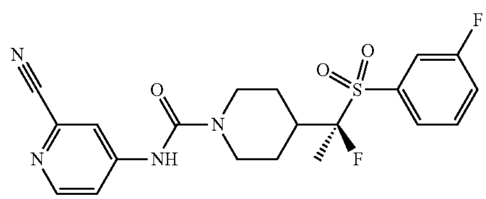 [SMILES: C[C@](F)(C1CCN(C(=O)Nc2ccnc(C#N)c2)CC1)S(=O)(=O)c1cccc(F)c1] | (R)-N-(2-cyano-pyridin-4-yl)-4-(1-fluoro-1-((3-fluoro-phenyl)sulfonyl)ethyl)piperidine-1-carboxamide | 293 | 6 | 435 | 1H NMR (400 MHz, DMSO-d6) δ ppm 9.38 (s, 1H), 8.47 (d, J = 5.75 Hz, 1H), 8.05 (d, J = 2.08 Hz, 1H), 7.68-7.86 (m, 5H), 4.18-4.30 (m, 3H), 2.80-2.94 (m, 2H), 2.39-2.48 (m, 1H), 2.04-2.14 (m, 1H), 1.67-1.78 (m, 1H), 1.34-1.62 (m, 5H) |
| 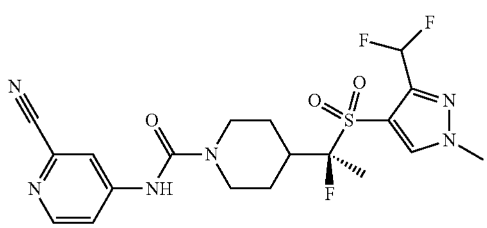 [SMILES: Cn1cc(S(=O)(=O)[C@@](C)(F)C2CCN(C(=O)Nc3ccnc(C#N)c3)CC2)c(C(F)F)n1] | (R)-N-(2-cyano-pyridin-4-yl)-4-(1-((3-(difluoro-methyl)-1-methyl-1H-pyrazol-4-yl)sulfonyl)-1-fluoro-ethyl)piperidine-1-carboxamide | 294 | 20 | 435 | 1H NMR (400 MHz, DMSO-d6) δ ppm 9.37 (s, 1H), 8.67 (s, 1H), 8.47 (d, J = 5.75 Hz, 1H), 8.06 (d, J = 2.20 Hz, 1H), 7.72 (dd, J = 2.20, 5.75 Hz, 1H), 7.05 (t, J = 52.00 Hz, 1H), 4.16-4.33 (m, 2H), 4.00 (s, 3H), 2.79-2.96 (m, 2H), 2.39-2.49 (m, 1H), 2.00-2.10 (m, 1H), 1.69-1.79 (m 1H), 1.57 (d, J = 23.00 Hz, 3H), 1.32-1.52 (m, 2H) |
| 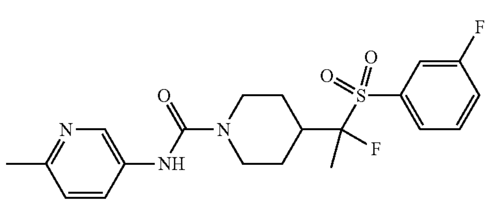 [SMILES: Cc1ccc(NC(=O)N2CCC(C(C)(F)S(=O)(=O)c3cccc(F)c3)CC2)cn1] | 4-(1-fluoro-1-((3-fluoro-phenyl)sulfonyl)ethyl)-N-(6-methyl-pyridin-3-yl)piperidine-1-carboxamide | 295 | 6 | 424 | 1H NMR (400 MHz, DMSO-d6) δ ppm 9.20 (s, 1H), 8.80 (d, J = 2.45 Hz, 1H), 8.20 (dd, J = 2.45, 8.80 Hz, 1H), 7.56-7.81 (m, 4H), 4.09-4.24 (m, 2H), 2.72-2.90 (m, 3H), 2.30-2.49 (m, 4H), 1.95-2.06 (m, 1H), 1.62- |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| | | | | | 1.75 (m, 1H), 1.26-1.56 (m, 5H) |
| | (R)-4-(1-fluoro-1-((1-methyl-3-(trifluoromethyl)-1H-pyrazol-5-yl)sulfonyl)ethyl)-N-(2-fluoropyridin-4-yl)piperidine-1-carboxamide | 296 | 18, 5 | 482 | 1H NMR (400 MHz, CD3CN) δ ppm 7.97 (d, J = 5.99 Hz, 1H), 7.82 (br. s., 1H), 7.39 (s, 1H), 7.26 (s, 2H), 4.20-4.31 (m, 2H), 4.17 (s, 3H), 2.82-3.00 (m, 2H), 2.47-2.63 (m, 1H), 2.06-2.18 (m, 1H), 1.79-1.90 (m, 1H), 1.41-1.73 (m, 5H) |
| | (R)-4-(1-((3-(difluoromethyl)-1-methyl-1H-pyrazol-4-yl)sulfonyl)-1-fluoroethyl)-N-(2-fluoropyridin-4-yl)piperidine-1-carboxamide | 297 | 20 | 464 | 1H NMR (400 MHz, CD3OD) δ ppm 8.38 (s, 1H), 7.96 (d, J = 5.87 Hz, 1H), 7.30 (td, J = 1.60, 5.84 Hz, 1H), 7.26 (d, J = 1.83 Hz, 1H), 6.99 (t, J = 52.00 Hz, 1H), 4.24-4.39 (m, 2H), 4.05 (s, 3H), 2.95 (dt, J = 2.57, 13.08 Hz, 2H), 2.49-2.63 (m, 1H), 2.18-2.29 (m, 1H), 1.84-1.94 (m, 1H), 1.43-1.69 (m, 5H) |
| | (S)-4-(1-((3-(difluoromethyl)-1-methyl-1H-pyrazol-4-yl)sulfonyl)-1-fluoroethyl)-N-(2-methylpyridin-4-yl)piperidine-1-carboxamide | 298 | 21 | 461 | 1H NMR (400 MHz, CD3CN) δ ppm 8.63 (br. s., 1H), 8.23 (d, J = 6.85 Hz, 1H), 8.16 (s, 1H), 7.78 (s, 1H), 7.71 (d, J = 6.97 Hz, 1H), 7.02 (t, J = 52.00 Hz, 1H), 4.18-4.33 (m, 2H), 4.00 (s, 3H), 2.87-3.04 (m, 2H), 2.62 (s, 3H), 2.46-2.58 (m, 1H), 2.11-2.22 (m, 1H), 1.80-1.91 (m, 1H), 1.41-1.66 (m, 5H) |
| | (R)-N-(6-cyanopyridin-3-yl)-4-(1-((3-(difluoromethyl)-1-methyl-1H-pyrazol-4-yl)sulfonyl)-1-fluoroethyl)piperidine-1-carboxamide | 299 | 20 | 471 | 1H NMR (400 MHz, CD3OD) δ ppm 9.03-9.09 (m, 1H), 8.71-8.77 (m, 1H), 8.38 (s, 1H), 8.10 (dd, J = 2.57, 8.68 Hz, 1H), 7.78 (d, J = 8.68 Hz, 1H), 6.99 (t, J = 52.00 Hz, 1H), 4.24-4.40 (m, 2H), 4.05 (s, 3H), 2.96 (dt, J = 2.57, 13.08 Hz, 2H), 2.51-2.64 (m, 1H), 2.20-2.29 (m, 1H), 1.84-1.95 (m, 1H), 1.44-1.68 (m, 5H) |

TABLE 1-continued

Representative compounds of the Invention and Analytical Data

| Structure | Name | Cmpd. No. | Ref. Example | Obs. Mass (M + H)+ | ¹H NMR |
|---|---|---|---|---|---|
| 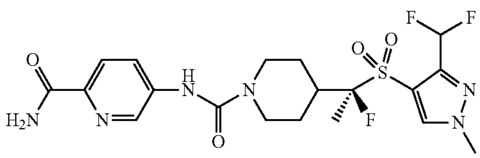 [SMILES: Cn1cc(S(=O)(=O)[C@@](C)(F)C2CCN(C(=O)Nc3ccc(C(N)=O)nc3)CC2)c(C(F)F)n1] | (R)-5-(4-(1-((3-(difluoro-methyl)-1-methyl-1H-pyrazol-4-yl)sulfonyl)-1-fluoro-ethyl)piperidine-1-carboxa-mido)picolinamide | 300 | 20 | 489 | 1H NMR (400 MHz, METHANOL-d4) δ ppm 8.70 (t, J = 1.47 Hz, 1H), 8.27 (s, 1H), 7.99 (d, J = 1.47 Hz, 2H), 6.88 (t, J = 52.00 Hz, 1H), 4.14-4.30 (m, 2H), 3.93 (s, 3H), 2.85 (dt, J = 2.38, 13.05 Hz, 2H), 2.39-2.52 (m, 1H), 2.07-2.18 (m, 1H), 1.74-1.84 (m, 1H), 1.33-1.57 (m, 5H) |
| 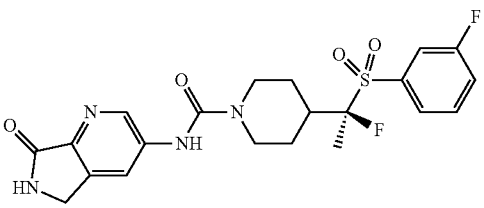 [SMILES: C[C@](F)(C1CCN(C(=O)Nc2cnc3c(c2)CNC3=O)CC1)S(=O)(=O)c1cccc(F)c1] | (R)-4-(1-fluoro-1-((3-fluoro-phenyl)sulfonyl)ethyl)-N-(7-oxo-6,7-dihydro-5H-pyrrolo[3,4-b]pyridin-3-yl)piperidine-1-carboxamide | 301 | 6 | 465 | 1H NMR (400 MHz, DMSO-d6) δ ppm 9.03 (s, 1H), 8.69-8.66 (m, 2H), 8.19-8.19 (m, 1H), 7.80-7.71 (m, 4H), 4.32-4.25 (m, 4H), 2.85-2.83 (m, 2H), 2.50-2.49 (m, 1H), 2.07-2.02 (m, 1H), 1.70-1.166 (m, 1H), 1.58-1.44 (m, 5H) |
| 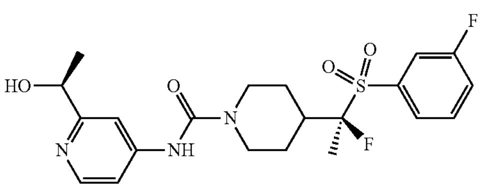 [SMILES: C[C@H](O)c1cc(NC(=O)N2CCC([C@](C)(F)S(=O)(=O)c3cccc(F)c3)CC2)ccn1] | 4-((R)-1-fluoro-1-((3-fluoro-phenyl)sulfonyl)ethyl)-N-(2-((S)-1-hydroxy-ethyl)pyridin-4-yl)piperidine-1-carboxamide | 302 | 6, 29 | 454 | 1H NMR (400 MHz, DMSO-d6) δ ppm 8.95 (s, 1H), 8.19-8.18 (m, 1H), 7.83-7.71 (m, 4H), 7.58 (s, 1H), 7.41-7.40 (m, 1H), 5.27-526 (m, 1H), 4.65-4.59 (m, 1H), 4.26-4.23 (m, 2H), 2.84-2.77 (m, 2H), 2.43-2.38 (m, 1H), 2.07-2.04 (m, 1H), 1.71-1.68 (m, 1H), 1.57-1.41 (m, 8H) |
| 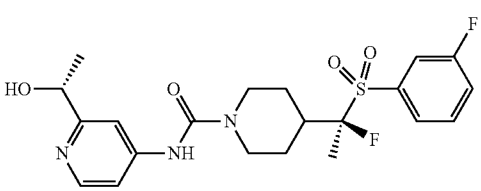 [SMILES: C[C@@H](O)c1cc(NC(=O)N2CCC([C@](C)(F)S(=O)(=O)c3cccc(F)c3)CC2)ccn1] | 4-((R)-1-fluoro-1-((3-fluoro-phenyl)sulfonyl)ethyl)-N-(2-((R)-1-hydroxy-ethyl)pyridin-4-yl)piperidine-1-carboxamide | 303 | 6, 29 | 454 | 1H NMR (400 MHz, DMSO-d6) δ ppm 8.95 (s, 1H), 8.19-8.18 (m, 1H), 7.80-7.71 (m, 4H), 7.58 (s, 1H), 7.41-7.39 (m, 1H), 5.27-5.26 (m, 1H), 4.63-4.61 (m, 1H), 4.26-4.23 (m, 2H), 2.81-2.79 (m, 2H), 2.50-2.49 (m, 1H), 2.07-2.04 (m, 1H), 1.71-1.68 (m, 1H), 1.52-1.23 (m, 8H) |
| 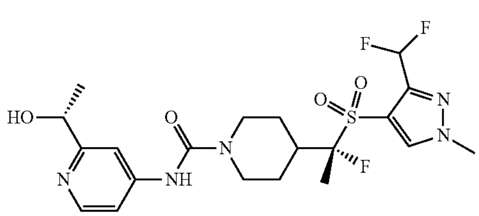 [SMILES: C[C@@H](O)c1cc(NC(=O)N2CCC([C@@](C)(F)S(=O)(=O)c3cn(C)nc3C(F)F)CC2)ccn1] | 4-((S)-1-((3-(difluoro-methyl)-1-methyl-1H-pyrazol-4-yl)sulfonyl)-1-fluoro-ethyl)-N-(2-((R)-1- | 304 | 29 | 490.2 | 1H NMR (400 MHz, CD3OD) δ ppm 8.33 (s, 1H), 8.18 (d, J = 5.8 Hz, 1H), 7.59 (d, J = 2.2 Hz, 1H), 7.38 (dd, J = 5.8, 2.2 Hz, 1H), 6.94 (t, J = 53.1 Hz, 1H), 4.76 (m, 1H), 4.27 (t, J = 14.0 Hz, 2H), 4.00 (s, 3H), 3.00-2.80 (m, |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| | hydroxy-ethyl)pyridin-4-yl)piperidine-1-carboxamide | | | | 2H), 2.52 (s, 1H), 2.18 (d, J = 13.4 Hz, 1H), 1.84 (d, J = 13.1 Hz, 1H), 1.65-1.36 (m, 8H). |
| 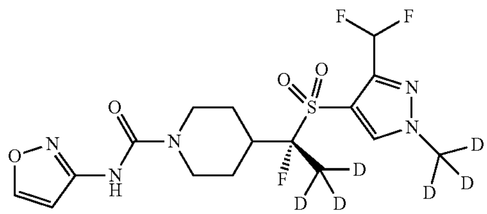 [SMILES: [2H]C([2H])([2H])n1cc(S(=O)(=O)[C@](F)(C2CCN(C(=O)Nc3ccon3)CC2)C([2H])([2H])[2H])c(C(F)F)n1] | (S)-4-(1-((3-(difluoro-methyl)-1-(methyl-d3)-1H-pyrazol-4-yl)sulfonyl)-1-fluoro-ethyl-2,2,2-d3)-N-(isoxazol-3-yl)piperidine-1-carboxamide | 305 | 20 | 442 | 1H NMR (400 MHz, CD3OD) δ ppm 8.33 (s, 1H), 8.25 (s, 1H), 6.87 (t, J = 53.1 Hz, 1H), 6.63 (s, 1H), 4.21-4.17 (m, 2H), 2.84-2.77 (m, 2H), 2.47-2.37 (m, 1H), 2.11-2.07 (m, 1H), 1.77-1.73 (m, 1H), 1.77-1.31 (m, 2H) |
| 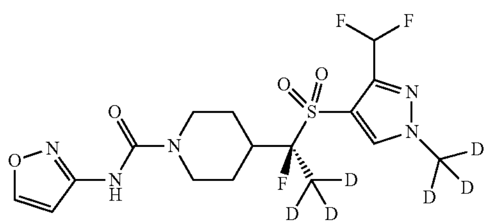 [SMILES: [2H]C([2H])([2H])n1cc(S(=O)(=O)[C@@](F)(C2CCN(C(=O)Nc3ccon3)CC2)C([2H])([2H])[2H])c(C(F)F)n1] | (R)-4-(1-((3-(difluoro-methyl)-1-(methyl-d3)-1H-pyrazol-4-yl)sulfonyl)-1-fluoro-ethyl-2,2,2-d3)-N-(isoxazol-3-yl)piperidine-1-carboxamide | 306 | 20 | 442 | 1H NMR (400 MHz, CD3OD) δ ppm 8.33 (s, 1H), 8.25 (s, 1H), 6.87 (t, J = 53.1 Hz, 1H), 6.63 (s, 1H), 4.21-4.17 (m, 2H), 2.84-2.77 (m, 2H), 2.47-2.37 (m, 1H), 2.11-2.07 (m, 1H), 1.77-1.73 (m, 1H), 1.77-1.31 (m, 2H) |
| 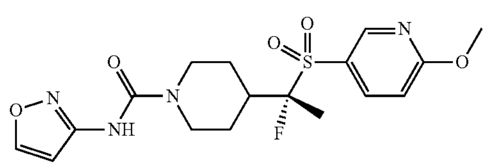 [SMILES: COc1ccc(S(=O)(=O)[C@](C)(F)C2CCN(C(=O)Nc3ccon3)CC2)cn1] | (S)-4-(1-fluoro-1-((6-methoxy-pyridin-3-yl)sulfonyl)ethyl)-N-(isoxazol-3-yl)piperidine-1-carboxamide | 307 | 9 | 435.0 (M + Na)+ | 1H NMR (300 MHz, DMSO-d6) δ ppm 9.73 (br s, 1H), 8.65 (s, 2H), 8.11-8.09 (m, 1H), 7.12 (d, J = 8.8 Hz, 1H), 6.77 (d, J = 1.6 Hz, 1H), 4.26-4.24 (m, 2H), 3.99 (s, 3H), 2.83-2.75 (m, 2H), 2.41-2.40 (m, 1H), 2.07-2.02 (m, 1H), 1.69-1.65 (m, 1H), 1.56 (d, J = 22.8 Hz, 3H), 1.42-1.35 (m, 2H) |
| 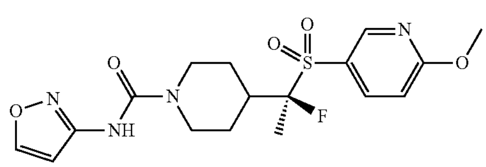 [SMILES: COc1ccc(S(=O)(=O)[C@@](C)(F)C2CCN(C(=O)Nc3ccon3)CC2)cn1] | (R)-4-(1-fluoro-1-((6-methoxy-pyridin-3-yl)sulfonyl)ethyl)-N-(isoxazol-3-yl)piperidine-1-carboxamide | 308 | 9 | 413 | 1H NMR (300 MHz, DMSO-d6) δ ppm 9.71 (br s, 1H), 8.63 (s, 2H), 8.10-8.07 (m, 1H), 7.10 (d, J = 8.7 Hz, 1H), 6.75-6.74 (m, 1H), 4.25-4.20 (m, 2H), 3.97 (s, 3H), 2.87-2.73 (m, 2H), 2.48-2.37 (m, 1H), 2.05-2.00 (m, 1H), 1.67-1.63 (m, 1H), 1.55 (d, J = 23.0 Hz, 3H), 1.44-1.27 (m, 2H) |

TABLE 1-continued

Representative compounds of the Invention and Analytical Data

| Structure | Name | Cmpd. No. | Ref. Example | Obs. Mass (M + H)+ | 1H NMR |
|---|---|---|---|---|---|
| 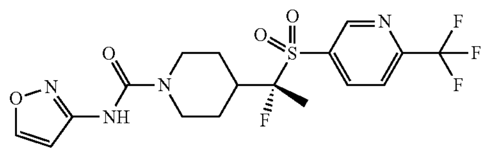 [SMILES: C[C@@](F)(C1CCN(C(=O)Nc2ccon2)CC1)S(=O)(=O)c1ccc(C(F)(F)F)nc1] | (S)-4-(1-fluoro-1-((6-(trifluoromethyl)pyridin-3-yl)sulfonyl)ethyl)-N-(isoxazol-3-yl)piperidine-1-carboxamide | 309 | 4, 6 | 451 | 1H NMR (400 MHz, DMSO-d6) δ ppm 9.73 (s, 1H), 9.24-9.21 (m, 1H), 8.68-8.59 (m, 2H), 8.26-8.24 (m, 1H), 6.75 (s, 1H), 4.25-4.22 (m, 2H), 2.83-2.77 (m, 2H), 2.65-2.59 (m, 1H), 2.05-2.00 (m, 1H), 1.68-1.51 (m, 4H), 1.47-1.34 (m, 2H) |
| 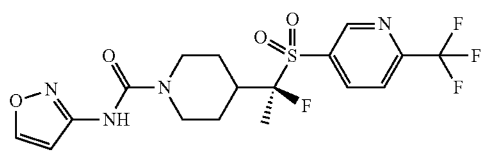 [SMILES: C[C@](F)(C1CCN(C(=O)Nc2ccon2)CC1)S(=O)(=O)c1ccc(C(F)(F)F)nc1] | (R)-4-(1-fluoro-1-((6-(trifluoromethyl)pyridin-3-yl)sulfonyl)ethyl)-N-(isoxazol-3-yl)piperidine-1-carboxamide | 310 | 4, 6 | 451 | 1H NMR (400 MHz, DMSO-d6) δ ppm 9.73 (s, 1H), 9.21 (s, 1H), 8.64-8.59 (m, 2H), 8.26-8.24 (m, 1H), 6.75 (s, 1H), 4.25-4.22 (m, 2H), 2.83-2.77 (m, 2H), 2.65-2.59 (m, 1H), 2.05-2.00 (m, 1H), 1.68-1.51 (m, 4H), 1.47-1.34 (m, 2H) |
| 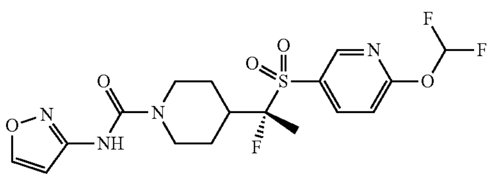 [SMILES: C[C@@](F)(C1CCN(C(=O)Nc2ccon2)CC1)S(=O)(=O)c1ccc(OC(F)F)nc1] | (S)-4-(1-((6-(difluoromethoxy)pyridin-3-yl)sulfonyl)-1-fluoroethyl)-N-(isoxazol-3-yl)piperidine-1-carboxamide | 311 | 14 | 449 | 1H NMR (400 MHz, DMSO-d6) δ ppm 9.88 (s, 1H), 8.73 (d, J = 2.4 Hz, 1H), 8.64 (s, 1H), 8.36-8.33 (m, 1H), 7.80 (t, J = 71.6 Hz, 1H), 7.40 (d, J = 8.8 Hz, 1H), 6.75 (s, 1H), 4.24-4.22 (m, 2H), 2.82-2.76 (m, 2H), 2.49-2.31 (m, 1H), 2.05-2.00 (m, 1H), 1.67-1.64 (m, 1H), 1.51 (d, J = 23.0 Hz, 3H), 1.42-1.31 (m, 2H) |
| 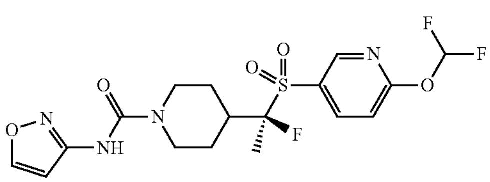 [SMILES: C[C@](F)(C1CCN(C(=O)Nc2ccon2)CC1)S(=O)(=O)c1ccc(OC(F)F)nc1] | (R)-4-(1-((6-(difluoromethoxy)pyridin-3-yl)sulfonyl)-1-fluoroethyl)-N-(isoxazol-3-yl)piperidine-1-carboxamide | 312 | 14 | 449 | 1H NMR (400 MHz, DMSO-d6) δ ppm 9.88 (s, 1H), 8.73 (d, J = 2.4 Hz, 1H), 8.64 (s, 1H), 8.36-8.33 (m, 1H), 7.80 (t, J = 71.6 Hz, 1H), 7.40 (d, J = 8.8 Hz, 1H), 6.75 (s, 1H), 4.24-4.22 (m, 2H), 2.82-2.76 (m, 2H), 2.49-2.31 (m, 1H), 2.05-2.00 (m, 1H), 1.67-1.64 (m, 1H), 1.51 (d, J = 23.0 Hz, 3H), 1.42-1.31 (m, 2H) |

Example 8. Myosin Activation Assay

Small molecule agents were assessed for their ability to activate the enzymatic activity of bovine cardiac myosin using a biochemical assay that couples the release of ADP (adenosine diphosphate) from cardiac myosin to an enzymatic coupling system consisting of pyruvate kinase and lactate dehydrogenase (PK/LDH) and monitoring the absorbance decrease of NADH (at 340 nm) as a function of time. PK converts ADP to ATP (adenosine triphosphate) by converting PEP (phosphoenolpyruvate) to pyruvate. Pyruvate is then converted to lactate by LDH by converting NADH (nicotinamide adenine dinucleotide) to NAD (oxidized nicotinamide adenine dinucleotide). The source of cardiac myosin was from bovine heart in the form of skinned myofibrils. Prior to testing small molecule agents, the bovine myofibrils were assessed for their calcium responsiveness and the calcium concentration that achieves either a 50% (pCa$_{50}$ or pCa=~6) or <5% (pCa=10) activation of the myofibril system was chosen as the final condition for assessing the activation activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM12 buffer). Final assay conditions were 1 mg/mL of bovine cardiac myofibrils, 0.4 mM PK/LDH, 50 uM ATP, 0.1 mg/mL BSA (bovine serum albumin), 10 ppm antifoam, 2 mM BME, 0.5 mM NADH, 1.5 mM PEP at the desired free calcium concentration required to achieve either 50% or <5% activation of the myofibrils.

A dilution series of compound was created in DMSO such that the final desired concentration of compound would be achieved in a volume of 100 μL with a fixed DMSO concentration of 3.3% (v/v). Typically a 1 μL of the dilution series was added to a 384 well plate to achieve a 10 point dose response. Following the addition of 14 μL of a solution containing bovine cardiac myofibrils, PK/LDH and a solution of calcium (that achieved the desired activation), the enzymatic reaction was started with the addition of 15 μL of a solution containing ATP, PEP and NADH. The reaction progress was followed in a PerkinElmer Envision plate reader at ambient temperature using clear bottom plates. The plate reader was configured to read absorbance at 340 nm in kinetics mode for 15 minutes. Data were recorded as the slope of the absorbance response to time. The slopes of the absorbance response as a function of time were normalized to slopes on the plate containing DMSO. This normalized rate was then plotted as a function of small molecule concentration and the data was fitted to a four-parameter fit using EXCEL XLfit. The concentration at which the total response is increased by twenty or fifty percent is reported as AC$_{20}$ or AC$_{50}$. Any agent that failed to achieve the corresponding percent activation at the highest concentration tested is reported as an AC$_{20}$ or AC$_{50}$ greater than the highest concentration tested (ie. AC$_{50}$>50 uM).

TABLE 2

Myosin Activation of Selected Compounds$^a$

| Compound No. | Myosin Activation |
|---|---|
| 1 | + |
| 2 | +++ |
| 3 | +++ |
| 4 | ++ |
| 5 | ++ |
| 6 | ++ |
| 7 | +++ |
| 8 | +++ |
| 9 | +++ |
| 10 | + |
| 11 | ++ |
| 12 | + |
| 13 | + |
| 13.1 | ++ |
| 14 | +++ |
| 15 | +++ |
| 16 | ++ |
| 17 | +++ |
| 18 | +++ |
| 19 | + |
| 20 | +++ |
| 21 | + |
| 22 | + |
| 23 | ++ |
| 24 | ++ |
| 25 | ++ |
| 26 | ++ |
| 27 | + |
| 28 | ++ |
| 29 | + |
| 30 | ++ |
| 31 | ++ |
| 32 | +++ |
| 33 | + |
| 34 | + |
| 35 | +++ |
| 36 | + |
| 37 | +++ |
| 38 | + |
| 39 | + |
| 40 | +++ |
| 40 | + |
| 42 | +++ |
| 43 | +++ |
| 44 | + |
| 45 | +++ |
| 46 | ++ |
| 47 | ++ |
| 48 | ++ |
| 49 | ++ |
| 50 | ++ |
| 51 | ++ |
| 52 | ++ |
| 53 | +++ |
| 54 | ++ |
| 55 | ++ |
| 56 | +++ |
| 57 | ++ |
| 58 | + |
| 59 | ++ |
| 60 | ++ |
| 61 | ++ |
| 62 | + |
| 63 | ++ |
| 64 | ++ |
| 65 | ++ |
| 66 | ++ |
| 67 | ++ |
| 68 | + |
| 69 | ++ |
| 70 | ++ |
| 71 | ++ |
| 72 | +++ |
| 73 | ++ |
| 74 | +++ |
| 75 | ++ |
| 76 | ++ |
| 77 | ++ |
| 78 | + |
| 79 | + |
| 80 | + |
| 81 | + |
| 82 | + |
| 83 | ++ |
| 84 | + |
| 85 | + |
| 86 | ++ |
| 87 | + |
| 88 | + |
| 89 | + |
| 90 | + |
| 91 | ++ |
| 92 | ++ |
| 93 | ++ |
| 94 | + |
| 95 | + |
| 96 | + |
| 97 | + |
| 98 | + |
| 99 | + |
| 100 | + |
| 101 | ++ |

TABLE 2-continued

Myosin Activation of Selected Compounds[a]

| Compound No. | Myosin Activation |
|---|---|
| 102 | + |
| 103 | ++ |
| 104 | + |
| 105 | +++ |
| 106 | ++ |
| 107 | ++ |
| 108 | ++ |
| 109 | + |
| 110 | ++ |
| 111 | ++ |
| 112 | ++ |
| 113 | + |
| 114 | +++ |
| 115 | ++ |
| 116 | +++ |
| 117 | ++ |
| 118 | +++ |
| 119 | ++ |
| 120 | ++ |
| 121 | + |
| 122 | +++ |
| 123 | ++ |
| 124 | + |
| 125 | + |
| 126 | ++ |
| 127 | ++ |
| 128 | ++ |
| 129 | +++ |
| 130 | ++ |
| 131 | + |
| 132 | + |
| 133 | ++ |
| 134 | ++ |
| 135 | + |
| 136 | + |
| 137 | +++ |
| 138 | + |
| 139 | + |
| 140 | +++ |
| 141 | + |
| 142 | + |
| 143 | + |
| 144 | + |
| 145 | + |
| 146 | ++ |
| 147 | + |
| 148 | + |
| 149 | ++ |
| 150 | + |
| 151 | ++ |
| 152 | ++ |
| 153 | + |
| 154 | + |
| 155 | ++ |
| 156 | + |
| 157 | +++ |
| 158 | +++ |
| 159 | ++ |
| 160 | ++ |
| 161 | + |
| 162 | + |
| 163 | + |
| 164 | +++ |
| 165 | +++ |
| 166 | ++ |
| 167 | +++ |
| 168 | +++ |
| 169 | +++ |
| 170 | +++ |
| 171 | ++ |
| 172 | + |
| 173 | + |
| 174 | +++ |
| 175 | +++ |
| 176 | + |
| 177 | + |
| 178 | +++ |
| 179 | +++ |
| 180 | ++ |
| 181 | ++ |
| 182 | +++ |
| 183 | ++ |
| 184 | ++ |
| 185 | + |
| 186 | +++ |
| 187 | +++ |
| 188 | +++ |
| 189 | +++ |
| 190 | ++ |
| 191 | +++ |
| 192 | +++ |
| 193 | +++ |
| 194 | ++ |
| 195 | ++ |
| 196 | ++ |
| 197 | +++ |
| 198 | + |
| 199 | + |
| 200 | ++ |
| 201 | + |
| 202 | +++ |
| 203 | +++ |
| 204 | + |
| 205 | +++ |
| 206 | +++ |
| 207 | +++ |
| 208 | ++ |
| 209 | ++ |
| 210 | +++ |
| 211 | +++ |
| 212 | +++ |
| 213 | +++ |
| 214 | + |
| 215 | ++ |
| 216 | +++ |
| 217 | +++ |
| 218 | ++ |
| 219 | + |
| 220 | + |
| 221 | ++ |
| 222 | + |
| 223 | + |
| 224 | ++ |
| 225 | ++ |
| 226 | + |
| 227 | + |
| 228 | ++ |
| 229 | + |
| 230 | + |
| 231 | + |
| 232 | +++ |
| 233 | +++ |
| 234 | +++ |
| 235 | +++ |
| 236 | ++ |
| 237 | + |
| 238 | + |
| 239 | ++ |
| 240 | ++ |
| 241 | + |
| 242 | ++ |
| 243 | ++ |
| 244 | + |
| 245 | ++ |
| 246 | ++ |
| 247 | + |
| 248 | + |
| 249 | ++ |
| 250 | ++ |
| 251 | ++ |
| 252 | ++ |
| 253 | +++ |

TABLE 2-continued

Myosin Activation of Selected Compounds[a]

| Compound No. | Myosin Activation |
|---|---|
| 254 | + |
| 255 | ++ |
| 256 | ++ |
| 257 | + |
| 258 | + |
| 259 | +++ |
| 260 | ++ |
| 261 | + |
| 262 | +++ |
| 263 | +++ |
| 264 | +++ |
| 265 | +++ |
| 266 | ++ |
| 267 | +++ |
| 268 | +++ |
| 269 | ++ |
| 270 | +++ |
| 271 | ++ |
| 272 | + |
| 273 | ++ |
| 274 | +++ |
| 275 | +++ |
| 276 | +++ |
| 277 | +++ |
| 278 | +++ |
| 279 | + |
| 280 | + |
| 281 | ++ |
| 282 | ++ |
| 283 | ++ |
| 284 | +++ |
| 285 | + |
| 286 | + |
| 287 | +++ |
| 288 | ++ |
| 289 | ++ |
| 290 | ++ |
| 291 | + |
| 292 | ++ |
| 293 | + |
| 294 | ++ |
| 295 | + |
| 296 | +++ |
| 297 | +++ |
| 298 | + |
| 299 | +++ |
| 300 | ++ |
| 301 | ++ |
| 302 | + |
| 303 | + |
| 304 | + |
| 305 | + |
| 306 | +++ |
| 307 | + |
| 308 | ++ |
| 309 | + |
| 310 | ++ |
| 311 | + |
| 312 | +++ |

[a] +++ represents myosin activation value $AC_{20} < 2$ μM; ++ represents myosin activation value $AC_{20}$ from 2 μM-5 μM; + represents myosin activation value $AC_{20} > 5$ μM.

Selectivity against rabbit skeletal myofibrils was assessed as described above with the exception that the source of myosin was that of fast skeletal myosin from rabbit in the form of myofibrils. Dose responses against rabbit skeletal myofibrils were also determined as described above.

Example 9. Cardiomyocyte Contractility Assay

Contractility of adult rat ventricular myocytes is determined by edge detection with an IonOptix contractility system. Aliquots of myocytes in Tyrode buffer (137 mM NaCl, 3.7 mM KCl, 0.5 mM $MgCl_2$, 1.5 mM $CaCl_2$), 4 mM HEPES, 11 mM glucose) are placed in a perfusion chamber (Series 20 RC-27NE; Warner Instruments), allowed to adhere to the coverslip, and then perfused with 37° C. Tyrode buffer. Myocytes are filed stimulated at 1 Hz and 10V. Only myocytes with clear striations, quiescent prior to pacing, with a cell length of 120-180 microns, a basal fractional shortening equal to 3-8% of the cell length, and a contraction velocity greater than 100 microns per second are used for contractility experiments. To determine the response to compounds, myocytes are first perfused for 60 seconds with Tyrodes buffer followed by 5 minutes of compound and a 140 second washout with Tyrodes buffer. Data is continuously recorded using IonOptix software. Contractility data is analyzed using Ionwizard software (IonOptix). For each cell, 10-20 contractility transients were averaged and compared under basal (no compound) and compound-treated conditions. Compound activity is measured by effects on fractional shortening (FS), where fractional shortening is the ratio of the peak length of the cell at contraction divided by the basal cell length normalized to 100% for an untreated cell.

TABLE 3

Activation of Cardiomyocyte Contraction by Selected Compounds[a]

| Compound No. | Activity at 10 uM | Activity at 3.0 uM | Activity at 1.0 uM |
|---|---|---|---|
| 5 | +++ | | ++ |
| 6 | ++ | | |
| 7 | ++ | | ++ |
| 18 | | | +++ |
| 20 | | ++ | + |
| 32 | | | ++ |
| 129 | | +++ | |
| 149 | | ++ | |
| 246 | | +++ | |
| 287 | | ++ | ++ |

[a] + represents fractional shorting activation <20% over basal. ++ represents fractional shorting activation values from 20% to 50% over basal. +++ represents fractional shortening activation values greater than 50% over basal.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

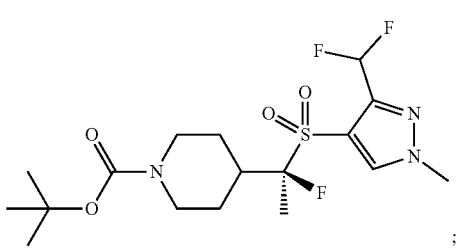

and
reacting the compound
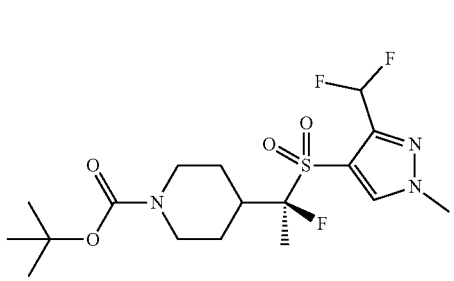
with HCl to produce a compound
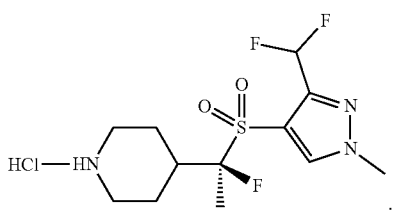
14. The method of claim 13, further comprising:
reacting a compound
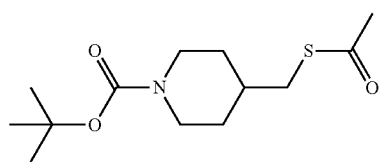
with a compound
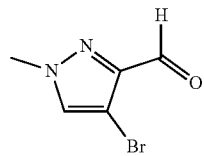
to produce a compound
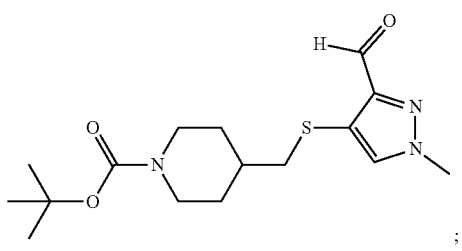
reacting the compound
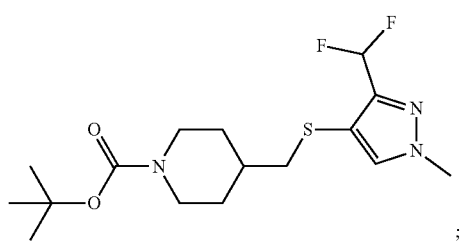
with diethylaminosulfur trifluoride (DAST) to produce a compound
reacting the compound
with N-butyllithium and perchloroethane to produce the compound
and
reacting the compound
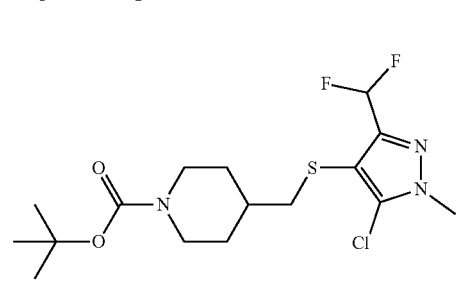

with sodium periodate to produce the compound
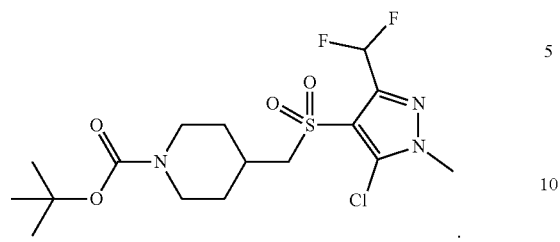

What is claimed is:

1. A method for preparing a compound of formula xi:

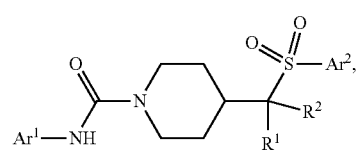

xi or a pharmaceutically acceptable salt thereof, the method comprising:

reacting a compound of formula ix

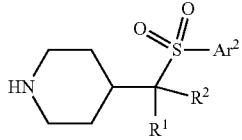

or a salt thereof, with a compound of formula x

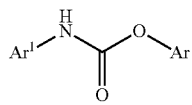

to produce the compound of formula xi, wherein:

Ar is aryl;

Ar$^1$ is selected from the group consisting of pyridyl, pyridazinyl, oxazolyl, isoxazolyl, 1,2,3-thiadiazolyl, isothiazolyl, and thiazolyl, each of which is optionally substituted with from 1-3R$^a$;

Ar$^2$ is selected from the group consisting of phenyl, pyridyl, pyrazolyl, and pyrazolo[1,5-a]pyridyl, each of which is optionally substituted with from 1-5R$^b$;

R$^1$ and R$^2$ are each independently a member selected from H, F, C$_1$-C$_4$ alkyl, C$_1$-C$_4$ deuteroalkyl, and C$_1$-C$_4$ haloalkyl; or optionally R$^1$ and R$^2$ can be combined to form a C$_3$-C$_5$ carbocyclic ring which is optionally substituted with one or two F;

each R$^a$ is independently selected from the group consisting of halo, CN, hydroxyl, C$_1$-C$_4$ alkyl, C$_1$-C$_4$ haloalkyl, C$_1$-C$_4$ hydroxyalkyl, C$_1$-C$_4$ alkoxy, C$_1$-C$_4$ haloalkoxy, —COR$^{a1}$, —CO$_2$R$^{a1}$, —SO$_2$R$^{a1}$, —SO$_2$NR$^{a1}$R$^{a2}$, and —CONR$^{a1}$R$^{a2}$, wherein each R$^{a1}$ and R$^{a2}$ is independently selected from the group consisting of H and C$_1$-C$_4$ alkyl or optionally R$^{a1}$ and R$^{a2}$ when attached to a nitrogen atom are combined to form a 4- to 6-membered ring; or optionally, two R$^a$ substituents on adjacent ring members are combined to form a 5- or 6-membered ring having 0, 1 or 2 ring members selected from O, N and S;

each R$^b$ is independently selected from the group consisting of halo, CN, hydroxyl, C$_1$-C$_4$ alkyl, C$_1$-C$_4$ deuteroalkyl, C$_1$-C$_4$ haloalkyl, C$_1$-C$_4$ alkoxy, C$_1$-C$_4$ haloalkoxy, C$_3$-C$_6$ cycloalkyl, —NR$^{b1}$R$^{b2}$, —COR$^{b1}$, —CO$_2$R$^{b1}$, —SO$_2$R$^{b1}$, —SO$_2$NR$^{b1}$R$^{b2}$, —CONR$^{b1}$R$^{b2}$, and a 5- or 6-membered heteroaryl which is optionally substituted with C$_1$-C$_4$ alkyl, and wherein each R$^{b1}$ and R$^{b2}$ is independently selected from the group consisting of H and C$_1$-C$_4$ alkyl or optionally R$^{b1}$ and R$^{b2}$ when attached to a nitrogen atom are combined to form a 4- to 6-membered ring; or optionally, two R$^b$ substituents on adjacent ring members are combined to form a 5- or 6-membered ring having 0, 1 or 2 ring members selected from O, N and S.

2. A method for preparing a compound having the formula:

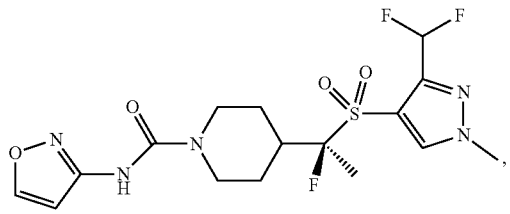 [SMILES: Cn1cc(S(=O)(=O)[C@@](C)(F)C2CCN(C(=O)Nc3ccon3)CC2)c(C(F)F)n1]

or a pharmaceutically acceptable salt thereof, the method comprising:

reacting a compound

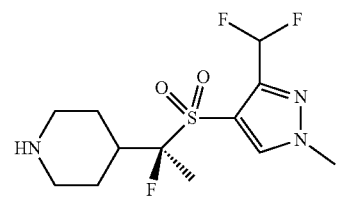 [SMILES: Cn1cc(S(=O)(=O)[C@@](C)(F)C2CCNCC2)c(C(F)F)n1]

or a salt thereof, with a compound

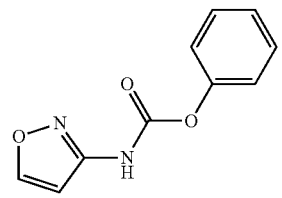 [SMILES: O=C(Nc1ccon1)Oc1ccccc1]

to produce the compound

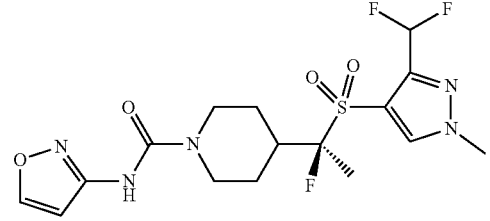 [SMILES: Cn1cc(S(=O)(=O)[C@@](C)(F)C2CCN(C(=O)Nc3ccon3)CC2)c(C(F)F)n1]

or a pharmaceutically acceptable salt thereof.

3. The method of claim 2, further comprising:

reacting a compound

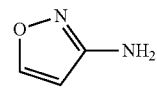

with phenyl chloroformate to produce the compound

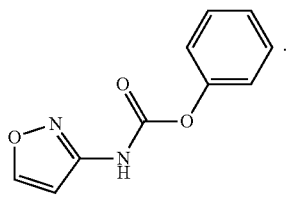 [SMILES: O=C(Nc1ccon1)Oc1ccccc1]

4. The method of claim 2, further comprising: reacting a compound

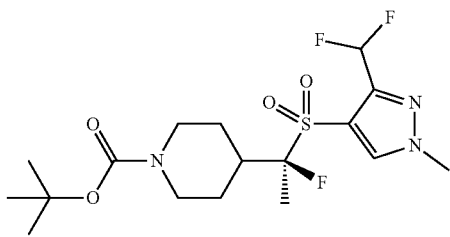 [SMILES: Cn1cc(S(=O)(=O)[C@@](C)(F)C2CCN(C(=O)OC(C)(C)C)CC2)c(C(F)F)n1]

with HCl to produce the compound

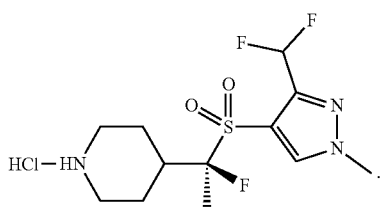

5. The method of claim 4, further comprising: performing a chiral separation of a compound

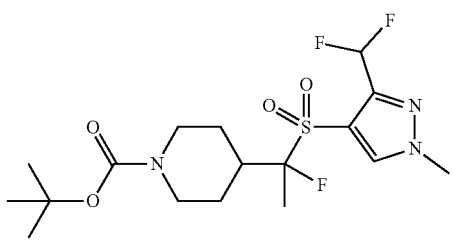 [SMILES: Cn1cc(S(=O)(=O)C(C)(F)C2CCN(C(=O)OC(C)(C)C)CC2)c(C(F)F)n1]

to isolate the compound

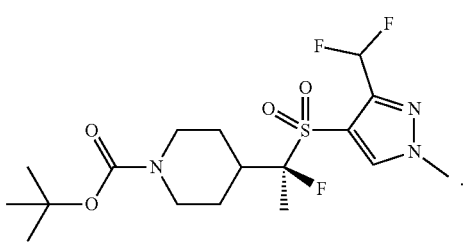 [SMILES: Cn1cc(S(=O)(=O)[C@@](C)(F)C2CCN(C(=O)OC(C)(C)C)CC2)c(C(F)F)n1]

6. The method of claim 5, further comprising: reacting a compound

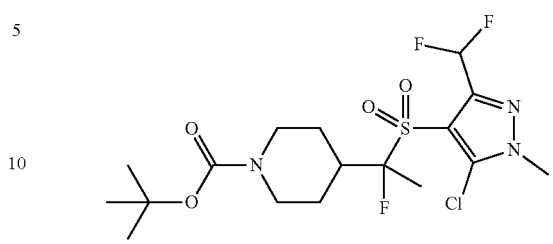

with n-Butyllithium to produce the compound

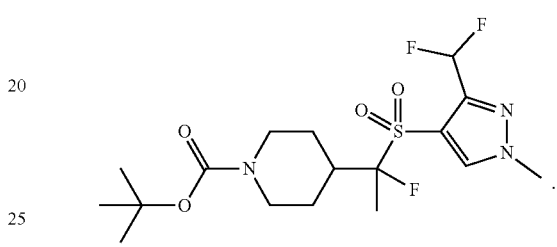

7. The method of claim 6, further comprising: reacting a compound

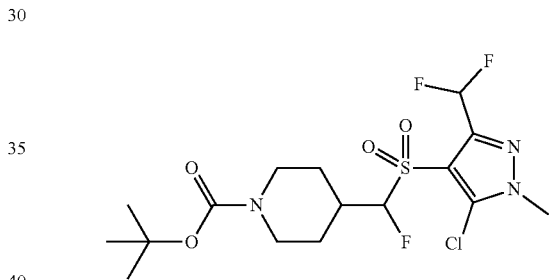

with iodomethane to produce the compound

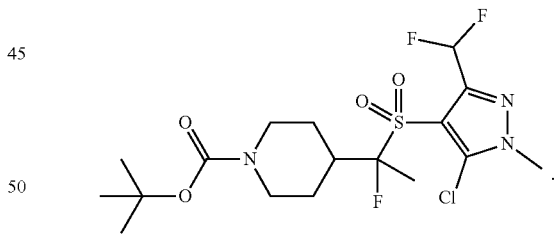

8. The method of claim 7, further comprising: reacting a compound

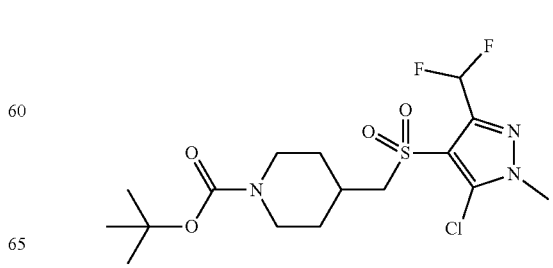

with lithium diisopropylamide (LDA) followed by N-Fluorobenzenesulfonimide (NFSI) to produce the compound

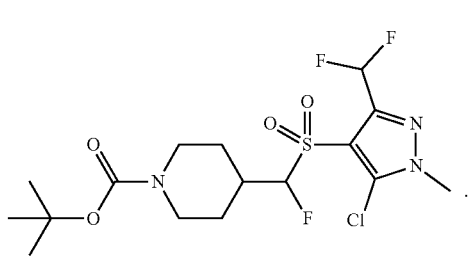 [SMILES: Cn1nc(C(F)F)c(S(=O)(=O)C(F)C2CCN(C(=O)OC(C)(C)C)CC2)c1Cl]

9. The method of claim 8, further comprising:

reacting a compound

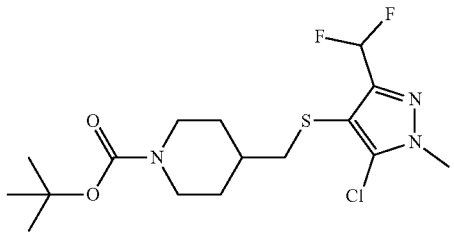 [SMILES: Cn1nc(C(F)F)c(SCC2CCN(C(=O)OC(C)(C)C)CC2)c1Cl]

with sodium periodate to produce the compound

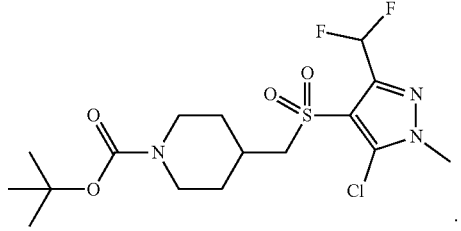 [SMILES: Cn1nc(C(F)F)c(S(=O)(=O)CC2CCN(C(=O)OC(C)(C)C)CC2)c1Cl]

10. The method of claim 9, further comprising:

reacting a compound

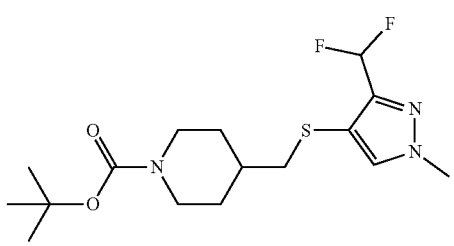

with N-butyllithium and perchloroethane to produce the compound

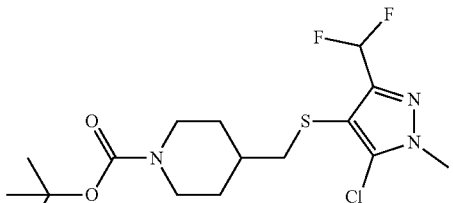

11. The method of claim 10, further comprising:

reacting a compound

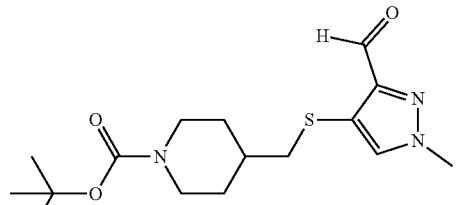

with diethylaminosulfur trifluoride (DAST) to produce the compound

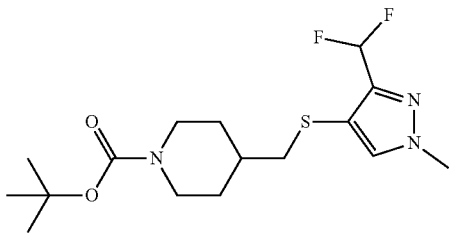 [SMILES: Cn1cc(SCC2CCN(C(=O)OC(C)(C)C)CC2)c(C(F)F)n1]

12. The method of claim 11, further comprising:

reacting a compound

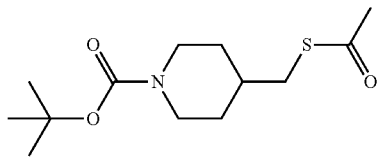

with a compound

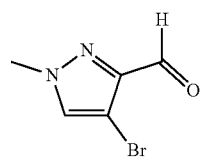

to produce the compound

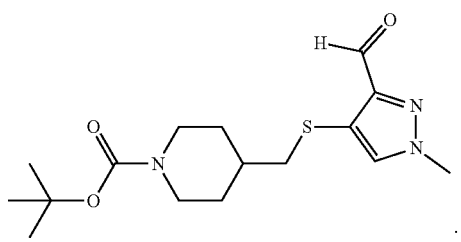 [SMILES: Cn1cc(SCC2CCN(C(=O)OC(C)(C)C)CC2)c(C=O)n1]

13. The method of claim 2, further comprising:
reacting a compound

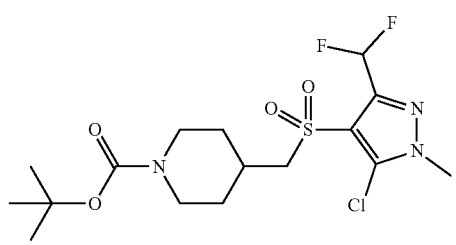 [SMILES: Cn1nc(C(F)F)c(S(=O)(=O)CC2CCN(C(=O)OC(C)(C)C)CC2)c1Cl]

with lithium diisopropylamide (LDA) followed by N-Fluorobenzenesulfonimide (NFSI) to produce a compound

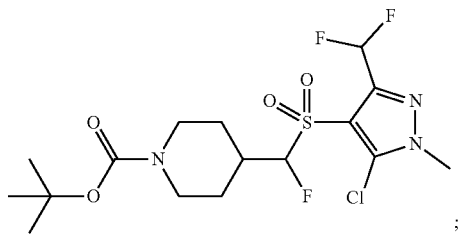

reacting the compound

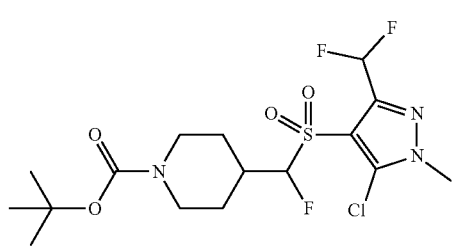 [SMILES: Cn1nc(C(F)F)c(S(=O)(=O)C(F)C2CCN(C(=O)OC(C)(C)C)CC2)c1Cl]

with iodomethane to produce a compound

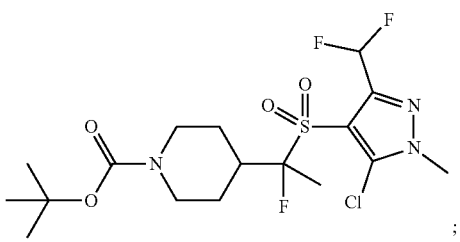 [SMILES: Cn1nc(C(F)F)c(S(=O)(=O)C(C)(F)C2CCN(C(=O)OC(C)(C)C)CC2)c1Cl]

reacting the compound

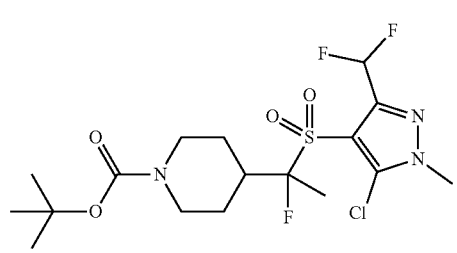

with n-Butyllithium to produce a compound

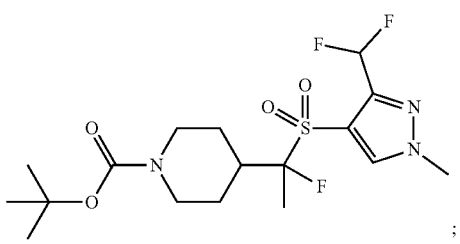 [SMILES: Cn1cc(S(=O)(=O)C(C)(F)C2CCN(C(=O)OC(C)(C)C)CC2)c(C(F)F)n1]

performing a chiral separation of the compound

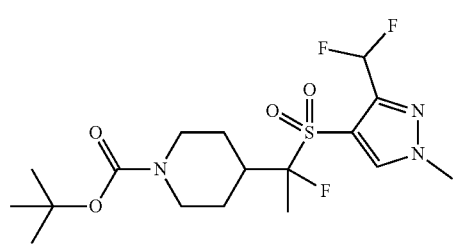

to isolate a compound